US012760073B2

(12) United States Patent
Brown et al.

(10) Patent No.: US 12,760,073 B2
(45) Date of Patent: Oct. 13, 2026

(54) COMPOSITIONS AND METHODS OF RIBONUCLEIC ACID RESPIRATORY SYNCYTIAL VIRUS (RSV) VACCINES

(71) Applicant: RNAimmune, Inc., Germantown, MD (US)

(72) Inventors: David Brown, Germantown, MD (US); Neeti Ananthaswamy, Germantown, MD (US); Renxiang Chen, Germantown, MD (US); Dong Shen, Germantown, MD (US)

(73) Assignee: RNAIMMUNE, INC., Germantown, MD (US)

(*) Notice: Subject to any disclaimer, the term of this patent is extended or adjusted under 35 U.S.C. 154(b) by 0 days.

(21) Appl. No.: 18/781,757

(22) Filed: Jul. 23, 2024

(65) Prior Publication Data

US 2024/0370011 A1 Nov. 7, 2024

Related U.S. Application Data

(63) Continuation of application No. 18/666,691, filed on May 16, 2024, now abandoned, which is a continuation of application No. PCT/US2022/050620, filed on Nov. 21, 2022.

(60) Provisional application No. 63/281,578, filed on Nov. 19, 2021.

(51) Int. Cl.

| | |
|---|---|
| ***C07K 14/005*** | (2006.01) |
| ***A61K 39/12*** | (2006.01) |
| ***A61P 31/14*** | (2006.01) |
| ***A61P 37/04*** | (2006.01) |
| ***C07K 14/135*** | (2006.01) |
| ***C12N 7/00*** | (2006.01) |
| ***G05B 23/02*** | (2006.01) |
| *A61K 39/00* | (2006.01) |

(52) U.S. Cl.

CPC ............ *C07K 14/005* (2013.01); *A61K 39/12* (2013.01); *A61P 31/14* (2018.01); *A61P 37/04* (2018.01); *C07K 14/135* (2013.01); *C12N 7/00* (2013.01); *G05B 23/0283* (2013.01); *A61K 39/00* (2013.01); *A61K 2039/51* (2013.01); *A61K 2039/53* (2013.01); *A61K 2039/55555* (2013.01); *C07K 2319/00* (2013.01); *C07K 2319/02* (2013.01); *C07K 2319/03* (2013.01); *C12N 2760/18522* (2013.01); *C12N 2760/18534* (2013.01); *C12N 2760/18541* (2013.01)

(58) Field of Classification Search

None

See application file for complete search history.

(56) References Cited

U.S. PATENT DOCUMENTS

| | | | | |
|---|---|---|---|---|
| 12,029,786 B2 * | 7/2024 | Tang | .................... | C07K 14/005 |
| 2014/0024076 A1 | 1/2014 | Tang et al. | | |
| 2014/0271699 A1 | 9/2014 | Kwong et al. | | |
| 2016/0046675 A1 * | 2/2016 | Kwong | ................ | C07K 14/005 530/400 |
| 2017/0319682 A1 | 11/2017 | Smith et al. | | |
| 2021/0170017 A1 * | 6/2021 | Lutz | ...................... | A61K 39/12 |

OTHER PUBLICATIONS

Comp to SEQ ID# 96 (Year: 2025).*
SEQ ID #5 to Kwong (Year: 2025).*
International Search Report and Written Opinion on PCT/US2022/050620 Dtd Aug. 4, 2023, 16 pages.

* cited by examiner

*Primary Examiner* — Shanon A. Foley
*Assistant Examiner* — Myron G Hill
(74) *Attorney, Agent, or Firm* — Foley & Lardner LLP

(57) ABSTRACT

Provided herein is a ribonucleic acid (RNA) encoding a fusion glycoprotein (F) protein or an immunogenic fragment thereof of a respiratory syncytial virus (RSV) comprising at least one non-naturally occurring amino acid mutation. Additionally provided are relevant polynucleotides, vectors, cells, compositions, kits, production methods and methods of use.

18 Claims, 33 Drawing Sheets

Specification includes a Sequence Listing.

RSV Vaccines

| Name | Name | Design | TM/Secreted | Conformation |
|---|---|---|---|---|
| A2-1 (WT RSVF) | F1 (optimized WT RSVF) |  | TM | Pre/Post |
| A2-2 | F2 |  | Secreted | Pre/Post |
| A2-3 | F3 |  | TM | Pre |
| A2-4 | F4 |  | Secreted | Pre |
| A2-5 | F5 |  | TM | Pre |
| A2-6 | F6 |  | Secreted | Pre |

| Animal Group | Formulation | mRNA | mRNA(ug/animal) | Number of Mice |
|---|---|---|---|---|
| 1 | LNP | RSVA2-F3 | 10 | 3 |
| 2 | LNP | RSVA2-F5 | 10 | 4 |
| 3 | LNP | RNAi Vaccine-F3 | 10 | 2 |
| 4 | LNP | RNAi Vaccine-F4 | 10 | 3 |
| 5 | LNP | RNAi Vaccine-F5 | 10 | 3 |
| 6 | LNP | RNAi Vaccine-F6 | 10 | 3 |

| Animal Group | Formulation | mRNA | mRNA(ug/animal) | Number of Mice |
|---|---|---|---|---|
| 1 | LNP | RNAi Vaccine-F3 | 10 | 5 |
| 2 | LNP | RNAi Vaccine-F6 | 10 | 5 |

COMPOSITIONS AND METHODS OF RIBONUCLEIC ACID RESPIRATORY SYNCYTIAL VIRUS (RSV) VACCINES

CROSS-REFERENCE TO RELATED APPLICATION

This application is continuation of U.S. patent application Ser. No. 18/666,691, filed on May 16, 2024, which is a bypass continuation of International Application No. PCT/US2022/050620, filed on Nov. 21, 2022, which claims priority under 35 U.S.C. § 119(e) and the Paris Convention to U.S. Provisional Application No. 63/281,578, filed Nov. 19, 2021, the contents of each which are incorporated herein by reference in their entireties.

INCORPORATION BY REFERENCE OF SEQUENCE LISTING

The instant application contains a Sequence Listing which has been submitted electronically in XML format and is hereby incorporated by reference in its entirety. Said XML copy, created on Mar. 31, 2023, is named 129774-3510.xml and is 187,114 bytes in size.

FIELD OF THE DISCLOSURE

Prophylactic and therapeutic agents for vaccination, prevention and treatment of respiratory syncytial virus (RSV) infections are provided.

SUMMARY OF THE DISCLOSURE

Provided herein is a fusion glycoprotein or immunogenic fragment thereof of a Respiratory Syncytial Virus (RSV) or a ribonucleic acid (RNA) encoding the fusion glycoprotein (F) protein or an immunogenic fragment thereof of the Respiratory Syncytial Virus (RSV) or an equivalent of each thereof. The F protein or immunogenic fragment thereof or an equivalent of each thereof encoded by the RSV RNA comprises or consists essentially of, or yet further consists of at least one non-naturally occurring amino acid mutation, for example, as compared to the amino acid sequence depicted in SEQ ID NO: 53 or 87.

In some embodiments, the RSV RNA encodes at least one non-naturally occurring amino acid mutation of the glycoprotein, fragment or equivalent thereof comprises, or alternatively consists essentially of, or yet further consists of one or more of: a cysteine (C) as the amino acid corresponding to S155 of SEQ ID NO: 87 or 53 (S155C), a phenylalanine (F) as the amino acid corresponding to S190 of SEQ ID NO: 87 or 53 (S190F), a leucine (L) as the amino acid corresponding to V207 of SEQ ID NO: 87 or 53 (V207L), a C as the amino acid corresponding to S290 of SEQ ID NO: 87 or 53 (S290C), or an equivalent thereof that maintains these amino acid mutations. In one aspect, the RSV RNA encodes a glycoprotein, fragment or equivalent thereof that comprises all four mutations, a non-limiting example of which is the optimized Vaccine F4 or Vaccine A2-4 without a transmembrane domain and optimized Vaccine F3 or Vaccine A2-3 with a transmembrane domain. Further provided is a polynucleotide encoding the fusion glycoprotein, the immunogenic fragment, or the equivalent thereof, that is DNA or RNA. Exemplary DNA sequence that encode a F protein are provided in SEQ ID NOS: 2, 4, 6, 8, 10, 12, 54, 57, 63, 66 or 69.

In some embodiments, the RSV RNA immunogenic fragment encodes: a fusion peptide, an heptad repeat A (HRA), a F protein, and a heptad repeat B (HRB), and optionally, an N-terminal signal peptide, an N-terminal heptad repeat C (HRC) peptide, wherein the immunogenic fragment further comprises an N-terminal p27 peptide, or wherein the immunogenic fragment optionally further comprises a C-terminal transmembrane domain and a cytoplasmic domain, or wherein the immunogenic fragment optionally further comprises a C-terminal trimerization domain.

The RSV RNA as disclosed herein can further comprising an RNA encoding a p27 peptide, e.g., the p27 peptide can comprise SEQ ID NO: 77 or comprises amino acids 110 to 137 of SEQ ID NO: 53.

In certain embodiments, the RSV RNA can further comprise an RNA encoding the HRC, e.g., wherein the HRC optionally comprises SEQ ID NO: 74 or optionally comprises the amino acids 27 to 109 of SEQ ID NO: 53.

In another aspect, the RSV RNA can further comprise an RNA encoding a signal peptide, e.g., the signal peptide of SEQ ID NO: 71 or the signal peptides of amino acids 1 to 26 of SEQ ID NO: 53.

In yet further embodiments, the at least one non-naturally occurring amino acid mutation encoded in the fusion glycoprotein, the fragment or equivalent thereof comprises, or alternatively consists essentially of, or yet further consists of one or more of: a histidine (H) as the amino acid corresponding to D486 of SEQ ID NO: 87 or 53 (D486H), a glutamine (Q) as the amino acid corresponding to E487 of SEQ ID NO: 87 or 53 (E487Q), a tryptophan (W) as the amino acid corresponding to F484 of SEQ ID NO: 87 or 53 (F484W), or a H as the amino acid corresponding to D489 of SEQ ID NO: 87 or 53 (D489H), or an equivalent thereof that maintains these amino acid mutations. Further provided is a polypeptide encoded by the RNA, or a polynucleotide encoding the fusion glycoprotein, the immunogenic fragment, or the equivalent thereof, that is DNA or RNA. Exemplary DNA sequence for the F protein are provided in SEQ ID NOS: 2, 4, 6, 8, 10, 12, 54, 57, 63, 66 or 69.

In some embodiments, the at least one non-naturally occurring amino acid mutation of the encoded glycoprotein, fragment or equivalent thereof comprises, or alternatively consists essentially of, or yet further consists of one or more of: a cysteine (C) as the amino acid corresponding to S155 of SEQ ID NO: 87 or 53 (S155C), a phenylalanine (F) as the amino acid corresponding to S190 of SEQ ID NO: 87 or 53 (S190F), a leucine (L) as the amino acid corresponding to V207 of SEQ ID NO: 87 or 53 (V207L), a C as the amino acid corresponding to S290 of SEQ ID NO: 87 or 53 (S290C), D486 of SEQ ID NO: 87 or 53 (D486H), a glutamine (Q) as the amino acid corresponding to E487 of SEQ ID NO: 87 or 53 (E487Q), a tryptophan (W) as the amino acid corresponding to F484 of SEQ ID NO: 87 or 53 (F484W), or a H as the amino acid corresponding to D489 of SEQ ID NO: 87 or 53 (D489H). In another aspect, the encoded glycoprotein, fragment or equivalent thereof comprises all eight mutations, an example of such is identified herein as optimized Vaccine F6 or Vaccine A2-6, without a transmembrane domain and optimized Vaccine F5 or Vaccine A2-5 with a transmembrane domain. Further provided is a polypeptide encoded by the RNA, or a polynucleotide encoding the fusion glycoprotein, the immunogenic fragment, or the equivalent thereof, that is DNA or RNA.

In some embodiments, the amino acid of the protein or immunogenic fragment or equivalent does not comprise SEQ ID NO: 53, or the fragment of SEQ ID NO: 53, and the polynucleotide does not encode SEQ ID NO: 53 or the fragment of SEQ ID NO: 53.

In some embodiments, the polynucleotide is RNA that is optionally a messenger RNA (mRNA).

In some embodiments, the fusion glycoprotein, fragment or equivalent of each thereof further comprises a RSV transmembrane domain, as well as DNA, RNA, e.g., mRNA, encoding the fusion glycoprotein, fragment or equivalent thereof and the transmembrane domain. In one aspect, the polynucleotide is RNA that comprises, or alternatively consists essentially of, or yet further consists of a polynucleotide such as SEQ ID NO: 97 or 61, or an equivalent thereof. In some embodiments, the RNA further comprises a three prime untranslated region (3' UTR), a polyadenylation (polyA) tail and a five prime untranslated region (5' UTR).

In another aspect of this disclosure, the immunogenic fragment of the RSV RNA further comprises a polynucleotide encoding: the N-terminal signal peptide, the N-terminal HRC peptide, and the N-terminal p27 peptide, or the immunogenic fragment further comprises the C-terminal a transmembrane domain and a cytoplasmic domain, or the C-terminal trimerization domain, or the immunogenic fragment further comprises the N-terminal signal peptide, the N-terminal HRC peptide, and the N-terminal p27 peptide and the C-terminal a transmembrane domain and a cytoplasmic domain, or a C-terminal trimerization domain.

In a further embodiment, the RSV RNA as disclosed above and herein, encodes at least one non-naturally occurring amino acid mutation comprises D486H, E487Q, F484W, and D489H and/or S155C, S190F, V207L, and S290C of SEQ ID NOs: 87 or 53, or an equivalent thereof that maintains the mutations.

In a further aspect, the RSV RNA encode an F protein that comprises the fusion peptide, the HRA, the F protein, and the trimerization domain of the optimized F4 vaccine (SEQ ID NO: 7) or an equivalent thereof, wherein the equivalent of SEQ ID NO: 7 comprises the mutations of S155C, S190F, V207L, and S290C or the F protein comprises the fusion peptide, the HRA, the F protein, and the trimerization domain of the A2-4 vaccine (amino acids 138 to 556 of SEQ ID NO: 62) or an equivalent thereof, wherein the equivalent of SEQ ID NO: 62 comprises the mutations of S155C, S190F, V207L, and S290C. Further provided is a polypeptide encoded by the RNA, or a polynucleotide encoding the fusion glycoprotein, the immunogenic fragment, or the equivalent thereof, that is DNA or RNA.

In some embodiments, the amino acid of the protein or immunogenic fragment or equivalent does not comprise SEQ ID NO: 53, or the fragment of SEQ ID NO: 53, and the polynucleotide does not encode SEQ ID NO: 53 or the fragment of SEQ ID NO: 53.

In another aspect, the RSV RNA encodes a F protein that comprises the fusion peptide, the HRA, the F protein, and the trimerization domain of the optimized F vaccine (SEQ ID NO: 11) or an equivalent thereof, wherein the equivalent of SEQ ID NO: 11 comprises the mutations of S155C, S190F, V207L, S290C, D486H, E487Q, F484W, and D489H or the F protein comprises the fusion peptide, the HRA, the F protein, and the trimerization domain of the A2-6 vaccine (amino acids 138 to 556 of SEQ ID NO: 68) or an equivalent thereof, wherein the equivalent of SEQ ID NO: 68 comprises the mutations of S155C, S190F, V207L, S290C, D486H, E487Q, F484W, and D489H. Further provided is a polypeptide encoded by the RNA, or a polynucleotide encoding the fusion glycoprotein, the immunogenic fragment, or the equivalent thereof, that is DNA or RNA.

In some embodiments, the amino acid of the protein or immunogenic fragment or equivalent does not comprise SEQ ID NO: 53, or the fragment of SEQ ID NO: 53, and the polynucleotide does not encode SEQ ID NO: 53 or the fragment of SEQ ID NO: 53.

In another aspect, RSV RNA encodes a F protein that comprises the fusion peptide, the HRA, the F protein, the transmembrane domain and a cytoplasmic domain of the optimized F vaccine (SEQ ID NO: 5) or an equivalent thereof, wherein the equivalent of SEQ ID NO: 5 comprises the mutations of S155C, S190F, V207L, and S290C, or the F protein comprises the fusion peptide, the HRA, the F protein, and the transmembrane domain and the cytoplasmic domain of the A2-3 vaccine (amino acids 138 to 574 of SEQ ID NO: 59) or an equivalent thereof, wherein the equivalent of SEQ ID NO: 59 comprises the mutations of S155C, S190F, V207L, and S290C. Further provided is a polypeptide encoded by the RNA, or a polynucleotide encoding the fusion glycoprotein, the immunogenic fragment, or the equivalent thereof, that is DNA or RNA.

In some embodiments, the amino acid of the protein or immunogenic fragment or equivalent does not comprise SEQ ID NO: 53, or the fragment of SEQ ID NO: 53, and the polynucleotide does not encode SEQ ID NO: 53 or the fragment of SEQ ID NO: 53.

In a further aspect, provided herein is an RSV RNA that encodes a F protein that comprises the fusion peptide, the HRA, the F protein, the transmembrane domain and the cytoplasmic domain of the optimized F vaccine (SEQ ID NO: 9) or an equivalent thereof, wherein the equivalent of SEQ ID NO: 9 comprises the mutations of S155C, S190F, V207L, S290C, D486H, E487Q, F484W, and D489H, or the F protein comprises the fusion peptide, the HRA, the F protein, and the transmembrane domain and the cytoplasmic domain of the A2-5 vaccine (amino acids 138 to 574 of SEQ ID NO: 65) or an equivalent thereof, wherein the equivalent of SEQ ID NO: 65 comprises the mutations of S155C, S190F, V207L, S290C, D486H, E487Q, F484W, and D489H. Further provided is a polypeptide encoded by the RNA, or a polynucleotide encoding the fusion glycoprotein, the immunogenic fragment, or the equivalent thereof, that is DNA or RNA.

In some embodiments, the amino acid of the protein or immunogenic fragment or equivalent does not comprise SEQ ID NO: 53, or the fragment of SEQ ID NO: 53, and the polynucleotide does not encode SEQ ID NO: 53 or the fragment of SEQ ID NO: 53.

In one aspect, provided is a polynucleotide, such as a DNA, encoding an RNA as disclosed herein. In a further aspect, provided is a vector comprising a polynucleotide as disclosed herein. In one embodiment, the vector is a plasmid, optionally comprising, or alternatively consisting essentially of, or yet further consisting of SEQ ID NO: 29 or an equivalent thereof. In yet a further aspect, provided is a cell comprising one or more of: a fusion glycoprotein, fragment or equivalent thereof as disclosed herein, an RNA as disclosed herein, a polynucleotide as disclosed herein, or a vector as disclosed herein. The cell can be a prokaryotic or a eukaryotic cell. In one aspect, provided is a composition comprising, or alternatively consisting essentially of, or yet further consisting of a carrier, optionally a pharmaceutically acceptable carrier and one or more of: a fusion glycoprotein, fragment or equivalent thereof, an RNA as disclosed herein, a polynucleotide as disclosed herein, a vector as disclosed herein, or a cell as disclosed herein.

Additionally provided is a method of producing a DNA, an RNA or a fusion glycoprotein, fragment or equivalent thereof, or a vector as disclosed herein. In some embodiments, the method comprises, or alternatively consists essentially of, or yet further consisting of culturing a cell as disclosed herein under conditions suitable for expressing or replicating the DNA, the RNA or the fusion glycoprotein, fragment or equivalent thereof, or the vector as disclosed. In other aspects, the DNA or RNA is replicated using chemical in vitro methods. In one embodiment, the method comprises, or alternatively consists essentially of, or yet further consists of contacting a polynucleotide or a vector as disclosed herein with an RNA polymerase, adenosine triphosphate (ATP), cytidine triphosphate (CTP), guanosine-5'-triphosphate (GTP), and uridine triphosphate (UTP) or a chemically modified UTP (such as N1-methyl pseudouridine trisphosphate) under conditions suitable for expressing or replicating the RNA. In further embodiments, a method as disclosed herein further comprises isolating the RNA, the DNA or fusion glycoprotein, fragment or equivalent thereof.

In one aspect, provided is a composition comprising, or alternatively consisting essentially of, or yet further consisting of an RNA as disclosed herein and a carrier such as a pharmaceutically acceptable carrier. In some embodiments, the pharmaceutically acceptable carrier comprises, or alternatively consists essentially of, or yet further consists of a polymeric nanoparticle. In further embodiments, the polymeric nanoparticle comprises, or alternatively consists essentially of, or yet further consists of a Histidine-Lysine co-polymer (HKP). In some embodiments, the pharmaceutically acceptable carrier further comprises a lipid, optionally one or more of: a cationic lipid (such as Dlin-MC3-DMA, i.e., MC3), a helper lipid, a cholesterol, or a PEGylated lipid. In some embodiments, the pharmaceutically acceptable carrier comprises, or alternatively consists essentially of, or yet further consists of a lipid nanoparticle (LNP). In some embodiments, the LNP comprises one or more of: 9-Heptadecanyl 8-{(2-hydroxyethyl)[6-oxo-6-(undecyloxy)hexyl]amino}octanoate (SM-102), 2,2-dilinoleyl-4-dimethylaminoethyl-[1,3]-dioxolane (DLin-KC2-DMA), dilinoleyl-methyl-4-dimethylaminobutyrate (DLin-MC3-DMA), di((Z)-non-2-en-1-yl) 9-((4-(dimethylamino)butanoyl)oxy)heptadecanedioate (L319), or an equivalent of each thereof. In further embodiments, the LNP further comprises one or more of: a helper lipid, a cholesterol, or a PEGylated lipid. A further pharmaceutically acceptable carrier can be added to the nanoparticle composition, e.g., phosphate buffered saline, preservative such as a cryopreservative and the like.

In further embodiments, the pharmaceutically acceptable carrier further comprises a dilute, an adjuvant, a binder, a stabilizer, a buffer, a salt, a lipophilic solvent, or a preservative. In some embodiments, the nanoparticle is a self-assembled nanoparticle. In a further aspect, provided is a composition comprising, or alternatively consisting essentially of, or yet further consisting of a self-assembled nanoparticle comprising an RNA as disclosed herein. In some embodiments, the nanoparticle encapsulates the RNA. In other embodiments, the nanoparticle is conveniently or non-covalently linked to the RNA.

In a further embodiments, provided is a method of producing the composition. In some embodiments, the method comprises, or alternatively consists essentially of, or yet further consists of contacting an RNA as disclosed herein with an HKP, thereby the RNA and the HKP are self-assembled into nanoparticles. Additionally or alternatively, the method comprises, or alternatively consists essentially of, or yet further consist of contacting an RNA as disclosed herein with a lipid, thereby the RNA and the lipid are self-assembled into nanoparticles. In further embodiment, the contacting step is performed in a microfluidic mixer.

In another aspect, provided is a method of one or more of: (a) preventing a subject from having a symptomatic RSV infection, (b) inducing an immune response to RSV in a subject in need thereof, (c) reducing the binding of an RSV or an F protein thereof in a subject in need thereof, (d) treating a subject infected with RSV, or (e) reducing a RSV viral load in a subject in need thereof. The method comprises, or alternatively consists essentially of, or yet further consists of administering to the subject one or more of: an RNA as disclosed herein, a polynucleotide as disclosed herein, a vector as disclosed herein, or a composition as disclosed herein. These methods can also be performed in vitro in a cell system. Such in vitro methods are useful to assay for efficacy and possible combination therapies. In one aspect, the subject is a human patient, selected from an infant, a pediatric patient, or a pregnant human or an adult 60 years old or older.

In one aspect, provided is an inhalation system comprising, or alternatively consisting essentially of, or yet further consisting of an RNA as disclosed herein, a polynucleotide as disclosed herein, a vector as disclosed herein, or a composition as disclosed herein, and a nebulizer.

Also provided is a kit for use in a method as described herein. In some embodiments, the kit comprises, or alternatively consists essentially of, or yet further consists of instructions for use and one or more of: a DNA as disclosed herein, a fusion glycoprotein, fragment or equivalent thereof as disclosed herein, an RNA as disclosed herein, a polynucleotide as disclosed herein, a vector as disclosed herein, a cell as disclosed herein, a composition as disclosed herein, and optionally an inhalation system as disclosed herein.

BRIEF DESCRIPTION OF THE DRAWINGS

FIG. 1B shows the assembly of resultant proteins.

FIG. 4A illustrates an X-Ray Crystallography diagram of a trimeric prefusion structure of an RSV F protein that undergoes conformational rearrangements. The figure is reproduced from: Bermingham, Imogen M et al. "The Heptad Repeat C Domain of the Respiratory Syncytial Virus Fusion Protein Plays a Key Role in Membrane Fusion." *Journal of virology* vol. 92, 4 e01323-17. 30 Jan. 2018, doi:10.1128/JVI.01323-17.

FIG. 4B illustrates an X-Ray Crystallography diagram of a postfusion form of the RSV F protein. The figure is reproduced from: Bermingham, Imogen M et al. "The Heptad Repeat C Domain of the Respiratory Syncytial Virus Fusion Protein Plays a Key Role in Membrane Fusion." *Journal of Virology* vol. 92, 4 e01323-17. 30 Jan. 2018, doi:10.1128/JVI.01323-17. F protein exists in multiple conformational forms. In the prefusion state (PreF), the protein exists in a trimeric form and contains the major antigenic site Ø. Ø serves as a primary target of neutralizing antibodies in a subject.

FIG. 11 shows mouse serum titration against RSV A2 at 35 DPI PRNT50.

DETAILED DESCRIPTION

Definitions

Figures 1A, 1B:
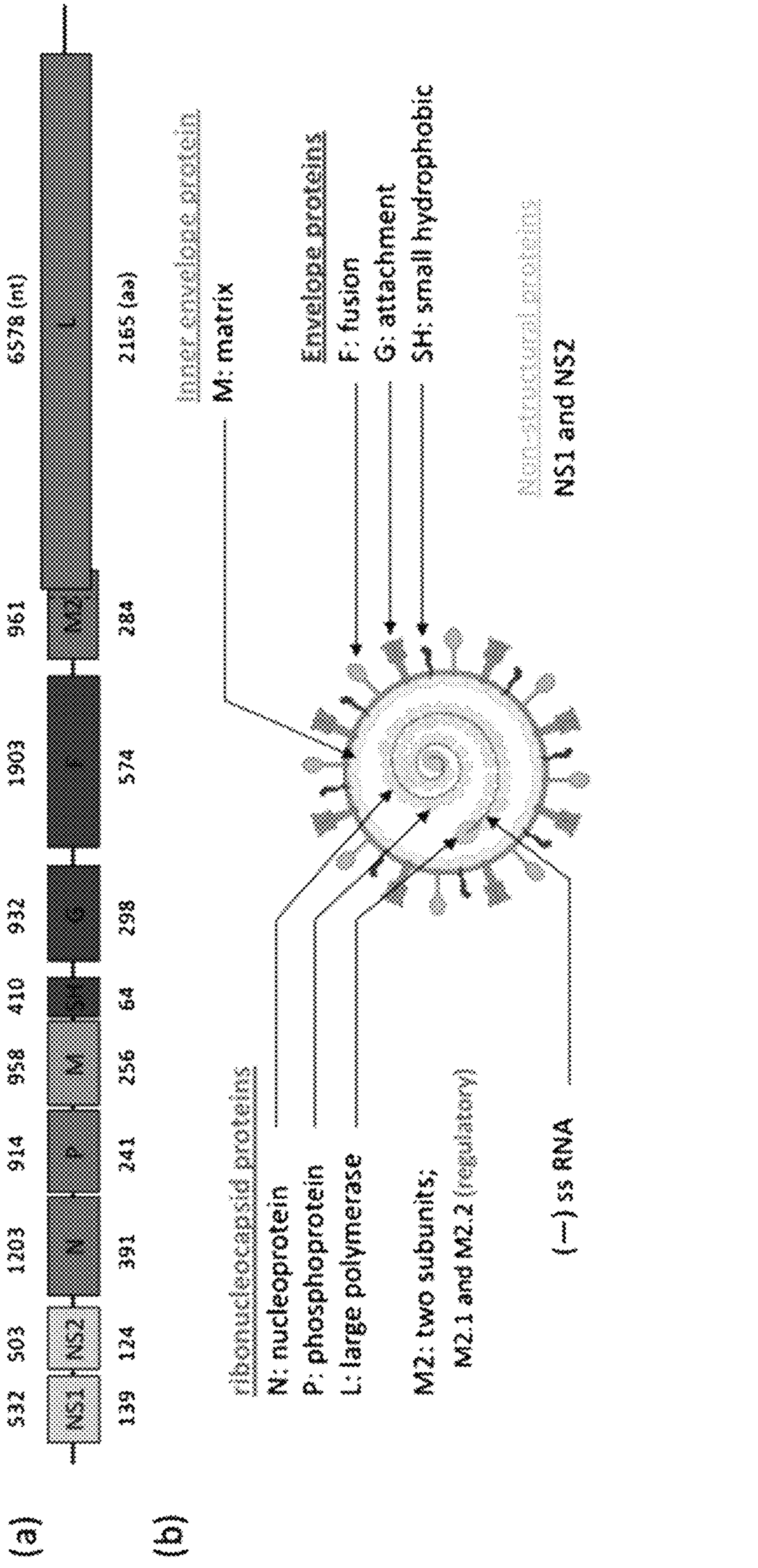
FIGS. 1A and 1B show the complete sequence of the RSV virus. RSV has a negative-sense, single-stranded RNA genome (FIG. 1A). The genome is linear and approximately 15,000 nucleotides in length.
Figure 2:
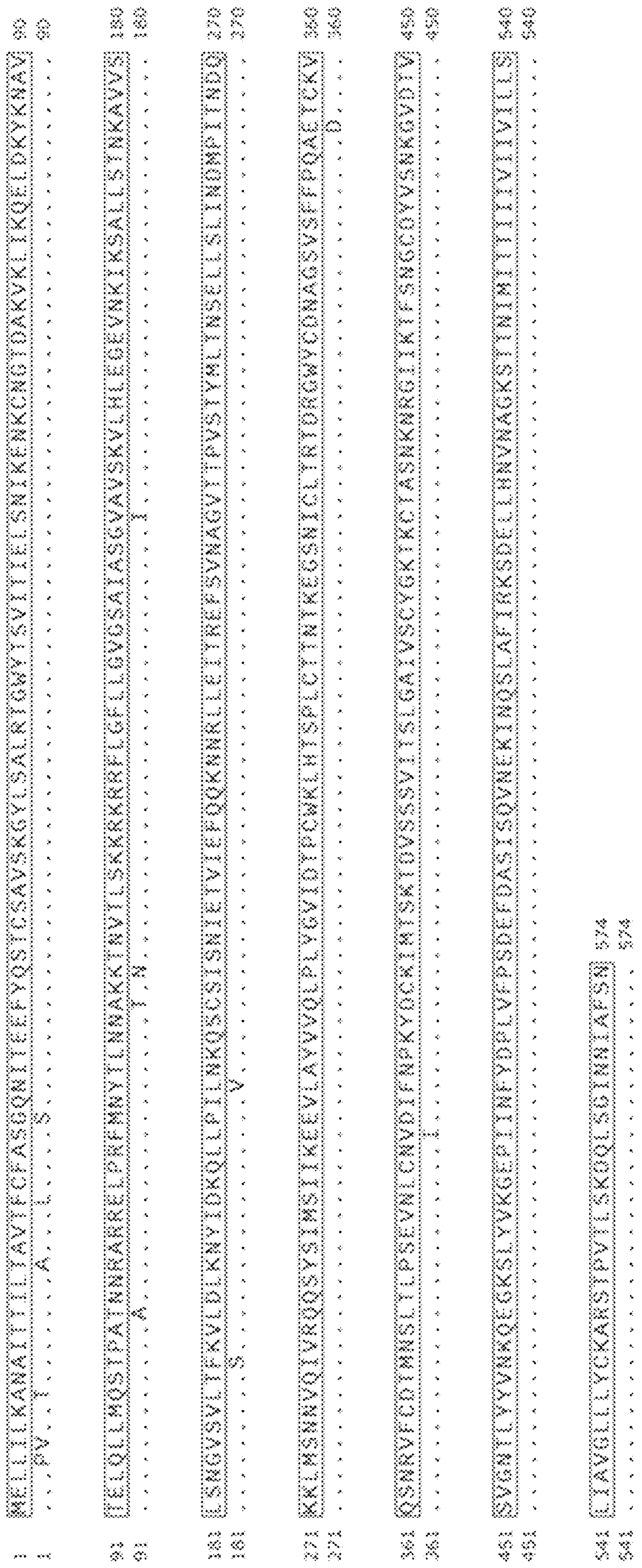
FIG. 2 shows the alignment of F1 from backbone 2A (SEQ ID NO: 53) (top) with optimized backbone (SEQ ID NO: 87) (bottom). Amino acid changes are indicated.
Figure 3B:
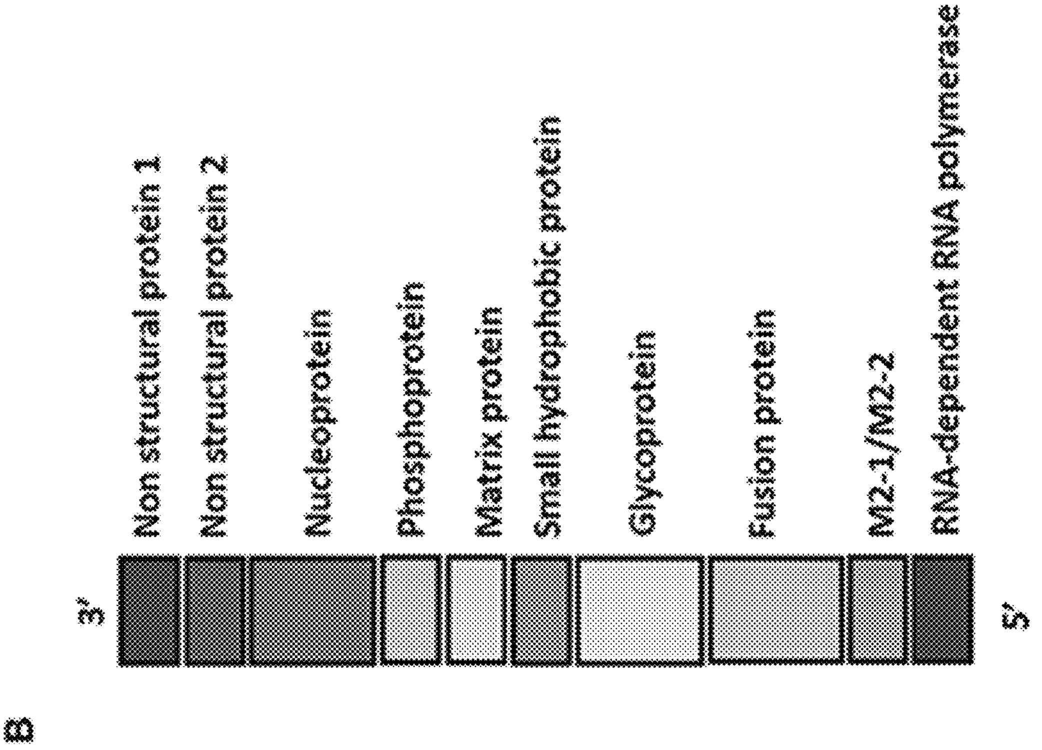
FIG. 3B illustrates the protein coding regions of the 11 proteins of the RSV viral genome.
Figure 3A:
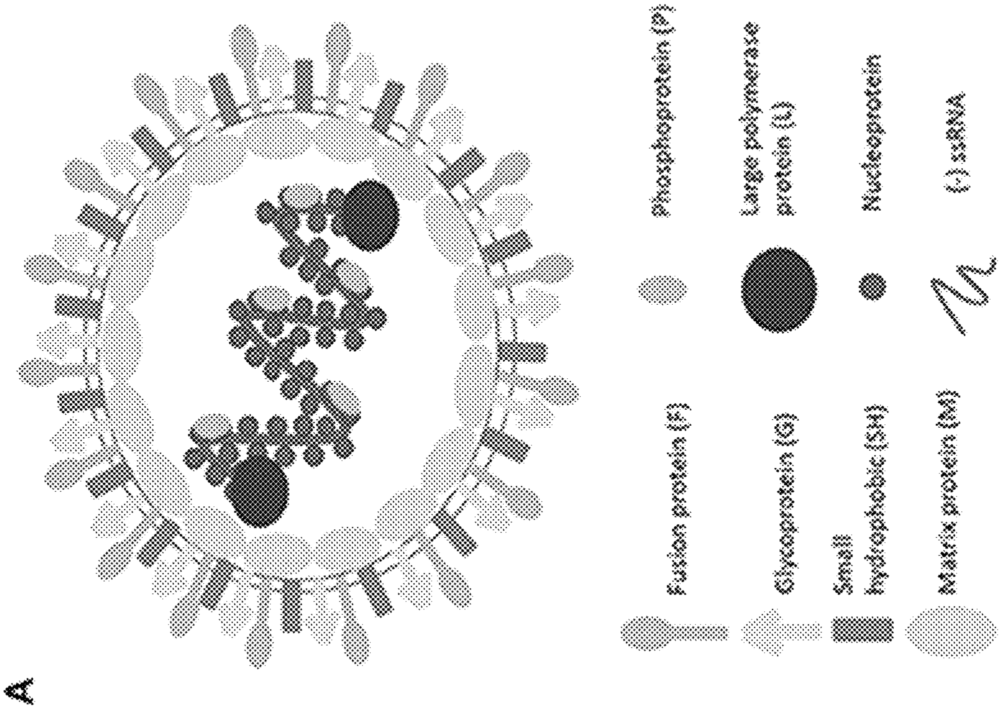
FIG. 3A is an illustration of the respiratory syncytial virus structure including the position of the membrane bound F protein of the RSV virus.
Figure 4A:
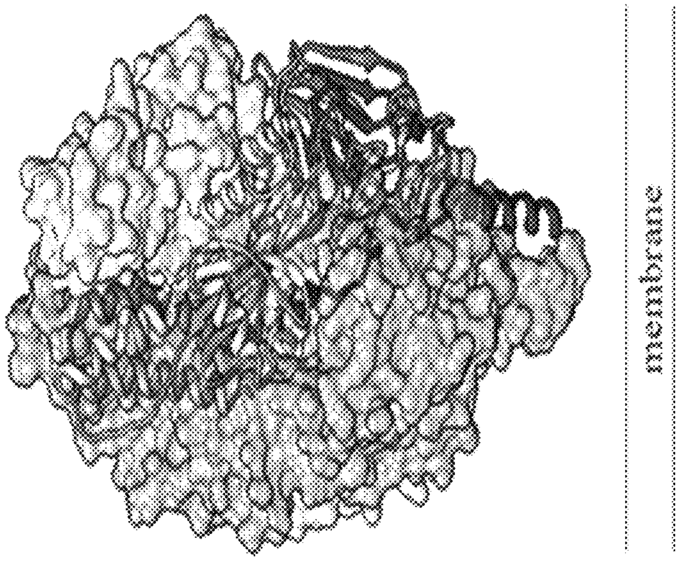
FIGS. 4A and 4B illustrate the pre- and post-fusion structure of RSV F protein.
Figure 4B:
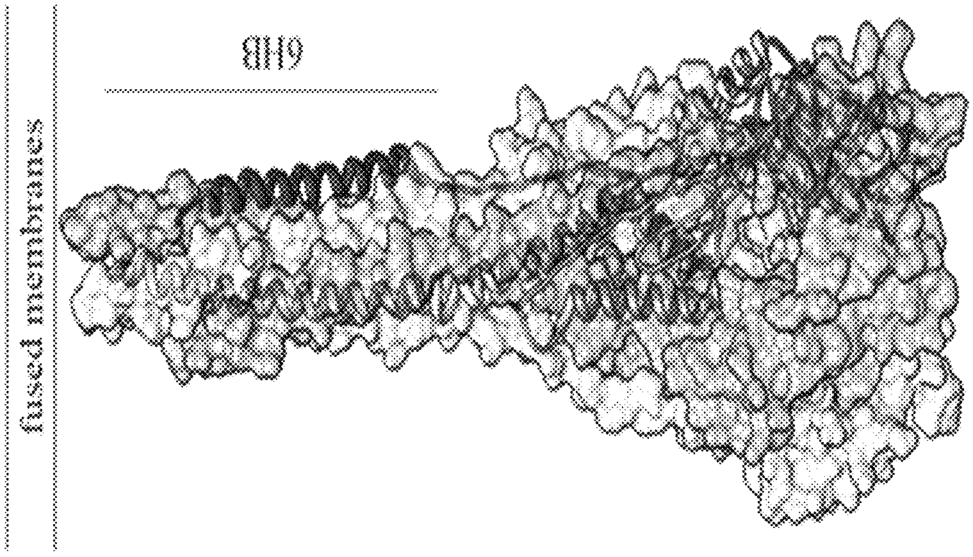

As it would be understood, the section or subsection headings as used herein is for organizational purposes only and are not to be construed as limiting and/or separating the subject matter described.

It is to be understood that this invention is not limited to particular embodiments described, as such may, of course, vary. It is also to be understood that the terminology used herein is for the purpose of describing particular embodiments only, and is not intended to be limiting, since the scope of this invention will be limited only by the appended claims.

Unless defined otherwise, all technical and scientific terms used herein have the same meanings as commonly understood by one of ordinary skill in the art to which this disclosure belongs. Although any methods and materials similar or equivalent to those described herein can be used in the practice or testing of the present disclosure, the preferred methods, devices, and materials are now described. All technical and patent publications cited herein are incorporated herein by reference in their entirety. Nothing herein is to be construed as an admission that the disclosure is not entitled to antedate such disclosure by virtue of prior disclosure.

The practice of the present disclosure will employ, unless otherwise indicated, conventional techniques of tissue culture, immunology, molecular biology, microbiology, cell biology and recombinant DNA, which are within the skill of the art. See, e.g., Sambrook and Russell eds. (2001) Molecular Cloning: A Laboratory Manual, 3rd edition; the series Ausubel et al. eds. (2007) Current Protocols in Molecular Biology; the series Methods in Enzymology (Academic Press, Inc., N.Y.); MacPherson et al. (1991) PCR 1: A Practical Approach (IRL Press at Oxford University Press); MacPherson et al. (1995) PCR 2: A Practical Approach; Harlow and Lane eds. (1999) Antibodies, A Laboratory Manual; Freshney (2005) Culture of Animal Cells: A Manual of Basic Technique, 5th edition; Gait ed. (1984) Oligonucleotide Synthesis; U.S. Pat. No. 4,683,195; Hames and Higgins eds. (1984) Nucleic Acid Hybridization; Anderson (1999) Nucleic Acid Hybridization; Hames and Higgins eds. (1984) Transcription and Translation; Immobilized Cells and Enzymes (IRL Press (1986)); Perbal (1984) A Practical Guide to Molecular Cloning; Miller and Calos eds. (1987) Gene Transfer Vectors for Mammalian Cells (Cold Spring Harbor Laboratory); Makrides ed. (2003) Gene Transfer and Expression in Mammalian Cells; Mayer and Walker eds. (1987) Immunochemical Methods in Cell and Molecular Biology (Academic Press, London); Herzenberg et al. eds (1996) Weir's Handbook of Experimental Immunology; Manipulating the Mouse Embryo: A Laboratory Manual, 3rd edition (Cold Spring Harbor Laboratory Press (2002)); Sohail (ed.) (2004) Gene Silencing by RNA Interference: Technology and Application (CRC Press); and Plotkin et al., Plotkin; Human Vaccines, $7^{th}$ edition (Elsevier).

As used in the specification and claims, the singular form "a," "an" and "the" include plural references unless the context clearly dictates otherwise. For example, the term "a cell" includes a plurality of cells, including mixtures thereof.

As used herein, the term "comprising" is intended to mean that the compounds, compositions and methods include the recited elements, but not exclude others. "Consisting essentially of" when used to define compounds, compositions and methods, shall mean excluding other elements of any essential significance to the combination. Thus, a composition consisting essentially of the elements as defined herein would not exclude trace contaminants, e.g., from the isolation and purification method and pharmaceutically acceptable carriers, preservatives, and the like. "Consisting of" shall mean excluding more than trace elements of other ingredients. Embodiments defined by each of these transition terms are within the scope of this technology.

All numerical designations, e.g., pH, temperature, time, concentration, and molecular weight, including ranges, are approximations which are varied (+) or (−) by increments of 1, 5, or 10%. It is to be understood, although not always explicitly stated that all numerical designations are preceded by the term "about." It also is to be understood, although not always explicitly stated, that the reagents described herein are merely exemplary and that equivalents of such are known in the art.

The term "about," as used herein when referring to a measurable value such as an amount or concentration and the like, is meant to encompass variations of 20%, 10%, 5%, 1%, 0.5%, or even 0.1% of the specified amount.

As used herein, comparative terms as used herein, such as high, low, increase, decrease, reduce, or any grammatical variation thereof, can refer to certain variation from the reference. In some embodiments, such variation can refer to about 10%, or about 20%, or about 30%, or about 40%, or about 50%, or about 60%, or about 70%, or about 80%, or about 90%, or about 1 fold, or about 2 fold, or about 3 fold, or about 4 fold, or about 5 fold, or about 6 fold, or about 7 fold, or about 8 fold, or about 9 fold, or about 10 fold, or about 20 fold, or about 30 fold, or about 40 fold, or about 50 fold, or about 60 fold, or about 70 fold, or about 80 fold, or about 90 fold, or about 100 fold or more higher than the reference. In some embodiments, such variation can refer to about 1%, or about 2%, or about 3%, or about 4%, or about 5%, or about 6%, or about 7%, or about 8%, or about 0%, or about 10%, or about 20%, or about 30%, or about 40%, or about 50%, or about 60%, or about 70%, or about 75%, or about 80%, or about 85%, or about 90%, or about 95%, or about 96%, or about 97%, or about 98%, or about 99% of the reference.

As will be understood by one skilled in the art, for any and all purposes, all ranges disclosed herein also encompass any and all possible subranges and combinations of subranges thereof. Furthermore, as will be understood by one skilled in the art, a range includes each individual member.

"Optional" or "optionally" means that the subsequently described circumstance may or may not occur, so that the description includes instances where the circumstance occurs and instances where it does not.

As used herein, "and/or" refers to and encompasses any and all possible combinations of one or more of the associated listed items, as well as the lack of combinations when interpreted in the alternative ("or").

"Substantially" or "essentially" means nearly totally or completely, for instance, 95% or greater of some given quantity. In some embodiments, "substantially" or "essentially" means 95%, 96%, 97%, 98%, 99%, 99.5%, or 99.9%.

The terms or "acceptable," "effective," or "sufficient" when used to describe the selection of any components, ranges, dose forms, etc. disclosed herein intend that said component, range, dose form, etc. is suitable for the disclosed purpose.

In some embodiments, the terms "first" "second" "third" "fourth" or similar in a component name are used to distinguish and identify more than one components sharing certain identity in their names. For example, "first RNA" and "second RNA" are used to distinguishing two RNAs.

Respiratory Syncytial Virus (RSV), also referred to as human respiratory syncytial virus (hRSV) or human orthopneumovirus is a common, contagious virus that causes infections of the respiratory tract. Syncytial refers to large cells known as syncytia that form when infected cells fuse together. RSV is an enveloped virus approximately 150 nanometers in size. The genome rests within a helical nucleocapsid and is surrounded by matrix protein and an envelope containing all viral glycoproteins. Following fusion of the viral and host cell membranes, the viral nucleocapsid (containing the viral genome) and the associated viral polymerase are delivered into the host cell cytoplasm. Transcription and translation both occur within the cytoplasm. RNA-dependent RNA polymerase transcribes the genome into 10 segments of messenger RNA (mRNA) which is translated into structural proteins by host cell machinery. RNA-dependent RNA polymerase synthesizes a positive-sense complement called the antigenome. This complementary strand is used as a template to construct genomic negative-sense RNA, which is packaged into nucleocapsids and transported to the plasma membrane for assembly and particle budding.

RSV is a negative-sense, single-stranded RNA virus. The genome is linear and approximately 15,000 nucleotides in length. It is non-segmented, which means that RSV cannot participate in genetic reassortment and antigenic shifts. RSV includes 10 genes encoding for 11 proteins. The gene order is NS1-N-P-M-SH-G-F-M2-L. NS1 and NS2 serve as non-structural promoter genes. See, e.g., FIGS. 1A and 1B.

The F protein from RSV is a type I transmembrane surface protein, which has an N-terminal cleaved signal peptide and a membrane anchor near the C-terminus. It is synthesized as an inactive 67-kD precursor denoted as F0. The F0 protein is activated by furin-like protease at two sites, yielding two disulfide-linked polypeptides, F2 and F1, from the N- and C-terminus, respectively. The 27amino acid peptide that is released is called "pep27". The F2 subunit consists of the heptad repeat C (HRC), while the F1 contains the fusion peptide (FP), heptad repeat A (HRA), heptad repeat B (HRB), transmembrane domain (TM) and cytoplasmic domain (CP).

F protein constructs which possess the transmembrane domain have the following regions: aa1 to aa26 is the "Signal peptide"; aa27 to aa109 is the "Heptad repeat C" and also known as "F2 protein"; aa110 to aa137 is "27 amino acid fragment released when F0 is cleaved into F1 and F2" or "p27"; aa138 . . . 574 is "F1 protein". F1 protein in turn has subregions: aa138 to aa155 is "fusion peptide"; aa156 to 214 is "Heptad repeat A"; aa475 to aa524 is "Heptad repeat B"; aa525 to aa550 is "transmembrane region"; and aa551 to aa574 is "cytoplasmic domain".

F protein constructs which do not possess the transmembrane domain have the following regions: aa1 to aa26 is the "Signal peptide"; aa27 to aa109 is the "Heptad repeat C" and also known as "F2 protein"; aa110 to aa137 is "27 amino acid fragment released when F0 is cleaved into F1 and F2" or "p27"; aa138 . . . 556 is "F1 protein". F1 protein in turn has subregions: aa138 to aa155 is "fusion peptide"; aa156 to 214 is "Heptad repeat A"; aa475 to aa524 is "Heptad repeat B"; aa525 to 556 is "trimerization domain".

The term "protein", "peptide" and "polypeptide" are used interchangeably and in their broadest sense to refer to a compound of two or more subunit amino acids, amino acid analogs or peptidomimetics. The subunits (which are also referred to as residues) may be linked by peptide bonds. In another embodiment, the subunit may be linked by other bonds, e.g., ester, ether, etc. A protein or peptide must contain at least two amino acids and no limitation is placed on the maximum number of amino acids which may comprise a protein's or peptide's sequence. As used herein the term "amino acid" refers to either natural and/or unnatural or synthetic amino acids, including glycine and both the D and L optical isomers, amino acid analogs and peptidomimetics.

As used herein, the terms "F protein" or "F glycoprotein" are used interchangeably, referring to the surface fusion protein responsible for fusion of RSV viral and host cell membranes, as well as syncytium formation between viral particles. In further embodiments, an F protein or an equivalent thereof as used herein also refers to an F protein mutant (for example, a mutated F protein as disclosed herein), an F protein fragment (such as an immunogenic fragment), or any combination thereof (such as, a naturally occurring variant engineered with additional mutation(s), or a fragment thereof).

The F protein has a highly conserved sequence between strains. The F protein exists in multiple conformational forms. In the native conformation of the prefusion state (PreF), the protein exists in a trimeric form. After binding to the target on a host cell surface, the PreF undergoes a conformational change to an elongated stable form that enables the protein to insert itself into the host cell membrane.

The surface protein G (glycoprotein) is responsible for viral attachment to host cells, and is highly variable between strains. The G protein may exist in both membrane-bound and secreted forms.

Along with the G protein, the F protein binds to and activates toll-like receptor 4 (TLR4), initiating the innate immune response and signal transduction.

As used herein, an amino acid (aa) or nucleotide (nt) residue position in a sequence of interest "corresponding to" an identified position in a reference sequence refers to that the residue position is aligned to the identified position in a sequence alignment between the sequence of interest and the reference sequence. Various programs are available for performing such sequence alignments, such as Clustal Omega and BLAST. In one aspect, equivalent polynucleotides, proteins and corresponding sequences can be determined using BLAST (accessible at blast.ncbi.nlm.nih.gov/Blast.cgi, last accessed on Aug. 1, 2021).

As used herein, an amino acid mutation is referred to herein as two letters separated by an integer, such as T19R. The first letter provides the one letter code of the original amino acid residue to be mutated; while the last letter provides the mutation, such as A indicating a deletion, or one letter code of the mutated amino acid residue. In some embodiments, the integer is the numbering of the to-be-mutated amino acid residue in the amino acid sequence free of the mutation, optionally counting from the N terminus to the C terminus. In some embodiments, the integer is the numbering of the mutated amino acid residue in the mutated amino acid sequence, optionally counting from the N terminus to the C terminus. In some embodiments, the integer is the numbering of the amino acid residue in SEQ ID NO: 53 that corresponds to (such as aligned to) the to-be-mutated residue or the mutated residue or both.

It is to be inferred without explicit recitation and unless otherwise intended, that when the present disclosure relates to a polypeptide, protein, polynucleotide, an equivalent or a biologically equivalent of such is intended within the scope of this disclosure. As used herein, the term "biological equivalent thereof" is intended to be synonymous with "equivalent thereof" when referring to a reference protein, polypeptide or nucleic acid, intends those having minimal homology while still maintaining desired structure or functionality. Unless specifically recited herein, it is contemplated that any polynucleotide, polypeptide or protein mentioned herein also includes equivalents thereof. For example, an equivalent intends at least about 70% homology or identity, or at least 80% homology or identity, or at least about 85% homology or identity, or alternatively at least about 90% homology or identity, or alternatively at least about 95% homology or identity, or alternatively at least about 96% homology or identity, or alternatively at least about 97% homology or identity, or alternatively at least about 98% homology or identity, or alternatively at least about 99% homology or identity (in one aspect, as determined using the Clustal Omega alignment program) and exhibits substantially equivalent biological activity to the reference protein, polypeptide or nucleic acid. Alternatively, when referring to polynucleotides, an equivalent thereof is a polynucleotide that hybridizes under stringent conditions to the reference polynucleotide or its complementary sequence.

An equivalent of a reference polypeptide comprises, consists essentially of, or alternatively consists of an polypeptide having at least 80%, or at least 85%, or at least 90%, or at least 95%, or at least about 96%, or at least 97%, or at least 98%, or at least 99% amino acid identity to the reference polypeptide (as determined, in one aspect using the Clustal Omega or BLAST alignment programs), or a polypeptide that is encoded by a polynucleotide that hybridizes under conditions of high stringency to the complementary sequence of a polynucleotide encoding the reference polypeptide, optionally wherein conditions of high stringency comprises incubation temperatures of about 55° C. to about 68° C.; buffer concentrations of about 1×SSC to about 0.1×SSC; formamide concentrations of about 55% to about 75%; and wash solutions of about 1×SSC, 0.1×SSC, or deionized water.

In some embodiments, a first sequence (nucleic acid sequence or amino acid) is compared to a second sequence, and the identity percentage between the two sequences can be calculated. In further embodiments, the first sequence can be referred to herein as an equivalent and the second sequence can be referred to herein as a reference sequence. In yet further embodiments, the identity percentage is calculated based on the full-length sequence of the first sequence. In other embodiments, the identity percentage is calculated based on the full-length sequence of the second sequence.

The terms "polynucleotide", "nucleic acid" and "oligonucleotide" are used interchangeably and refer to a polymeric form of nucleotides of any length, either deoxyribonucleotides or ribonucleotides or analogs thereof. Polynucleotides can have any three-dimensional structure and may perform any function, known or unknown. The following are non-limiting examples of polynucleotides: a gene or gene fragment (for example, a probe, primer, EST or SAGE tag), exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes and primers. A polynucleotide can comprise modified nucleotides, such as methylated nucleotides and nucleotide analogs. If present, modifications to the nucleotide structure can be imparted before or after assembly of the polynucleotide. The sequence of nucleotides can be interrupted by non-nucleotide components. A polynucleotide can be further modified after polymerization, such as by conjugation with a labeling component. The term also refers to both double- and single-stranded molecules. Unless otherwise specified or required, any embodiment of this disclosure that is a polynucleotide encompasses both the double-stranded form and each of two complementary single-stranded forms known or predicted to make up the double-stranded form.

A polynucleotide is composed of a specific sequence of four nucleotide bases: adenine (A); cytosine (C); guanine (G); thymine (T); and uracil (U) for thymine when the polynucleotide is RNA. Thus, the term "polynucleotide sequence" is the alphabetical representation of a polynucleotide molecule. This alphabetical representation can be input into databases in a computer having a central processing unit and used for bioinformatics applications such as functional genomics and homology searching.

The term "RNA" as used herein refers to its generally accepted meaning in the art. Generally, the term RNA refers to a polynucleotide comprising at least one ribofuranoside moiety. The term can include double-stranded RNA, single-stranded RNA, isolated RNA such as partially purified RNA, essentially pure RNA, synthetic RNA, recombinantly produced RNA, as well as altered RNA that differs from naturally occurring RNA by the addition, deletion, substitution and/or alteration of one or more nucleotides. Such alterations can include addition of non-nucleotide material, for example at one or more nucleotides of the RNA. Nucleotides in the nucleic acid molecules can also comprise non-standard nucleotides, such as non-naturally occurring nucleotides or chemically synthesized nucleotides or deoxynucleotides. These altered RNAs can be referred to as analogs or analogs of naturally-occurring RNA. In some embodiments, the RNA is a messenger RNA (mRNA).

"Messenger RNA" (mRNA) refers to any polynucleotide that encodes a (at least one) polypeptide (a naturally-occurring, non-naturally-occurring, or modified polymer of amino acids) and can be translated to produce the encoded polypeptide in vitro, in vivo, in situ or ex vivo. In some embodiments, an mRNA as disclosed herein comprises, or consists essentially of, or yet further consists of at least one coding region, a 5' untranslated region (UTR), a 3' UTR, a 5' cap and a poly-A tail.

Vaccination is the most successful medical approach to disease prevention and control. The successful development and use of vaccines has saved thousands of lives and large amounts of money. A key advantage of RNA vaccines is that RNA can be produced in the laboratory from a DNA template using readily available materials, less expensively and faster than conventional vaccine production, which can require the use of chicken eggs or other mammalian cells. In addition, mRNA vaccines have the potential to streamline vaccine discovery and development, and facilitate a rapid response to emerging infectious diseases, see, for example, Maruggi et al., *Mol Ther.* 2019; 27(4):757-772.

Preclinical and clinical trials have shown that mRNA vaccines provide a safe and long-lasting immune response in animal models and humans. mRNA vaccines against infectious diseases may be developed as prophylactic or therapeutic treatments. mRNA vaccines expressing antigens of infectious pathogens have been shown to induce potent T cell and humoral immune responses. See, for example, Pardi et al., *Nat Rev Drug Discov.* 2018; 17:261-279. The production procedure to generate mRNA vaccines is cell-free, simple, and rapid, compared to production of whole microbe, live attenuated, and subunit vaccines. This fast and simple manufacturing process makes mRNA a promising bio-product that can potentially fill the gap between emerging infectious disease and the desperate need for effective vaccines.

The term "isolated" as used herein with respect to nucleic acids, such as DNA or RNA, refers to molecules separated from other DNAs or RNAs, respectively that are present in the natural source of the macromolecule. The term "isolated nucleic acid" is meant to include nucleic acid fragments which are not naturally occurring as fragments and would not be found in the natural state. The term "isolated" is also used herein to refer to polypeptides, proteins and/or host cells that are isolated from other cellular proteins and is meant to encompass both purified and recombinant polypeptides. In other embodiments, the term "isolated" means separated from constituents, cellular and otherwise, in which the cell, tissue, polynucleotide, peptide, polypeptide, or protein, which are normally associated in nature. For example, an isolated cell is a cell that is separated form tissue or cells of dissimilar phenotype or genotype. As is apparent to those of skill in the art, a non-naturally occurring polynucleotide, peptide, polypeptide, or protein, does not require "isolation" to distinguish it from its naturally occurring counterpart.

In some embodiments, the term "engineered" or "recombinant" refers to having at least one modification not normally found in a naturally occurring protein, polypeptide, polynucleotide, strain, wild-type strain or the parental host strain of the referenced species. In some embodiments, the term "engineered" or "recombinant" refers to being synthetized by human intervention. As used herein, the term "recombinant protein" refers to a polypeptide which is produced by recombinant DNA techniques, wherein generally, DNA encoding the polypeptide is inserted into a suitable expression vector which is in turn used to transform a host cell to produce the heterologous protein.

As used herein, "complementary" sequences refer to two nucleotide sequences which, when aligned anti-parallel to each other, contain multiple individual nucleotide bases which pair with each other. Paring of nucleotide bases forms hydrogen bonds and thus stabilizes the double strand structure formed by the complementary sequences. It is not necessary for every nucleotide base in two sequences to pair with each other for sequences to be considered "complementary". Sequences may be considered complementary, for example, if at least 30%, 40%, 50%, 55%, 60%, 65%, 70%, 75%, 80%, 85%, 90%, 95%, 98%, 99%, or 100% of the nucleotide bases in two sequences pair with each other. In some embodiments, the term complementary refers to 100% of the nucleotide bases in two sequences pair with each other. In addition, sequences may still be considered "complementary" when the total lengths of the two sequences are significantly different from each other. For example, a primer of 15 nucleotides may be considered "complementary" to a longer polynucleotide containing hundreds of nucleotides if multiple individual nucleotide bases of the primer pair with nucleotide bases in the longer polynucleotide when the primer is aligned anti-parallel to a particular region of the longer polynucleotide. Nucleotide bases paring is known in the field, such as in DNA, the purine adenine (A) pairs with the pyrimidine thymine (T) and the pyrimidine cytosine (C) always pairs with the purine guanine (G); while in RNA, adenine (A) pairs with uracil (U) and guanine (G) pairs with cytosine (C). Further, the nucleotide bases aligned anti-parallel to each other in two complementary sequences, but not a pair, are referred to herein as a mismatch.

A "gene" refers to a polynucleotide containing at least one open reading frame (ORF) that is capable of encoding a particular polypeptide or protein after being transcribed and translated.

The term "express" refers to the production of a gene product, such as mRNA, peptides, polypeptides or proteins. As used herein, "expression" refers to the process by which polynucleotides are transcribed into mRNA or the process by which the transcribed mRNA is subsequently being translated into peptides, polypeptides, or proteins. If the polynucleotide is derived from genomic DNA, expression may include splicing of the mRNA in a eukaryotic cell.

A "gene product" or alternatively a "gene expression product" refers to the amino acid (e.g., peptide or polypeptide) generated when a gene is transcribed and translated. In some embodiments, the gene product may refer to an mRNA or other RNA, such as an interfering RNA, generated when a gene is transcribed.

The term "encode" as it is applied to polynucleotides refers to a polynucleotide which is said to "encode" a polypeptide if, in its native state or when manipulated by methods well known to those skilled in the art, it can be transcribed to produce the mRNA for the polypeptide or a fragment thereof, and optionally translated to produce the polypeptide or a fragment thereof. The antisense strand is the complement of such a nucleic acid, and the encoding sequence can be deduced therefrom. Further, as used herein an amino acid sequence coding sequence refers to a nucleotide sequence encoding the amino acid sequence.

The terms "chemical modification" and "chemically modified" refer to modification with respect to adenosine (A), guanosine (G), uridine (U), thymidine (T) or cytidine (C) ribonucleosides or deoxyribnucleosides in at least one of their position, pattern, percent or population. In some embodiments, the term refers to the ribonucleotide modifications in naturally occurring 5'-terminal mRNA cap moieties. In further embodiments, the chemical modification is selected from pseudouridine, N1-methylpseudouridine, N1-ethylpseudouridine, 2-thiouridine, 4'-thiouridine, 5-methylcytosine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methyluridine, 5-methoxyuridine, or 2'-O-methyl uridine. In some embodiments the extent of incorporation of chemically modified nucleotides has been optimized for improved immune responses to the vaccine formulation. In other embodiments, the term excludes the ribonucleotide modifications in naturally occurring 5'-terminal mRNA cap moieties.

Polynucleotides (e.g., RNA polynucleotides, such as mRNA polynucleotides), in some embodiments, comprise non-natural modified nucleotides that are introduced during synthesis or post-synthesis of the polynucleotides to achieve desired functions or properties. The modifications may be present on an internucleotide linkages, purine or pyrimidine bases, or sugars. The modification may be introduced with chemical synthesis or with a polymerase enzyme at the terminal of a chain or anywhere else in the chain. Any of the regions of a polynucleotide may be chemically modified.

In some embodiments, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or higher percentage of residues of the RNA is chemically modified by one or more of modifications as disclosed herein. In some embodiments, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or higher percentage of uridine residues of the RNA is chemically modified by one or more of modifications as disclosed herein.

In some embodiments, an RNA as disclosed herein is optimized. Optimization, in some embodiments, may be used to match codon frequencies in target and host organisms to ensure proper folding; bias GC content to increase mRNA stability or reduce secondary structures; minimize tandem repeat codons or base runs that may impair gene construction or expression; customize transcriptional and translational control regions; insert or remove protein trafficking sequences; remove/add post translation modification sites in encoded protein (e.g. glycosylation sites); add, remove or shuffle protein domains; insert or delete restriction sites; modify ribosome binding sites and mRNA degradation sites; adjust translational rates to allow the various domains of the protein to fold properly; or to reduce or eliminate problem secondary structures within the polynucleotide.

A "3' untranslated region" (3' UTR) refers to a region of an mRNA that is directly downstream (i.e., 3') from the stop codon (i.e., the codon of an mRNA transcript that signals a termination of translation) that does not encode a polypeptide. In some embodiments, a 3' UTR as used herein comprises, or consists essentially of, or yet further consists of one or more of SEQ ID NOs: 18, 22, or 24.

A "5' untranslated region" (5' UTR) refers to a region of an RNA that is directly upstream (i.e., 5') from the start codon (i.e., the first codon of an mRNA transcript translated by a ribosome) that does not encode a polypeptide. In some embodiments, a 5' UTR as used herein comprises, or consists essentially of, or yet further consists of one or both of SEQ ID NO: 20 or 26.

A "polyA tail" is a region of mRNA that is downstream, e.g., directly downstream (i.e., 3'), from the 3' UTR that contains multiple, consecutive adenosine monophosphates. A polyA tail may contain 10 to 300 adenosine monophosphates (SEQ ID NO: 118). Additionally or alternatively, in a relevant biological setting (e.g., in cells, in vivo) the polyA tail functions to protect mRNA from enzymatic degradation, e.g., in the cytoplasm, and aids in transcription termination, export of the mRNA from the nucleus and translation. In some embodiments, a polyA tail as used herein comprises, or consists essentially of, or yet further consists of one or more of: SEQ ID NOs: 27 28, or 16.

In vitro transcription (IVT) methods permit template-directed synthesis of RNA molecules of almost any sequence. The size of the RNA molecules that can be synthesized using IVT methods range from short oligonucleotides to long nucleic acid polymers of several thousand bases. IVT methods permit synthesis of large quantities of RNA transcript (e.g., from microgram to milligram quantities) (Beckert et al., *Methods Mol Biol.* 703:29-41(2011); Rio et al. RNA: A Laboratory Manual. Cold Spring Harbor: Cold Spring Harbor Laboratory Press, 2011, 205-220; and Cooper, Geoffery M. The Cell: A Molecular Approach. 4th ed. Washington D.C.: ASM Press, 2007, 262-299). Generally, IVT utilizes a DNA template featuring a promoter sequence upstream of a sequence of interest. The promoter sequence is most commonly of bacteriophage origin (ex. the T7, T3 or SP6 promoter sequence) but many other promotor sequences can be tolerated including those designed de novo. Transcription of the DNA template is typically best achieved by using the RNA polymerase corresponding to the specific bacteriophage promoter sequence. Exemplary RNA polymerases include, but are not limited to T7 RNA polymerase, T3 RNA polymerase, or SP6 RNA polymerase, among others. IVT is generally initiated at a dsDNA but can proceed on a single strand.

It will be appreciated that an RNA as disclosed herein can be made using any appropriate synthesis method. For example, in some embodiments, an RNA is made using IVT from a single bottom strand DNA as a template and complementary oligonucleotide that serves as promotor. The single bottom strand DNA may act as a DNA template for in vitro transcription of RNA, and may be obtained from, for example, a plasmid, a PCR product, or chemical synthesis. In some embodiments, the single bottom strand DNA is linearized from a circular template. The single bottom strand DNA template generally includes a promoter sequence, e.g., a bacteriophage promoter sequence, to facilitate IVT. Methods of making RNA using a single bottom strand DNA and a top strand promoter complementary oligonucleotide are known in the art. An exemplary method includes, but is not limited to, annealing the DNA bottom strand template with the top strand promoter complementary oligonucleotide (e.g., T7 promoter complementary oligonucleotide, T3 promoter complementary oligonucleotide, or SP6 promoter complementary oligonucleotide), followed by IVT using an RNA polymerase corresponding to the promoter sequence, e.g., a T7 RNA polymerase, a T3 RNA polymerase, or an SP6 RNA polymerase.

IVT methods can also be performed using a double-stranded DNA template. For example, in some embodiments, the double-stranded DNA template is made by extending a complementary oligonucleotide to generate a complementary DNA strand using strand extension techniques available in the art. In some embodiments, a single bottom strand DNA template containing a promoter sequence and sequence encoding one or more epitopes of interest is annealed to a top strand promoter complementary oligonucleotide and subjected to a PCR-like process to extend the top strand to generate a double-stranded DNA template. Alternatively or additionally, a top strand DNA containing a sequence complementary to the bottom strand promoter sequence and complementary to the sequence encoding one or more epitopes of interest is annealed to a bottom strand promoter oligonucleotide and subjected to a PCR-like process to extend the bottom strand to generate a double-stranded DNA template. In some embodiments, the number of PCR-like cycles ranges from 1 to 20 cycles, e.g., 3 to 10 cycles. In some embodiments, a double-stranded DNA template is synthesized wholly or in part by chemical synthesis methods. The double-stranded DNA template can be subjected to in vitro transcription as described herein.

"Under transcriptional control", which is also used herein as "directing expression of" or any grammatical variation thereof, is a term well understood in the art and indicates that transcription and optionally translation of a polynucleotide sequence, usually a DNA sequence, depends on its being operatively linked to an element which contributes to the initiation of, or promotes, transcription.

"Operatively linked" intends the polynucleotides are arranged in a manner that allows them to function in a cell.

The term "a regulatory sequence", "an expression control element" or "promoter" as used herein, intends a polynucleotide that is operatively linked to a target polynucleotide to be transcribed or replicated, and facilitates the expression or replication of the target polynucleotide.

A promoter is an example of an expression control element or a regulatory sequence. Promoters can be located 5' or upstream of a gene or other polynucleotide, that provides a control point for regulated gene transcription. In some embodiments, a promoter as used herein is corresponding to the RNA polymerase. In further embodiments, a promoter as sued herein comprises, or consists essentially of, or yet further consists of a T7 promoter, or a SP6 promoter, or a T3 promoter. Non-limiting examples of suitable promoters are provided in WO2001009377A1.

An "RNA polymerase" refers to an enzyme that produces a polyribonucleotide sequence, complementary to a pre-existing template polynucleotide (DNA or RNA). In some embodiments, the RNA polymerase is a bacteriophage RNA polymerase, optionally a T7 RNA polymerase, or a SP6 RNA polymerase, or a T3 RNA polymerase. Non-limiting examples of suitable polymerase are further detailed in U.S. Ser. No. 10/526,629B2.

In some embodiments, the term "vector" intends a recombinant vector that retains the ability to infect and transduce non-dividing and/or slowly-dividing cells and optionally integrate into the target cell's genome. Non-limiting examples of vectors include a plasmid, a nanoparticle, a liposome, a virus, a cosmid, a phage, a BAC, a YAC, etc. In some embodiments, plasmid vectors may be prepared from commercially available vectors. In other embodiments, viral vectors may be produced from baculoviruses, retroviruses, adenoviruses, AAVs, etc. according to techniques known in the art. In one embodiment, the viral vector is a lentiviral vector. In one embodiment, the viral vector is a retroviral vector. In one embodiment, the vector is a plasmid. In one embodiment, the vector is a nanoparticle, optionally a polymeric nanoparticle or a lipid nanoparticle.

Vectors that contain both a promoter and a cloning site into which a polynucleotide can be operatively linked are well known in the art. Such vectors are capable of transcribing RNA in vitro or in vivo, and are commercially available from sources such as Stratagene (La Jolla, Calif.) and Promega Biotech (Madison, Wis.). In order to optimize expression and/or in vitro transcription, it may be necessary to remove, add or alter 5' and/or 3' untranslated portions of the clones to eliminate extra, potential inappropriate alternative translation initiation codons or other sequences that may interfere with or reduce expression, either at the level of transcription or translation. Alternatively, consensus ribosome binding sites can be inserted immediately 5' of the start codon to enhance expression.

A “plasmid” is an extra-chromosomal DNA molecule separate from the chromosomal DNA which is capable of replicating independently of the chromosomal DNA. In many cases, it is circular and double-stranded. Plasmids provide a mechanism for horizontal gene transfer within a population of microbes and typically provide a selective advantage under a given environmental state. Plasmids may carry genes that provide resistance to naturally occurring antibiotics in a competitive environmental niche, or alternatively the proteins produced may act as toxins under similar circumstances. Many plasmids are commercially available for such uses. The gene to be replicated is inserted into copies of a plasmid containing genes that make cells resistant to particular antibiotics and a multiple cloning site (MCS, or polylinker), which is a short region containing several commonly used restriction sites allowing the easy insertion of DNA fragments at this location. Another major use of plasmids is to make large amounts of proteins. In this case, researchers grow bacteria containing a plasmid harboring the gene of interest. Just as the bacterium produces proteins to confer its antibiotic resistance, it can also be induced to produce large amounts of proteins from the inserted gene. This is a cheap and easy way of mass-producing a gene or the protein it then codes for.

A “viral vector” is defined as a recombinantly produced virus or viral particle that comprises a polynucleotide to be delivered into a host cell, either in vivo, ex vivo or in vitro. As is known to those of skill in the art, there are 6 classes of viruses. The DNA viruses constitute classes I and II. The RNA viruses and retroviruses make up the remaining classes. Class III viruses have a double-stranded RNA genome. Class IV viruses have a positive single-stranded RNA genome, the genome itself acting as mRNA Class V viruses have a negative single-stranded RNA genome used as a template for mRNA synthesis. Class VI viruses have a positive single-stranded RNA genome but with a DNA intermediate not only in replication but also in mRNA synthesis. Retroviruses carry their genetic information in the form of RNA; however, once the virus infects a cell, the RNA is reverse-transcribed into the DNA form which integrates into the genomic DNA of the infected cell. The integrated DNA form is called a provirus. Examples of viral vectors include retroviral vectors, lentiviral vectors, adenovirus vectors, adeno-associated virus vectors, alphavirus vectors and the like. Alphavirus vectors, such as Semliki Forest virus-based vectors and Sindbis virus-based vectors, have also been developed for use in gene therapy and immunotherapy. See, Schlesinger and Dubensky (1999) Curr. Opin. Biotechnol. 5:434-439 and Ying, et al. (1999) Nat. Med. 5(7):823-827. As used herein, Multiplicity of infection (MOI) refers to the number of viral particles that are added per cell during infection.

Vectors that contain both a promoter and a cloning site into which a polynucleotide can be operatively linked are well known in the art. Such vectors are capable of transcribing RNA in vitro or in vivo, and are commercially available from sources such as Stratagene (La Jolla, Calif.) and Promega Biotech (Madison, Wis.). In order to optimize expression and/or in vitro transcription, it may be necessary to remove, add or alter 5' and/or 3' untranslated portions of the clones to eliminate extra, potential inappropriate alternative translation initiation codons or other sequences that may interfere with or reduce expression, either at the level of transcription or translation. Alternatively, consensus ribosome binding sites can be inserted immediately 5' of the start codon to enhance expression.

A retrovirus such as a gammaretrovirus and/or a lentivirus comprises (a) envelope comprising lipids and glycoprotein, (b) a vector genome, which is a RNA (usually a dimer RNA comprising a cap at the 5' end and a polyA tail at the 3' end flanked by LTRs) derived to the target cell, (c) a capsid, and (d) proteins, such as a protease. U.S. Pat. No. 6,924,123 discloses that certain retroviral sequence facilitate integration into the target cell genome. This patent teaches that each retroviral genome comprises genes called gag, pol and env which code for virion proteins and enzymes. These genes are flanked at both ends by regions called long terminal repeats (LTRs). The LTRs are responsible for proviral integration, and transcription. They also serve as enhancer-promoter sequences. In other words, the LTRs can control the expression of the viral genes. Encapsidation of the retroviral RNAs occurs by virtue of a psi sequence located at the 5' end of the viral genome. The LTRs themselves are identical sequences that can be divided into three elements, which are called U3, R and U5. U3 is derived from the sequence unique to the 3' end of the RNA. R is derived from a sequence repeated at both ends of the RNA, and U5 is derived from the sequence unique to the 5'end of the RNA. The sizes of the three elements can vary considerably among different retroviruses. For the viral genome, the site of poly (A) addition (termination) is at the boundary between R and U5 in the right hand side LTR. U3 contains most of the transcriptional control elements of the provirus, which include the promoter and multiple enhancer sequences responsive to cellular and in some cases, viral transcriptional activator proteins.

With regard to the structural genes gag, pol and env themselves, gag encodes the internal structural protein of the virus. Gag protein is proteolytically processed into the mature proteins MA (matrix), CA (capsid) and NC (nucleocapsid). The pol gene encodes the reverse transcriptase (RT), which contains DNA polymerase, associated RNase H and integrase (IN), which mediate replication of the genome.

For the production of viral vector particles, the vector RNA genome is expressed from a DNA construct encoding it, in a host cell. The components of the particles not encoded by the vector genome are provided in trans by additional nucleic acid sequences (the “packaging system”, which usually includes either or both of the gag/pol and env genes) expressed in the host cell. The set of sequences required for the production of the viral vector particles may be introduced into the host cell by transient transfection, or they may be integrated into the host cell genome, or they may be provided in a mixture of ways. The techniques involved are known to those skilled in the art.

The term "adeno-associated virus" or "AAV" as used herein refers to a member of the class of viruses associated with this name and belonging to the genus dependoparvovirus, family Parvoviridae. Multiple serotypes of this virus are known to be suitable for gene delivery; all known serotypes can infect cells from various tissue types. At least 11 sequentially numbered, AAV serotypes are known in the art. Non-limiting exemplary serotypes useful in the methods disclosed herein include any of the 11 serotypes, e.g., AAV2, AAV8, AAV9, or variant or synthetic serotypes, e.g., AAV-DJ and AAV PHP.B. The AAV particle comprises, alternatively consists essentially of, or yet further consists of three major viral proteins: VP1, VP2 and VP3. In one embodiment, the AAV refers to of the serotype AAV1, AAV2, AAV4, AAV5, AAV6, AAV7, AAV8, AAV9, AAV10, AAV11, AAV12, AAV13, AAV PHP.B, or AAV rh74. These vectors are commercially available or have been described in the patent or technical literature.

Gene delivery vehicles also include DNA/liposome complexes, micelles and targeted viral protein-DNA complexes. Liposomes that also comprise a targeting antibody or fragment thereof can be used in the methods disclosed herein. In addition to the delivery of polynucleotides to a cell or cell population, direct introduction of the proteins described herein to the cell or cell population can be done by the non-limiting technique of protein transfection, alternatively culturing conditions that can enhance the expression and/or promote the activity of the proteins disclosed herein are other non-limiting techniques.

The term "a regulatory sequence" "an expression control element" or "promoter" as used herein, intends a polynucleotide that is operatively linked to a target polynucleotide to be transcribed and/or replicated, and facilitates the expression and/or replication of the target polynucleotide. A promoter is an example of an expression control element or a regulatory sequence. Promoters can be located 5' or upstream of a gene or other polynucleotide, that provides a control point for regulated gene transcription. Polymerase II and III are examples of promoters.

A polymerase II or "pol II" promoter catalyzes the transcription of DNA to synthesize precursors of mRNA, and most shRNA and microRNA. Examples of pol II promoters are known in the art and include without limitation, the phosphoglycerate kinase ("PGK") promoter; EF1-alpha; CMV (minimal cytomegalovirus promoter); and LTRs from retroviral and lentiviral vectors.

An enhancer is a regulatory element that increases the expression of a target sequence. A "promoter/enhancer" is a polynucleotide that contains sequences capable of providing both promoter and enhancer functions. For example, the long terminal repeats of retroviruses contain both promoter and enhancer functions. The enhancer/promoter may be "endogenous" or "exogenous" or "heterologous." An "endogenous" enhancer/promoter is one which is naturally linked with a given gene in the genome. An "exogenous" or "heterologous" enhancer/promoter is one which is placed in juxtaposition to a gene by means of genetic manipulation (i.e., molecular biological techniques) such that transcription of that gene is directed by the linked enhancer/promoter.

"Hybridization" refers to a reaction in which one or more polynucleotides react to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. A hybridization reaction may constitute a step in a more extensive process, such as the initiation of a PCR reaction, or the enzymatic cleavage of a polynucleotide by a ribozyme.

Hybridization reactions can be performed under conditions of different "stringency".

In general, a low stringency hybridization reaction is carried out at about 40° C. in 10×SSC or a solution of equivalent ionic strength/temperature. A moderate stringency hybridization is typically performed at about 50° C. in 6×SSC, and a high stringency hybridization reaction is generally performed at about 60° C. in 1×SSC. Hybridization reactions can also be performed under "physiological conditions" which is well known to one of skill in the art. A non-limiting example of a physiological condition is the temperature, ionic strength, pH and concentration of $Mg^{2+}$ normally found in a cell.

Examples of stringent hybridization conditions include: incubation temperatures of about 25° C. to about 37° C.; hybridization buffer concentrations of about 6×SSC to about 10× SSC; formamide concentrations of about 0% to about 25%; and wash solutions from about 4×SSC to about 8×SSC. Examples of moderate hybridization conditions include: incubation temperatures of about 40° C. to about 50° C.; buffer concentrations of about 9×SSC to about 2×SSC; formamide concentrations of about 30% to about 50%; and wash solutions of about 5×SSC to about 2×SSC. Examples of high stringency conditions include: incubation temperatures of about 55° C. to about 68° C.; buffer concentrations of about 1×SSC to about 0.1×SSC; formamide concentrations of about 55% to about 75%; and wash solutions of about 1×SSC, 0.1×SSC, or deionized water. In general, hybridization incubation times are from 5 minutes to 24 hours, with 1, 2, or more washing steps, and wash incubation times are about 1, 2, or 15 minutes. SSC is 0.15 M NaCl and 15 mM citrate buffer. It is understood that equivalents of SSC using other buffer systems can be employed.

When hybridization occurs in an antiparallel configuration between two single-stranded polynucleotides, the reaction is called "annealing" and those polynucleotides are described as "complementary." A double-stranded polynucleotide can be "complementary" or "homologous" to another polynucleotide, if hybridization can occur between one of the strands of the first polynucleotide and the second. "Complementarity" or "homology" (the degree that one polynucleotide is complementary with another) is quantifiable in terms of the proportion of bases in opposing strands that are expected to form hydrogen bonding with each other, according to generally accepted base-pairing rules.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, or alternatively less than 25% identity, with one of the sequences of the present disclosure. In some embodiments, the identity is calculated between two peptides or polynucleotides over their full-length, or over the shorter sequence of the two, or over the longer sequence of the two.

A polynucleotide or polynucleotide region (or a polypeptide or polypeptide region) has a certain percentage (for example, 70%, 75%, 80%, 85%, 90%, 95%, 98% or 99%) of "sequence identity" to another sequence means that, when aligned, that percentage of bases (or amino acids) are the same in comparing the two sequences. This alignment and the percent homology or sequence identity can be determined using software programs known in the art, for example, those described in Ausubel et al. eds. (2007) Current Protocols in Molecular Biology. Preferably, default parameters are used for alignment. One alignment program is BLAST, using default parameters. In particular, programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Details of these programs can be found at the following Internet address: blast.ncbi.nlm.nih.gov/Blast.cgi, last accessed on Aug. 1, 2021.

In some embodiments, the polynucleotide as disclosed herein is a RNA or an analog thereof. In some embodiments, the polynucleotide as disclosed herein is a DNA or an analog thereof. In some embodiments, the polynucleotide as disclosed herein is a hybrid of DNA and RNA or an analog thereof.

In some embodiments, an equivalent to a reference nucleic acid, polynucleotide or oligonucleotide encodes the same sequence encoded by the reference. In some embodiments, an equivalent to a reference nucleic acid, polynucleotide or oligonucleotide hybridizes to the reference, a complement reference, a reverse reference, or a reverse-complement reference, optionally under conditions of high stringency.

Additionally or alternatively, an equivalent nucleic acid, polynucleotide or oligonucleotide is one having at least 70% sequence identity, or at least 75% sequence identity, or at least 80% sequence identity, or alternatively at least 85% sequence identity, or alternatively at least 90% sequence identity, or alternatively at least 92% sequence identity, or alternatively at least 95% sequence identity, or alternatively at least 97% sequence identity, or alternatively at least 98% sequence, or alternatively at least 99% sequence identity to the reference nucleic acid, polynucleotide, or oligonucleotide, or alternatively an equivalent nucleic acid hybridizes under conditions of high stringency to a reference polynucleotide or its complementary. In one aspect, the equivalent must encode the same protein or a functional equivalent of the protein that optionally can be identified through one or more assays described herein. In addition or alternatively, the equivalent of a polynucleotide would encode a protein or polypeptide of the same or similar function as the reference or parent polynucleotide.

The term "transduce" or "transduction" refers to the process whereby a foreign nucleotide sequence is introduced into a cell. In some embodiments, this transduction is done via a vector, viral or non-viral.

"Detectable label", "label", "detectable marker" or "marker" are used interchangeably, including, but not limited to radioisotopes, fluorochromes, chemiluminescent compounds, dyes, and proteins, including enzymes. Detectable labels can also be attached to a polynucleotide, polypeptide, protein or composition described herein.

As used herein, the term "label" or a detectable label intends a directly or indirectly detectable compound or composition that is conjugated directly or indirectly to the composition to be detected, e.g., N-terminal histidine tags (N-His), magnetically active isotopes, e.g., $^{115}Sn$, $^{117}Sn$ and $^{119}Sn$, a non-radioactive isotopes such as $^{13}C$ and $^{15}N$, polynucleotide or protein such as an antibody so as to generate a "labeled" composition. The term also includes sequences conjugated to the polynucleotide that will provide a signal upon expression of the inserted sequences, such as green fluorescent protein (GFP) and the like. The label may be detectable by itself (e.g., radioisotope labels or fluorescent labels) or, in the case of an enzymatic label, may catalyze chemical alteration of a substrate compound or composition which is detectable. The labels can be suitable for small scale detection or more suitable for high-throughput screening. As such, suitable labels include, but are not limited to magnetically active isotopes, non-radioactive isotopes, radioisotopes, fluorochromes, chemiluminescent compounds, dyes, and proteins, including enzymes. The label may be simply detected, or it may be quantified. A response that is simply detected generally comprises a response whose existence merely is confirmed, whereas a response that is quantified generally comprises a response having a quantifiable (e.g., numerically reportable) value such as an intensity, polarization, or other property. In luminescence or fluorescence assays, the detectable response may be generated directly using a luminophore or fluorophore associated with an assay component actually involved in binding, or indirectly using a luminophore or fluorophore associated with another (e.g., reporter or indicator) component. Examples of luminescent labels that produce signals include, but are not limited to bioluminescence and chemiluminescence. Detectable luminescence response generally comprises a change in, or an occurrence of a luminescence signal. Suitable methods and luminophores for luminescently labeling assay components are known in the art and described for example in Haugland, Richard P. (1996) Handbook of Fluorescent Probes and Research Chemicals (6th ed). Examples of luminescent probes include, but are not limited to, aequorin and luciferases.

As used herein, the term "immunoconjugate" comprises an antibody or an antibody derivative associated with or linked to a second agent, such as a cytotoxic agent, a detectable agent, a radioactive agent, a targeting agent, a human antibody, a humanized antibody, a chimeric antibody, a synthetic antibody, a semisynthetic antibody, or a multispecific antibody.

Examples of suitable fluorescent labels include, but are not limited to, fluorescein, rhodamine, tetramethylrhodamine, eosin, erythrosin, coumarin, methyl-coumarins, pyrene, Malacite green, stilbene, Lucifer Yellow, Cascade Blue™, and Texas Red. Other suitable optical dyes are described in the Haugland, Richard P. (1996) Handbook of Fluorescent Probes and Research Chemicals (6th ed.).

In some embodiments, the fluorescent label is functionalized to facilitate covalent attachment to a cellular component present in or on the surface of the cell or tissue such as a cell surface marker. Suitable functional groups, include, but are not limited to, isothiocyanate groups, amino groups, haloacetyl groups, maleimides, succinimidyl esters, and sulfonyl halides, all of which may be used to attach the fluorescent label to a second molecule. The choice of the functional group of the fluorescent label will depend on the site of attachment to either a linker, the agent, the marker, or the second labeling agent.

As used herein, a purification label or maker refers to a label that may be used in purifying the molecule or component that the label is conjugated to, such as an epitope tag (including but not limited to a Myc tag, a human influenza hemagglutinin (HA) tag, a FLAG tag), an affinity tag (including but not limited to a glutathione-S transferase (GST), a poly-Histidine (His) tag, Calmodulin Binding Protein (CBP), or Maltose-binding protein (MBP)), or a fluorescent tag.

A "selection marker" refers to a protein or a gene encoding the protein necessary for survival or growth of a cell grown in a selective culture regimen. Typical selection markers include sequences that encode proteins, which confer resistance to selective agents, such as antibiotics, herbicides, or other toxins. Examples of selection markers include genes for conferring resistance to antibiotics, such as spectinomycin, streptomycin, tetracycline, ampicillin, kanamycin, G 418, neomycin, bleomycin, hygromycin, methotrexate, dicamba, glufosinate, or glyphosate.

The term "culturing" refers to the in vitro or ex vivo propagation of cells or organisms on or in media of various kinds. It is understood that the descendants of a cell grown in culture may not be completely identical (i.e., morphologically, genetically, or phenotypically) to the parent cell.

In some embodiments, the cell as disclosed herein is a eukaryotic cell or a prokaryotic cell. In some embodiments, the cell is a human cell. In some embodiments, the cell is a cell line, such as a human embryonic kidney 293 cell (HEK 293 cell or 293 cell), a 293T cell, or an a549 cell.

"Host cell" refers not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein. The host cell can be a prokaryotic or a eukaryotic cell. In some embodiments, the host cell is a cell line, such as a human embryonic kidney 293 cell (HEK 293 cell or 293 cell), a 293T cell, or an a549 cell.

"Eukaryotic cells" comprise all of the life kingdoms except monera. They can be easily distinguished through a membrane-bound nucleus. Animals, plants, fungi, and protists are eukaryotes or organisms whose cells are organized into complex structures by internal membranes and a cytoskeleton. The most characteristic membrane-bound structure is the nucleus. Unless specifically recited, the term "host" includes a eukaryotic host, including, for example, yeast, higher plant, insect and mammalian cells. Non-limiting examples of eukaryotic cells or hosts include simian, canine, bovine, porcine, murine, rat, avian, reptilian and human.

"Prokaryotic cells" that usually lack a nucleus or any other membrane-bound organelles and are divided into two domains, bacteria and archaea. Additionally, instead of having chromosomal DNA, these cells' genetic information is in a circular loop called a plasmid. Bacterial cells are very small, roughly the size of an animal mitochondrion (about 1-2 m in diameter and 10 μm long). Prokaryotic cells feature three major shapes: rod shaped, spherical, and spiral. Instead of going through elaborate replication processes like eukaryotes, bacterial cells divide by binary fission. Examples include but are not limited to *bacillus* bacteria, *E. coli* bacterium, and *Salmonella* bacterium.

A "composition" is intended to mean a combination of active agent and another compound or composition, inert (for example, a detectable agent or label) or active, such as an adjuvant, diluent, binder, stabilizer, buffers, salts, lipophilic solvents, preservative, adjuvant or the like and include pharmaceutically acceptable carriers.

Carriers also include pharmaceutical excipients and additives proteins, peptides, amino acids, lipids, and carbohydrates (e.g., sugars, including monosaccharides, di-, tri, tetra-oligosaccharides, and oligosaccharides; derivatized sugars such as alditols, aldonic acids, esterified sugars and the like; and polysaccharides or sugar polymers), which can be present singly or in combination, comprising alone or in combination 1-99.99% by weight or volume. Exemplary protein excipients include serum albumin such as human serum albumin (HSA), recombinant human albumin (rHA), gelatin, casein, and the like. Representative amino acid components, which can also function in a buffering capacity, include alanine, arginine, glycine, arginine, betaine, histidine, glutamic acid, aspartic acid, cysteine, lysine, leucine, isoleucine, valine, methionine, phenylalanine, aspartame, and the like. Carbohydrate excipients are also intended within the scope of this technology, examples of which include but are not limited to monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol) and myoinositol.

A composition as disclosed herein can be a pharmaceutical composition. A "pharmaceutical composition" is intended to include the combination of an active agent with a carrier, inert or active, making the composition suitable for diagnostic or therapeutic use in vitro, in vivo or ex vivo.

"Pharmaceutically acceptable carriers" refers to any diluents, excipients, or carriers that may be used in the compositions disclosed herein. Pharmaceutically acceptable carriers include ion exchangers, alumina, aluminum stearate, lecithin, serum proteins, such as human serum albumin, buffer substances, such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Suitable pharmaceutical carriers are described in Remington's Pharmaceutical Sciences, Mack Publishing Company, a standard reference text in this field. They may be selected with respect to the intended form of administration, that is, oral tablets, capsules, elixirs, syrups and the like, and consistent with conventional pharmaceutical practices.

As used herein, the term "excipient" refers to a natural or synthetic substance formulated alongside the active ingredient of a medication, included for the purpose of long-term stabilization, bulking up solid formulations, or to confer a therapeutic enhancement on the active ingredient in the final dosage form, such as facilitating drug absorption, reducing viscosity, or enhancing solubility.

The compositions used in accordance with the disclosure can be packaged in dosage unit form for ease of administration and uniformity of dosage. The term "unit dose" or "dosage" refers to physically discrete units suitable for use in a subject, each unit containing a predetermined quantity of the composition calculated to produce the desired responses in association with its administration, i.e., the appropriate route and regimen. The quantity to be administered, both according to number of treatments and unit dose, depends on the result and/or protection desired. Precise amounts of the composition also depend on the judgment of the practitioner and are peculiar to each individual. Factors affecting dose include physical and clinical state of the subject, route of administration, intended goal of treatment (alleviation of symptoms versus cure), and potency, stability, and toxicity of the particular composition. Upon formulation, solutions are administered in a manner compatible with the dosage formulation and in such amount as is therapeutically or prophylactically effective. The formulations are easily administered in a variety of dosage forms, such as the type of injectable solutions described herein.

A combination as used herein intends that the individual active ingredients of the compositions are separately formulated for use in combination, and can be separately packaged with or without specific dosages. The active ingredients of the combination can be administered concurrently or sequentially.

The four-branched histidine-lysine (HK) peptide polymer H2K4b has been shown to be a good carrier of large molecular weight DNA plasmids (Leng et al. *Nucleic Acids Res* 2005; 33:e40), but a poor carrier of relatively low molecular weight siRNA (Leng et al. *J Gene Med* 2005; 7:977-986). Two histidine-rich peptides analogs of H2K4b, namely H3K4b and H3K(+H)4b, were shown to be effective carriers of siRNA (Leng et al. *J Gene Med* 2005; 7: 977-986. Chou et al. *Biomaterials* 2014; 35:846-855), although H3K(+H)4b appeared to be modestly more effective (Leng et al. *Mol Ther* 2012; 20:2282-2290). Moreover, the H3K4b carrier of siRNA induced cytokines to a significantly greater degree in vitro and in vivo than H3K(+H)4b siRNA polyplexes (Leng et al. *Mol Ther* 2012; 20:2282-2290). Suitable HK polypeptides are described in WO/2001/047496, WO/2003/090719, and WO/2006/060182, the contents of each of which are incorporated herein in their entireties. These polypeptides have a lysine backbone (three lysine residues) where the lysine side chain ε-amino groups and the N-terminus are coupled to various HK sequences. HK polypeptide carriers can be synthesized by methods that are well-known in the art including, for example, solid-phase synthesis.

It was found that such histidine-lysine peptide polymers ("HK polymers" or "HKP") were surprisingly effective as mRNA carriers, and that they can be used, alone or in combination with liposomes, to provide effective delivery of mRNA into target cells. Similar to PEI and other carriers, initial results suggested HK polymers differ in their ability to carry and release nucleic acids. However, because HK polymers can be reproducibly made on a peptide synthesizer, their amino acid sequence can be easily varied, thereby allowing fine control of the binding and release of RNAs, as well as the stability of polyplexes containing the HK polymers and RNA (Chou et al. *Biomaterials* 2014; 35:846-855. Midoux et al. *Bioconjug Chem* 1999; 10:406-411. Henig et al. *Journal of American Chemical Society* 1999; 121:5123-5126). When mRNA molecules are admixed with one or more HKP carriers the components self-assemble into nanoparticles.

As described herein, advantageously the HK polymer comprises four short peptide branches linked to a three-lysine amino acid core. The peptide branches consist of histidine and lysine amino acids, in different configurations. The general structure of these histidine-lysine peptide polymers (HK polymers) is shown in Formula I, where R represents the peptide branches and K is the amino acid L-lysine.

Formula I

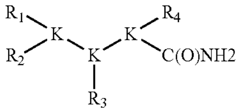

In Formula I where K is L-lysine and each of $R_1$, $R_2$, $R_3$ and $R_4$ is independently a histidine-lysine peptide. The $R_{1-4}$ branches may be the same or different in the HK polymers of the invention. When an R branch is "different", the amino acid sequence of that branch differs from each of the other R branches in the polymer. Suitable R branches used in the HK polymers of the invention shown in Formula I include, but are not limited to, the following R branches $R_A$-$R_{-J}$:

$R_A$ = KHKHHKHHKHHKHHKHHKHK- (SEQ ID NO: 31)

$R_B$ = KHHHKHHHKHHHKHHHK- (SEQ ID NO: 32)

$R_C$ = KHHHKHHHKHHHHKHHHK- (SEQ ID NO: 33)

$R_D$ = kHHHHHHHHHHHHHk- (SEQ ID NO: 34)

$R_E$ = HKHHHKHHHKHHHHKHHHK- (SEQ ID NO: 35)

$R_F$ = HHKHHHKHHHKHHHHKHHHK- (SEQ ID NO: 36)

$R_G$ = KHHHHKHHHHKHHHHKHHHHK- (SEQ ID NO: 37)

$R_H$ = KHHHKHHHKHHHKHHHHK- (SEQ ID NO: 38)

$R_I$ = KHHHKHHHHKHHHKHHHK- (SEQ ID NO: 39)

$R_J$ = KHHHKHHHHKHHHKHHHHK- (SEQ ID NO: 40)

Specific HK polymers that may be used in the mRNA compositions include, but are not limited to, HK polymers where each of $R_1$, $R_2$, $R_3$ and $R_4$ is the same and selected from $R_A$-$R_J$ (Table 1). These HK polymers are termed H2K4b, H3K4b, H3K(+H)4b, H3k(+H)4b, H-H3K(+H)4b, HH-H3K(+H)4b, H4K4b, H3K(1+H)4b, H3K(3+H)4b and H3K(1,3+H)4b, respectively. In each of these 10 examples, upper case "K" represents an L-lysine, and lower case "k" represents D-lysine. Extra histidine residues, in comparison to H3K4b, are underlined within the branch sequences. Nomenclature of the HK polymers is as follows:

1) for H3K4b, the dominant repeating sequence in the branches is -HHHK- (SEQ ID NO: 45), thus "H3K" (SEQ ID NO: 45) is part of the name; the "4b" refers to the number of branches;
2) there are four -HHHK- (SEQ ID NO: 45) motifs in each branch of H3K4b and analogues; the first -HHHK- motif (SEQ ID NO: 45) ("1") is closest to the lysine core;

3) H3K(+H)4b is an analogue of H3K4b in which one extra histidine is inserted in the second -HHHK- motif (SEQ ID NO: 45) (motif 2) of H3K4b;
4) for H3K(1+H)4b and H3K(3+H)4b peptides, there is an extra histidine in the first (motif 1) and third (motif 3) motifs, respectively;
5) for H3K(1,3+H)4b, there are two extra histidines in both the first and the third motifs of the branches.

TABLE 1

| Polymer | Branch Sequence | Sequence Identifier |
|---|---|---|
| H2K4b | $R_A$ = KHKHHKHHKHHKHHKHHKHK-<br>4 3 2 1 | (SEQ ID NO: 31) |
| H3K4b | $R_B$ = KHHHKHHHKHHHKHHHK- | (SEQ ID NO: 32) |
| H3K(+H)4b | $R_C$ = KHHHKHHHKHHHHKHHHK- | (SEQ ID NO: 33) |
| H3k(+H)4b | $R_D$ = kHHHkHHHkHHHHkHHHk- | (SEQ ID NO: 34) |
| H-H3K(+H)4b | $R_E$ = HKHHHKHHHKHHHHKHHHK- | (SEQ ID NO: 35) |
| HH-H3K(+H)4b | $R_F$ = HHKHHHKHHHKHHHHKHHHK- | (SEQ ID NO: 36) |
| H4K4b | $R_G$ = KHHHHKHHHHKHHHHKHHHHK- | (SEQ ID NO: 37) |
| H3K(1 +H)4b | $R_H$ = KHHHKHHHKHHHKHHHHK- | (SEQ ID NO: 38) |
| H3K(3 +H)4b | $R_I$ = KHHHKHHHHKHHHKHHHK- | (SEQ ID NO: 39) |
| H3K(1,3 +H)4b | $R_J$ = KHHHKHHHHKHHHKHHHHK- | (SEQ ID NO: 40) |

Methods well known in the art, including gel retardation assays, heparin displacement assays and flow cytometry can be performed to assess performance of different formulations containing HK polymer plus liposome in successfully delivering mRNA. Suitable methods are described in, for example, Gujrati et al, *Mol. Pharmaceutics* 11:2734-2744 (2014), and Pärnaste et al., *Mol Ther Nucleic Acids.* 7: 1-10 (2017).

Detection of mRNA uptake into cells can also be achieved using SMARTFLARE® technology (Millipore Sigma). These smart flares are beads that have a sequence attached that, when recognizing the RNA sequence in the cell, produce an increase in fluorescence that can be analyzed with a fluorescent microscope.

Other methods include measuring protein expressions from an mRNA, for example, an mRNA encoding luciferase can be used to measure the efficiency of transfection. See, for example, He et al (*J Gene Med.* 2021 February; 23(2): e3295) demonstrating the efficacy of delivering mRNA using a HKP and liposome formulation.

The combination of H3K(+H)4b and DOTAP (a cationic lipid) surprisingly was synergistic in its ability to carry mRNA into MDA-MB-231 cells (H3K(+H)4b/liposomes vs liposomes, $P<0.0001$). The combination was about 3-fold and 8-fold more effective as carriers of mRNA than the polymer alone and the cationic lipid carrier, respectively. Not all HK peptides demonstrated the synergistic activity with DOTAP lipid. For example, the combination of H3K4b and DOTAP was less effective than the DOTAP liposomes as carriers of luciferase mRNA. Besides DOTAP, other cationic lipids that may be used with HK peptides include Lipofectin (ThermoFisher), Lipofectamine (ThermoFisher), and DOSPER.

The D-isomer of H3k (+H)4b, in which the L-lysines in the branches are replaced with D-lysines, was the most effective polymeric carrier (H3k(+H)4b vs. H3K(+H)4b, $P<0.05$). The D-isomer/liposome carrier of mRNA was nearly 4-fold and 10-fold more effective than the H3k(+H)4b alone and liposome carrier, respectively. Although the D-H3k(+H)4b/lipid combination was modestly more effective than the L-H3K(+H)4b/lipid combination, this comparison was not statistically different.

Both H3K4b and H3K(+H)4b can be used as carriers of nucleic acids in vitro See, for example, Leng et al. *J Gene Med* 2005; 7: 977-986; and Chou et al., *Cancer Gene Ther* 2011; 18: 707-716. Despite these previous findings, H3K(+H)4b was markedly better as a carrier of mRNA compared to other similar analogues (Table 2).

TABLE 2

| Polymer | Ratio(wt:wt; mRNA:Polymer) | RLU/ug-Protein |
|---|---|---|
| H3K(+H)4b | 1:4 | 1532.9 ± 122.9 |
| | 1:8 | 1656.3 ± 202.5 |
| | 1:12 | 1033.4 ± 197 |
| H3k(+H)4b | 1:4 | 1851.6 ± 138.3 |
| | 1:8 | 1787.2 ± 195.2 |
| | 1:12 | 1982.3 ± 210.7 |
| H3K4b | 1:4 | 156.8 ± 41.8 |
| | 1:8 | 62.1 ± 13.2 |
| | 1:12 | 18.1 ± 4.0 |
| H3K(3 + H)4b | 1:4 | 61.7 ± 5.7 |
| | 1:8 | 68.7 ± 3.1 |
| | 1:12 | 59.0 ± 7.5 |
| H3K(1 + H)4b | 1:4 | 24.3 ± 4.5 |
| | 1:8 | 15.0 ± 3.6 |
| | 1:12 | 7.3 ± 2.5 |
| H-H3K(+H)4b | 1:4 | 1107.5 ± 140.4 |
| | 1:8 | 874.6 ± 65.2 |
| | 1:12 | 676.4 ± 25.7 |
| HH-H3K(+H)4b | 1:4 | 1101.9 ± 106.6 |
| | 1:8 | 832.2 ± 75.3 |
| | 1:12 | 739.8 ± 105.4 |
| H4K4b | 1:4 | 896.4 ± 112.6 |
| | 1:8 | 821.8 ± 115.6 |
| | 1:12 | 522.4 ± 69.2 |
| H3K(1,3 + H)4b | 1:4 | 518.3 ± 134.7 |
| | 1:8 | 427.7 ± 18.1 |
| | 1:12 | 378 ± 5.2 |

TABLE 2-continued

| Polymer | Ratio(wt:wt; mRNA:Polymer) | RLU/ug-Protein |
|---|---|---|
| H2K4b | 1:4 | 546.7 ± 70.1 |
| | 1:8 | 132.3 ± 58.5 |
| | 1:12 | 194.7 ± 18.4 |

Especially, it has higher mRNA transfection efficiency than H3K4b in various weight:weight (HK:mRNA) ratios. At a 4:1 ratio, luciferase expression was 10-fold higher with H3K(+H)4b than H3K4b in MDA-MB-231 cells without significant cytotoxicity. Moreover, the buffering capacity does not seem to be an essential factor in their transfection differences since the percent of histidines (by weight) in H3K4b and H3K(+H)4b is 68.9 and 70.6%, respectively.

Gel retardation assays show that the electrophoretic mobility of mRNA was delayed by the HK polymers. The retardation effect increased with higher peptide to mRNA weight ratios. However, mRNA was completely retarded in 2:1 ratio of H3K(+H)4b, whereas it was not completely retarded by H3K4b. This suggested that H3K(+H)4b could form a more stable polyplex, which was advantageous for its ability to be a suitable carrier for mRNA delivery.

Further confirmation that the H3K(+H)4b peptide binds more tightly to mRNA was demonstrated with a heparin-displacement assay. Various concentrations of heparin was added into the polyplexes formed with mRNA and HK and it was observed that, particularly at the lower concentrations of heparin, mRNA was released by the H3K4b polymer more readily than the H3K(+H)4b polymer. These data suggest H3K(+H)4b could bind to mRNA and form a more stable polyplex than H3K4b.

With the mRNA labeled with cyanine-5, the uptake of H3K4b and H3K(+H)4b polyplexes into MDA-MB-231 cells was compared using flow cytometry. At different time points (1, 2, and 4 h), the H3K(+H)4b polyplexes were imported into the cells more efficiently than H3K4b polyplexes. Similar to these results, fluorescent microscopy indicated that H3K(+H)4b polyplexes localized within the acidic endosomal vesicles significantly more than H3K4b polyplexes (H3K4b vs. H3K(+H)4b, P<0.001). Interestingly, irregularly-shaped H3K4b polyplexes, which did not overlap endocytic vesicles, were likely extracellular and were not observed with H3K(+H)4b polyplexes.

It is known both that HK polymers and cationic lipids (i.e., DOTAP) significantly and independently increase transfection with plasmids. See, for example, Chen et al. *Gene Ther* 2000; 7: 1698-1705. Consequently, whether these lipids together with HK polymers enhanced mRNA transfection was investigated. Notably, the H3K(+H)4b and H3k (+H)4b carriers were significantly better carriers of mRNA than the DOTAP liposomes. The combination of H3K(+H) 4b and DOTAP lipid was synergistic in the ability to carry mRNA into MDA-MB-231 cells. The combination was about 3-fold and 8-fold more effective as carriers of mRNA than the polymer alone and the liposome carrier, respectively (H3K(+H)4b/lipid vs. liposomes or H3K(+H)4b). Notably, not all HK peptides demonstrated improved activity with DOTAP lipid. The combination of H3K4b and DOTAP carriers was less effective than the DOTAP liposomes as carriers of luciferase mRNA. The combination of DOTAP and H3K(+H)4b carriers were found to be synergistic in their ability to carry mRNA into cells. See, for example, He et al. *J Gene Med.* 2020 Nov. 10:e3295.

In some embodiments, the carrier, such as the NKP nanoparticle, further comprises a cationic lipid, a PEG-modified lipid, a sterol and a non-cationic lipid. In some embodiments, a cationic lipid is an ionizable cationic lipid and the non-cationic lipid is a neutral lipid, and the sterol is a cholesterol. In some embodiments, a cationic lipid is selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA, or MC3), and di((Z)-non-2-en-1-yl) 9-((4-(dimethylamino)butanoyl)oxy) heptadecanedioate (L319).

In some embodiments, the carrier is a lipid nanoparticle (LNP). In some embodiments, the LNP has a mean diameter of about 50 nm to about 200 nm. In some embodiments, Lipid nanoparticle carriers/formulations typically comprise, or alternatively consist essentially of, or yet further consist of a lipid, in particular, an ionizable cationic lipid, for example, SM-102 as disclosed herein, 2,2-dilinoleyl-4-dimethylaminoethyl-[1,3]-dioxolane (DLin-KC2-DMA), dilinoleyl-methyl-4-dimethylaminobutyrate (DLin-MC3-DMA), or di((Z)-non-2-en-1-yl) 9-((4-(dimethylamino) butanoyl)oxy)heptadecanedioate (L319). In some embodiments, the LNP carriers/formulations further comprise a neutral lipid, a sterol (such as a cholesterol) and a molecule capable of reducing particle aggregation, for example a PEG or PEG-modified lipid (also referred to herein as PEGylated lipid). Additional exemplary lipid nanoparticle compositions and methods of making same are described, for example, in Semple et al. (2010) Nat. Biotechnol. 28:172-176; Jayarama et al. (2012), Angew. Chem. Int. Ed., 51:8529-8533; and Maier et al. (2013) Molecular Therapy 21:1570-1578, the contents of each of which are incorporated herein by reference in their entirety.

In one embodiment, the term "disease" or "disorder" as used herein refers to a RSV infection, a status of being diagnosed with a RSV infection, a status of being suspect of having a RSV infection, or a status of at high risk of having a RSV infection. In one embodiment, the term "disease" or "disorder" as used herein refers to a symptomatic RSV infection, a status of being diagnosed with a symptomatic RSV infection, a status of being suspect of having a symptomatic RSV infection, or a status of at high risk of having a symptomatic RSV infection.

As used herein, the term "animal" refers to living multi-cellular vertebrate organisms, a category that includes, for example, mammals and birds. The term "mammal" includes both human and non-human mammals such as non-human primates (e.g., apes, gibbons, chimpanzees, orangutans, monkeys, macaques, and the like), domestic animals (e.g., dogs and cats), farm animals (e.g., horses, cows, goats, sheep, pigs) and experimental animals (e.g., mouse, bat, rat, rabbit, guinea pig).

The term "subject," "host," "individual," and "patient" are as used interchangeably herein to refer to animals, typically mammalian animals. Any suitable mammal can be treated by a method described herein. Non-limiting examples of mammals include humans, non-human primates (e.g., apes, gibbons, chimpanzees, orangutans, monkeys, macaques, and the like), domestic animals (e.g., dogs and cats), farm animals (e.g., horses, cows, goats, sheep, pigs) and experimental animals (e.g., mouse, rat, bat, rabbit, guinea pig). In some embodiments, a mammal is a human. A mammal can be any age or at any stage of development (e.g., an adult, teen, child, infant, or a mammal in utero). A mammal can be male or female. In some embodiments, a subject is a human. In some embodiments, a subject has or is diagnosed of having or is suspected of having a disease.

As used herein, "treating" or "treatment" of a disease in a subject refers to (1) preventing the symptoms or disease from occurring in a subject that is predisposed or does not yet display symptoms of the disease; (2) inhibiting the disease or arresting its development; or (3) ameliorating or causing regression of the disease or the symptoms of the disease. As understood in the art, "treatment" is an approach for obtaining beneficial or desired results, including clinical results. For the purposes of the present technology, beneficial or desired results can include one or more, but are not limited to, alleviation or amelioration of one or more symptoms, diminishment of extent of a condition (including a disease), stabilized (i.e., not worsening) state of a condition (including disease), delay or slowing of condition (including disease), progression, amelioration or palliation of the condition (including disease), states and remission (whether partial or total), whether detectable or undetectable. In one aspect, treatment excludes prophylaxis.

In some embodiments, the terms "treating," "treatment," and the like, as used herein, mean ameliorating a disease, so as to reduce, ameliorate, or eliminate its cause, its progression, its severity, or one or more of its symptoms, or otherwise beneficially alter the disease in a subject. Reference to "treating," or "treatment" of a patient is intended to include prophylaxis. Treatment may also be preemptive in nature, i.e., it may include prevention of disease in a subject exposed to or at risk for the disease. Prevention of a disease may involve complete protection from disease, for example as in the case of prevention of infection with a pathogen, or may involve prevention of disease progression. For example, prevention of a disease may not mean complete foreclosure of any effect related to the diseases at any level, but instead may mean prevention of the symptoms of a disease to a clinically significant or detectable level. Prevention of diseases may also mean prevention of progression of a disease to a later stage of the disease.

"Immune response" broadly refers to the antigen-specific responses of lymphocytes to foreign substances. The terms "immunogen" and "immunogenic" refer to molecules with the capacity to elicit an immune response. All immunogens are antigens, however, not all antigens are immunogenic. An immune response disclosed herein can be humoral (via antibody activity) or cell-mediated (via T cell activation). The response may occur in vivo or in vitro. The skilled artisan will understand that a variety of macromolecules, including proteins, nucleic acids, fatty acids, lipids, lipopolysaccharides and polysaccharides have the potential to be immunogenic. The skilled artisan will further understand that nucleic acids encoding a molecule capable of eliciting an immune response necessarily encode an immunogen. The artisan will further understand that immunogens are not limited to full-length molecules, but may include partial molecules.

As used herein, "viral load", also known as "viral burden," "viral titer", "viral level" or "viral expression" in some embodiments, is a measure of the severity of a viral infection, and can be calculated by estimating the amount of virus in an infected organism, an involved body fluid, or a biological sample.

As used herein, a biological sample, or a sample, is obtained from a subject. Exemplary samples include, but are not limited to, cell sample, tissue sample, biopsy, liquid samples such as blood and other liquid samples of biological origin, including, but not limited to, anterior nasal swab, ocular fluids (aqueous and vitreous humor), peripheral blood, sera, plasma, ascites, urine, cerebrospinal fluid (CSF), sputum, saliva, bone marrow, synovial. fluid, aqueous humor, amniotic fluid, cerumen, breast milk, broncheoalveolar lavage fluid, semen, prostatic fluid, cowper's fluid or pre-ejaculatory fluid, female ejaculate, sweat, tears, cyst fluid, pleural and peritoneal fluid, pericardial fluid, ascites, lymph, chyme, chyle, bile, interstitial fluid, menses, pus, sebum, vomit, vaginal secretions/flushing, synovial fluid, mucosal secretion, stool water, pancreatic juice, lavage fluids from sinus cavities, bronchopulmonary aspirates, blastocyl cavity fluid, or umbilical cord blood.

In some embodiments, the sample may be an upper respiratory specimen, such as a nasopharyngeal (NP) specimen, an oropharyngeal (OP) specimen, a nasal mid-turbinate swab, an anterior nares (nasal swab) specimen, or nasopharyngeal wash/aspirate or nasal wash/aspirate (NW) specimen.

In some embodiments, the samples include fluid from a subject, including, without limitation, blood or a blood product (e.g., serum, plasma, or the like), umbilical cord blood, amniotic fluid, cerebrospinal fluid, spinal fluid, lavage fluid (e.g., bronchoalveolar, gastric, peritoneal, ductal, ear, arthroscopic), washings of female reproductive tract, urine, feces, sputum, saliva, nasal mucous, prostate fluid, lavage, semen, lymphatic fluid, bile, tears, sweat, breast milk, breast fluid, the like or combinations thereof. In some embodiments, a liquid biological sample is a blood plasma or serum sample. The term "blood" as used herein refers to a blood sample or preparation from a subject. The term encompasses whole blood, blood product or any fraction of blood, such as serum, plasma, buffy coat, or the like as conventionally defined. In some embodiments, the term "blood" refers to peripheral blood. Blood plasma refers to the fraction of whole blood resulting from centrifugation of blood treated with anticoagulants. Blood serum refers to the watery portion of fluid remaining after a blood sample has coagulated. Fluid samples often are collected in accordance with standard protocols hospitals or clinics generally follow. For blood, an appropriate amount of peripheral blood (e.g., between 3-40 milliliters) often is collected and can be stored according to standard procedures prior to or after preparation.

The term "adjuvant" refers to a substance or mixture that enhances the immune response to an antigen. As non-limiting example, the adjuvant can comprise dimethyldioctadecylammonium-bromide, dimethyldioctadecylammonium-chloride, dimethyldioctadecylammonium-phosphate or dimethyldioctadecylammonium-acetate (DDA) and an apolar fraction or part of said apolar fraction of a total lipid extract of a *mycobacterium* (See e.g., U.S. Pat. No. 8,241,610). In another embodiment, the synthetic nanocarrier may comprise at least one polynucleotide and an adjuvant. As a non-limiting example, the synthetic nanocarrier comprising and adjuvant can be formulated by the methods described in WO2011150240 and US20110293700, each of which is herein incorporated by reference in its entirety.

The term "contacting" means direct or indirect binding or interaction between two or more. A particular example of direct interaction is binding. A particular example of an indirect interaction is where one entity acts upon an intermediary molecule, which in turn acts upon the second referenced entity. Contacting as used herein includes in solution, in solid phase, in vitro, ex vivo, in a cell and in vivo. Contacting in vivo can be referred to as administering, or administration.

"Administration" or "delivery" of a cell or vector or other agent and compositions containing same can be performed in one dose, continuously or intermittently throughout the course of treatment. Methods of determining the most effective means and dosage of administration are known to those of skill in the art and will vary with the composition used for therapy, the purpose of the therapy, the target cell being treated, and the subject being treated. Single or multiple administrations can be carried out with the dose level and pattern being selected by the treating physician or in the case of animals, by the treating veterinarian. In some embodiments, administering or a grammatical variation thereof also refers to more than one doses with certain interval. In some embodiments, the interval is 1 day, 2 days, 3 days, 4 days, 5 days, 6 days, 1 week, 10 days, 2 weeks, 3 weeks, 1 month, 2 months, 3 months, 4 months, 5 months, 6 months, 1 year or longer. In some embodiments, one dose is repeated for once, twice, three times, four times, five times, six times, seven times, eight times, nine times, ten times or more. Suitable dosage formulations and methods of administering the agents are known in the art. Route of administration can also be determined and method of determining the most effective route of administration are known to those of skill in the art and will vary with the composition used for treatment, the purpose of the treatment, the health condition or disease stage of the subject being treated, and target cell or tissue. Non-limiting examples of route of administration include oral administration, intraperitoneal, infusion, nasal administration, inhalation, injection, and topical application. In some embodiments, the administration is an infusion (for example to peripheral blood of a subject) over a certain period of time, such as about 30 minutes, about 1 hour, about 2 hours, about 3 hours, about 4 hours, about 5 hours, about 6 hours, about 7 hours, about 8 hours, about 9 hours, about 10 hours, about 11 hours, about 12 hours, about 24 hours or longer.

The term administration shall include without limitation, administration by oral, parenteral (e.g., intramuscular, intraperitoneal, intravenous, intracerebroventricular (ICV), intrathecal, intracisternal injection or infusion, subcutaneous injection, or implant), by inhalation spray nasal, vaginal, rectal, sublingual, urethral (e.g., urethral suppository) or topical routes of administration (e.g., gel, ointment, cream, aerosol, etc.) and can be formulated, alone or together, in suitable dosage unit formulations containing conventional non-toxic pharmaceutically acceptable carriers, adjuvants, excipients, and vehicles appropriate for each route of administration. The disclosure is not limited by the route of administration, the formulation or dosing schedule.

In some embodiments, an RNA, polynucleotide, vector, cell or composition as disclosed herein is administered in an effective amount. An "effective amount" is an amount sufficient to effect beneficial or desired results. An effective amount can be administered in one or more administrations, applications or dosages. Such delivery is dependent on a number of variables including the time period for which the individual dosage unit is to be used, the bioavailability of the therapeutic agent, the route of administration, etc. It is understood, however, that specific dose levels of the therapeutic agents disclosed herein for any particular subject depends upon a variety of factors including the activity of the specific agent employed, bioavailability of the agent, the route of administration, the age of the animal and its body weight, general health, sex, the diet of the animal, the time of administration, the rate of excretion, the drug combination, and the severity of the particular disorder being treated and form of administration. In general, one will desire to administer an amount of the agent that is effective to achieve a serum level commensurate with the concentrations found to be effective in vivo. These considerations, as well as effective formulations and administration procedures are well known in the art and are described in standard textbooks.

Modes for Carrying Out the Disclosure

Prophylactic and therapeutic agents for vaccination, prevention and treatment of a Respiratory Syncytial Virus (RSV) disease are provided.

Fusion Glycoproteins, DNA and RNA

Provided herein is a fusion glycoprotein or immunogenic fragment thereof of a Respiratory Syncytial Virus (RSV) or polynucleotide encoding the RSV, such as a DNA or RNA, e.g., mRNA encoding the fusion glycoprotein (F) protein or an immunogenic fragment thereof of the Respiratory Syncytial Virus (RSV), or an equivalent of each thereof. In one aspect, the F protein or immunogenic fragment thereof or an equivalent of each thereof comprises or consists essentially of, or yet further consists of at least one non-naturally occurring amino acid mutation, for example, as compared to SEQ ID NOS: 1, 87, or amino acids 138 to 574 of SEQ ID NO: 53, or SEQ ID NO: 53, or a polynucleotide encoding the same.

In some embodiments, the at least one non-naturally occurring amino acid mutation of the glycoprotein, fragment or equivalent thereof comprises, or alternatively consists essentially of, or yet further consists of one or more of, two or more, three or more, or all four of: a cysteine (C) as the amino acid corresponding to S155 of SEQ ID NO: 53 or 87 (S155C), a phenylalanine (F) as the amino acid corresponding to S190 of SEQ ID NO: 53 or 87 (S190F), a leucine (L) as the amino acid corresponding to V207 of SEQ ID NO: 53 or 87 (V207L), or a C as the amino acid corresponding to S290 of SEQ ID NO: 53 or 87 (S290C). In one aspect, the glycoprotein, fragment or equivalent thereof comprises, or alternatively consists essentially of, or yet further consists of all of: a cysteine (C) as the amino acid corresponding to S155 of SEQ ID NO: 53 or 87 (S155C), a phenylalanine (F) as the amino acid corresponding to S190 of SEQ ID NO: 53 or 87 (S190F), a leucine (L) as the amino acid corresponding to V207 of SEQ ID NO: 53 or 87 (V207L), and a C as the amino acid corresponding to S290 of SEQ ID NO: 53 or 87 (S290C), see e.g. optimized Vaccine F4 (without a transmembrane domain and cytoplasmic domain) and optimized Vaccine F3 (with a transmembrane and cytoplasmic domains.) Further provided is a polynucleotide encoding the fusion glycoprotein, the immunogenic fragment, or the equivalent thereof, that is DNA or RNA. An exemplary DNA sequence for the A2 F protein is provided in SEQ ID NO: 54, which does not have these specific mutations. An exemplary DNA sequence for the optimized F protein scaffold or backbone is provided in SEQ ID NO: 88.

In another aspect, provided herein is a fusion glycoprotein, the fragment or equivalent thereof that comprises one or more non-naturally occurring amino acid mutations in the fusion glycoprotein, the fragment or equivalent thereof that comprises, or alternatively consists essentially of, or yet further consists of one or more, two or more, three or more, or all four of: a histidine (H) as the amino acid corresponding to D486 of SEQ ID NO: 53 or 87 (D486H), a glutamine (Q) as the amino acid corresponding to E487 of SEQ ID NO: 53 or 87 (E487Q), a tryptophan (W) as the amino acid corresponding to F484 of SEQ ID NO: 53 or 87 (F484W), and/or a H as the amino acid corresponding to D489 of SEQ ID NO: 53 or 87 (D489H) In another aspect, provided herein is a fusion glycoprotein, the fragment or equivalent thereof that comprises all four one or more non-naturally occurring amino acid mutations in the fusion glycoprotein, the fragment or equivalent thereof that comprises, or alternatively consists essentially of, or yet further consists of all of: a histidine (H) as the amino acid corresponding to D486 of SEQ ID NO: 53 or 87 (D486H), a glutamine (Q) as the amino acid corresponding to E487 of SEQ ID NO: 53 or 87 (E487Q), a tryptophan (W) as the amino acid corresponding to F484 of SEQ ID NO: 53 or 87 (F484W), and a H as the amino acid corresponding to D489 of SEQ ID NO: 53 or 87 (D489H).

Figure 5:
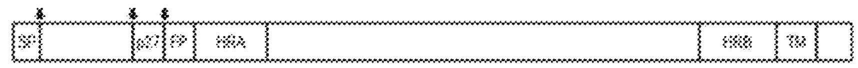
FIG. 5 shows provides a protein mapping diagram for respiratory syncytial virus (RSV) F protein mRNA optimized vaccine candidates. Optimized F1 is an RSV F protein scaffold lacking any mutations (SEQ ID NO: 87). F2 to F6 indicate alternative RSV optimized vaccine constructs. The column "TM/Secreted" indicates the vaccine is transmembrane or secreted. Conformation column indicates that the three dimensional confirmation of the vaccine, whether it is in the pre- and post-fusion structure of RSV F protein. F1 through F6 are the same protein mapping diagrams for the "A" or "A2" RSV Vaccines (A2-1 through A2-6, respectively), only the backbone structures are different, see FIG. 2 for a sequence comparison.
Figure 5:
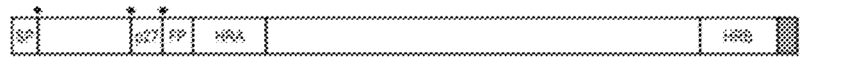
Figure 5:
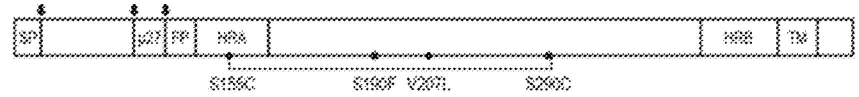
Figure 5:
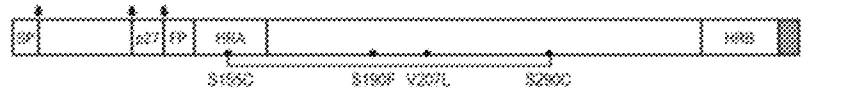
Figure 5:
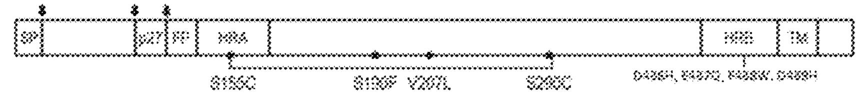
Figure 5:
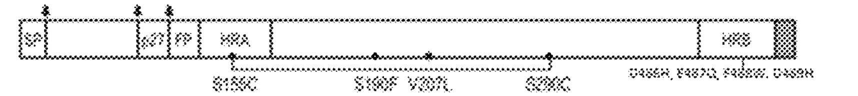

In some embodiments, the at least one non-naturally occurring amino acid mutation of the glycoprotein, fragment or equivalent thereof comprises, or alternatively consists essentially of, or yet further consists of one, or two, or three, or four, or five, or six, or seven, or all eight of: a cysteine (C) as the amino acid corresponding to S155 of SEQ ID NO: 53 or 87 (S155C), a phenylalanine (F) as the amino acid corresponding to S190 of SEQ ID NO: 53 or 87 (S190F), a leucine (L) as the amino acid corresponding to V207 of SEQ ID NO: 53 or 87 (V207L), a C as the amino acid corresponding to S290 of SEQ ID NO: 53 or 87 (S290C), D486 of SEQ ID NO: 53 or 87 (D486H), a glutamine (Q) as the amino acid corresponding to E487 of SEQ ID NO: 53 or 87 (E487Q), a tryptophan (W) as the amino acid corresponding to F484 of SEQ ID NO: 53 or 87 (F484W), or a H as the amino acid corresponding to D489 of SEQ ID NO: 53 or 87 (D489H). Optimized Vaccine F6 comprises all eight mutations without a transmembrane and cytoplasmic domain, but comprises the trimerization domain and optimized vaccine F5 comprises all eight mutations with a transmembrane domain and cytoplasmic domain. See FIG. 5 for the maps of the optimized vaccines F2 through F6 as well as vaccines A-2 through A-6. In another aspect, the glycoprotein, fragment or equivalent thereof comprises all eight mutations and is identified herein as optimized Vaccine F5 or F6.

Further provided are polynucleotides encoding the fusion glycoproteins, the immunogenic fragments, or the equivalents thereof, that is DNA or RNA. An exemplary DNA sequence for the F protein is provided in SEQ ID NO. 54 absent these specific mutations.

Further provided is a polynucleotide encoding the fusion glycoprotein, the immunogenic fragment, or the equivalent thereof, that is DNA or RNA. An exemplary DNA sequence for the A2 F protein is provided in SEQ ID NO. 54 absent these specific mutations.

In some embodiments, the amino acid of the protein or fragment or equivalent does not comprise SEQ ID NO: 54.

The disclosure also provides a ribonucleic acid (RNA) encoding a fusion (F) protein or a fragment thereof (such as an immunogenic fragment) of a Respiratory Syncytial Virus (RSV). The F protein or fragment comprises, or consists essentially of, or yet further consists of, at least one non-naturally occurring amino acid mutation, as in one aspect, is disclosed herein.

In some embodiments, the fragment or immunogenic fragment comprises, or alternatively consists essentially of, or yet further consists of a Heptad Repeat B (HRB) domain of the F protein or an equivalent thereof, such as a fragment corresponding (such as aligning) to aa 476 to aa 524 of SEQ ID NO: 53. In some embodiment, the fragment or immunogenic fragment is at least about 5 amino acids long, or at least about 8 amino acids long, or at least about 10 amino acids long, or at least about 15 amino acids long, or at least about 20 amino acids long, or at least about 25 amino acids long, or at least about 30 amino acids long, or at least about 40 amino acids long, or at least about 50 amino acids long, or at least about 60 amino acids long, or at least about 70 amino acids long, or at least about 80 amino acids long, or at least about 100 amino acids long, or at least about 125 amino acids long, or at least about 150 amino acids long, or at least about 160 amino acids long, or at least about 170 amino acids long, or at least about 180 amino acids long, or at least about 190 amino acids long, or at least about 200 amino acids long, or at least about 250 amino acids long, or at least about 300, or longer. The immunogenic fragment is useful for inducing an immune response to the RSV, or reducing or inhibiting the binding of RSV to its receptor, or both and a fragment that is non-immunogenic is useful as a control in the assays as provided herein. The immunogenic fragment and glycoproteins can be used in vitro cell assays to reduce or inhibit the binding of RSV to its receptor, or both, for efficacy analysis against new viral serotypes and for assaying for combination therapies.

In some embodiments, the at least one non-naturally occurring amino acid mutation comprises, or alternatively consists essentially of, or yet further consists of a mutation. In some embodiments, the at least one non-naturally occurring amino acid mutation comprises, or alternatively consists essentially of, or yet further consists of one or more of: a cysteine (C) as the amino acid corresponding to S155 of SEQ ID NO: 53 or 87 (S155C), a phenylalanine (F) as the amino acid corresponding to S190 of SEQ ID NO: 53 or 87 (S190F), a leucine (L) as the amino acid corresponding to V207 of SEQ ID NO: 53 or 87 (V207L), a C as the amino acid corresponding to S290 of SEQ ID NO: 53 or 87 (S290C).

In some embodiments, the at least one non-naturally occurring amino acid mutation comprises, or alternatively consists essentially of, or yet further consists of one or more of: a histidine (H) as the amino acid corresponding to D486 of SEQ ID NO: 53 or 87 (D486H), a glutamine (Q) as the amino acid corresponding to E487 of SEQ ID NO: 53 or 87 (E487Q), a tryptophan (W) as the amino acid corresponding to F484 of SEQ ID NO: 53 or 87 (F484W), or a H as the amino acid corresponding to D489 of SEQ ID NO: 53 or 87 (D489H).

In some embodiments, the at least one non-naturally occurring amino acid mutation comprises, or alternatively consists essentially of, or yet further consists of a cysteine (C) as the amino acid corresponding to S155 of SEQ ID NO: 53 or 87 (S155C), a phenylalanine (F) as the amino acid corresponding to S190 of SEQ ID NO: 53 or 87 (S190F), a leucine (L) as the amino acid corresponding to V207 of SEQ ID NO: 53 or 87 (V207L), and a C as the amino acid corresponding to S290 of SEQ ID NO: 53 or 87 (S290C). In some embodiments, the at least one non-naturally occurring amino acid mutation comprises, or alternatively consists essentially of, or yet further consists of a histidine (H) as the amino acid corresponding to D486 of SEQ ID NO: 53 or 87 (D486H), a glutamine (Q) as the amino acid corresponding to E487 of SEQ ID NO: 53 or 87 (E487Q), a tryptophan (W) as the amino acid corresponding to F484 of SEQ ID NO: 53 or 87 (F484W), and a H as the amino acid corresponding to D489 of SEQ ID NO: 53 or 87 (D489H).

In some embodiments, the polynucleotide as RNA or mRNA encodes an F protein comprising the polypeptide of SEQ ID NO: 5, 7 or 95 or an equivalent thereof, wherein the equivalent of SEQ ID NO: 5, 7 or 95 comprises the mutations of S155C, S190F, V207L, and S290C. In some embodiments, the RNA encodes an F protein comprising the polypeptide of SEQ ID NO: 11 or 104 or an equivalent thereof, wherein the equivalent of SEQ ID NO: 11 or 104, respectively maintains the mutations of S155C, S190F, V207L, S290C, D486H, E487Q, F484W, and D489H, as compared to SEQ ID NO: 53.

In some embodiments, the fusion glycoprotein, fragment or equivalent of each thereof further comprises a RSV transmembrane domain or a RSV transmembrane and cytoplasmic domain, as well as DNA, RNA, e.g., mRNA, encoding the fusion glycoprotein, fragment or equivalent thereof and the transmembrane domain.

In some embodiments, the polynucleotide is RNA encoding an RSV transmembrane domain. An exemplary RSV transmembrane domain comprises the sequence (SEQ ID NO: 117)
IMITTIIIVIIVILLSLIAVGLLLYCKARSTPVTLSKDQLSGINNIAFSN.

In further embodiments, the RNA encodes an RSV transmembrane comprising SEQ ID NO: 14 or 90.

In some embodiments, the RNA encodes an F protein comprising the polypeptide of SEQ ID NO: 5 or an equivalent thereof, wherein the equivalent of SEQ ID NO: 5 comprises the mutations of S155C, S190F, V207L, and S290C. In some embodiments, the RNA encodes an F protein comprising the polypeptide of SEQ ID NO: 9 or an equivalent thereof, wherein the equivalent of SEQ ID NO: 9 maintains the mutations of S155C, S190F, V207L, S290C, D486H, E487Q, F484W, and D489H as compared to SEQ ID NO: 53.

In some embodiments, the RNA further comprises an RNA encoding a p27 peptide. In some embodiments, the p27 peptide comprises SEQ ID NO: 77. In some embodiments, the RNA further comprises an RNA encoding a heptad repeat. In some embodiments, the heptad repeat comprises SEQ ID NO: 74. In some embodiments, the RNA further comprises an RNA encoding a signal peptide. In some embodiments, the signal peptide comprises SEQ ID NO: 71.

In some embodiments, the equivalent is at least about 80%, or at least about 85%, or at least about 90%, or at least about 91%, or at least about 92%, or at least about 93%, or at least about 94%, or at least about 95%, or at least about 96%, or at least about 97%, or at least about 98%, or at least about 99%, or more identical to the full-length reference sequence as determined by Clustal Omega or BLAST.

In some embodiments, the RNA further comprises a 3' UTR. In further embodiments, the 3'UTR comprises, or alternatively consists essentially of, or consists of any one of SEQ ID NOs: 18, 22, or 24.

In some embodiments, the RNA further comprises a 5' UTR. In further embodiments, the 5' UTR comprises, or alternatively consists essentially of, or consists of SEQ ID NO: 20 or 26.

In some embodiments, the RNA further comprises a polyA tail. In further embodiments, the polyA tail comprises any one of SEQ ID NOs: 27, 28, or 16.

In some embodiments, the RNA further comprises a 5' cap. In further embodiments, the 5' cap comprises, or alternatively consists of, or yet further consists of a 5' CleanCap. This structure uses an initiating capped trimer to yield a naturally occurring 5' cap structure.

In some embodiments, the RNA comprises, or alternatively consists essentially of, or consist of, optionally from 5' to 3', a 5'UTR, a coding sequence encoding an F protein or a fragment as disclosed herein, a 3'UTR and a polyA. In further embodiments, the RNA comprises, or alternatively consists essentially of, or consists of SEQ ID NO: 16.

In some embodiments, the RNA encodes SEQ ID NO: 5, and comprises a 3' UTR selected from SEQ ID NOs: 18, 22, or 24, a 5' UTR selected from SEQ ID NOs: 20 or 26, and a polyA tail selected from SEQ ID NOs: 27, 28, or 16.

In some embodiments, the RNA is a messenger RNA (mRNA).

Also provided are DNA encoding the RNA as disclosed herein.

In some embodiments, the RNA is chemically modified. In further embodiments, the modification comprises, or alternatively consists essentially of, or consists of modifying a uridine (U) residue to an N1-methyl-pseudouridine residue. Additionally or alternatively, the modification comprises, or alternatively consists essentially of, or consist of modifying a U residue to a pseudouridine residue.

In some embodiments, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or higher percentage of residues of the RNA is chemically modified.

In some embodiments, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or higher percentage of uridine residues of the RNA is chemically modified, optionally to N1-methyl pseudouridine or pseudouridine. In further embodiments, at least about 50%, or at least about 70%, or about 100% of the uridine residues in the RNA are N1-methyl pseudouridine or pseudouridine.

In some embodiments, all or some of uridine residues are replaced by pseudouridines during in vitro transcription. This modification stabilizes the mRNA against enzymatic degradation in the cell, leading to enhanced translation efficiency of the mRNA. The pseudouridines used can be N1-methyl-pseudouridine, or other modifications that are well known in the art such as N6m-ethyladenosine (m6A), inosine, pseudouridine, 5-methylcytidine (m5C), 5-hydroxymethylcytidine (hm5C), and N1-methyladenosine (m1A). The modification optionally is made throughout the entire mRNA. The skilled artisan will recognize that other modified RNA residues can be used to stabilize the protein's 3 dimensional structure and increase protein translation.

Without wishing to be bound by the theory, an RNA encoding a naturally occurring F protein activates an endosomal RNA sensing pathway such as TLR3, TLR7, and TLR8 (Toll-like receptor), thereby induces innate immunity which in turn inhibits fusion protein translation. In addition, a secreted IFN-β provokes tumor cell death upon binding of cognate receptor expressed on the cell surface by activation of the downstream apoptotic pathway. However, an optimized RNA expressing a mutated F protein as disclosed herein avoids this disadvantage, and thus presents an improved translation efficiency (innate immunity) which in turn inhibits fusion protein translation. In some embodiments, the optimized RNA can be administered to a subject in need thereof, expressing the mutated F protein in vivo. In further embodiments, the expressed F protein can induce an immune response in the subject, which in turns preventing or treating a RSV infection as disclosed herein. Additionally or alternatively, the optimized RNA expresses the mutated F protein in vitro and optionally such expressed F protein can activate an immune cell in vitro. The activated immune cells can then be used to treat a subject in need thereof.

In another aspect, provided is a method of producing a fusion (F) protein or an immunogenic fragment thereof of RSV In some embodiments, the method is an in vitro method. The method comprises, or alternatively consists essentially of, or yet further consists of culturing a cell as disclosed herein under conditions suitable for expressing the F protein or immunogenic fragment thereof. In further embodiments, the method herein further comprises isolating the F protein or immunogenic fragment thereof. In some embodiments, the cell is a host cell as disclosed herein.

The mechanism of action of mRNA vaccine can be found, for example, in Wadhwa et al. *Pharmaceutics.* 2020 Jan. 28; 12(2):102. Briefly, in some embodiments, the mRNA is in vitro transcribed (IVT) from a DNA template in a cell-free system. IVT mRNA is subsequently transfected into dendritic cells (DCs) via endocytosis. Entrapped mRNA undergoes endosomal escape and is released into the cytosol. Using the translational machinery of host cells (ribosomes), the mRNA is translated into antigenic proteins. The translated antigenic protein undergoes post-translational modification and can act in the cell where it is generated. Alternatively, the protein is secreted from the host cell. Antigen protein is degraded by the proteasome in the cytoplasm. The generated antigenic peptide epitopes are transported into the endoplasmic reticulum and loaded onto major histocompatibility complex (MHC) class I molecules (MHC I). The loaded MHC I-peptide epitope complexes are presented on the surface of cells, eventually leading to the induction of antigen-specific CD8+ T cell responses after T-cell receptor recognition and appropriate co-stimulation. Exogenous proteins are taken up DCs. They are degraded in endosomes and presented via the MHC II pathway. Moreover, to obtain cognate T-cell help in antigen-presenting cells, the protein should be routed through the MHC II pathway. The generated antigenic peptide epitopes are subsequently loaded onto MHC II molecules. The loaded MHC II-peptide epitope complexes are presented on the surface of cells, leading to the induction of the antigen-specific CD4+ T cell responses. Exogenous antigens can also be processed and loaded onto MHC class I molecules via a mechanism known as cross-presentation.

Without wishing to be bound by the theory, expression of a neoantigen on a cell surface is more desirable from the perspective of inducing an immune response against the neoantigen, compared to secretion of the neoantigen outside of a cell, or expression of a neoantigen in a cell (such as on an organelle membrane inside of a cell). Signal peptides have been used to direct the transport and localization of the protein expressed by a cell. Accordingly, the combination with signal peptide was investigated and uses of a human immunoglobulin heavy chain signal peptide H7 lead to an unexpected high expression of a polypeptide of interest (an RSV derived peptide as disclosed herein) on cell surface. See, the Examples.

In some embodiments, the fragment or immunogenic fragment comprises, or alternatively consists essentially of, or yet further consists of a heptad repeat B (HRB) domain of the F protein or an equivalent thereof, such as a fragment corresponding (such as aligning) to aa 476 to aa 524 of SEQ ID NO: 53. In other embodiments, the fragment or immunogenic fragment comprises, or alternatively consists essentially of, or yet further consists of the F2 cleavage product, corresponding to aa 137 to 574 of SEQ ID NO: 53.

In some embodiments, the fragment or immunogenic fragment is at least about 5 amino acids long, or at least about 8 amino acids long, or at least about 10 amino acids long, or at least about 15 amino acids long, or at least about 20 amino acids long, or at least about 25 amino acids long, or at least about 30 amino acids long, or at least about 40 amino acids long, or at least about 50 amino acids long, or at least about 60 amino acids long, or at least about 70 amino acids long, or at least about 80 amino acids long, or at least about 100 amino acids long, or at least about 125 amino acids long, or at least about 150 amino acids long, or at least about 160 amino acids long, or at least about 170 amino acids long, or at least about 180 amino acids long, or at least about 190 amino acids long, or at least about 200 amino acids long, or at least about 250 amino acids long, or at least about 300, or longer. The immunogenic fragment is useful for inducing an immune response to the RSV, or reducing or inhibiting the binding of RSV, or both and a fragment that is non-immunogenic is useful as a control in the assays as provided herein.

In some embodiments, the RNA is chemically modified. In some embodiments, the chemical modification comprises, or consists essentially or, or yet further consists of one or both of the incorporation of an N1-methyl-pseudouridine residue or a pseudouridine residue. In some embodiments, at least about 50% to about 100% of the uridine residues in the RNA are N1-methyl pseudouridine or pseudouridine. In some embodiments, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at east about 90%, at least about 91%, at least about 92%, at least about 93%, at least about 94%, at least about 95%, at least about 96%, at least about 97%, at least about 98%, at least about 99%, or higher percentage of residues of the RNA is chemically modified by one or more of modifications as disclosed herein. In some embodiments, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or higher percentage of uridine residues of the RNA is chemically modified by one or more of modifications as disclosed herein. In some embodiments, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or higher percentage of uridine residues of the RNA is N1-methyl pseudouridine or pseudouridine.

In some embodiments, all or some of uridine residues are replaced by pseudouridines during in vitro transcription. This modification stabilizes the mRNA against enzymatic degradation in the cell, leading to enhanced translation efficiency of the mRNA. The pseudouridines used can be N1-methyl-pseudouridine, or other modifications that are well known in the art such as N6m-ethyladenosine (m6A), inosine, pseudouridine, 5-methylcytidine (m5C), 5-hydroxymethylcytidine (hm5C), and N1-methyladenosine (m1A). The modification optionally is made throughout the entire mRNA. The skilled artisan will recognize that other modified RNA residues can be used to stabilize the protein's 3 dimensional structure and increase protein translation.

Polynucleotides, Vectors, Cells and Related Methods

Further provided is a polynucleotide encoding an RNA as disclosed herein, or a polynucleotide complementary thereto, or both. In some embodiments, the polynucleotide is selected from the group of: a deoxyribonucleic acid (DNA), an RNA, a hybrid of DNA and RNA, or an analog of each thereof. In further embodiments, the analog comprises, or consists essentially of, or yet further consists of a peptide nucleic acid or a locked nucleic acid or both.

In some embodiments, the polynucleotide comprises SEQ ID NO: 8, or an equivalent thereof, wherein the equivalent of SEQ ID NO: 8 encodes SEQ ID NO: 7 or an equivalent thereof. In some embodiments, the polynucleotide comprises SEQ ID NO: 12 or an equivalent thereof, wherein the equivalent of SEQ ID NO: 12 encodes SEQ ID NO: 11 or an equivalent thereof. In some embodiments, the polynucleotide comprises SEQ ID NO: 6 or an equivalent thereof, wherein the equivalent of SEQ ID NO: 6 encodes SEQ ID NO: 5 or an equivalent thereof. In some embodiments, the polynucleotide comprises SEQ ID NO: 10 or an equivalent thereof, wherein the equivalent of SEQ ID NO: 10 encodes SEQ ID NO: 9 or an equivalent thereof.

In still further embodiments, the polynucleotide may encode a fusion peptide. In some embodiments, the fusion peptide comprises SEQ ID NO: 81. In some embodiments, the polynucleotide may encode a p27 peptide. In some embodiments, the p27 peptide comprises SEQ ID NO: 78. In some embodiments, the polynucleotide may encode a heptad repeat. In some embodiments, the heptad repeat comprises SEQ ID NO: 75. In some embodiments, the polynucleotide may encode a signal peptide. In some embodiments, the signal peptide comprises SEQ ID NO: 72.

In a further aspect, provided is a vector comprising, or alternatively consisting essentially of, or consisting of a polynucleotide as disclosed herein.

In some embodiments, the vector further comprises a regulatory sequence operatively linked to the polynucleotide to direct the transcription thereof. In some embodiments, the regulatory sequence is suitable for use in an in vitro transcription system. In further embodiments, the regulatory sequence comprises, or alternatively consists essentially of, or consists of a promotor. In yet further embodiments, the promoter is an RNA polymerase promoter, optionally a bacteriophage RNA polymerase promoter. In some embodiment, the promoter comprises, or consists essentially of, or further consists of a T7 promoter, or a SP6 promoter, or a T3 promoter. In some embodiments, the T7 promoter comprises, or consists essentially of, or yet further consists of TAATACGACTCACTATAA (SEQ ID NO: 86). In some embodiments, the regulatory sequence is suitable for use in a cell to expressing an RNA as disclosed herein. In further embodiments, the regulatory sequence comprises, or alternatively consists essentially of, or yet further consists of a promotor, or an enhancer or both.

In some embodiments, the vector further comprises a regulatory sequence operatively linked to the polynucleotide to direct the replication thereof. In further embodiments, the regulatory sequence comprises, or alternatively consists essentially of, or yet further consists of one or more of the following: an origin of replication or a primer annealing site, a promoter, or an enhancer.

In some embodiments, an RNA, or a polynucleotide, or a vector further comprises a marker selected from a detectable marker, a purification marker, or a selection marker.

In some embodiments, the vector is a non-viral vector, optionally a plasmid, or a liposome, or a micelle. In some embodiments, the plasmid comprises, or alternatively consists essentially of, or consists of SEQ ID NO: 29 or an equivalent thereof. In some embodiments, the vector is a viral vector, optionally an adenoviral vector, or an adeno-associated viral vector, or a retroviral vector, or a lentiviral vector, or a plant viral vector.

In some embodiments, a polynucleotide or a vector as disclosed herein is suitable for producing (such as transcribing or expressing or replicating) an RNA as disclosed herein. Such production can be in vivo or in vitro. For example, the polynucleotide or vector can be used to produce or replicate the RNA in vitro. Such RNA is then administrated to a subject in need thereof optionally with a suitable pharmaceutical acceptable carrier. Alternatively, the polynucleotide or vector can be used as a gene therapy and directly administrated to a subject in need thereof optionally with a suitable pharmaceutical acceptable carrier. In further embodiments, the gene therapy can additionally deliver other prophylactic or therapeutic agent to the subject.

In another aspect, a cell comprising one or more of: an RNA as disclosed herein, a polynucleotide as disclosed herein, or a vector as disclosed herein. In some embodiments, the cell is a prokaryotic cell, optionally an *Escherichia coli* cell. In some embodiments, the cell is a eukaryotic cell, optionally a mammal cell, an insect cell, or a yeast cell. In some embodiments, the cell is a human embryonic kidney 293 cell (HEK 293 cell or 293 cell) or a 293T cell.

In some embodiments, a cell as disclosed herein is suitable for producing (such as transcribing or expressing) an RNA as disclosed herein. Such production can be in vivo or in vitro. For example, the cell can be used to produce the RNA in vitro. Such RNA is then administrated to a subject in need thereof optionally with a suitable pharmaceutical acceptable carrier. Alternatively, the cell can be used as a cell therapy and directly administrated to a subject in need thereof optionally with a suitable pharmaceutical acceptable carrier. In further embodiments, the cell therapy can additionally deliver other prophylactic or therapeutic agent to the subject.

In yet another aspect, provided is a composition comprising, or alternatively consisting essentially of, or yet further consisting of a carrier, optionally a pharmaceutically acceptable carrier, and one or more of: an RNA as disclosed herein, a polynucleotide as disclosed herein, a vector as disclosed herein, or a cell as disclosed herein.

In some embodiments, the composition further comprises an additional prophylactic or therapeutic agent. In one aspect, that agent comprises an additional viral polynucleotide, e.g., a infection viral polynucleotide, optionally selected from a corona virus, a COVID-19 virus, an influenza virus, a papillomavirus, an Hepatitis A, an Hepatitis B, an Hepatitis C, a polio virus, a chickenpox varicella virus, a measles virus, the virus responsible for mumps, rubella, or a rotavirus or an human immune deficiency virus (HIV), for example.

In some embodiments, the additional prophylactic or therapeutic agent is suitable for preventing or treating a RSV related disease as disclosed herein. In further embodiments, the additional prophylactic or therapeutic agent comprises, or alternatively consists essentially of, or yet further consists of an anti-viral agent, optionally remdesivir, lopinavir, ritonavir, ivermectin, tamiflu, or favipiravir; an anti-inflammatory agent, optionally dexamethasone, tocilizumab, kevzara, colcrys, hydroxychloroquine, chloroquine, or a kinase inhibitor; a covalescent plasma from a subject recovered from a RSV infection; an antibody binding to RSV, optionally bamlanivimab, etesevimab, casirivimab, or imdevimab; or an antibiotic agent, optionally azithromycin.

In some embodiments, the additional prophylactic agent is suitable for preventing a disease that is not related to RSV. For example, the additional prophylactic agent comprises, or alternatively consists essentially of, or yet further consists of a vaccine for another virus. Additionally or alternatively, the additional prophylactic agent comprises, or alternatively consists essentially of, or yet further consists of a vaccine for another virus, such as an influenza (flu) vaccine, a papillomavirus vaccine, an Hepatitis A vaccine, an Hepatitis B vaccine, an Hepatitis c vaccine, a polio vaccine, a chickenpox varicella vaccine, a measles vaccine, a mumps vaccine, a rubella vaccine, a rotavirus vaccine. In some embodiments, the additional prophylactic agent comprises, or alternatively consists essentially of, or yet further consists of a vaccine for a bacterium or other pathogen, such as a diphtheria vaccine, a *Haemophilus influenzae* type b vaccine, a Pertussis vaccine, a pneumococcus vaccine, a Tetanus vaccine, or a Meningococcal vaccine. In some embodiments, the additional prophylactic agent comprises, or alternatively consists essentially of, or yet further consists of a vaccine for a non-infectious disease, such as a cancer.

In some embodiments, the composition further comprises an adjuvant.

In one aspect, provided is a method of producing an RNA as disclosed herein. In some embodiments, the method comprises, or alternatively consists essentially of, or yet further consists of culturing a cell as disclosure herein under conditions suitable for expressing and/or replicating the RNA. In further embodiments, the RNA is produced by a plasmid DNA (pDNA) vector delivery system. In yet further embodiments, the plasmid vectors can be adapted for mRNA vaccine production. Commonly used plasmids include pSFV1, pcDNA3 and pTK126, which are all commercially available. One unique mRNA expression system is pEVL (see, Grier et al. *Mol Ther Nucleic Acids.* 19; 5:e306 (2016)).

In some embodiments, the method comprises, or alternatively consists essentially of, or yet further consists of contacting a polynucleotide as disclosed herein or a vector as disclosed herein with an RNA polymerase, adenosine triphosphate (ATP), cytidine triphosphate (CTP), guanosine-5'-triphosphate (GTP), and uridine triphosphate (UTP) or a chemically modified UTP under conditions suitable for expressing the RNA. In some embodiments, the RNA is produced in a linear in vitro transcription (IVT) system from a linear DNA template comprising a bacteriophage promoter, UTRs and a coding sequence, by using a RNA polymerase (T7, T3 or SP6) and a mix of the different nucleosides. In some embodiments, the method further comprises isolating the RNA. In further embodiments, the method further comprises storing the RNA.

In some embodiments, the polypeptide comprises, or consists essentially of, or yet further consists of any one or more of the following amino acid sequences shown in Table 2. In some embodiments, the polypeptide further comprises a fusion peptide. In some embodiments, the polypeptide further comprises a p27 peptide. In some embodiments, the polypeptide further comprises a heptad repeat. In some embodiments, the polypeptide further comprises a signal peptide.

In some embodiments, the fusion peptide comprises SEQ ID NO: 80. In some embodiments, the p27 peptide comprises SEQ ID NO: 77. In some embodiments, the heptad repeat comprises SEQ ID NO: 74. In some embodiments, the signal peptide comprises SEQ ID NO: 71.

Further provided is a respiratory syncytial virus (RSV) ribonucleic acid (RNA) encoding an RSV fusion glycoprotein (F) protein or an immunogenic fragment thereof, the RNA encoding a peptide comprising one or more non-naturally occurring amino acid mutations selected from: a cysteine (C) as the amino acid corresponding to S155 of SEQ ID NOS: 87 or 53 (S155C), a phenylalanine (F) as the amino acid corresponding to S190 of SEQ ID NOS: 87 or 53 (S190F), a leucine (L) as the amino acid corresponding to V207 of SEQ ID NOS: 87 or 53 (V207L), a cysteine (C) as the amino acid corresponding to S290 of SEQ ID NOS: 87 or 53 (S290C).

In another aspect, the RNA RSV encodes an immunogenic fragment that comprises: a fusion peptide, an heptad repeat A (HRA), a F protein, and a heptad repeat B, and optionally: wherein the immunogenic fragment further comprises a N-terminal signal peptide, or wherein the immunogenic fragment further comprises a N-terminal HRC peptide, or wherein the immunogenic fragment further comprises a N-terminal p27 peptide, or wherein the immunogenic fragment further comprises a C-terminal transmembrane domain and a cytoplasmic domain, or wherein the immunogenic fragment comprises further a C-terminal trimerization domain.

In another aspect, the RSV RNA encodes an F protein that comprises one or more non-naturally occurring amino acid mutations selected from: a histidine (H) as the amino acid corresponding to D486 of SEQ ID NOS: 87 or 53 (D486H), a glutamine (Q) as the amino acid corresponding to E487 of SEQ ID NOS: 87 or 53 (E487Q), a tryptophan (W) as the amino acid corresponding to F484 of SEQ ID NOS: 87 or 53 (F484W), or a H as the amino acid corresponding to D489 of SEQ ID NOS: 87 or 53 (D489H).

In a further embodiment, the RSV RNA encodes an immunogenic fragment that comprises: a fusion peptide, an heptad repeat A (HRA), a F protein, and a heptad repeat B (HRB), and optionally: wherein the immunogenic fragment further comprises a N-terminal signal peptide, or wherein the immunogenic fragment further comprises a N-terminal HRC peptide, or wherein the immunogenic fragment further comprises a N-terminal p27 peptide, or wherein the immunogenic fragment comprises further a C-terminal a transmembrane domain and a cytoplasmic domain, or wherein the immunogenic fragment comprises further a C-terminal trimerization domain.

In one aspect, the RSV RNA encodes an immunogenic fragment that further comprises: the N-terminal signal peptide, the N-terminal HRC peptide, and the N-terminal p27 peptide, or wherein the immunogenic fragment further comprises further the C-terminal a transmembrane domain and a cytoplasmic domain, or the C-terminal trimerization domain, or wherein the immunogenic fragment further comprises the N-terminal signal peptide, the N-terminal HRC peptide, and the N-terminal p27 peptide and the C-terminal a transmembrane domain and a cytoplasmic domain, or a C-terminal trimerization domain.

In a further embodiment the RSV RNA encodes a polypeptide having at least one non-naturally occurring amino acid mutation from the group of D486H, E487Q, F484W, and D489H and/or S155C, S190F, V207L, and S290C of SEQ ID NOs: 87 or 53.

In another aspect, the RSV RNA encodes a F protein that comprises the fusion peptide, the HRA, the F protein, and the trimerization domain of the optimized F4 vaccine (SEQ ID NO: 7) or an equivalent thereof, wherein the equivalent of SEQ ID NO: 7 comprises the mutations of S155C, S190F, V207L, and S290C or the F protein comprises the fusion peptide, the HRA, the F protein, and the trimerization domain of the A2-4 vaccine (amino acids 138 to 556 of SEQ ID NO: 62) or an equivalent thereof, wherein the equivalent of SEQ ID NO: 62 comprises the mutations of S155C, S190F, V207L, and S290C.

In another aspect, the RSV RNA encodes a F protein that comprises the fusion peptide, the HRA, the F protein, and the trimerization domain of the optimized F vaccine (SEQ ID NO: 11) or an equivalent thereof, wherein the equivalent of SEQ ID NO: 11 comprises the mutations of S155C, S190F, V207L, S290C, D486H, E487Q, F484W, and D489H or the F protein comprises the fusion peptide, the HRA, the F protein, and the trimerization domain of the A2-6 vaccine (amino acids 138 to 556 of SEQ ID NO: 68) or an equivalent thereof, wherein the equivalent of SEQ ID NO: 68 comprises the mutations of S155C, S190F, V207L, S290C, D486H, E487Q, F484W, and D489H. Alternatively, the RSV RNA encodes a F protein that comprises the fusion peptide, the HRA, the F protein, the transmembrane domain and the cytoplasmic domain of the optimized F vaccine (SEQ ID NO: 5) or an equivalent thereof, wherein the equivalent of SEQ ID NO: 5 comprises the mutations of S155C, S190F, V207L, and S290C or the F protein comprises the fusion peptide, the HRA, the F protein, and the transmembrane domain and the cytoplasmic domain of the A2-3 vaccine (amino acids 138 to 574 of SEQ ID NO: 59) or an equivalent thereof, wherein the equivalent of SEQ ID NO: 59 comprises the mutations of S155C, S190F, V207L, and S290C. Yet further, the RSV RNA encodes a F protein that comprises the fusion peptide, the HRA, the F protein, the transmembrane domain and the cytoplasmic domain of the optimized F vaccine (SEQ ID NO: 9) or an equivalent thereof, wherein the equivalent of SEQ ID NO: 9 comprises the mutations of S155C, S190F, V207L, S290C, D486H, E487Q, F484W, and D489H or the F protein comprises the fusion peptide, the HRA, the F protein, and the transmembrane domain and the cytoplasmic domain of the A2-5 vaccine (amino acids 138 to 574 of SEQ ID NO: 65) or an equivalent thereof, wherein the equivalent of SEQ ID NO: 65 comprises the mutations of S155C, S190F, V207L, S290C, D486H, E487Q, F484W, and D489H.

The RSV RNA of this disclosure can further comprise an RNA encoding a p27 peptide such as for example, the p27 peptide that comprises SEQ ID NO: 77 or comprises the amino acids 110 to 137 of SEQ ID NO: 53.

The RSV RNA of this disclosure can further comprise an RNA encoding the HRC, e.g., SEQ ID NO: 74 or comprises the amino acids 27 to 109 of SEQ ID NO: 53.

In another aspect, the RSV RNA of this disclosure can further comprise an RNA encoding a signal peptide, e.g., a signal peptide that comprises SEQ ID NO: 71 or comprises the amino acids 1 to 26 of SEQ ID NO: 53.

As used herein, equivalents comprise at least about 80%, or at least about 85%, or at least about 90%, or at least about 91%, or at least about 92%, or at least about 93%, or at least about 94%, or at least about 95%, or at least about 96%, or at least about 97%, or at least about 98%, or at least about 99%, or more identical to the full-length reference sequence.

In a yet further aspect, the RSV RNA further comprises a 3' UTR, e.g., a 3'UTR is selected from SEQ ID NOs: 18, 22, or 24 and/or a 5' UTR selected from SEQ ID NO: 20 or 26, and/or a polyA tail, e.g., a polyA tail is selected from SEQ ID NOs: 27, 28, or 16.

In a further aspect, provided herein is a RSV RNA that encodes an F protein fragment comprising SEQ ID NO: 5, a fusion peptide comprising SEQ ID NO: 80, a p27 peptide comprising SEQ ID NO: 77, an HRC comprising SEQ ID NO: 74, and a signal peptide comprising SEQ ID NO: 71 (SEQ ID NO: 95) and further comprises a 3' UTR selected from SEQ ID NOs: 18, 22, or 24, a 5' UTR selected from SEQ ID NOs: 20 or 26, and a polyA tail selected from SEQ ID NOs: 27, 28, or 16.

In another aspect, provided herein is an RSV RNA selected from the RNA of any one of SEQ ID NOS: 61, 64, 67, 70, 97, 100, 103, or 106.

Provided herein is a polynucleotide comprising SEQ ID NO: 8, or an equivalent thereof, wherein the equivalent of SEQ ID NO: 8 encodes SEQ ID NO: 7 or an equivalent thereof, or a polynucleotide comprising SEQ ID NO: 12 or an equivalent thereof, wherein the equivalent of SEQ ID NO: 12 encodes SEQ ID NO: 11 or an equivalent thereof, or a polynucleotide comprising SEQ ID NO: 6 or an equivalent thereof, wherein the equivalent of SEQ ID NO: 6 encodes SEQ ID NO: 5 or an equivalent thereof, or a polynucleotide comprising SEQ ID NO: 10 or an equivalent thereof, wherein the equivalent of SEQ ID NO: 10 encodes SEQ ID NO: 9 or an equivalent thereof.

Further provided is a polypeptide selected from the polypeptide of any one of SEQ ID NOs: 59, 62, 65, 68, 88, 95, 98, 101, or 104, or polynucleotide of any one of SEQ ID NOs: 60, 63, 66, 69, 93, 96, 99, 102, or 105.

For the purpose of this disclosure, an equivalent is at least about 80%, or at least about 85%, or at least about 90%, or at least about 91%, or at least about 92%, or at least about 93%, or at least about 94%, or at least about 95%, or at least about 96%, or at least about 97%, or at least about 98%, or at least about 99%, or more identical to the full-length reference sequence.

In the aspects of this disclosure, the RSV RNA is optionally chemically modified and optionally comprises one or more of: an N1-methyl-pseudouridine residue or a pseudouridine residue, and optionally wherein at least about 50%, or at least about 70%, or about 100% of the uridine residues in the RNA are N1-methyl pseudouridine or pseudouridine.

Also provided is a polypeptide or protein, encoded by the RNA as disclosed herein, as well as a DNA encoding same, e.g. mRNA. Alternatively, the polynucleotide of this disclosure is a hybrid of DNA and RNA, or an analog of each thereof.

Further provided is an optimized F protein scaffold peptide, comprising SEQ ID NO: 87 or SEQ ID NO: 92, as well as an DNA or RNA (e.g., mRNA) encoding the optimized F protein scaffold comprising SEQ ID NO: 89 or SEQ ID NO: 94.

In some embodiments, the polynucleotide further comprises a regulatory sequence directing the transcription thereof. In some embodiments, the regulatory sequence is suitable for use in an in vitro transcription system. In further embodiments, the regulatory sequence comprises, or consists essentially of, or yet further consists of a promotor. In yet further embodiments, the promoter comprises, or consists essentially of, or yet further consists of: a bacteriophage RNA polymerase promoter, such as a T7 promoter, or a SP6 promoter, or a T3 promoter. In some embodiments, the polynucleotide comprises a marker selected from a detectable marker, a purification marker, or a selection marker.

In a further aspect, provided is a vector comprising, or consisting essentially of, or yet further consisting of a polynucleotide as disclosed herein.

In some embodiments, the vector further comprises a regulatory sequence operatively linked to the polynucleotide to direct the transcription thereof. In some embodiments, the regulatory sequence is suitable for use in an in vitro transcription system. In further embodiments, the regulatory sequence comprises, or consists essentially of, or yet further consists of a promotor. In yet further embodiments, the promoter comprises, or consists essentially of, or yet further consists of: a bacteriophage RNA polymerase promoter, such as a T7 promoter, or a SP6 promoter, or a T3 promoter. In some embodiments, the vector further comprises a marker selected from a detectable marker, a purification marker, or a selection marker.

In some embodiments, the vector further comprises a regulatory sequence operatively linked to the polynucleotide to direct the replication thereof. In further embodiments, the regulatory sequence comprises, or alternatively consists essentially of, or yet further consists of one or more of the following: an origin of replication or a primer annealing site, a promoter, or an enhancer.

In some embodiments, the vector is a non-viral vector. In further embodiments, the non-viral vector is a plasmid, or a liposome, or a micelle. In some embodiments, the vector is pUC57, or pSFV1, or pcDNA3, or pTK126, or another plasmid available at addgene or Standard European Vector Architecture (SEVA). In some embodiments, the vector comprises, or consists essentially of, or yet further consists of any one of SEQ ID NO: 29 or an equivalent thereof. In some embodiments, the equivalent of SEQ ID NOs: 29 still expresses the same polypeptide.

In some embodiments, the vector is a viral vector. In further embodiments, the viral vector is selected from the group consisting of an adenoviral vector, or an adeno-associated viral vector, or a retroviral vector, or a lentiviral vector, or a plant viral vector.

In yet a further aspect, provided is a cell comprising one or more of: an RNA as disclosed herein, a polynucleotide as disclosed herein, or a vector as disclosed herein. In some embodiments, the cell is suitable for replicating any one or more of: the RNA, the polynucleotide, or the vector, thereby producing the one or more of: the RNA, the polynucleotide, or the vector. In some embodiments, the cell is suitable for transcribing the polynucleotide or the vector to the RNA, thereby producing the RNA.

In some embodiments, the cell is a prokaryotic cell. In further embodiments, the prokaryotic cell is an *Escherichia coli* cell.

In some embodiments, the cell is a eukaryotic cell. In further embodiments, the eukaryotic cell is any one of a mammal cell, an insect cell, or a yeast cell. In some embodiments, the cell is a 293T cell. In some embodiments, the cell is a HEp-2 cell.

In some embodiments, a cell as disclosed herein is suitable for producing (such as transcribing or expressing) an RNA as disclosed herein. Such production can be in vivo or in vitro. For example, the cell can be used to produce the RNA in vitro. Such RNA is then administrated to a subject in need thereof optionally with a suitable pharmaceutical acceptable carrier. Alternatively, the cell can be used as a cell therapy and directly administrated to a subject in need thereof optionally with a suitable pharmaceutical acceptable carrier. In further embodiments, the cell therapy can additionally deliver other prophylactic or therapeutic agent to the subject. In some embodiments, the cell used as a cell therapy is an immune cell, such as a T cell, a B cell, an NK cell, an NKT cell, a dendritic cell, a myeloid cell, a monocyte, or a macrophage.

In one aspect, provided is a composition comprising, or consisting essentially of, or yet further consisting of a carrier, and one or more of: an RNA as disclosed herein, a polynucleotide as disclosed herein, a vector as disclosed herein, or a cell as disclosed herein. In some embodiments, the carrier is a pharmaceutically acceptable carrier. In some embodiments, the composition further comprises an additional anti-viral therapy. Additionally or alternatively, the composition further comprises an adjuvant.

Formulation and Related Methods

Accordingly, in one aspect, provided is a composition (such as an immunogenic composition) comprising, or consisting essentially of, or yet further consisting of, for example an effective amount of, an RNA as disclosed herein formulated in a pharmaceutically acceptable carrier. In some embodiments, the composition comprises, or consists essentially of, or yet further consists of the RNA and the pharmaceutically acceptable carrier.

In some embodiments, the pharmaceutically acceptable carrier comprises, or consists essentially of, or yet further consists of a nanoparticle. In some embodiments, the nanoparticle is a polymeric nanoparticle or a liposomal nanoparticle or both. In some embodiments, the nanoparticle is a lipid nanoparticle (LNP). In some embodiments, the pharmaceutically acceptable carrier comprises, or consists essentially of, or yet further consists of a polymeric nanoparticle or a liposomal nanoparticle or both.

In some embodiments, the polymeric nanoparticle carrier comprises, or consists essentially of, or yet further consists of a Histidine-Lysine co-polymer (HKP). In further embodiments, the HKP comprises, or consists essentially of, or yet further consists of H3K(+H)4b. In yet further embodiments, the HKP comprises, or consists essentially of, or yet further consists of H3k(+H)4b. In some embodiments, the HKP comprises a side chain selected from SEQ ID NOs: 31-44.

In some embodiments, the mass ratio of HKP and the RNA in the composition is about 10:1 to about 1:10, including any range or ratio there between, for example, about 5:1 to 1:5, about 5:1 to 1:1, about 10:1, about 9.5:1, about 9:1, about 8.5:1, about 8:1, about 7.5:1, about 7:1, about 6.5:1, about 6:1, about 5.5:1, about 5:1, about 4.5:1, about 4:1, about 3.5:1, about 3:1, about 2:5:1, about 2:1, about 1.5:1, about 1:1, about 1:1.5, about 1:2, about 1:2.5, about 1:3, about 1:3.5, about 1:4, about 1:4.5, about 1:5, about 1:5.5, about 1:6, about 1:6.5, about 1:7, about 1:7.5, about 1:8, about 1:8.5, about 1:9, about 1:9.5, or about 1:10. In one embodiment, the mass ratio of HKP and the RNA in the composition is about 2.5:1. In another embodiment, the mass ratio of HKP and the RNA in the composition is about 4:1.

In some embodiments, the polymeric nanoparticle carrier further comprises a lipid. In further embodiments, the lipid is a cationic lipid. In yet further embodiments, the cationic lipid is ionizable.

In some embodiments, the cationic lipid comprises, or consists essentially of, or yet further consists of Dlin-MC3-DMA (MC3) or dioleoyloxy-3-(trimethylammonio)propane (DOTAP) or both.

In some embodiments, the lipid further comprises one or more of: a helper lipid, a cholesterol, or a PEGylated lipid. In some embodiments, the lipid further comprises PLA or PLGA.

In some embodiments, the HKP and the mRNA self-assemble into nanoparticles upon admixture.

In some embodiments, the pharmaceutical acceptable carrier is a lipid nanoparticle (LNP). In some embodiments, the LNP comprises, or consists essentially of, or yet further consists of one or more of: 9-Heptadecanyl 8-{(2-hydroxyethyl)[6-oxo-6-(undecyloxy)hexyl]amino}octanoate (SM-102), 2,2-dilinoleyl-4-dimethylaminoethyl-[1,3]-dioxolane (DLin-KC2-DMA), dilinoleyl-methyl-4-dimethylaminobutyrate (DLin-MC3-DMA), di((Z)-non-2-en-1-yl) 9-((4-(dimethylamino)butanoyl)oxy)heptadecanedioate (L319), or an equivalent of each thereof. In some embodiments, the LNP further comprises one or more of: a helper lipid, a cholesterol, or a PEGylated lipid. In some embodiments, the lipid is a cationic lipid. In further embodiments, the cationic lipid is ionizable.

In some embodiments, the mass ratio of LNP and the RNA in the composition is about 10:1 to about 1:10, including any range or ratio there between, for example, about 5:1 to 1:5, about 5:1 to 1:1, about 10:1, about 9.5:1, about 9:1, about 8.5:1, about 8:1, about 7.5:1, about 7:1, about 6.5:1, about 6:1, about 5.5:1, about 5:1, about 4.5:1, about 4:1, about 3.5:1, about 3:1, about 2:5:1, about 2:1, about 1.5:1, about 1:1, about 1:1.5, about 1:2, about 1:2.5, about 1:3, about 1:3.5, about 1:4, about 1:4.5, about 1:5, about 1:5.5, about 1:6, about 1:6.5, about 1:7, about 1:7.5, about 1:8, about 1:8.5, about 1:9, about 1:9.5, or about 1:10. In one embodiment, the mass ratio of LNP and the RNA in the composition is about 2.5:1. In another embodiment, the mass ratio of LNP and the RNA in the composition is about 4:1.

In some embodiments, the helper lipid comprises, or consists essentially of, or yet further consists of one or more of: disteroylphosphatidyl choline (DSPC), Dipaimitoylphosphatidylcholine (DPPC), (2R)-3-(Hexadecanoyloxy)-2-{[(9Z)-octadec-9-enoyl]oxy}propyl 2-(trimethylazaniumyl)ethyl phosphate (POPC), or dioleoyl phosphatidylethanolamine (DOPE).

In some embodiments, the cholesterol comprises, or consists essentially of, or yet further consists of a plant cholesterol or an animal cholesterol or both.

In some embodiments, the PEGylated lipid comprises, or consists essentially of, or yet further consists of one or more of: PEG-c-DOMG (R-3-[(ω-methoxy-poly(ethyleneglycol)2000)carbamoyl)]-1,2-dimyristyloxypropyl-3-amine), PEG-DSG (1,2-Distearoyl-sn-glycerol, methoxypolyethylene glycol), PEG-DMG (1,2-Dimyristoyl-sn-glycerol) optionally PEG2000-DMG ((1,2-dimyristoyl-sn-glycero-3-phophoethanolamine-N-[methoxy(polyethylene glycol)-2000)], or PEG-DPG (1,2-Dipalmitoyl-sn-glycerol, methoxypolyethylene glycol).

In some embodiments, the mass ratio of the cationic lipid and the helper lipid is about 10:1 to about 1:10, including any range or ratio there between, for example, about 5:1 to 1:5, about 5:1 to 1:1, about 10:1, about 9.5:1, about 9:1, about 8.5:1, about 8:1, about 7.5:1, about 7:1, about 6.5:1, about 6:1, about 5.5:1, about 5:1, about 4.5:1, about 4:1, about 3.5:1, about 3:1, about 2:5:1, about 2:1, about 1.5:1, about 1:1, about 1:1.5, about 1:2, about 1:2.5, about 1:3, about 1:3.5, about 1:4, about 1:4.5, about 1:5, about 1:5.5, about 1:6, about 1:6.5, about 1:7, about 1:7.5, about 1:8, about 1:8.5, about 1:9, about 1:9.5, or about 1:10. In one embodiment, the mass ratio of the cationic lipid and the helper lipid is about 1:1.

In some embodiments, the mass ratio of the cationic lipid and cholesterol is about 10:1 to about 1:10, including any range or ratio there between, for example, about 5:1 to 1:5, about 5:1 to 1:1, about 10:1, about 9.5:1, about 9:1, about 8.5:1, about 8:1, about 7.5:1, about 7:1, about 6.5:1, about 6:1, about 5.5:1, about 5:1, about 4.5:1, about 4:1, about 3.5:1, about 3:1, about 2:5:1, about 2:1, about 1.5:1, about 1:1, about 1:1.5, about 1:2, about 1:2.5, about 1:3, about 1:3.5, about 1:4, about 1:4.5, about 1:5, about 1:5.5, about 1:6, about 1:6.5, about 1:7, about 1:7.5, about 1:8, about 1:8.5, about 1:9, about 1:9.5, or about 1:10. In one embodiment, the mass ratio of the cationic lipid and cholesterol is about 1:1.

In some embodiments, the mass ratio of the cationic lipid and PEGylated lipid is about 10:1 to about 1:10, including any range or ratio there between, for example, about 5:1 to 1:5, about 5:1 to 1:1, about 10:1, about 9.5:1, about 9:1, about 8.5:1, about 8:1, about 7.5:1, about 7:1, about 6.5:1, about 6:1, about 5.5:1, about 5:1, about 4.5:1, about 4:1, about 3.5:1, about 3:1, about 2:5:1, about 2:1, about 1.5:1, about 1:1, about 1:1.5, about 1:2, about 1:2.5, about 1:3, about 1:3.5, about 1:4, about 1:4.5, about 1:5, about 1:5.5, about 1:6, about 1:6.5, about 1:7, about 1:7.5, about 1:8, about 1:8.5, about 1:9, about 1:9.5, or about 1:10. In one embodiment, the mass ratio of the cationic lipid and PEGylated lipid is about 1:1.

The mass ratio of the cationic lipid, helper lipid, cholesterol and PEGylated lipid can be calculated by one of skill in the art based on the ratios of the cationic lipid and the helper lipid, the cationic lipid and the cholesterol and the cationic lipid and the PEGylated lipid as disclosed herein.

In some embodiments, the LNP comprises, or consists essentially of, or yet further consists of SM-102, DSPC, cholesterol and PEG2000-DMG. In some embodiments, the mass ratio of the SM-102, DSPC, cholesterol and PEG200-DMG is about 1:1:1:1. In some embodiments, the molar ratio of the SM-102, DSPC, cholesterol and PEG2000-DMG is about 50:10:38.5:1.5.

In some embodiments, the liposomal nanoparticle carrier comprises, or consists essentially of, or yet further consists of a Spermine-Lipid Cholesterol (SLiC). In some embodiments, the SLiC is selected from any one of TM1-TM5 as illustrated below.

-continued
TM1
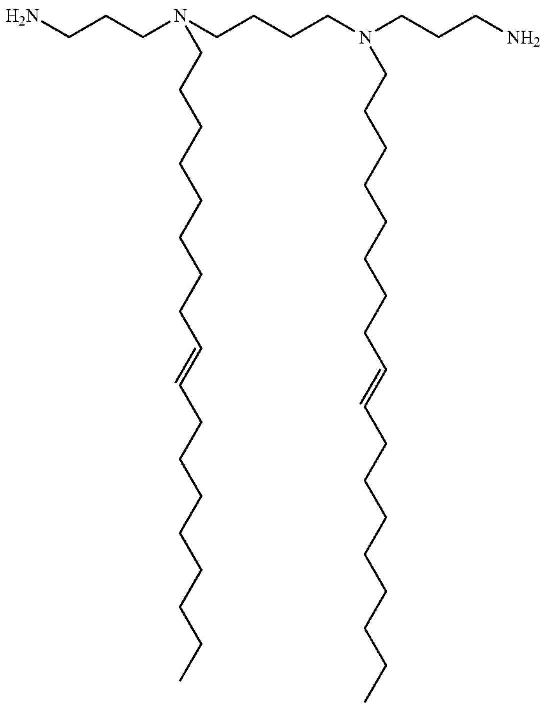
TM3
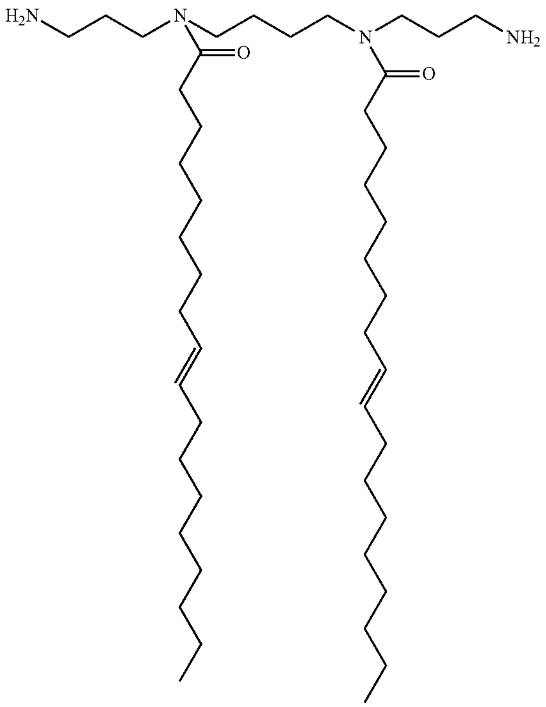
TM2
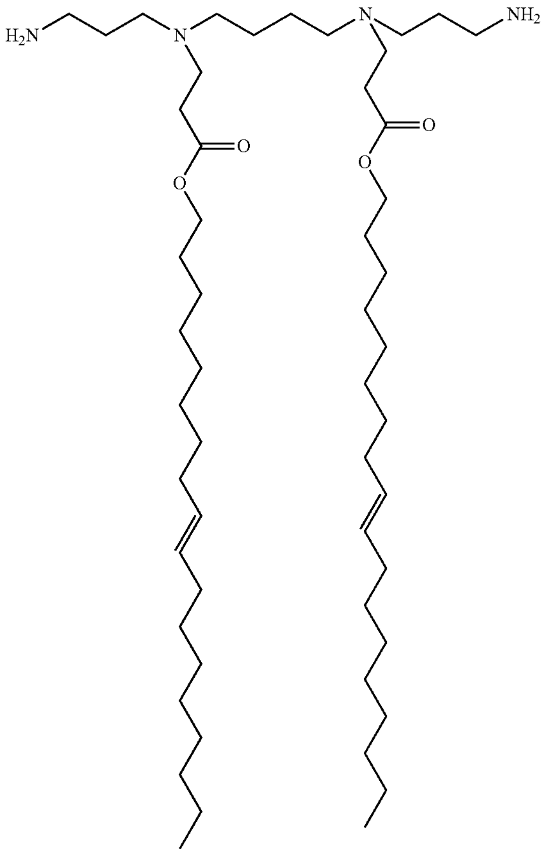
TM4
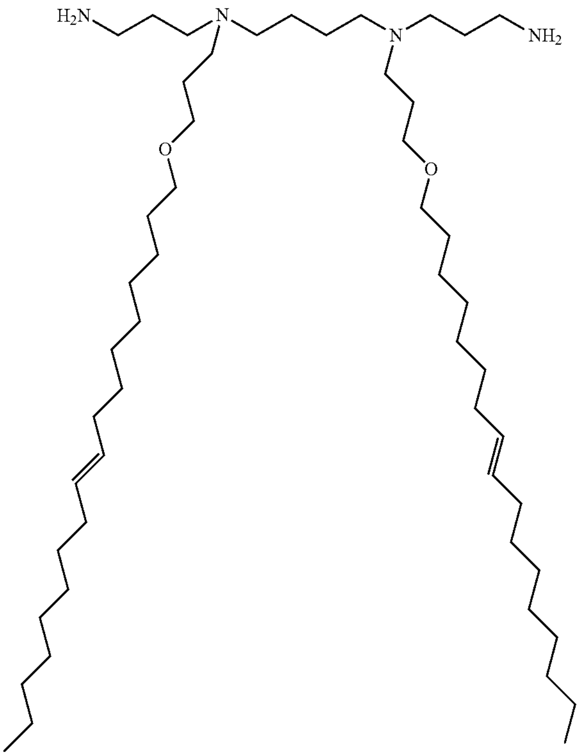

-continued

TM5

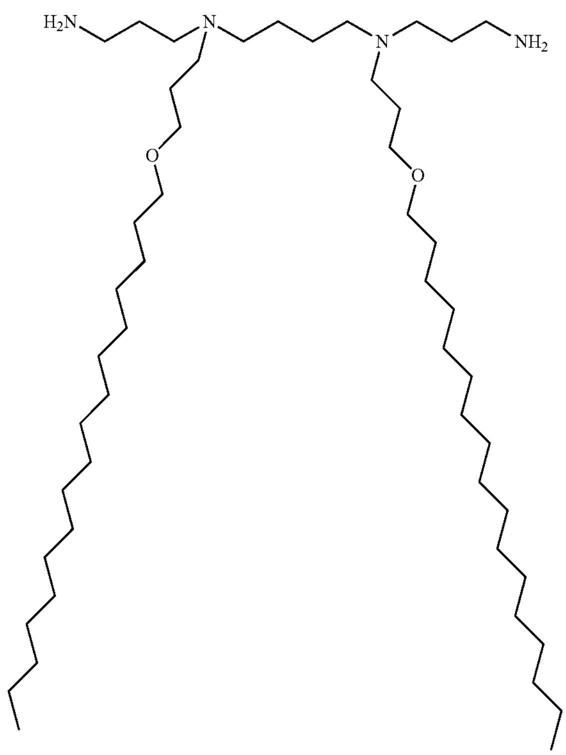

In some embodiments, a mass ratio as provided here can be substituted with another parameter, such as a molar ratio, a weight percentage over the total weight, a component's weight over the total volume, or a molar percentage over the total molar amount. Knowing the component and its molecular weight, one of skill in the art would have no difficulty in converting a mass ratio to a molar ratio or other equivalent parameters.

In a further aspect, provided is a method of producing a composition as disclosed herein. The method comprises, or consists essentially of, or yet further consists of contacting an RNA as disclosed herein with an HKP, thereby the RNA and the HKP are self-assembled into nanoparticles.

In some embodiments, the mass ratio of HKP and the RNA in the contacting step is about 10:1 to about 1:10, including any range or ratio there between, for example, about 5:1 to 1:5, about 5:1 to 1:1, about 10:1, about 9.5:1, about 9:1, about 8.5:1, about 8:1, about 7.5:1, about 7:1, about 6.5:1, about 6:1, about 5.5:1, about 5:1, about 4.5:1, about 4:1, about 3.5:1, about 3:1, about 2:5:1, about 2:1, about 1.5:1, about 1:1, about 1:1.5, about 1:2, about 1:2.5, about 1:3, about 1:3.5, about 1:4, about 1:4.5, about 1:5, about 1:5.5, about 1:6, about 1:6.5, about 1:7, about 1:7.5, about 1:8, about 1:8.5, about 1:9, about 1:9.5, or about 1:10. In one embodiment, the mass ratio of HKP and the RNA in the contacting step is about 2.5:1. In another embodiment, the mass ratio of HKP and the RNA in the contacting step is about 4:1.

In some embodiments, the method further comprises contacting the HKP and RNA with a cationic lipid. In further embodiments, the cationic lipid comprises, or consists essentially of, or yet further consists of Dlin-MC3-DMA (MC3) or DOTAP (dioleoyloxy-3-(trimethylammonio)propane) or both. In yet further embodiments, the mass ratio of the cationic lipid and the RNA in the contacting step is about 10:1 to about 1:10, including any range or ratio there between, for example, about 5:1 to 1:5, about 5:1 to 1:1, about 10:1, about 9.5:1, about 9:1, about 8.5:1, about 8:1, about 7.5:1, about 7:1, about 6.5:1, about 6:1, about 5.5:1, about 5:1, about 4.5:1, about 4:1, about 3.5:1, about 3:1, about 2:5:1, about 2:1, about 1.5:1, about 1:1, about 1:1.5, about 1:2, about 1:2.5, about 1:3, about 1:3.5, about 1:4, about 1:4.5, about 1:5, about 1:5.5, about 1:6, about 1:6.5, about 1:7, about 1:7.5, about 1:8, about 1:8.5, about 1:9, about 1:9.5, or about 1:10. In one embodiment, the mass ratio of the RNA and the cationic lipid in the contacting step is about 1:1. Accordingly, the mass ratio of the HKP, the RNA and the cationic lipid in the contacting step can be calculated based on the ratio between the HKP and the RNA and the ratio between the RNA and the cationic lipid. For example, if the ratio of the HKP to the RNA is about 4:1 and the ratio of the RNA to the cationic lipid is about 1:1, the ratio of the HKP to the RNA to the cationic lipid is about 4:1:1.

In yet a further aspect, provided is a method of producing a composition as disclosed herein. The method comprises, or consists essentially of, or yet further consists of contacting an RNA as disclosed herein with a lipid, thereby the RNA and the lipid are self-assembled into lipid nanoparticles (LNPs).

In some embodiments, the LNPs comprise, or consist essentially of, or yet further consist of one or more of: 9-Heptadecanyl 8-{(2-hydroxyethyl)[6-oxo-6-(undecyloxy) hexyl]amino}octanoate (SM-102), 2,2-dilinoleyl-4-dimethylaminoethyl-[1,3]-dioxolane (DLin-KC2-DMA), dilinoleyl-methyl-4-dimethylaminobutyrate (DLin-MC3-DMA), di((Z)-non-2-en-1-yl) 9-((4-(dimethylamino)butanoyl)oxy) heptadecanedioate (L319), or an equivalent of each thereof.

In some embodiments, the LNPs further comprise one or more of: a helper lipid, a cholesterol, or a PEGylated lipid. In some embodiments, the helper lipid comprises, or consists essentially of, or yet further consists of one or more of: disteroylphosphatidyl choline (DSPC), Dipalmitoylphosphatidylcholine (DPPC), (2R)-3-(Hexadecanoyloxy)-2-{[(9Z)-octadec-9-enoyl]oxy}propyl 2-(trimethylazaniumyl) ethyl phosphate (POPC), or dioleoyl phosphatidylethanolamine (DOPE). In some embodiments, the cholesterol comprises, or consists essentially of, or yet further consists of a plant cholesterol or an animal cholesterol or both. In some embodiments, the PEGylated lipid comprises, or consists essentially of, or yet further consists of one or more of: PEG-c-DOMG (R-3-[((ω-methoxy-poly (ethyleneglycol)2000)carbamoyl)]-1,2-dimyristyloxypropyl-3-amine), PEG-DSG (1,2-Distearoyl-sn-glycerol, methoxypolyethylene glycol), PEG-DMG (1,2-Dimyristoyl-sn-glycerol) optionally PEG2000-DMG ((1,2-dimyristoyl-sn-glycero-3-phophoethanolamine-N-[methoxy(polyethylene glycol)-2000)], or PEG-DPG (1,2-Dipalmitoyl-sn-glycerol, methoxypolyethylene glycol).

In some embodiments, the LNPs comprise, or consist essentially of, or yet further consist of SM-102, DSPC, cholesterol and PEG2000-DMG. In some embodiments, the mass ratio of the SM-102, DSPC, cholesterol and PEG200-DMG is about 1:1:1:1. Additionally or alternatively, the molar ratio of the SM-102, DSPC, cholesterol and PEG2000-DMG is about 50:10:38.5:1.5.

In some embodiments, the contacting step is performed in a microfluidic mixer. In further embodiments, the microfluidic mixer is a slit interdigital micromixer, or a staggered herringbone micromixer (SHM).

In some embodiments, the composition is for use in raising an immune response in a patient.

Also provided is a composition produced by a method as disclosed herein.

Methods of Treatment

In one aspect, provided is a method for preventing or treating a disease as disclosed herein. Additionally or alternatively, provided is a method of one or more of: (a) preventing a subject from having a symptomatic RSV infection; (b) preventing a subject from hospitalization after infection by a RSV; (c) preventing a subject from requiring intensive care (such as in an intensive care unit (ICU)) or a ventilator or both after infection by a RSV; (d) inducing an immune response to RSV in a subject in need thereof; (e) reducing the binding of a RSV or an F protein thereof with its receptor, in a subject in need thereof; (f) treating a subject infected with RSV; or (g) reducing a RSV viral load in a subject in need thereof.

The method comprises, or alternatively consists essentially of, or yet further consists of administering to the subject, optionally an effective amount of, one or more of: an RNA as disclosed herein, a polynucleotide as disclosed herein, a vector as disclosed herein, a cell as disclosed herein, or a composition as disclosed herein.

In some embodiments, the method further comprises treating the subject in need thereof, such as administering to the subject, an additional prophylactic or therapeutic agent.

In some embodiments, the additional prophylactic or therapeutic agent is suitable for preventing or treating a RSV related disease as disclosed herein. In further embodiments, the additional prophylactic or therapeutic agent comprises, or alternatively consists essentially of, or yet further consists of an anti-viral agent, optionally remdesivir, lopinavir, ritonavir, ivermectin, tamiflu, or favipiravir; an anti-inflammatory agent, optionally dexamethasone, tocilizumab, kevzara, colcrys, hydroxychloroquine, chloroquine, or a kinase inhibitor; a covalescent plasma from a subject recovered from a RSV infection; an antibody binding to RSV, optionally bamlanivimab, etesevimab, casirivimab, or imdevimab; or an antibiotic agent, optionally azithromycin.

In some embodiments, the additional prophylactic agent is suitable for preventing a disease that is not related to RSV. Additionally or alternatively, the additional prophylactic agent comprises, or alternatively consists essentially of, or yet further consists of a vaccine for another virus, such as a coronavirus, an influenza (flu) vaccine, a papillomavirus vaccine, an Hepatitis A vaccine, an Hepatitis B vaccine, an Hepatitis c vaccine, a polio vaccine, a chickenpox varicella vaccine, a measles vaccine, a mumps vaccine, a rubella vaccine, a rotavirus vaccine. In some embodiments, the additional prophylactic agent comprises, or alternatively consists essentially of, or yet further consists of a vaccine for a bacterium or other pathogen, such as a diphtheria vaccine, a *Haemophilus influenzae* type b vaccine, a Pertussis vaccine, a pneumococcus vaccine, a Tetanus vaccine, or a Meningococcal vaccine. In some embodiments, the additional prophylactic agent comprises, or alternatively consists essentially of, or yet further consists of a vaccine for a non-infectious disease, such as a cancer.

In some embodiments, the subject does not have a RSV infection when administrated with the RNA or the composition. In some embodiments, a RSV infection can be diagnosed using a conventional method, such as a nucleic acid amplification test (NAATs), an antigen test, or an antibody test. NAATs for RSV specifically identify the RNA (ribonucleic acid) sequences that comprise the genetic material of the virus, including but not limited to reverse transcription polymerase chain reaction (RT-PCR), or an isothermal amplification (such as nicking endonuclease amplification reaction (NEAR), transcription mediated amplification (TMA), loop-mediated isothermal amplification (LAMP), helicase-dependent amplification (HDA), clustered regularly interspaced short palindromic repeats (CRISPR) or strand displacement amplification (SDA)). Antigen tests are immunoassays that detect the presence of a specific viral antigen, which implies current viral infection. Antibody or serology tests look for antibodies in blood that fight RSV, and are commonly used to indicate a past infection or a successful vaccination.

In some embodiments, the subject is at risk of having a disease as disclosed herein, such as RSV infection. In some embodiments, the subject has not been exposed to RSV. In some embodiments, the subject is at risk of exposing to RSV.

In some embodiments, the subject is more likely than others to become severely ill after being infected by RSV. For example, they can require hospitalization, intensive care, or a ventilator, or die, after the infection. In some embodiments, the subject is over age 65. In some embodiments, the subject is over age 45. In some embodiments, the subject has one or more of the following medical conditions: a cancer, a chronic kidney disease, a chronic lung diseases (such as chronic obstructive pulmonary disease (COPD), asthma (moderate-to-severe), interstitial lung disease, cystic fibrosis, or pulmonary hypertension), dementia or other neurological conditions, diabetes (type 1 or type 2), Down syndrome, a heart condition (such as heart failure, coronary artery disease, cardiomyopathies or hypertension), an HIV infection, an immunocompromised state (weakened immune system), a liver disease, overweight, obesity, pregnancy, a sickle cell disease, thalassemia, smoking (current or former), a solid organ or blood stem cell transplant, stroke or cerebrovascular disease (such as those affecting blood flow to the brain), or a substance use disorder.

In some embodiments, the administrations is by inhalation. In further embodiments, the RNA or the composition is atomized by a nebulizer inhalation system prior to or during administration. In yet further embodiments, the nebulizer system is a portable nebulizer for whole respiratory tract drug delivery.

In some embodiments, the administration is by subcutaneous injection. In some embodiments, the administration is by intramuscular injection. In some embodiments, the administration is by intraperitoneal injection (i.p).

In some embodiments, a composition as disclosed herein can be in the form of an aerosol, dispersion, solution, or suspension and can be formulated for inhalation, intramuscular, oral, sublingual, buccal, parenteral, nasal, subcutaneous, intradermal, or topical administration. The term parenteral as used herein includes percutaneous, subcutaneous, intravascular (e.g., intravenous), intramuscular, or intrathecal injection or infusion techniques and the like.

As used herein, an effective dose of an RNA, or polynucleotide, or vector, or cell or composition as disclosed herein is the dose required to produce a protective immune response in the subject to be administered. A protective immune response in the present context is one that prevents or ameliorates disease in a subject challenged with RSV or a pseudovirus thereof. The RNA, or polynucleotide, or vector, or cell or composition as disclosed herein can be administered one or more times. An initial measurement of an immune response to the vaccine may be made by measuring production of antibodies in the subject receiving the RNA, or polynucleotide, or vector, or cell, or composition. Methods of measuring antibody production in this manner are also well known in the art, is that dose required to prevent, inhibit the occurrence, or treat (alleviate a symptom to some extent, preferably all of the symptoms) of a disease state. The pharmaceutically effective dose depends on the type of disease, the composition used, the route of administration, the type of mammal being treated, the physical characteristics of the specific mammal under consideration, concurrent medication, and other factors that those skilled in the medical arts will recognize. Generally, an amount between 0.1 mg/kg and 100 mg/kg body weight/day of active ingredients is administered dependent upon potency of the formulated composition.

In a further aspect, provided is an inhalation system comprising, or alternatively consisting essentially of, or yet further consisting of an RNA as disclosed herein, a polynucleotide as disclosed herein, a vector as disclosed herein, or a composition as disclosed herein and a nebulizer. In further embodiments, the nebulizer is a portable nebulizer for whole respiratory tract drug delivery.

In some embodiments, the RNA compositions can be administered at dosage levels sufficient to deliver 0.0001 mg/kg to 100 mg/kg, 0.001 mg/kg to 0.05 mg/kg, 0.005 mg/kg to 0.05 mg/kg, 0.001 mg/kg to 0.005 mg/kg, 0.05 mg/kg to 0.5 mg/kg, 0.01 mg/kg to 50 mg/kg, 0.1 mg/kg to 40 mg/kg, 0.5 mg/kg to 30 mg/kg, 0.01 mg/kg to 10 mg/kg, 0.1 mg/kg to 10 mg/kg, or 1 mg/kg to 25 mg/kg, of subject body weight per day, one or more times a day, per week, per month, etc. to obtain the desired therapeutic or prophylactic effect. The desired dosage can be delivered three times a day, two times a day, once a day, every other day, every third day, every week, every two weeks, every three weeks, every four weeks, every 2 months, every three months, every 6 months, etc. In certain embodiments, the desired dosage can be delivered using multiple administrations (e.g., two, three, four, five, six, seven, eight, nine, ten, eleven, twelve, thirteen, fourteen, or more administrations). When multiple administrations are employed, split dosing regimens such as those described herein can be used. In some embodiments, the RNA compositions can be administered at dosage levels sufficient to deliver 0.0005 mg/kg to 0.01 mg/kg, e.g., about 0.0005 mg/kg to about 0.0075 mg/kg, e.g., about 0.0005 mg/kg, about 0.001 mg/kg, about 0.002 mg/kg, about 0.003 mg/kg, about 0.004 mg/kg or about 0.005 mg/kg. In some embodiments, the RNA compositions can be administered once or twice (or more) at dosage levels sufficient to deliver 0.025 mg/kg to 0.250 mg/kg, 0.025 mg/kg to 0.500 mg/kg, 0.025 mg/kg to 0.750 mg/kg, or 0.025 mg/kg to 1.0 mg/kg.

In some embodiments, the RNA compositions can be administered twice (e.g., Day 0 and Day 7, Day 0 and Day 14, Day 0 and Day 21, Day 0 and Day 28, Day 0 and Day 60, Day 0 and Day 90, Day 0 and Day 120, Day 0 and Day 150, Day 0 and Day 180, Day 0 and 3 months later, Day 0 and 6 months later, Day 0 and 9 months later, Day 0 and 12 months later, Day 0 and 18 months later, Day 0 and 2 years later, Day 0 and 5 years later, or Day 0 and 10 years later) at a total dose of or at dosage levels sufficient to deliver a total dose of 0.0100 mg, 0.025 mg, 0.050 mg, 0.075 mg, 0.100 mg, 0.125 mg, 0.150 mg, 0.175 mg, 0.200 mg, 0.225 mg, 0.250 mg, 0.275 mg, 0.300 mg, 0.325 mg, 0.350 mg, 0.375 mg, 0.400 mg, 0.425 mg, 0.450 mg, 0.475 mg, 0.500 mg, 0.525 mg, 0.550 mg, 0.575 mg, 0.600 mg, 0.625 mg, 0.650 mg, 0.675 mg, 0.700 mg, 0.725 mg, 0.750 mg, 0.775 mg, 0.800 mg, 0.825 mg, 0.850 mg, 0.875 mg, 0.900 mg, 0.925 mg, 0.950 mg, 0.975 mg, or 1.0 mg. Higher and lower dosages and frequency of administration are encompassed by the present disclosure. For example, the RNA composition can be administered three or four times.

Kits

In one aspect, provided is a kit for use in a method as disclosed herein.

In some embodiments, the kit comprises, or alternatively consists essentially of, or yet further consist of instructions for use and one or more of: a RNA as disclosed herein, a polynucleotide as disclosed herein, a vector as disclosed herein, a composition as disclosed herein, or an inhalation system as disclosed herein. In further embodiments, the kit is suitable for use in a method of treatment as disclosed herein.

In some embodiments, the kit comprises, or alternatively consists essentially of, or yet further consist of instructions for use and one or more of: an RNA as disclosed herein, a polynucleotide as disclosed herein, a vector as disclosed herein, a cell as disclosed herein, a composition as disclosed herein, an HKP, or a lipid optionally a cationic lipid. In further embodiments, the kit is suitable for use in a method producing an RNA or a composition as disclosed herein.

In some embodiments, the kit comprises, or alternatively consists essentially of, or yet further consist of instructions of use, a polynucleotide or a vector as disclosed herein, an RNA polymerase, ATP, CTP, GTP, and UTP or a chemically modified UTP. In further embodiments, the kit is suitable for use in an in vitro method producing an RNA or a composition as disclosed herein.

Also provided is a kit for use in a method as described herein. In some embodiments, the kit comprises, or alternatively consists essentially of, or yet further consists of instructions for use and one or more of: a DNA as disclosed herein, a fusion glycoprotein, fragment or equivalent thereof as disclosed herein, an RNA as disclosed herein, a polynucleotide as disclosed herein, a vector as disclosed herein, a cell as disclosed herein, a composition as disclosed herein, and optionally an inhalation system as disclosed herein.

The following examples are provided to illustrate but not limit the inventions of this disclosure.

EXPERIMENTAL METHODS

The following examples are illustrative of procedures which can be used in various instances in carrying the disclosure into effect.

Example 1: In Vitro Transcription (IVT) Assay

In vitro transcription was performed following RNAimmune's In vitro transcription SOP. Briefly, the RSV mRNA producing plasmid was linearized using BspQI (NEB) at 37 C for 4 h and the linearized plasmid was purified using QIAquick PCR purification kit following manufacturer's instruction (Qiagen). After purification, in vitro transcription reaction was performed. In a 20 μl reaction, all the components added in the order as following: 1 μg of linearized DNA; 1 μl of ATP, CTP, GTP and N1-methyl-pseudouridine tri phosphate; 0.8 μl CleanCap AG (3'Ome); 2 μl 10×IVT reaction buffer; 0.5 μl Murine RNase Inhibitor; 0.4 μl *E. coli* Inorganic Pyrophosphatase; and 3.2 μl T7 RNA polymerase. The IVT reaction was incubated at 37C for 4 h. The components of 10X Transcription Buffer include: 400 mM Tris-HCL (pH 8), 100 mM DTT, 20 mM Spermidine, 0.02% Triton X, 165 mM Magnesium Acetate, and DNase/RNase-Free Water.

After in vitro transcription reaction, the mRNA was purified using RNeasy Mini Kit following manufacturer's instruction (Qiagen). The IVT reaction was adjusted to a volume of 100 μl with RNase-free water. Then, mRNA was mixed well with 350 μl buffer RLT. 250 μl of 100% ethanol was then added to the mixture, mix well by pipetting, and 700 μl of the sample was transferred to an RNeasy Mini spin column, centrifuged for 15s at ≥8000×g (≥10,000 rpm). After discard the flow-through, spin column was washed twice with 500 μl Buffer RPE. Then transfer the spin column to a 1.5 ml collection tube (kit supplied), elute mRNA with 30 μl RNase-free water. If the expected RNA yield is >30 μg, repeat elution step using another 30 μl RNase-free water. RNA gel electrophoresis. The quality of purified mRNA was evaluated using 1% agarose gel in NorthernMax™-Gly Gel Prep with Sybr Gold (1:20,000).

The running buffer was prepared by diluting Northern-Max™-Gly Gel Prep from 10× stock solution in DEPC-treated ultrapure water. RNA sample was prepared by adding one volume of RNA (up to 30 μg total RNA) to one volume NortherMax®-Gly Sample Loading Buffer and incubated at 65 C for 30 min to prevent formation of secondary structure. Gel markers also treated similarly. Then run RNA sample and markers on 1% agarose gel at 5V/cm. Once the bromophenol blue dye front migrated approximately ¾ the length of the gel, electrophoresis was stopped, and mRNA was visualized with blue light.

Example 2: Lipid Nanoparticle Formulation

To make a 4× stock solution of each component in ethanol, each component was prepared as following: 100 mg of SM-102 in 5.63 ml 100% ethanol; 39.5 mg of DSPC in 10 ml 100% ethanol; 74.4 mg of Cholesterol in 100% ethanol; and 18.8 mg of DMG-PEG2000 in 100% ethanol. The final concentration of 4× stock is 25 mM SM-102, 5 mM DSPC, 19.5 mM Cholesterol and 0.75 mM DMG-PEG2000. Each lipid component was then added to a 5 ml tube at a ratio of 1:1:1:1 to make a 1× working solution. The final concentration of working concentration is 6.25 mM SM-102, 1.25 mM DSPC, 4.815 mM Cholesterol, and 0.1875 mM DMG-PEG2000. To make mRNA working concentration, the mRNA stock solution was diluted in 25 mM Sodium Acetate pH5.0 at a final concentration of 0.13 mg per ml. The formulation of lipid nanoparticles was done using NanoAssmblr Ignite (PNI) following manufacturer's instructions with mRNA:lipid ratio 3:1. After formulation, the formulated LNPs were transferred into pre-soaked dialysis cassette and dialyze in 20 mM Tris-HCl, 8% sucrose dialysis buffer for at least 18 hours at 4 C. After dialysis, remove LNPs from dialysis cassette using a 3-5 ml syringe, filter sterilize the LNPs using acrodisc filter (0.2 M pore size) and fill the top compartment of an Amicon® Ultra-15 centrifugal filtration tube. Spin the tube at 2000×g at 4° C. until the solution is re-concentrated to desired volume. Transfer the LNPs to a new tube and characterize LNPs by Dynamic Light Scattering to measure particle size, polydispersity and zeta potential using Zetasizer Ultra (Malven Panalytical). The encapsulation efficiency was measured using Ribogreen assay (Invitrogen). The mRNA concentration was measured using Ribogreen assay and Nanodrop. Store the final LNPs at −80C for future use.

Example 3: Western Blot Analysis

To test the in vitro expression of optimized vaccine candidates, Western blot analysis was used to examine the expression of RSV optimized vaccine candidates. 293T cell was transfected with various forms of RSV mRNA with His-tag using Lipofectamin MessengerMax transfection reagents. Forty-eight hours post transfection, cells were collected, cell lysates were prepared, and the protein concentration was determined using BCA assay. The expression level of each construct was compared using Western Blot analysis with anti-His antibody.

Figure 8:
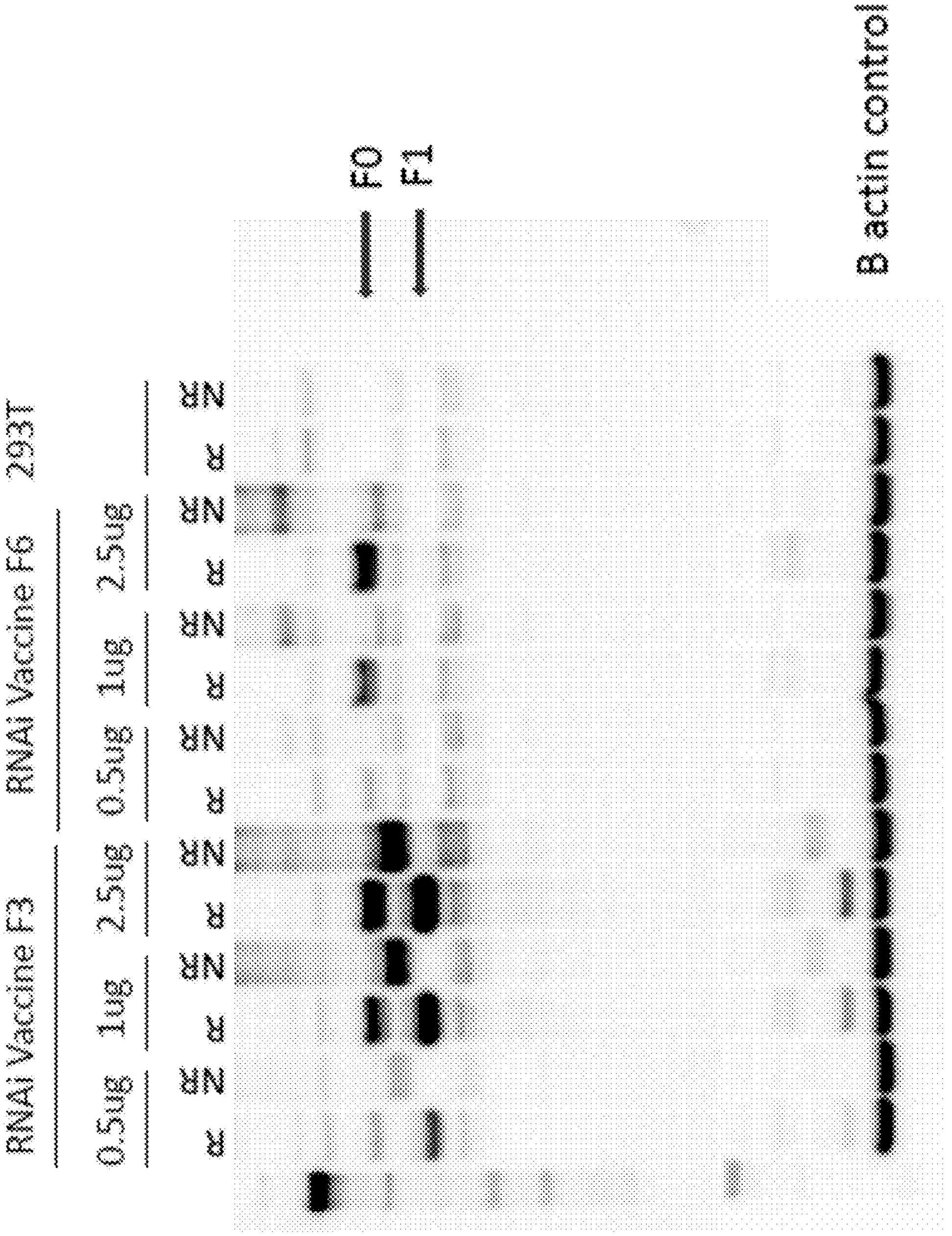
FIG. 8 shows expression levels of optimized Vaccine F3 and optimized Vaccine F6 His-tagged constructs. Anti-His antibody was used for detection of expression. Proteins were measured under reducing conditions (R) and non-reducing conditions (NR).
Figure 9:
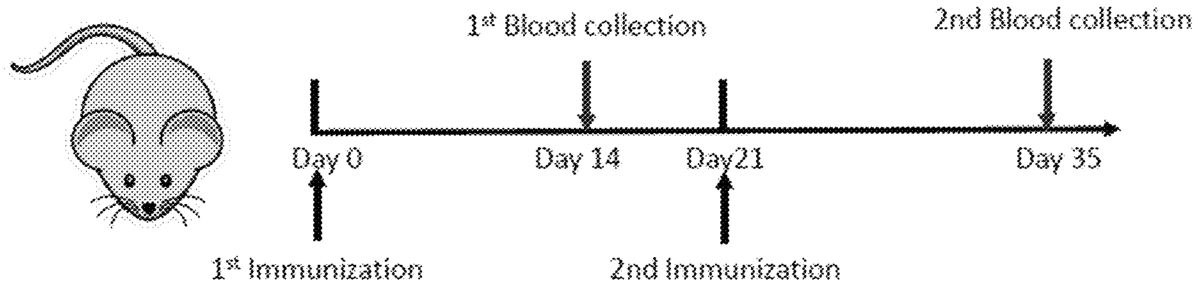
FIG. 9 depicts an exemplary challenge study.

FIG. 8 shows the relative expression levels of optimized Vaccine-F3 and optimized Vaccine-F6 as determined by anti-His antibody staining.

Example 4: Flow Cytometry

To test the expression of native form of RSV pre-fusion F protein expression, flow cytometry was used. After transfection, Expi293F cells ($2\times10^5$ cells) were pelleted in a U-bottom 96-well plate and resuspended in PBS (200 μL). Cells were pelleted, washed twice with cell staining buffer (200 μL/well, Biolegend), and were resuspended in cell staining buffer with D25-Alexa Fluor 488 or AM14-Alexa Fluor 488 and Palivizumab-Alexa Fluor 647, or isotype control antibodies (each at 5 μg/mL) and incubated for 1 h at 4 C in the dark. Cells were then pelleted and washed twice with cell staining buffer (200 μL/well), then stained with DAPI in cell staining buffer (0.25 μg/mL, 100 μL/well) at 4 C in the dark for 15 min. After incubation, cells were pelleted, washed twice with PBS (200 μL/well), and were resuspended in PBS (200 μL/well). Cells were acquired using BD Celesta Flow cytometer (BD Biosciences) and flow cytometry data were analyzed using FlowJo software.

The Alexa488 to Alexa647 ratio indicates the ratio of PreFusion form of F protein to pre and post fusion protein. In this experiment, the mRNA expressed mainly in prefusion form. In the prefusion form, a greater number of antigenic sites are exposed, which is advantageous for vaccine design.

Figure 7:
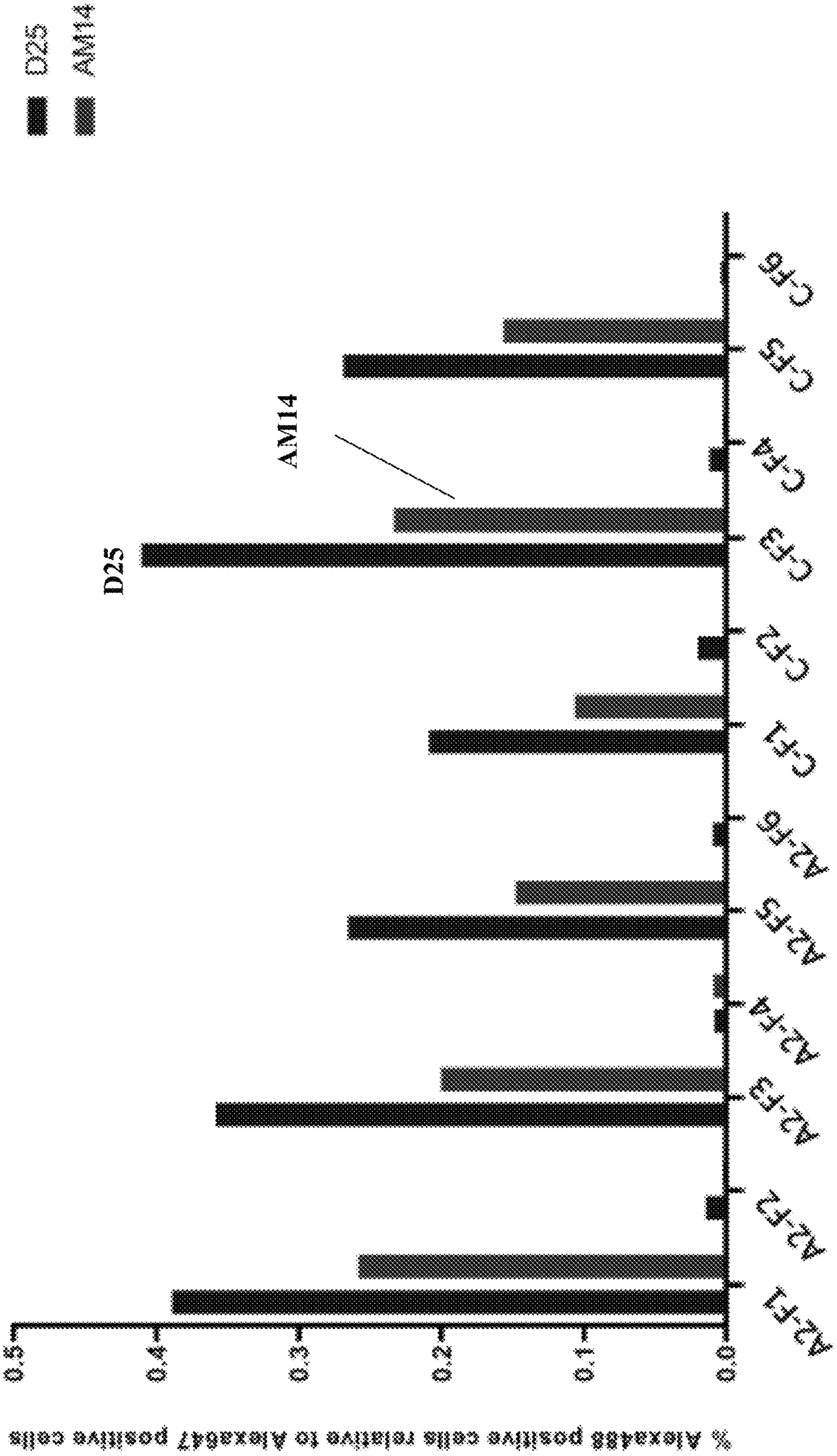
FIG. 7 shows FACS analysis of RSVF binding to a prefusion specific antibody. A2 and optimized vaccines and controls were bound to D25 and AM14 antibodies. FACS analysis demonstrated that transmembrane prefusion F protein in both optimized and A2 sequence backgrounds can bind to prefusion F specific antibodies, D25 and AM14. RNAi optimized Vaccine F3 has highest binding activity among all these vaccine candidates.

FACS analysis results from FIG. 7 were used to determine that RSV A2-F3, RSV A2-F5, RSV-Optimized-F3, RSV-Optimized-F4, RSV-Optimized-F5, and RSV-Optimized-F6 were suitable to continue into animal studies.

Example 5: Sandwich ELISA Assay

Cell supernatants were collected and analyzed following standard sandwich ELISA protocol. Briefly, 96-well flat bottom plates (MaxiSorp ELISA plates, Nunc) were incubated with rabbit anti-Human RSV-F monoclonal antibody in PBS (2 μg/mL, 100 μL/well) at 4° C. overnight. Plates were washed three times with PBS-T, then incubated with 1×ELISA diluent buffer (Biolegend) at RT for 1 h. After three washes with PBS-T, cell supernatants were added to the wells at 1:5, 1:25 or 1:125 dilutions (100 μL/well) in 1×ELISA diluent buffer and incubated at RT for 2 h. After 2 h room temperature incubation, plates were washed three times with PBS-T and incubated with rabbit anti-Human RSV-F monoclonal antibody conjugated to horseradish-peroxidase (HRP) (detection antibody) (0.1 μg/mL, 100 μL/well in 1×ELISA diluent buffer) at RT for 1 h. The color reaction was developed with TMB substrate (Biolegend) for 15 min at room temperature and then stopped with IN HCl. The absorbance was detected at 450 nm.

Figure 6A:
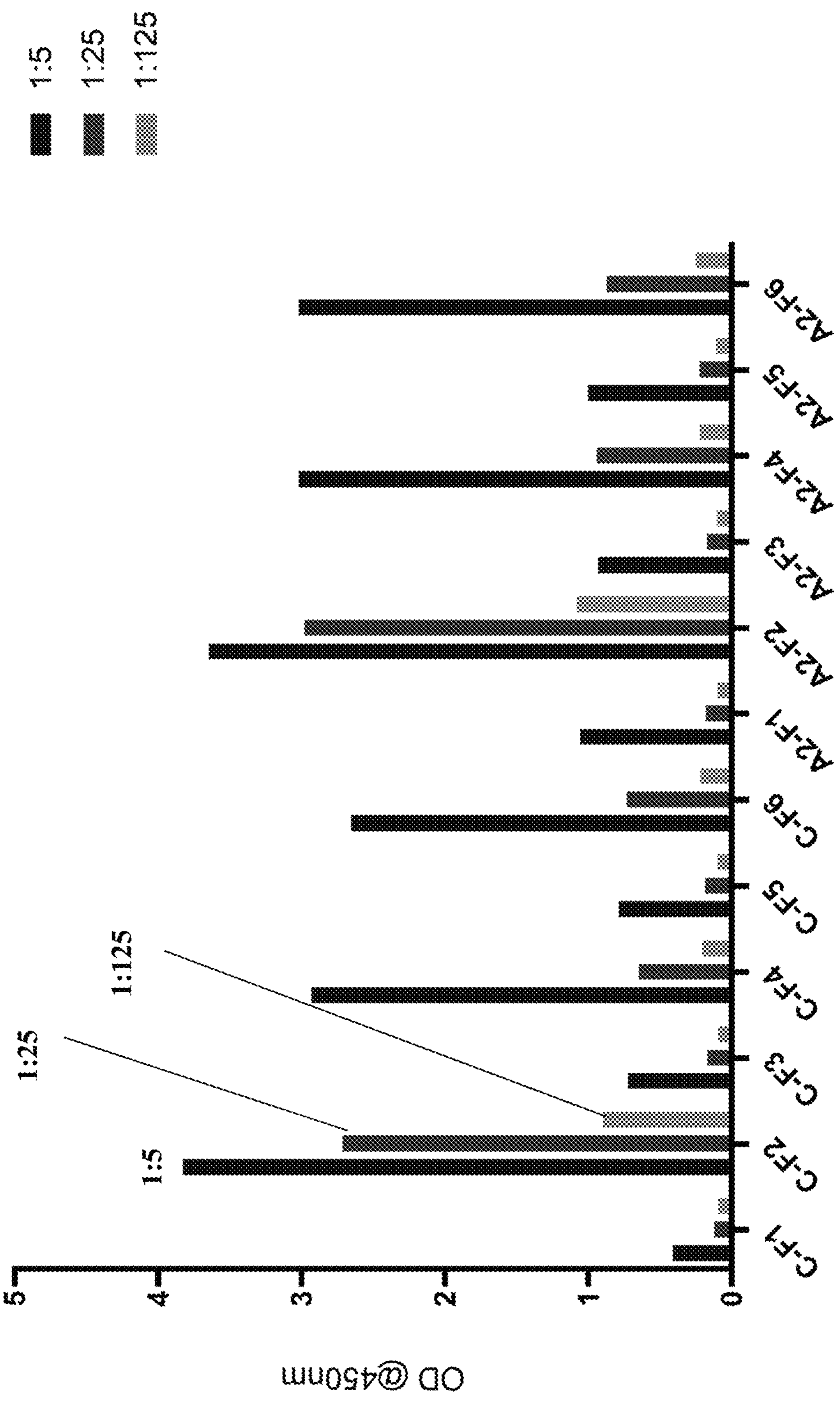
FIGS. 6A and B show sandwich ELISA results for secreted RSVF constructs. Sandwich ELISA was used for measuring the in vitro expression of secreted form of A2 and optimized vaccine candidates. Cell supernatant was diluted in ELISA blocking buffer at 1:5, 1:25, and 1:125 dilution. The results show that secreted pre-fusion F protein in both optimized and A2 sequence backgrounds has comparable expression level. Data for RSV-optimized candidates and A2 strain background are shown in bar format (FIG. 6A) and line format (FIG. 6B).
Figure 6B:
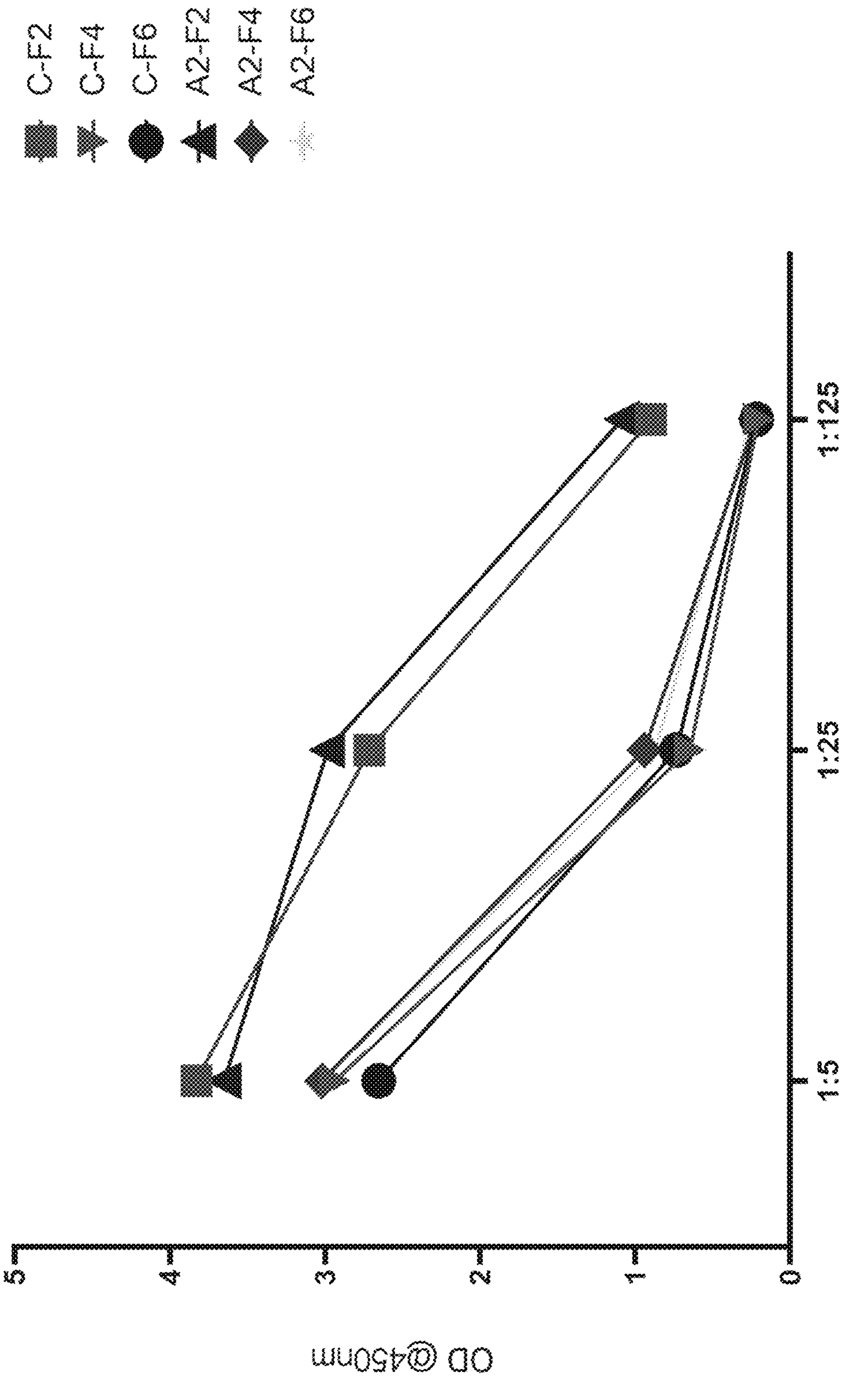

Sandwich ELISA results for secreted candidate A2 and optimized vaccines in FIGS. 6A and 6B show the relative antibody levels as compared to A2 strain backgrounds. Sandwich ELISA was used for measuring the in vitro expression of secreted form of A2 and optimized vaccine candidates. Cell supernatant was diluted in ELISA blocking buffer at 1:5, 1:25, and 1:125 dilution. The result shows that secreted pre-fusion F protein in both optimized and A2 sequence backgrounds has comparable expression level.

Example 6: ELISA Assay

Balb/c female mice were immunized at week 0 and week 3 with 10 μg of RSV A2 and optimized vaccine candidates.

Sera were collected 2 weeks post-immunization. The total IgG was analyzed following standard ELISA protocol. Briefly, 96-well plates were coated with 1 μg/mL of RSV A2 F (Sino Biological), RSVB F (Sino Biological) and PreF protein (in-house) per well and incubated overnight at 4 C. For measuring total IgG, individual sera were diluted starting 1:200 in 1×ELISA diluent buffer (Biolegnd) with 3-fold dilution up to 1:437400 dilution and incubated for 2 h at room temperature. Subsequently, 100 μl of horseradish peroxidase (HRP) conjugated goat anti-mouse IgG (Jackson ImmunoResearch) at dilution of 1:5000 was added, followed by incubation for 1 hr at room temperature. The color reaction was developed with TMB substrate (Biolegend) for 15 min at room temperature and then stopped with IN HCl. The absorbance was detected at 450 nm.

Figure 10A:
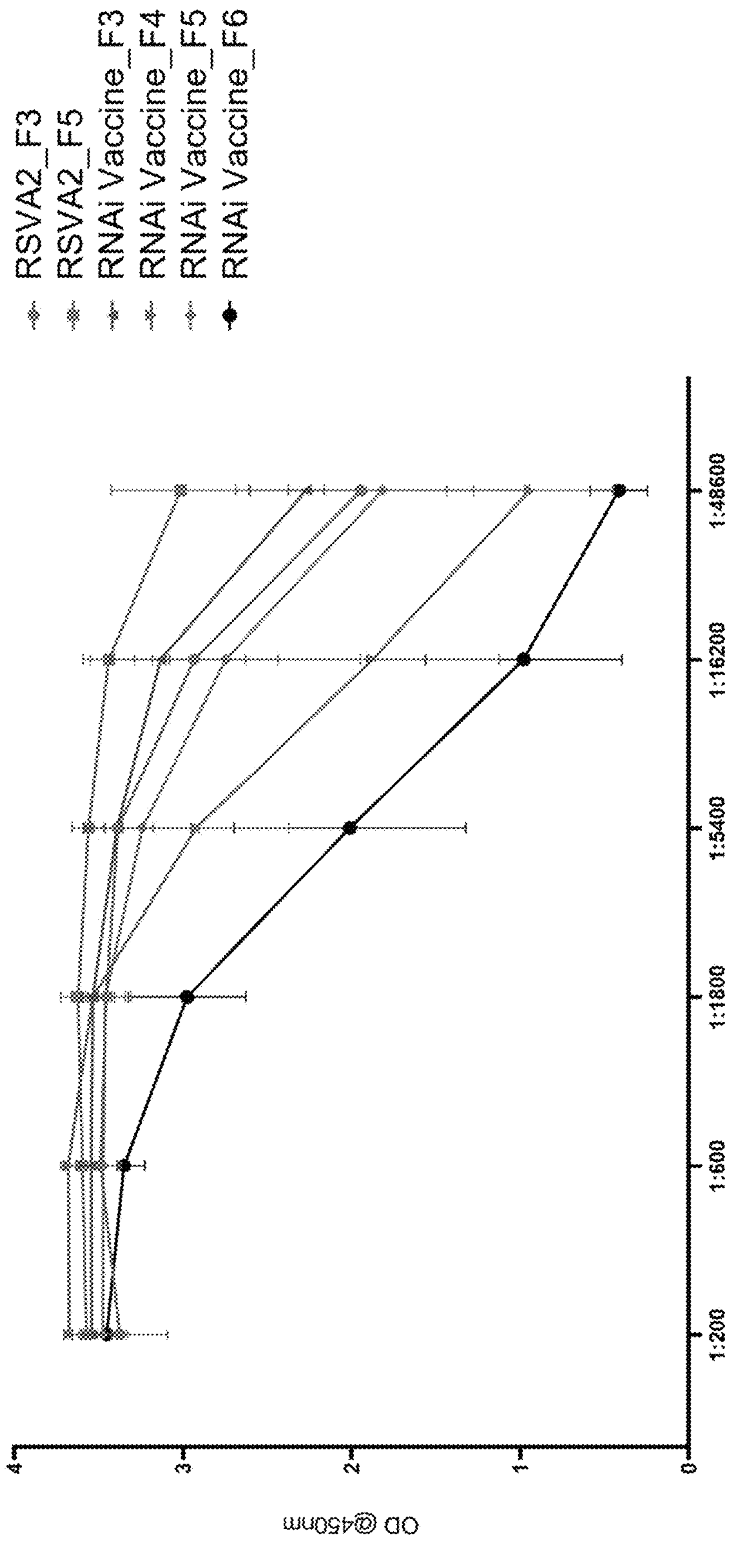
FIGS. 10A and 10B show the immunogenicity and neutralization activity of A2 and optimized vaccine candidates. The amount of IgG titer at 35 DPI for RSV A2 F protein (FIG. 10A) and Pre-F protein (FIG. 10B) are shown.
Figure 10B:
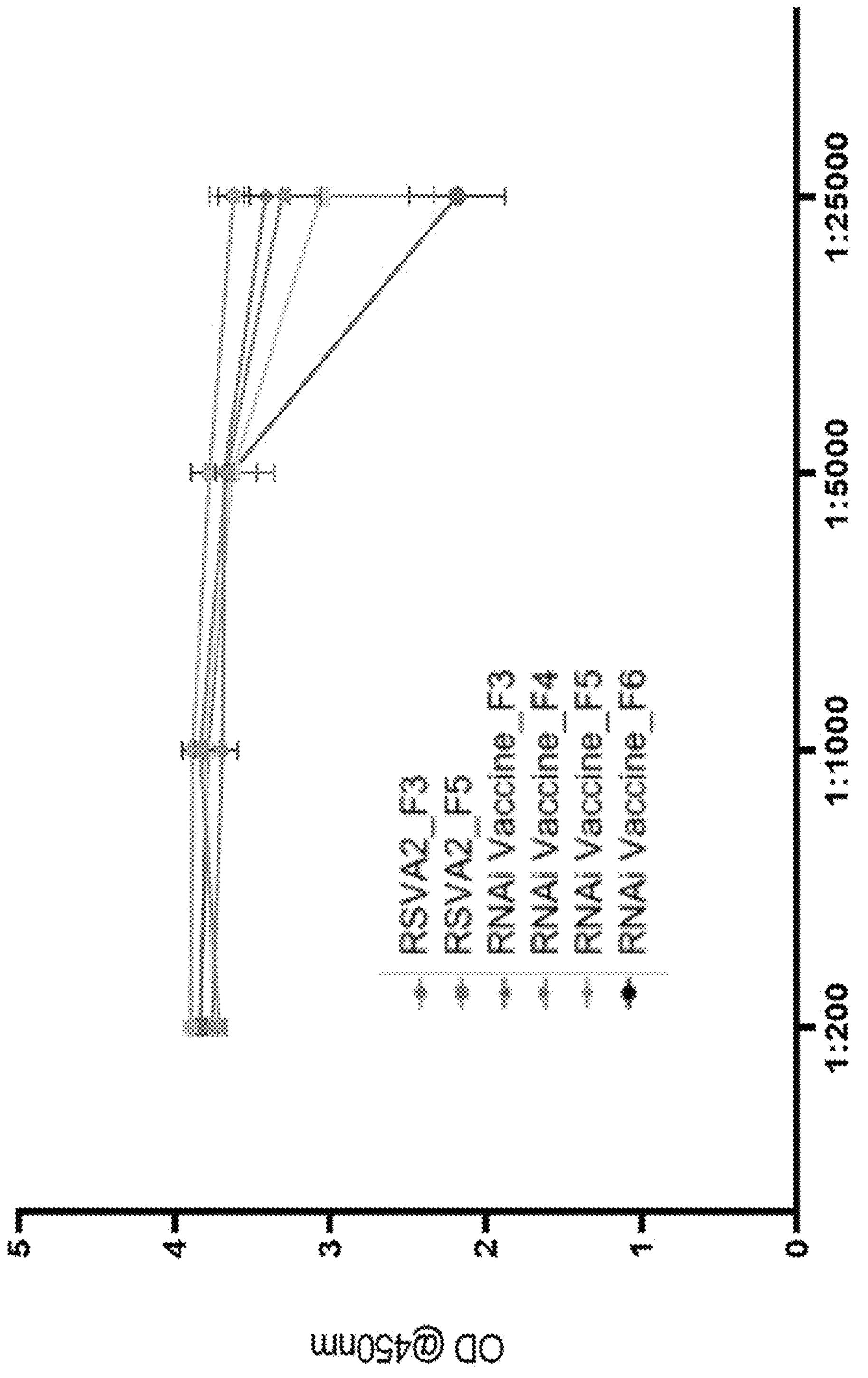

FIGS. 10A and 10B show that the optimized RSV Candidate-F3 and optimized RSV Candidate-F6 possessed the best properties as measured by this assay. Six vaccine candidates were subjected to the first animal study. Two weeks after second immunization, serum was collected for measuring immunogenicity and neutralization activity. ELISA using RSV A2 F protein as antigen showed that all six vaccine candidates had comparable IgG titer when sera were diluted to 1:600. When using in-house Prefusion F protein as antigen, all six vaccine candidates showed very similar IgG titer when the dilution factor as high as 1:5000.

Figure 13A:
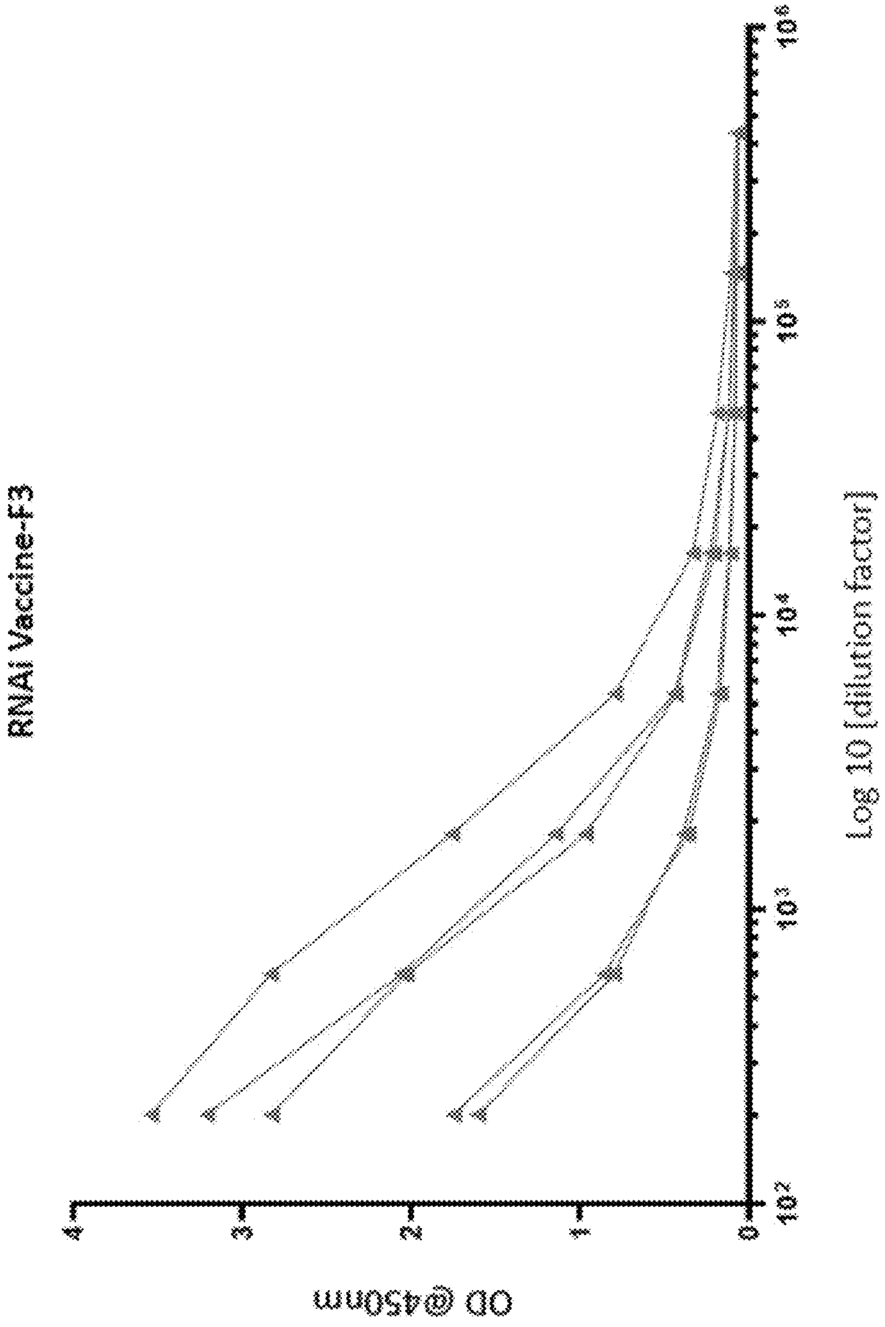
FIGS. 13A and 13B show immunization ELISA results for optimized Vaccine F3 (FIG. 13A) and optimized Vaccine F6 (FIG. 13B) candidates.
Figure 13B:
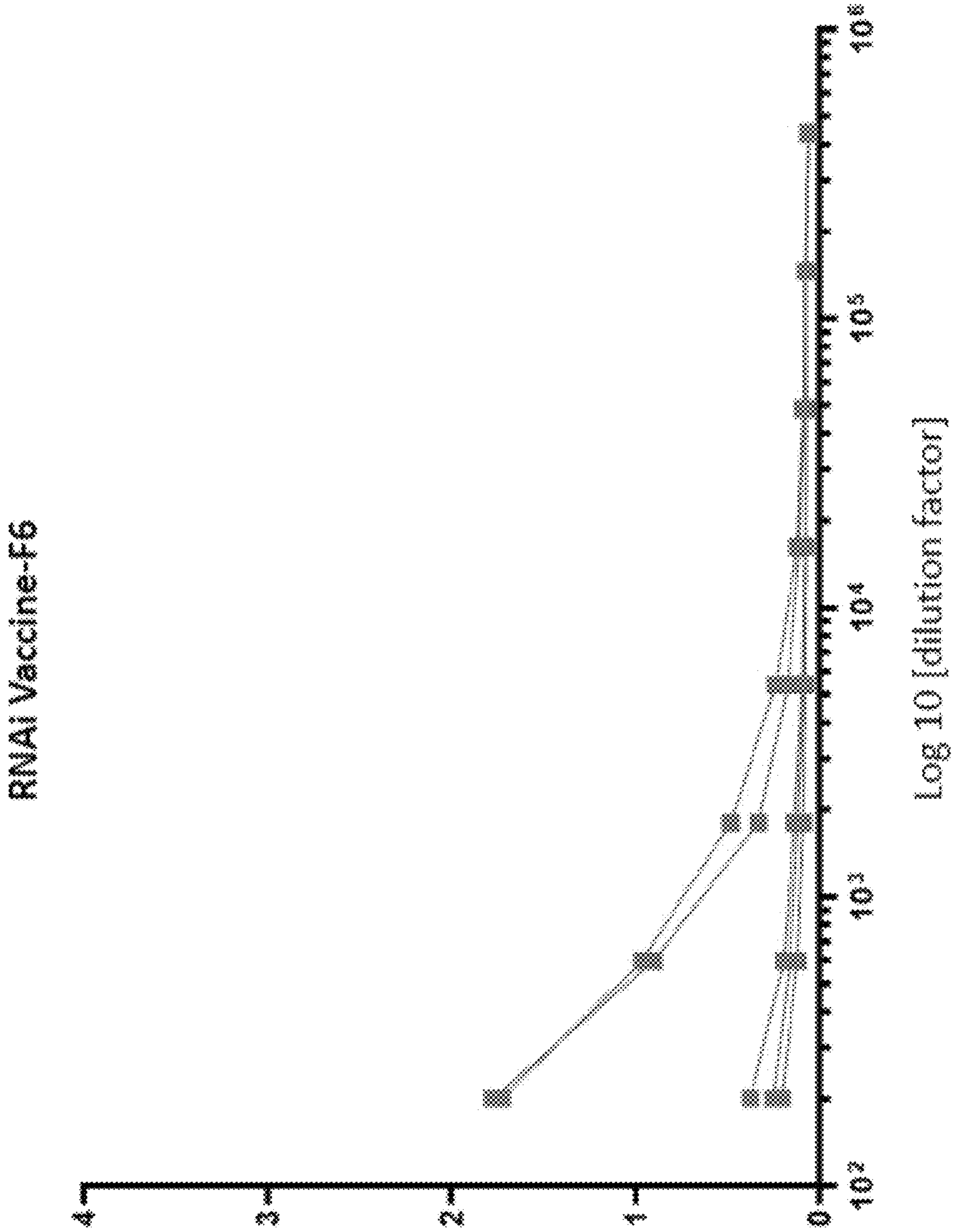

FIGS. 13A-13B show the immunogenicity of RNAi optimized Vaccine F3 and RNAi optimized Vaccine F6 after first immunization. Two weeks after first immunization, serum was collected for measuring IgG titer. In-house His-tagged Prefusion F protein was used as antigen. Results shown here are the IgG titer of individual mouse in each group. This result indicated that RNAi Vaccine F3 induced higher IgG titer after $1^{st}$ immunization.

Figure 14A:
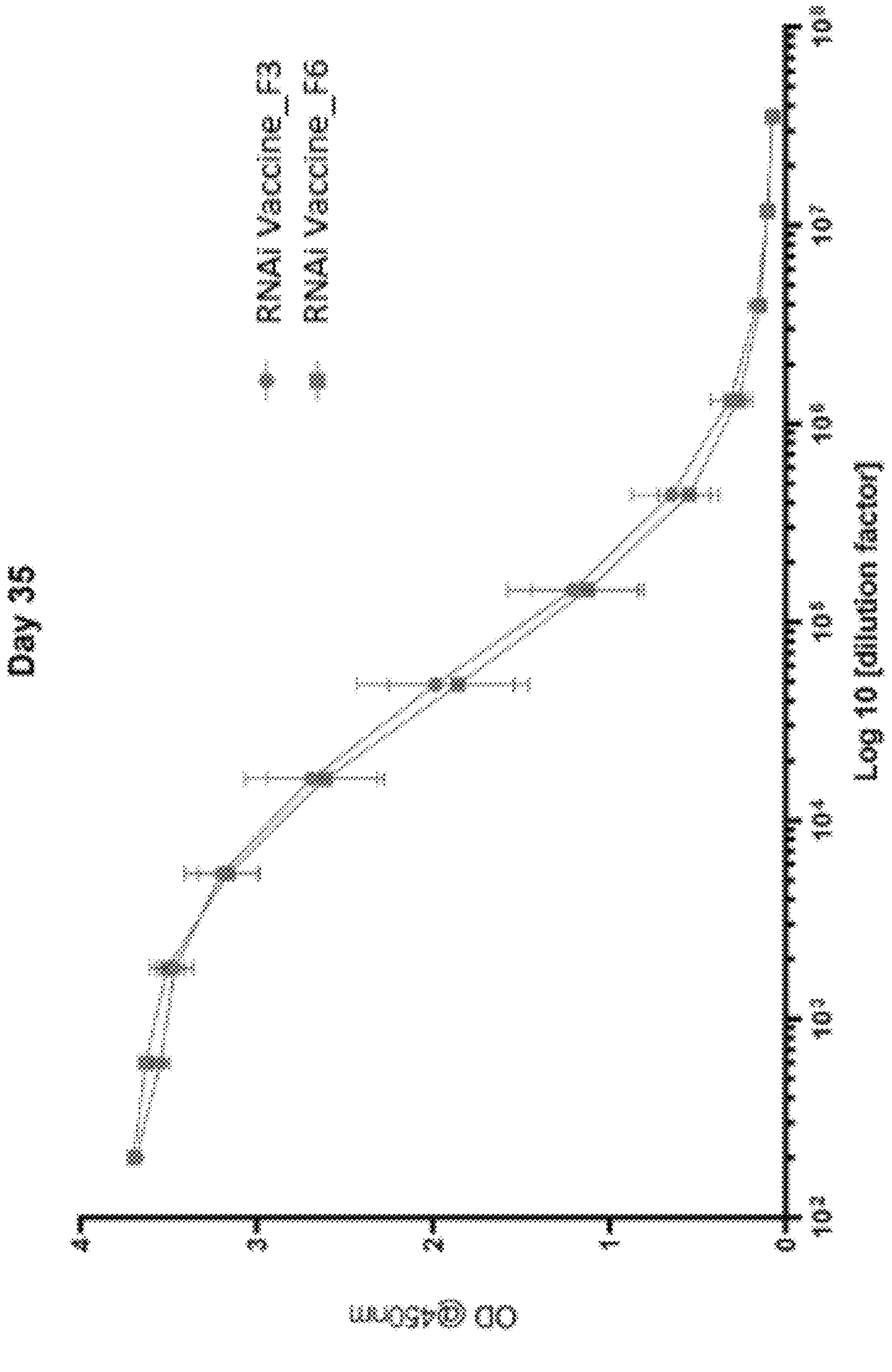
FIGS. 14A and 14B show the immunogenicity of RNAi optimized Vaccine-F3 and RNAi optimized Vaccine-F6 after second immunization. ELISA Data was collected after 35 days with PreF protein as antigen (FIG. 14A) and day 35 with RSV A2 F protein as antigen (FIG. 14B).
Figure 14B:
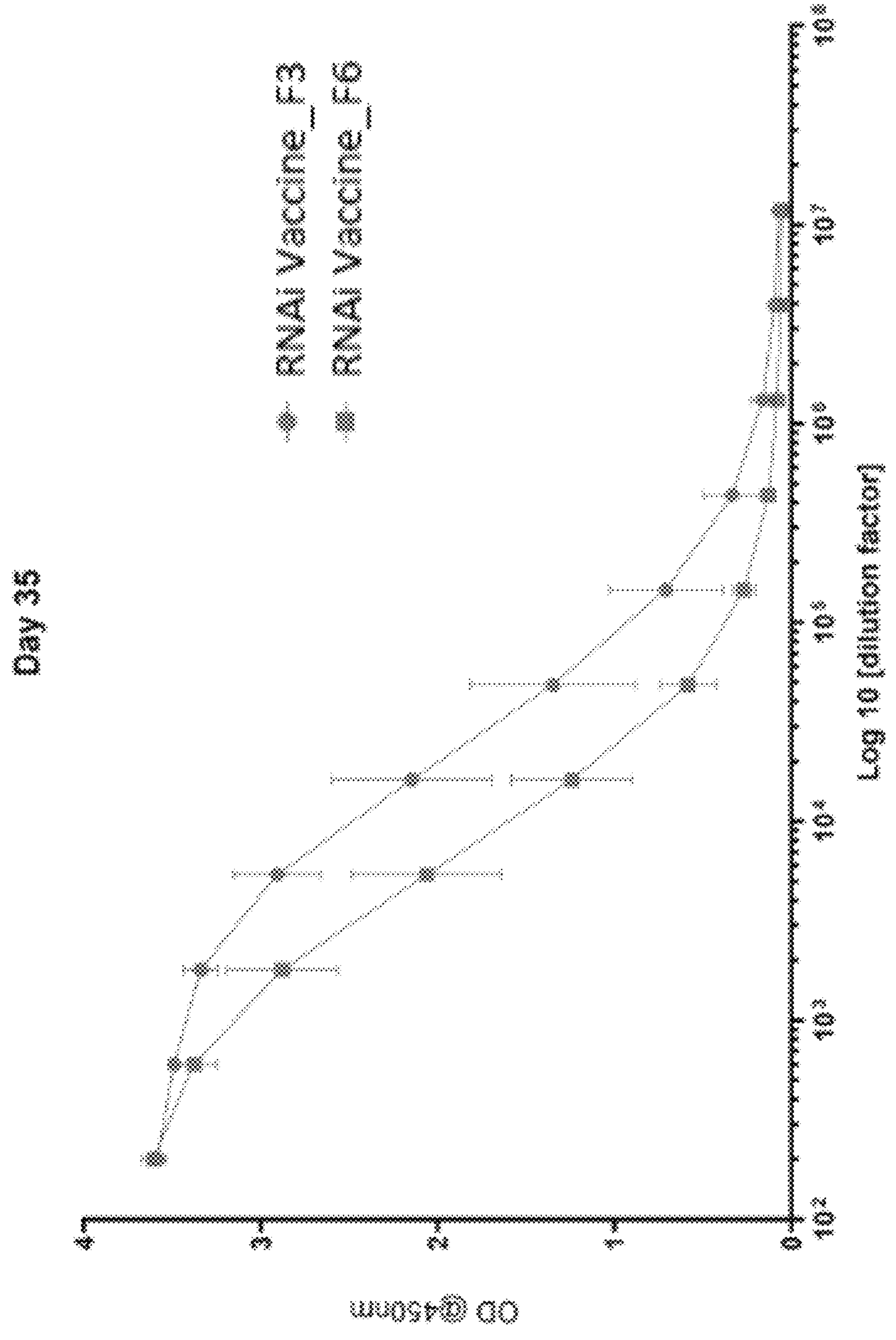

Immunogenicity of RNAi optimized Vaccine F3 and RNAi optimized Vaccine F6 after second immunization. Two weeks after second immunization, serum was collected for measuring IgG titer. In-house His-tagged Prefusion F protein and RSV A2 F protein were used as antigen. Results showed that the IgG titer of RNAi optimized Vaccine F3 and RNAi optimized Vaccine F6 are comparable when we use prefusion F specific protein as antigen (FIG. 14A). When we used RSV A2 F protein as antigen, RNAi optimized Vaccine F3 had higher IgG titer than that of RNAi optimized Vaccine F6 (FIG. 14B)

Figure 15:
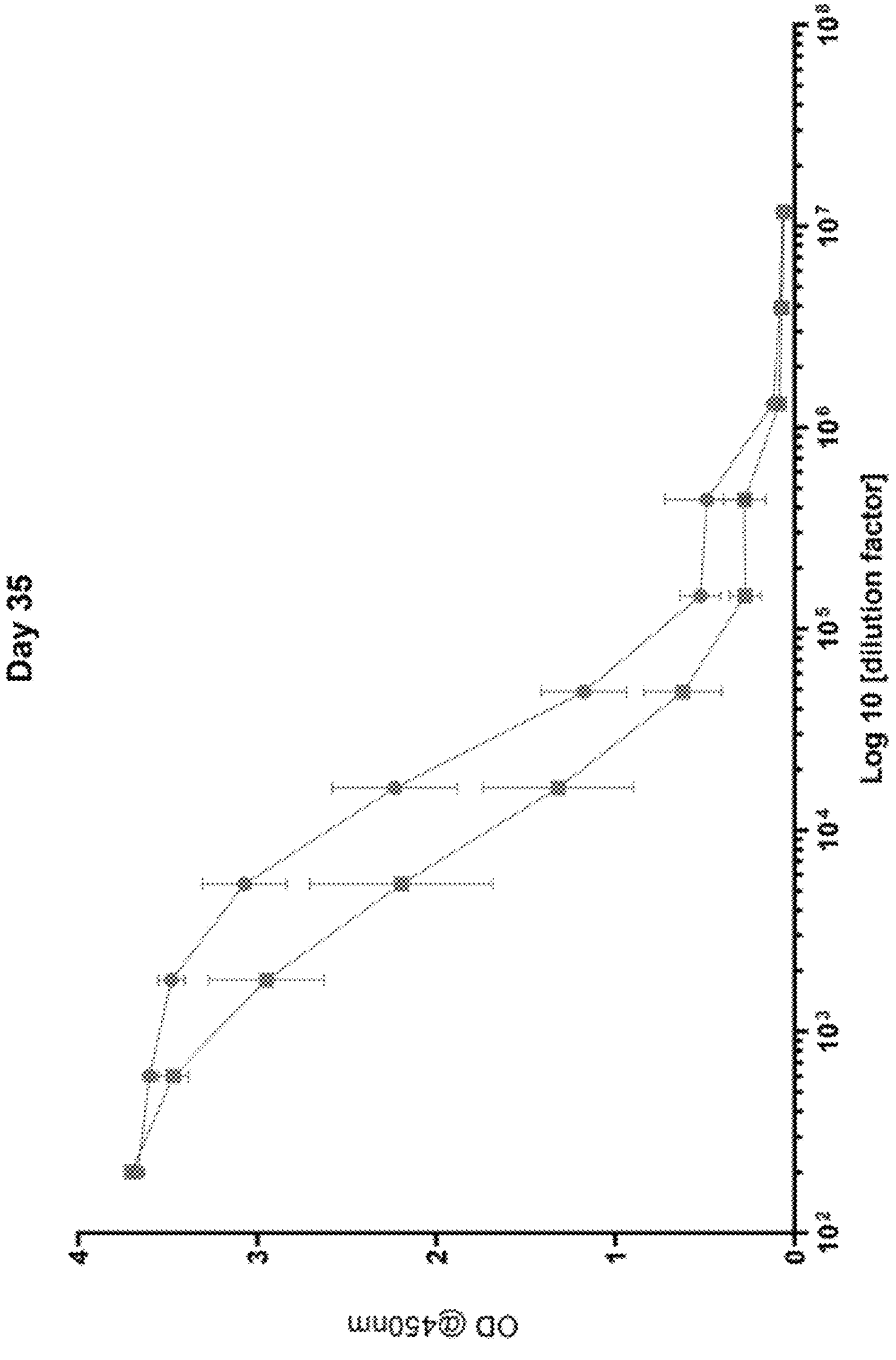
FIG. 15 shows IgG titer induced by RNAi optimized Vaccine-F3 and RNAi optimized Vaccine-F6 after second immunization was measured using RSVB F protein as antigen.
Figure 16A:
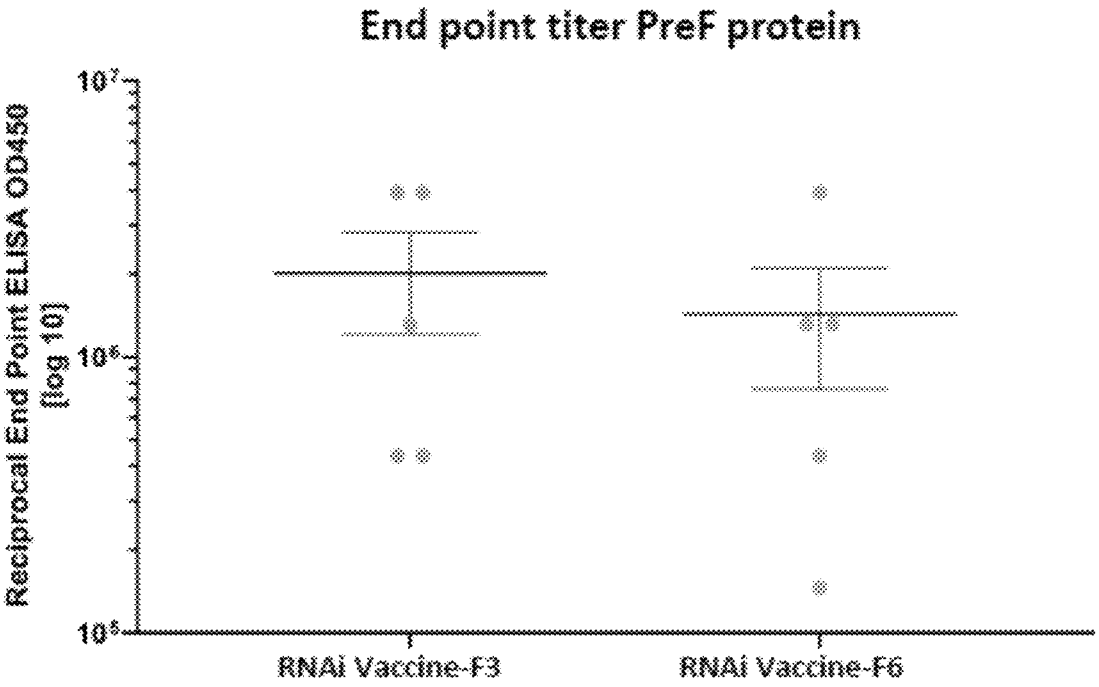
FIGS. 16A and 16B show end point titer results for optimized Vaccine F3 and optimized F6 against Pre-F protein (FIG. 16A) and A2 F protein (FIG. 16B).
Figure 16B:
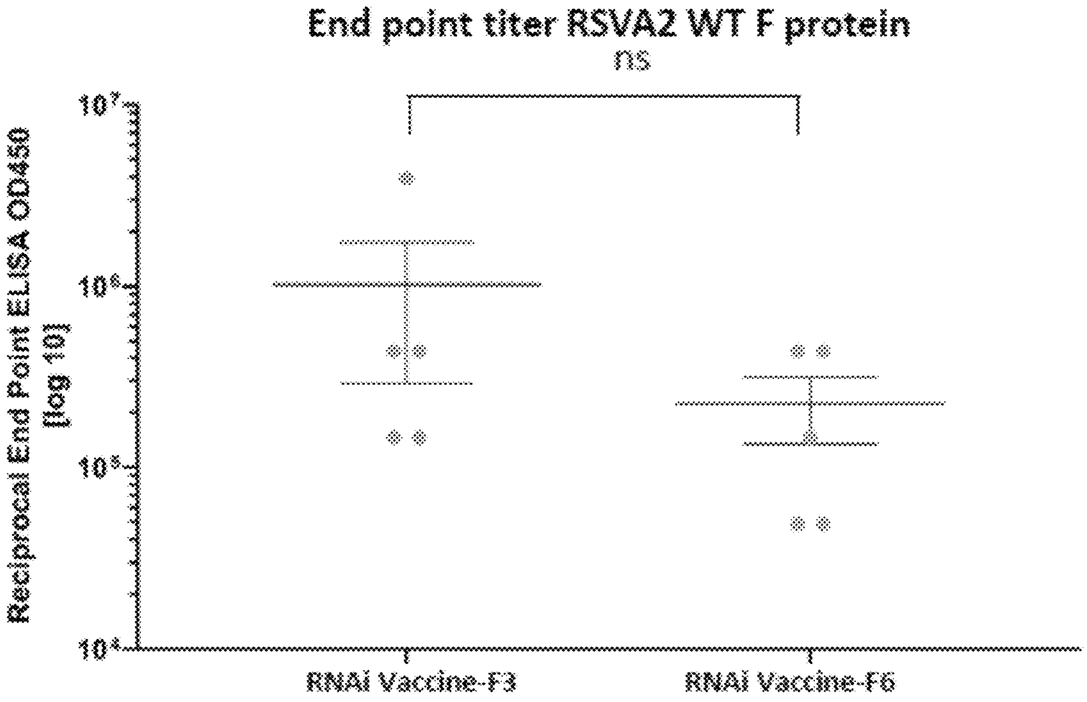
Figure 17A:
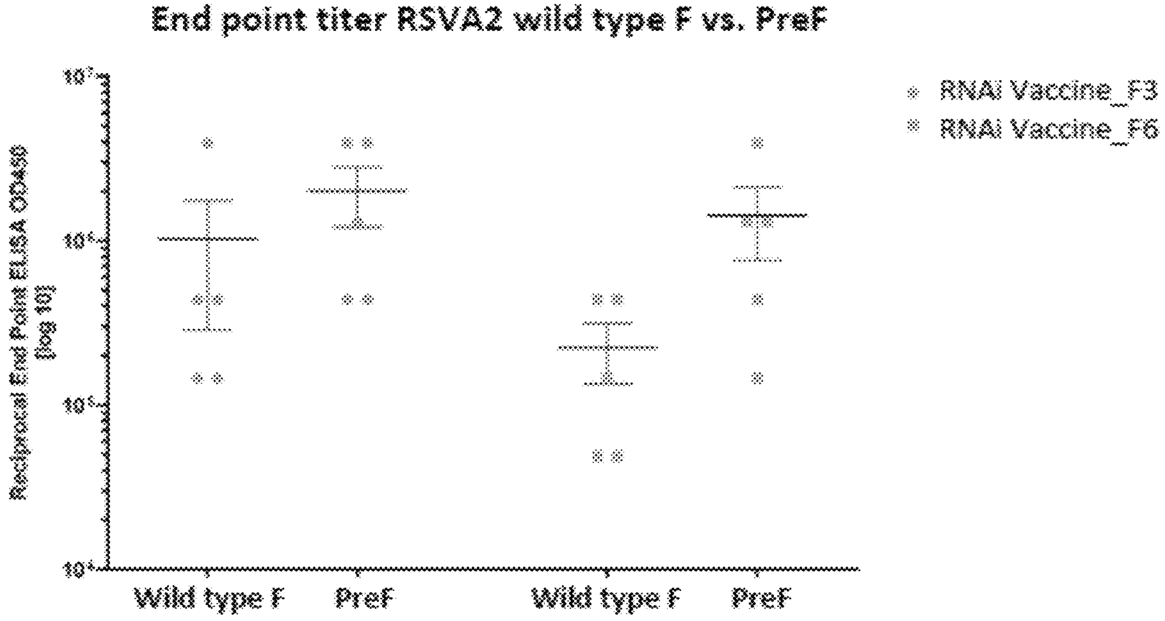
FIGS. 17A and 17B show end point titer results which compare optimized Vaccine F3 and optimized Vaccine F6 in the context of A2 F protein and PreF protein (FIG. 17A) and end point titer results which compare optimized Vaccine F3 and optimized Vaccine F6 in the context of RSV A2 F protein and RSVB F protein (FIG. 17B).
Figure 17B:
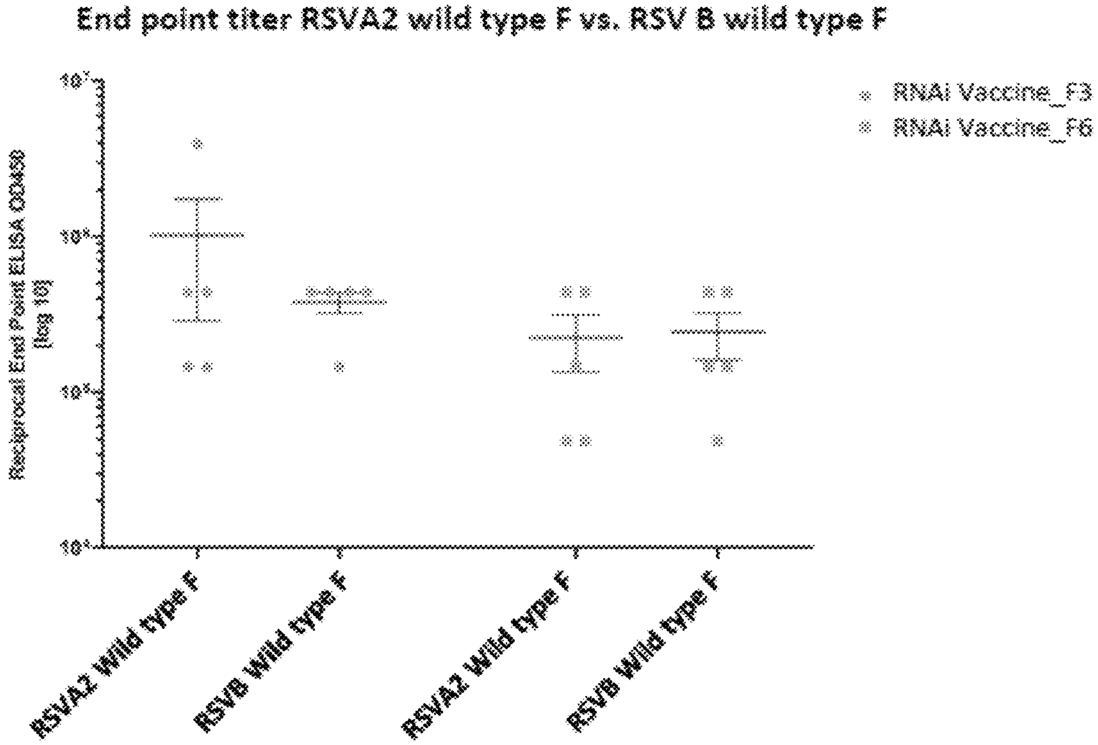
Figure 18A:
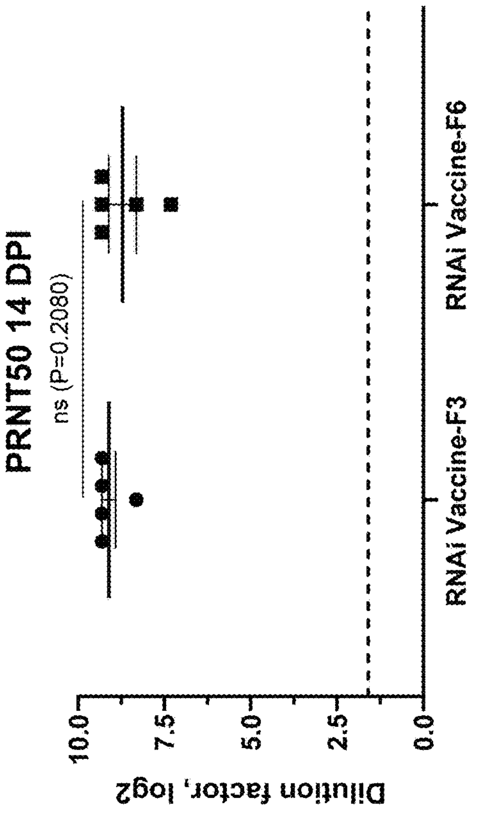
FIGS. 18A and 18B show the efficiency of optimized Vaccine-F3 and optimized Vaccine-F6 in 14 DPI mouse serums. PRNT50 14 DPI (FIG. 18A) and PRNT90 14 DPI (FIG. 18B) were examined.
Figure 18B:
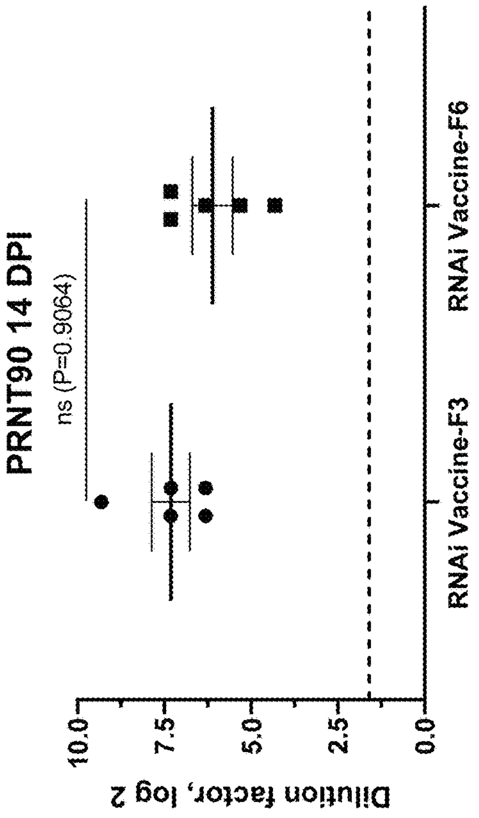
Figure 19B:
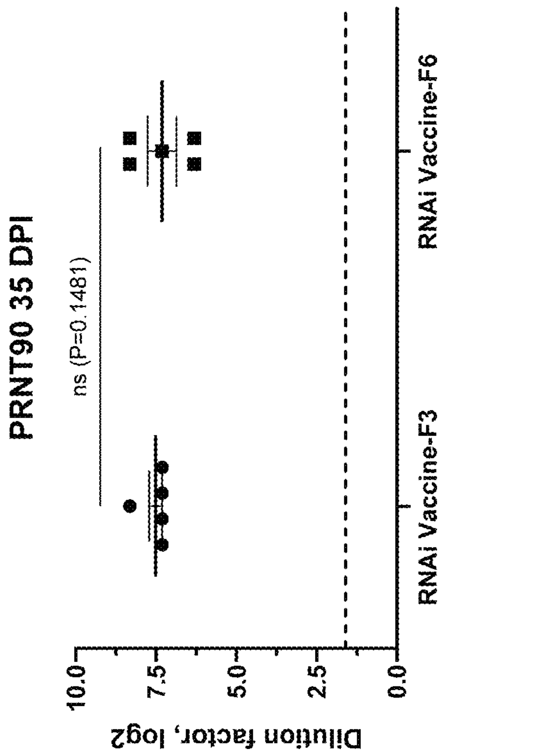
FIGS. 19A and 19B show the efficiency of optimized Vaccine-F3 and optimized Vaccine-F6 in 35 DPI mouse serums. PRNT50 35 DPI (FIG. 18A) and PRNT90 35 DPI (FIG. 18B) were examined.
Figure 19A:
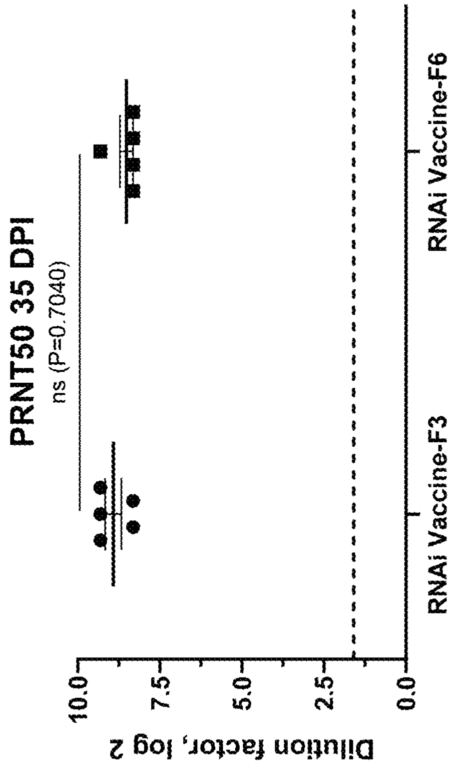

In FIG. 15, IgG titer induced by RNAi optimized Vaccine F3 and RNAi optimized Vaccine F6 after second immunization was measured using RSVB F protein as antigen. Two weeks after second immunization, serum was collected for measuring IgG titer. Results showed that RNAi optimized Vaccine F3 had higher IgG titer than that of RNAi optimized Vaccine F6. This result suggested that the optimized vaccine has broad cross-reactivity among different RSV subtypes FIGS. 16A-16B and 17A-17B show end point IgG titer induced by RNAi optimized Vaccine F3 and RNAi optimized Vaccine F6 after second immunization. The end point IgG titer of RNAi optimized Vaccine F3 and RNAi optimized Vaccine F6 was decided based on the ELISA results from FIGS. 14A-14B and 15. In FIGS. 16A-16B, results showed that RNAi optimized Vaccine F3 has higher IgG titer than RNAi optimized Vaccine F6 regardless which protein is used as antigen. In FIGS. 17A-17B, we compared the end point IgG titer which were measured using different antigens within each vaccine groups. These results showed that 1) RNAi optimized Vaccine F3 has higher IgG titer than RNAi optimized Vaccine F6 and 2) using a different antigen, the IgG titers are comparable.

Figure 20:
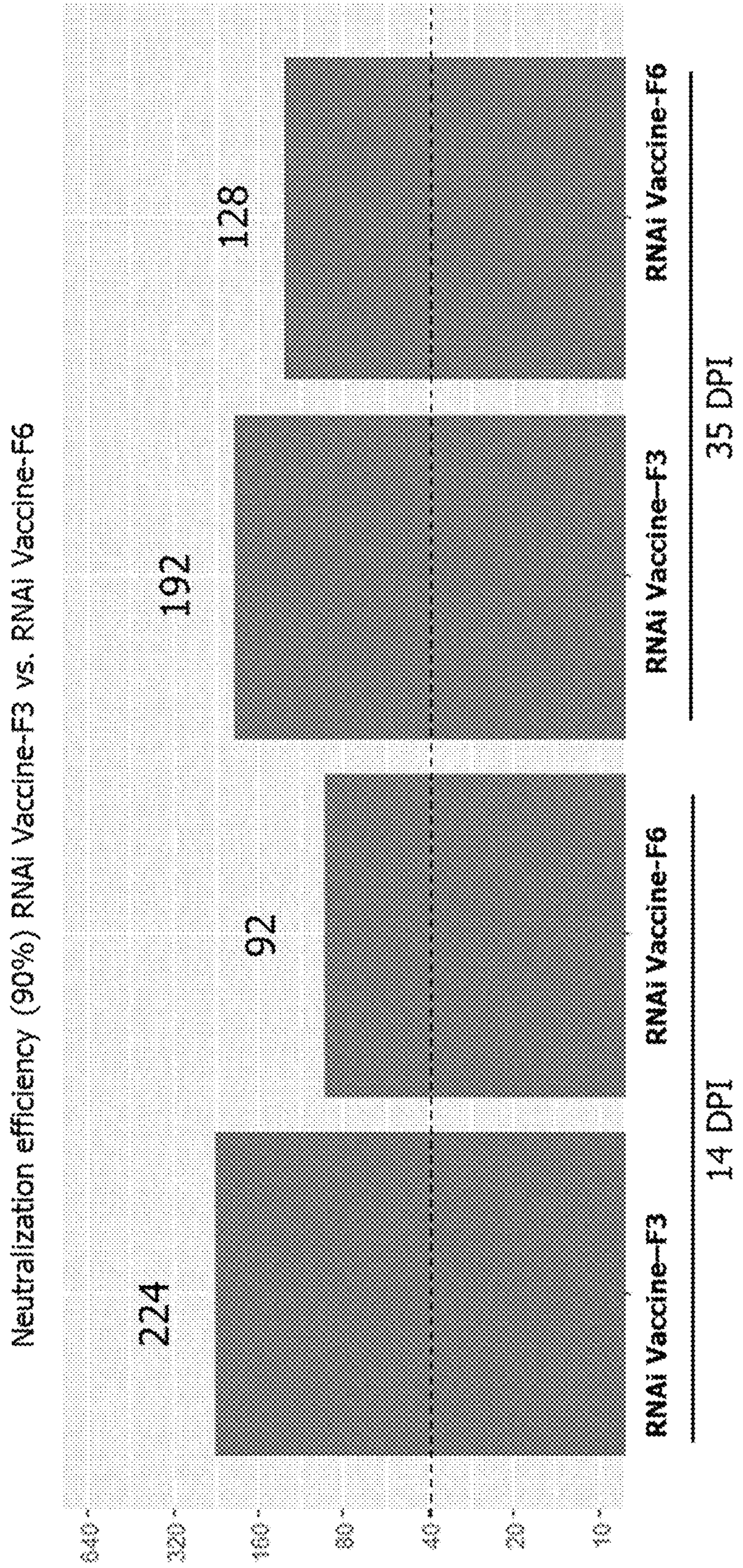
FIG. 20 shows a comparison of optimized Vaccine-F3 and optimized Vaccine-F6 neutralization efficiencies. The neutralizing titer of the test serum samples defined as the reciprocal of the highest serum dilution for which the virus infectivity is reduces 90% and higher.

FIG. 20 shows a summary of 90% of neutralization efficiency (PRNT90). The neutralizing titer of the test serum samples defined as the reciprocal of the highest serum dilution for which the virus infectivity is reduces 90% and higher.

Example 7: ELISpot Assay

Eight weeks after the final boost immunization, the spleens of the mice were collected, dissociated into single cell suspension mechanically, passed through a 70-μm cell strainer (Miltenyi Biotec), and lysed by ACK lysis buffer (KD Medical). The cells were then resuspended in RPMI supplemented with 10% FBS, 1× Pen/Strep and 1×2-Mercaptoethanol, counted and adjusted to $2\times10^6$ cells/ml. After this, 100 μl of splenocytes were added to a well of IFN-γ coated 96-well ELISpot plate (Mabtech). Splenocytes were then incubated for 16 hours in cell culture incubator with (stimulated) or without (unstimulated) stimulation of human RSVB PepMix that was prepared according to manufacturer's instruction (JPT peptide). After incubation, following manufacturer's instruction, biotinylated anti-IFN-γ R4-A2-biotin monoclonal antibody was used as detecting Ab; and streptavidin-ALP complex and BCIP/NBT-plus substrate (Mabtech) were used to reveal the presence of spots. Spots formed by IFN-γ-secreting cells were counted using Cytation 7 (Biotek) and results are presented as spot-forming cells per $2\times10^5$ splenocytes.

Figure 21:
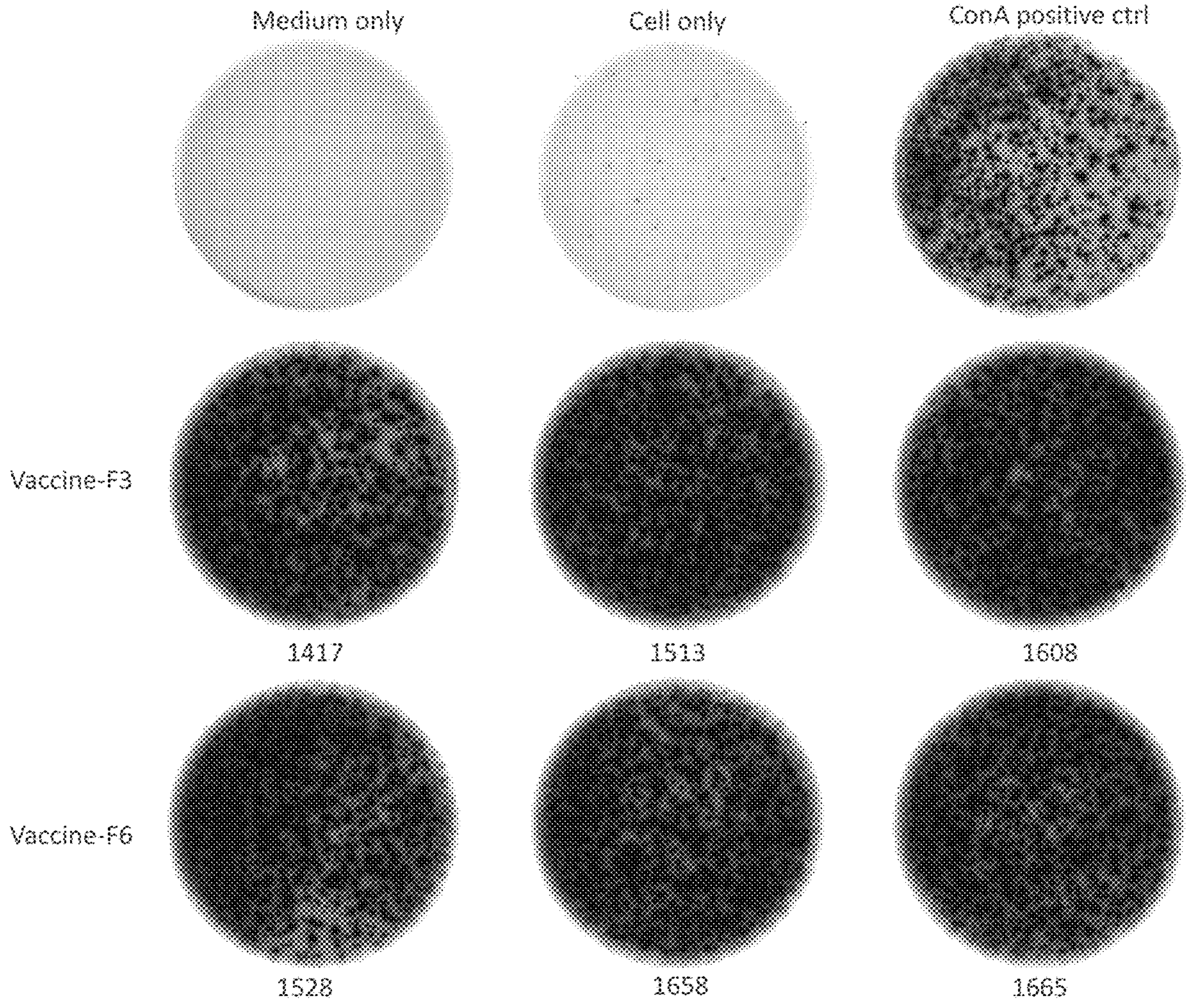
FIG. 21 shows the results of ELISpot analysis of RSV optimized Vaccines F3 and F6.
Figure 22:
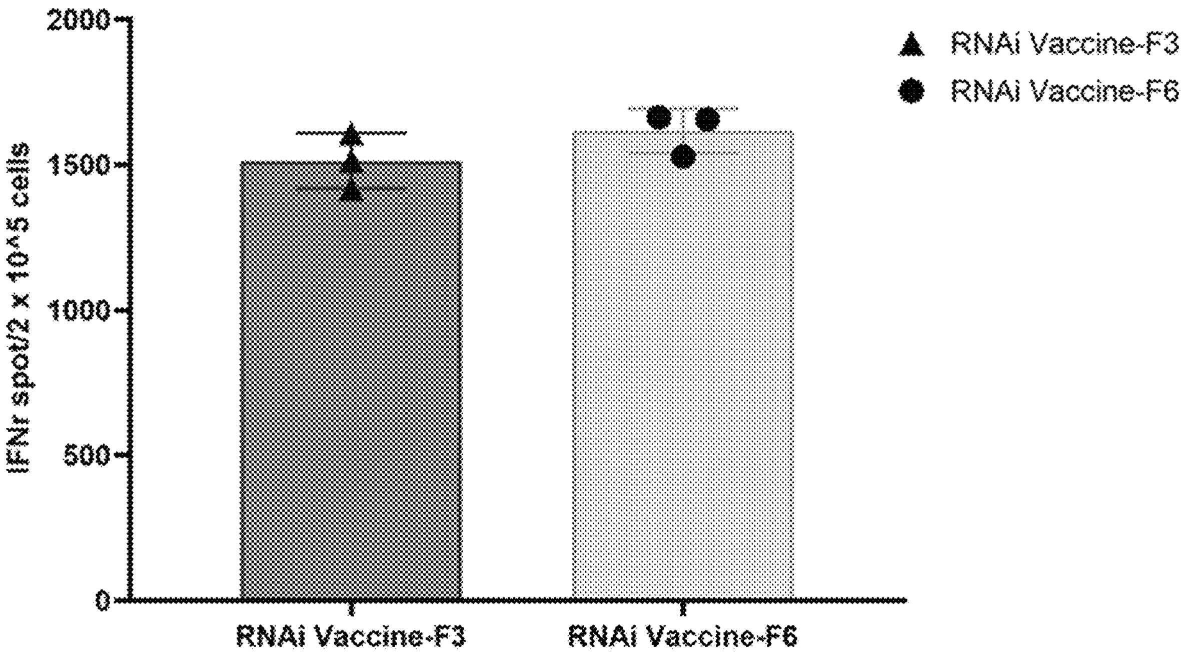
FIG. 22 shows the analysis of IFN-γ-secreting cells yielded by the ELISpot assay.
Figure 23A:
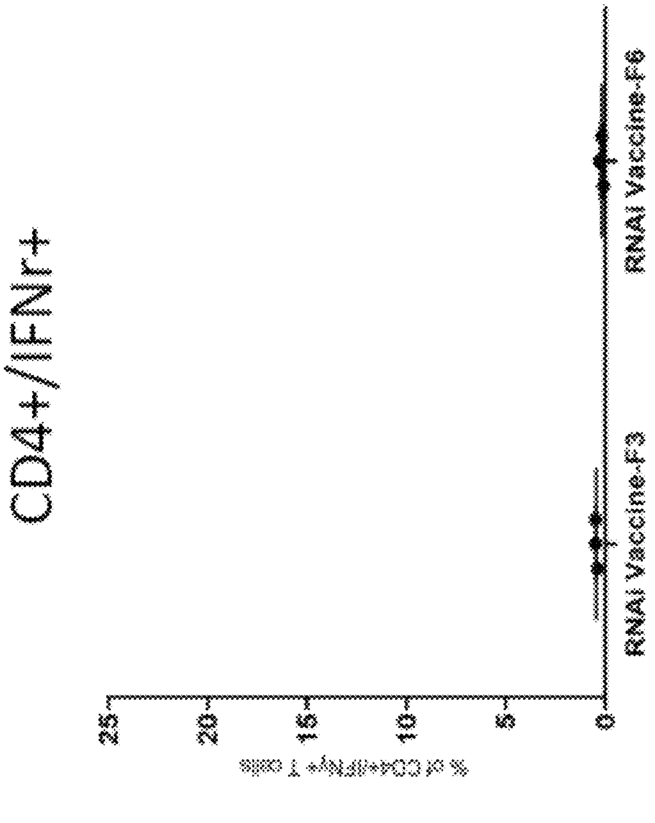
FIGS. 23A-D show T-cell response for optimized Vaccine F3 and optimized Vaccine F6 as determined by intracellular staining.
Figure 23B:
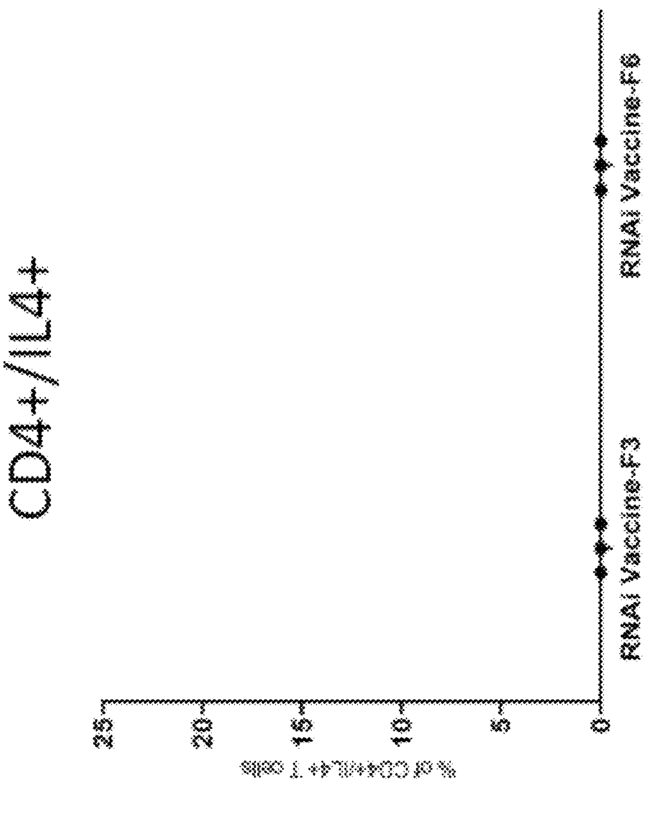
Figure 23C:
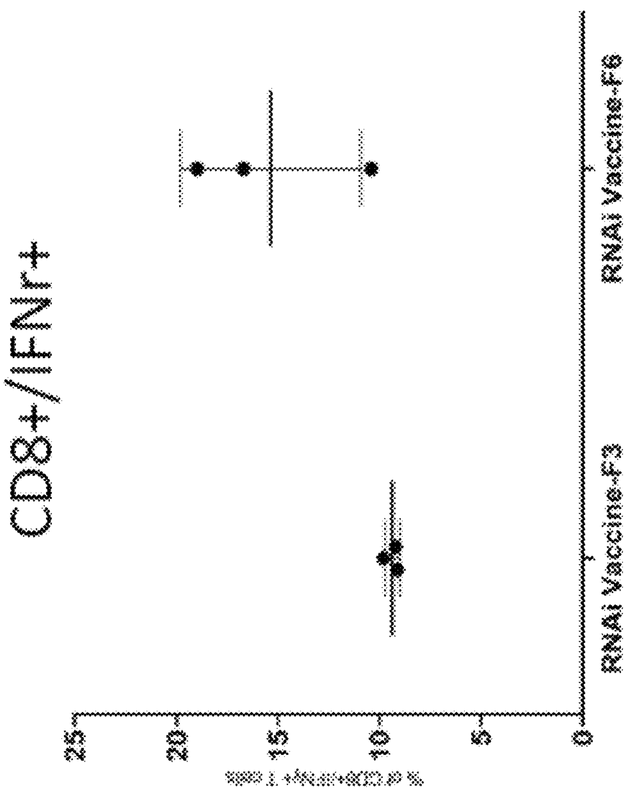
Figure 23D:
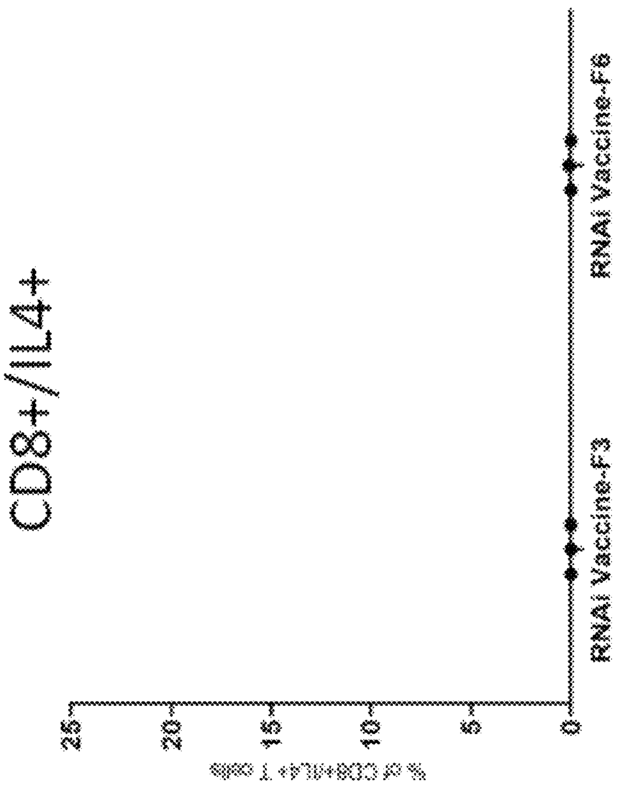
Figure 24A:
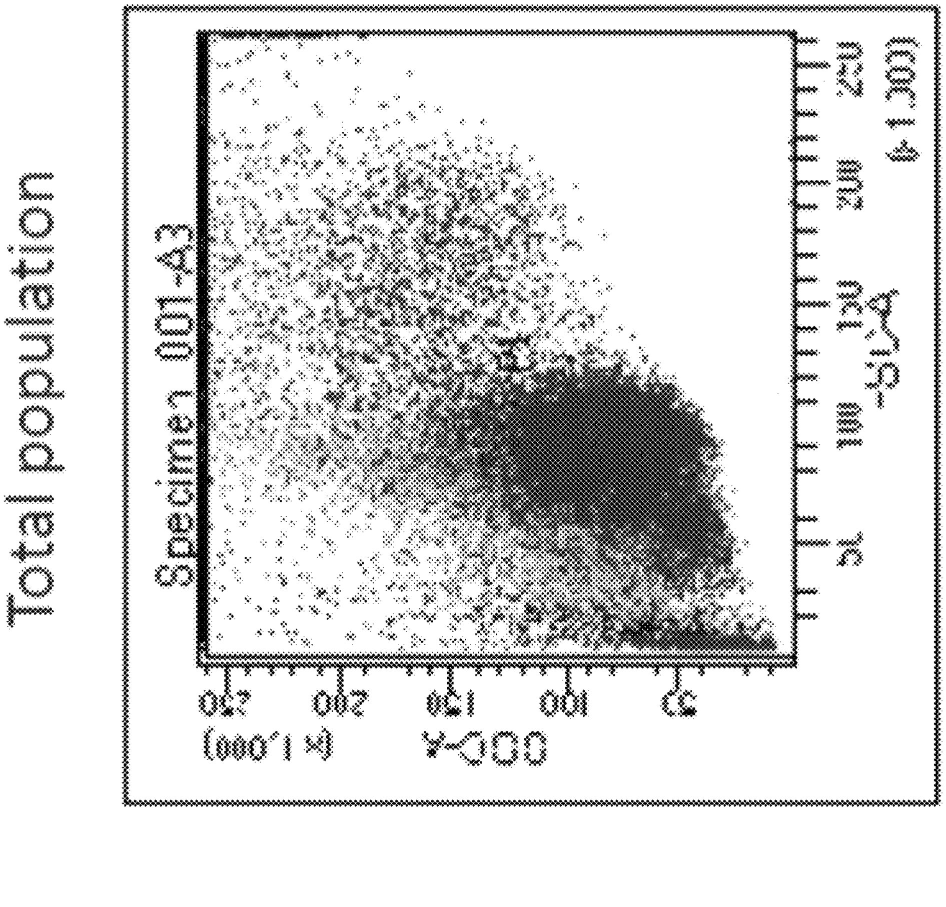
FIGS. 24A-I show the gating strategy for the flow cytometry analysis of the intracellular staining experiment. Total population (FIG. 24A), Single cell (FIG. 24B), and Live/Dead cells (FIGS. 24C-I) were included in the strategy.
Figure 24B:
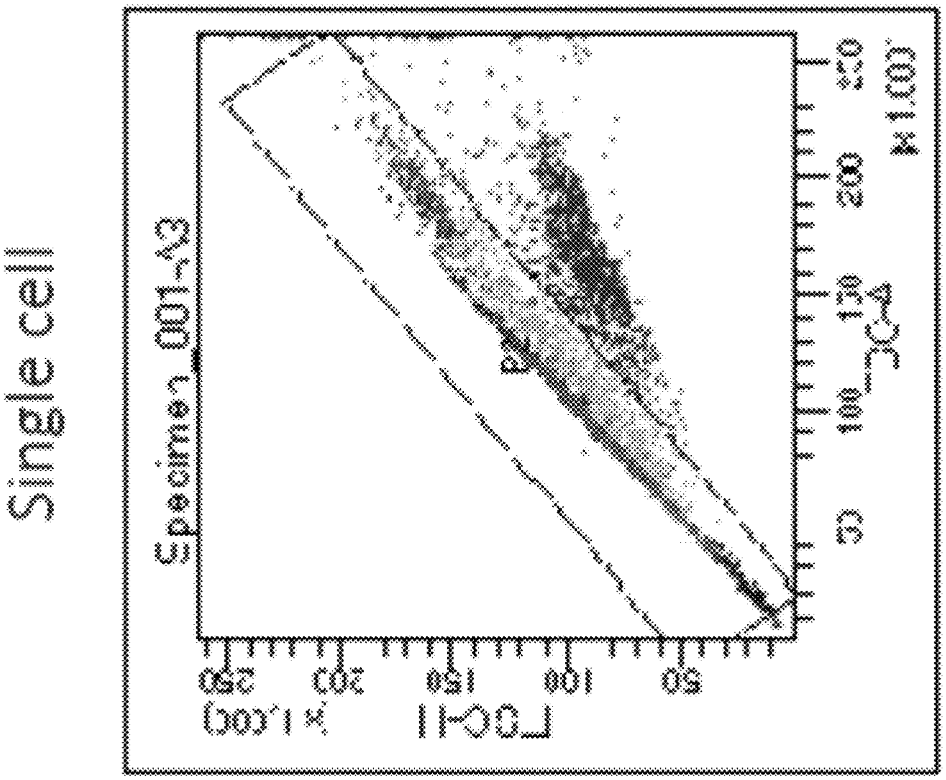
Figure 24D:
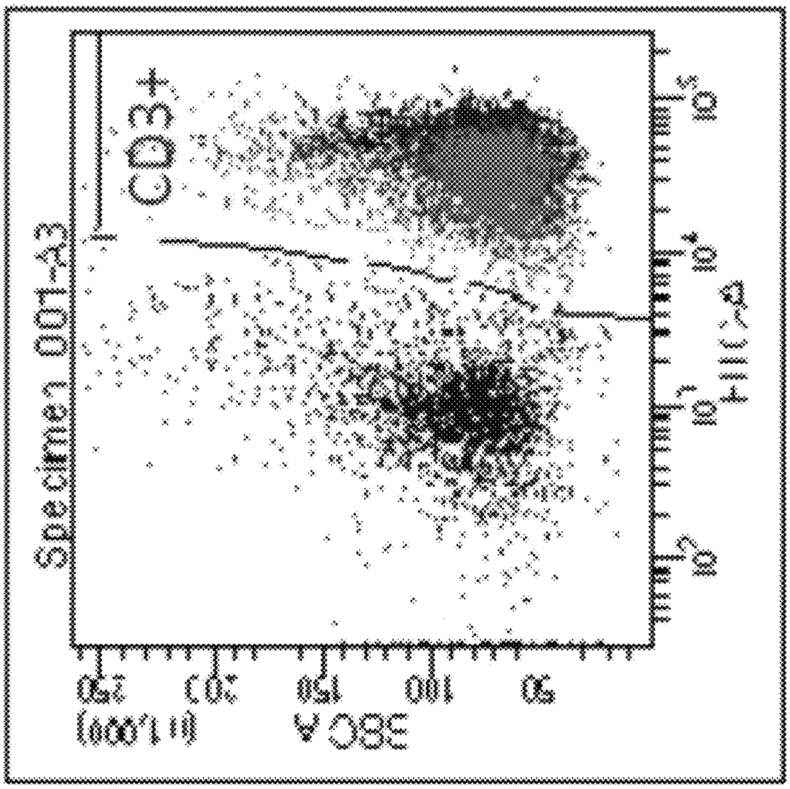
Figure 24C:
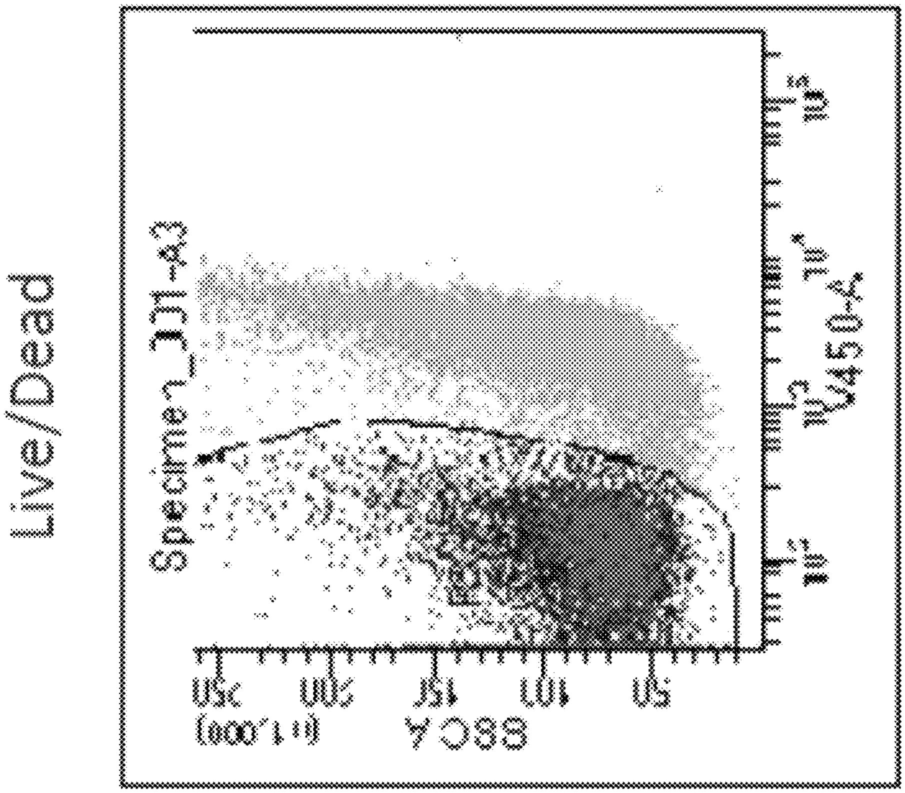
Figure 24E:
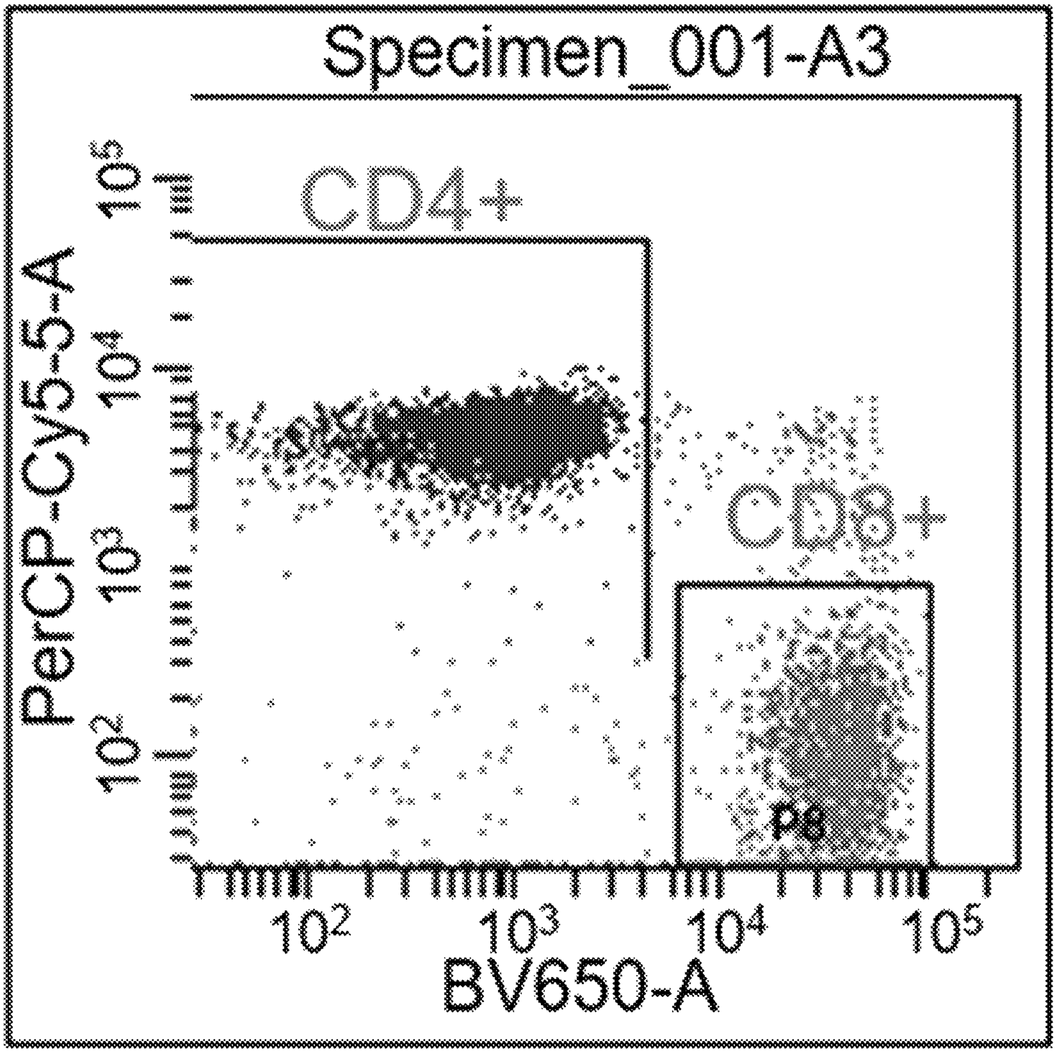
Figure 24F:
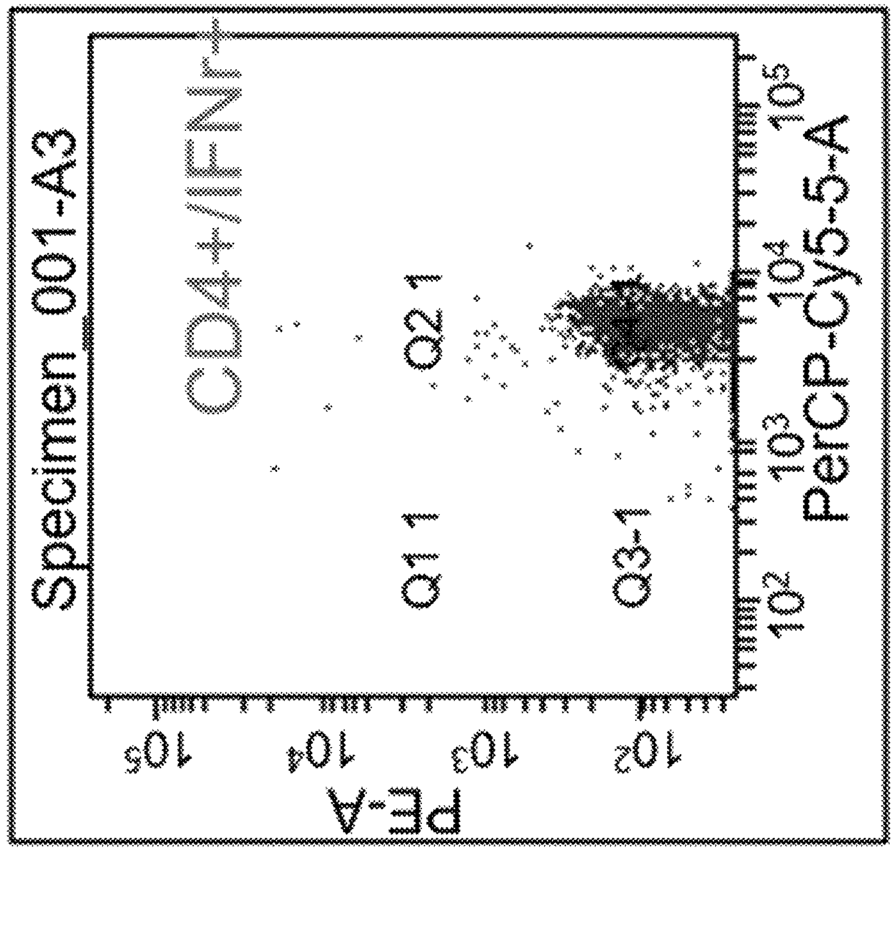
Figure 24G:
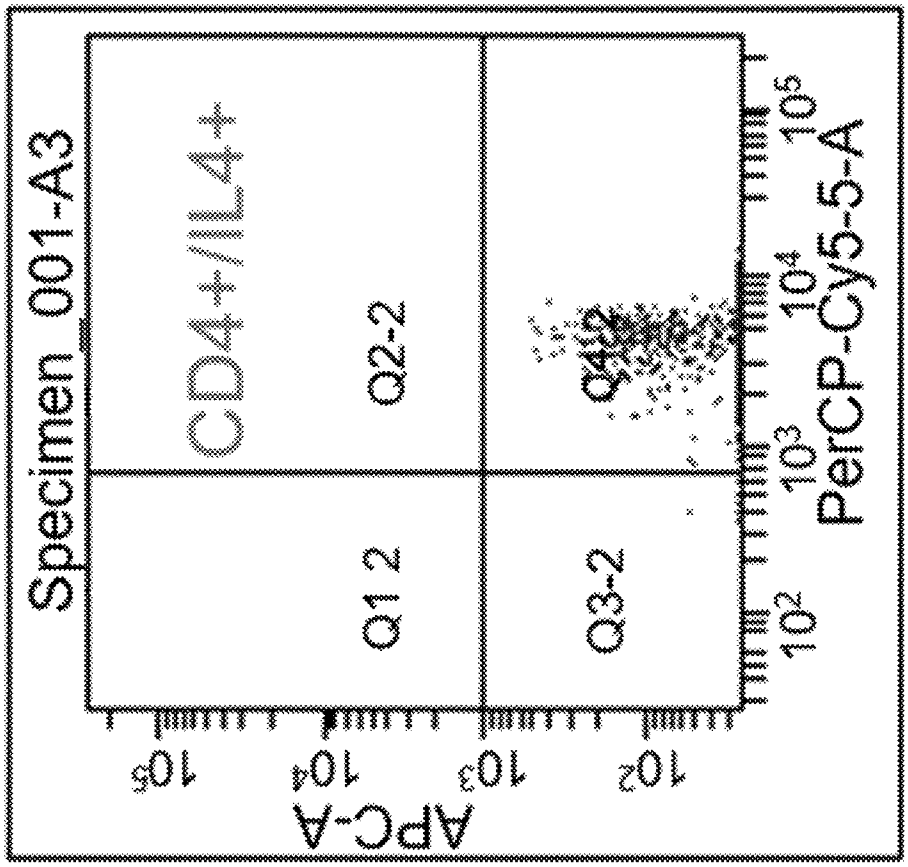
Figure 24H:
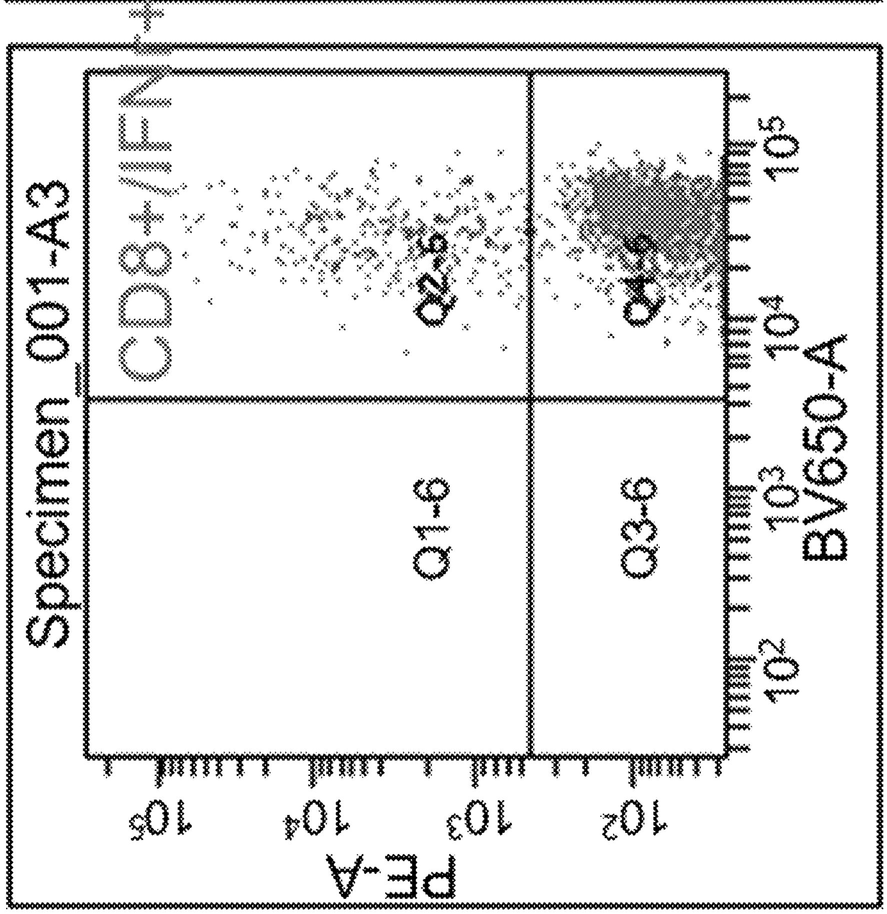
Figure 24I:
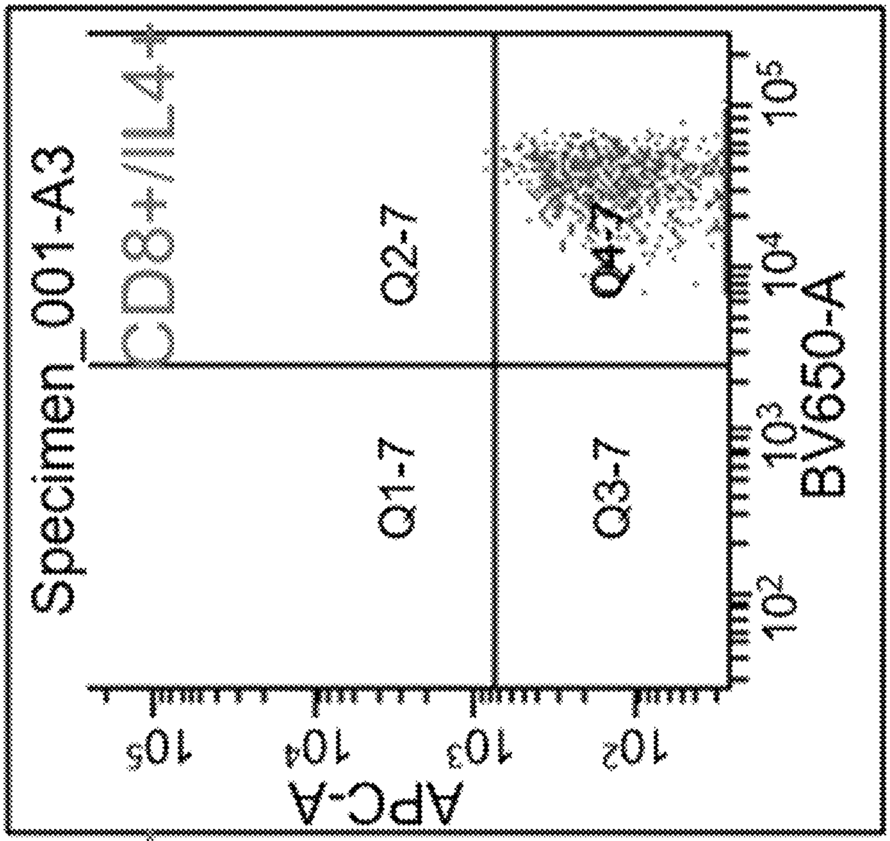

FIGS. 21 and 22 show the results of ELSIpot assay for optimized Vaccine F3 and optimized Vaccine F6. The ELISpot assay measures T cell response induced by RNAi optimized Vaccine F3 and RNAi optimized Vaccine F6. In this assay, human RSVB PepMix was used to stimulate splenocytes. The IFNr secreting spots were counted. The results showed that RNAi optimized Vaccine F3 and RNAi optimized Vaccine F6 induced comparable T cell response. RSV-F3 yielded a cell viability of 81.4% and RSV-F6 yielded a cell viability of 43.8%.

Example 8: Intracellular Staining (ICS) Assay

Induction of antigen-specific T cells was determined using ICS. Splenocytes were prepared as described above. $1\times10^6$ splenocytes were added in 12×75 mm plastic tubes in the presence of protein transport inhibitor, brefeldin A (BioLegend) with (stimulated) or without (unstimulated) stimulation of human RSVB PepMix that was prepared according to manufacturer's instruction (JPT peptide). After 16 h incubation, FACS analysis was performed to determine cytokines splenocytes. Cell surface staining was performed using antibodies against CD3 (FITC), CD4 (BV421) and CD8 (BV650). Intracellular staining was performed using antibodies against IL-4 (APC), and IFN-γ (PE). eFluor450 was used to distinguish live/dead cells (Invitrogen). Cells were acquired using BD Celesta Flow cytometer (BD Biosciences) and flow cytometry data were analyzed using FlowJo software.

Intracellular staining was employed to measure subtype T cell response. Human RSVB PepMix stimulated splenocytes were subjected to FACS analysis. The result showed that IFNr secreting cells are mainly CD8+ T cells, indicating that T cell response induced by RNAi optimized Vaccine F3 and RNAi optimized Vaccine F6 is mediated by CD8+ T cells.

FIGS. 23A-23D demonstrate that Vaccine F6 induced a stronger T-cell response than Vaccine F3. However, as shown by the above cell viability assay, Vaccine F6 may have greater cell toxicity. FIGS. 24A-24I lay out the overall gating strategy for the ICS assay.

Example 9: RSV Plaque Reduction Neutralization Assay

Neutralization activity was determined via plaque assay on HEp-2 cells. Briefly, sera were heat inactivated and diluted and added in duplicate to 6-well plates using the traditional plaque assay. HEp-2 cells were pre-seeded and incubated at 37° C. on the day before the assay. On the assay day, virus was added to confluent cell monolayers for 1 h at 37° C., the liquid was aspirated, washed twice with PBS and 0.4% agarose was added. Following 8 days at 37° C., cells were fixed and stained with anti-RSV antibody. Viral plaques were counted, and titers were expressed as pfu/ml of serum.

Figure 11:
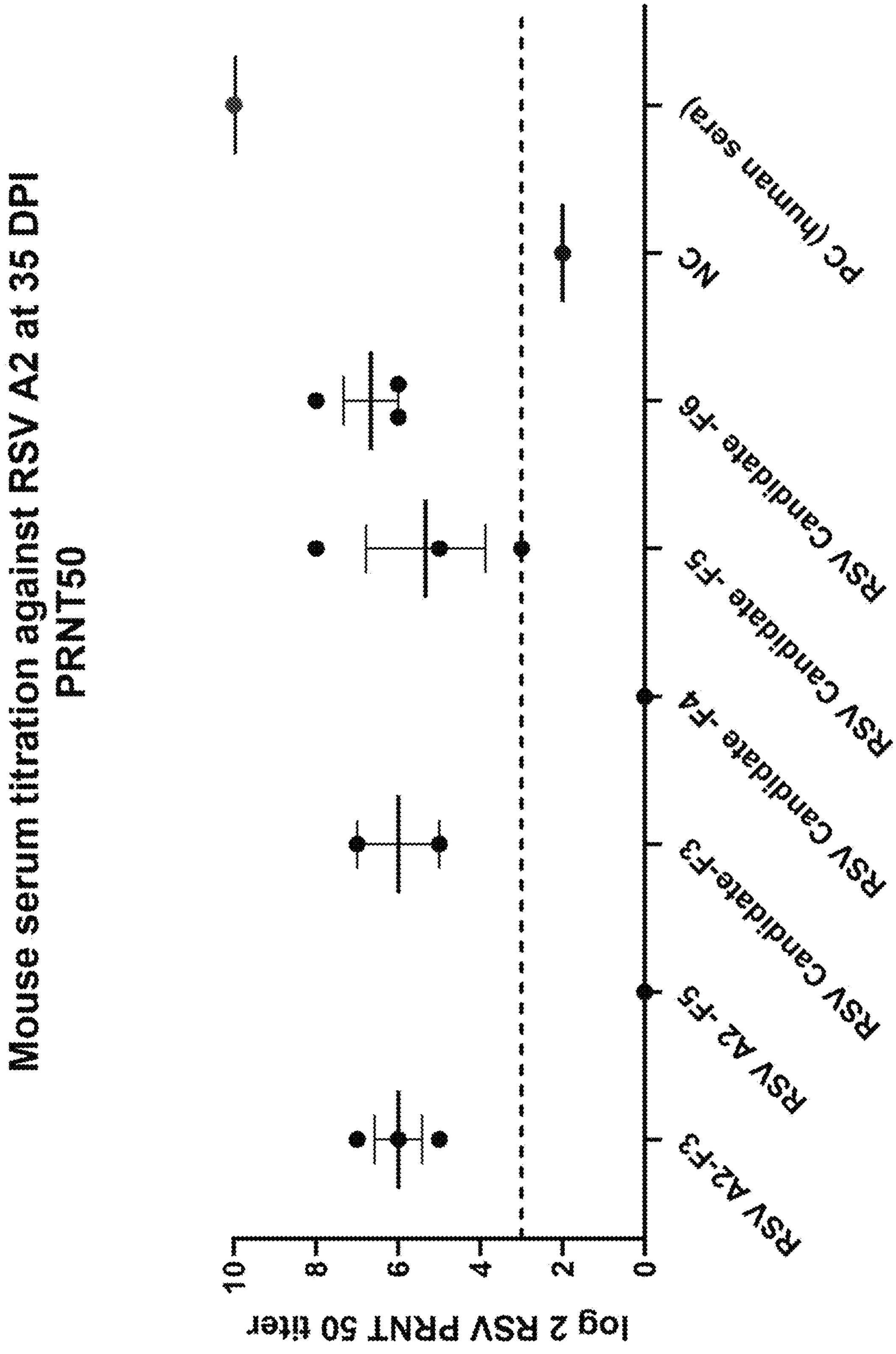
FIG. 11 shows immunogenicity and neutralization activity of A2 and optimized vaccine candidates.
Figure 12:
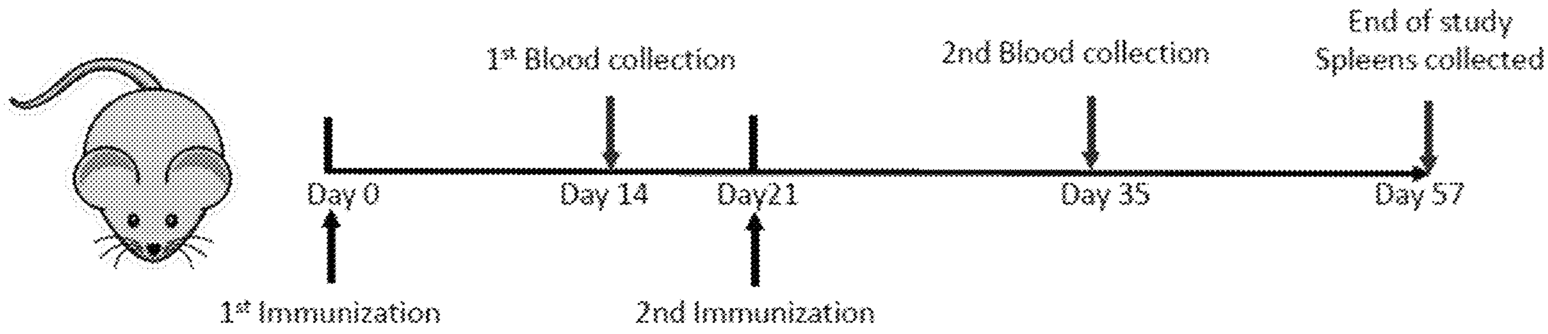
FIG. 12 depicts an alternative exemplary challenge study.

FIG. 11 shows the neutralization activity of these six vaccine candidates were determined using plaque assay to against RSV A2 isolate. The PRNT (plaque reduction neutralization titer) 50 were determined based on the plaque assay results. In this experiment, optimized RNAi Vaccine F3 and optimized RNAi Vaccine F6 showed higher PRNT50 titer when compared with other vaccine candidates. Based on the ELISA results and Plaque assay results, RNAi Vaccine F3 and RNAi Vaccine F6 were chosen for further study. FIG. 20 shows that Vaccine F3 achieves 90% neutralization at greater dilution factors than Vaccine F6 using this assay.

FIGS. 18A-18B and 19A-19B show the neutralization activity of RNAi optimized Vaccine F3 and RNAi optimized Vaccine F6 as determined using plaque assay to against RSV A2 isolate. The plaque reduction neutralization titer (PRNT) 50 and PRNT 90 were determined based on the plaque assay results. In this experiment, RNAi optimized Vaccine F3 and RNAi optimized Vaccine F6 showed similar PRNT50, while RNAi optimized Vaccine F3 has higher PRNT90 than that of RNAi optimized Vaccine F6 in both 14 and 35 DPI.

Example 10: RSV Cotton Rat Study

Groups of five female cotton rats (SAGE) aged 3-7 weeks are immunized twice intramuscularly with 25 μg and 10 μg RSV-F3 mRNA/LNP vaccine on days 0 and 21 of the study, or with a single intranasal administration of $10^{5.5}$ pfu RSV A2.

Animals are bled for serology prior to the first immunization and on days 21, 28, 42, and 56. On day 56 (4 weeks following the second immunization), all animals in the study are challenged intranasally with $5.9\times10^5$ pfu of RSV A2 or B 18537 strains delivered in a 0.1 mL volume. Four days following the RSV challenge, animals are euthanized, and lung and nose tissue are isolated for quantification of viral load.

The cotton rat vaccine-associated enhanced respiratory disease (VERD) study is conducted. Groups of 10 female cotton rats aged 3-7 weeks are immunized with the vaccine candidates RSV-F3 mRNA/LNP (25 μg and 10 μg), or with the following controls: empty LNP (or PBS) with no mRNA, FI-RSV Lot 100 from the original FI-RSV clinical trial, and two unvaccinated groups. One of the unvaccinated groups is challenged to serve as a control for the pathological changes associated with natural infection, while the second is left unchallenged to serve as a control for natural cotton rat physiology. The cotton rats are immunized twice intramuscularly at a 3-week interval, and all groups, with the exception of one of the unvaccinated groups which is left untreated as a control for normal cotton rat pathology, are challenged intranasally 4 weeks after the second immunization with $10^{5.5}$ pfu of RSV A2 in 0.1 mL volume. Five days following the challenge, animals are sacrificed. Noses are harvested for virus quantification, and lungs from each animal are trisected and processed for virus quantification, pathology, and cytokine mRNA analysis.

Example 11: RSV Human Study

Healthy volunteers are recruited to participate in the RSV challenge study through an active screening protocol at an appropriate facility. Subjects of interest include pediatric subjects, adult subjects, pregnant subjects, and seniors 60+. Subjects who meet inclusion criteria are asked for informed consent. Subjects who provide informed consent are prescreened for anti-RSV antibodies approximately 2 weeks prior to the study start date.

On the day prior to inoculation, subjects repeat RSV antibody testing. Subjects also undergo laboratory studies, including complete blood count, serum chemistries, and hepatic enzymes.

On the day of inoculation, dose of RSV vaccine manufactured and processed under current good manufacturing practices are inoculated per standard methods.

Subjects are admitted to the quarantine facility for 48 hours following RSV inoculation and shall remain for 48 hours following inoculation. Blood is collected for further study at predetermined intervals post-inoculation.

Samples are obtained from each subject daily for RSV titers to accurately gauge the success and timing of the RSV inoculation. 48 hours after inoculation, subjects are released from quarantine and returned for three consecutive mornings for sample acquisition and symptom score ascertainment. One metric for vaccine efficacy is prevention of hospitalization.

EQUIVALENTS

Unless otherwise defined, all technical and scientific terms used herein have the same meaning as commonly understood by one of ordinary skill in the art to which this technology belongs.

The present technology illustratively described herein may suitably be practiced in the absence of any element or elements, limitation or limitations, not specifically disclosed herein. Thus, for example, the terms “comprising,” “including,” “containing,” etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the present technology claimed.

Thus, it should be understood that the materials, methods, and examples provided here are representative of preferred aspects, are exemplary, and are not intended as limitations on the scope of the present technology.

It should be understood that although the present invention has been specifically disclosed by certain aspects, embodiments, and optional features, modification, improvement and variation of such aspects, embodiments, and optional features can be resorted to by those skilled in the art, and that such modifications, improvements and variations are considered to be within the scope of this disclosure.

The present technology has been described broadly and generically herein. Each of the narrower species and subgeneric groupings falling within the generic disclosure also form part of the present technology. This includes the generic description of the present technology with a proviso or negative limitation removing any subject matter from the genus, regardless of whether or not the excised material is specifically recited herein.

In addition, where features or aspects of the present technology are described in terms of Markush groups, those skilled in the art will recognize that the present technology is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

Other aspects are set forth within the following claims.

SEQUENCES

| Designation | Amino Acid Sequence | DNA Sequence | RNA Sequence |
|---|---|---|---|
| F protein Optimized (F1) fragment | SEQ ID NO: 1 | SEQ ID NO: 2 | SEQ ID NO: 48 |
| F protein Optimized no TM (F2) fragment | SEQ ID NO: 3 | SEQ ID NO: 4 | SEQ ID NO: 49 |
| F protein Optimized with s155C, S190F, V207L, and S290C mutations and transmembrane domain (F3) fragment | SEQ ID NO: 5 | SEQ ID NO: 6 | SEQ ID NO: 50 |
| F protein Optimized with s155C, S190F, V207L, and S290C mutations no transmembrane domain (F4) fragment | SEQ ID NO: 7 | SEQ ID NO: 8 | SEQ ID NO: 51 |
| F Protein Optimized with s155C, S190F, V207L, S290C, D486H, E487Q, F484W, and D489H and TM domain (F5) fragment | SEQ ID NO: 9 | SEQ ID NO: 10 | SEQ ID NO: 13 |
| F Protein Optimized with s155C, S190F, V207L, S290C, D486H, E487Q, F484W, and D489H No TM Domain (F6) fragment | SEQ ID NO: 11 | SEQ ID NO: 12 | SEQ ID NO: 52 |
| A2 protein (A2-1) | SEQ ID NO: 53 | SEQ ID NO: 54 | SEQ ID NO: 55 |
| A2 protein no TM (A2-2) | SEQ ID NO: 56 | SEQ ID NO: 57 | SEQ ID NO: 58 |
| A2 protein with s155C, S190F, V207L, and S290C mutations and transmembrane domain (A2-3) | SEQ ID NO: 59 | SEQ ID NO: 60 | SEQ ID NO: 61 |
| A2 protein with s155C, S190F, V207L, and S290C mutations no transmembrane domain (A2-4) | SEQ ID NO: 62 | SEQ ID NO: 63 | SEQ ID NO: 64 |
| A2 protein with S155C, S190F, V207L, S290C, D486H, E487Q, F484W, and D489H and TM domain (A2-5) | SEQ ID NO: 65 | SEQ ID NO: 66 | SEQ ID NO: 67 |
| A2 protein with S155C, S190F, V207L, S290C, D486H, E487Q, F484W, and D489H No TM Domain (A2-6) | SEQ ID NO: 68 | SEQ ID NO: 69 | SEQ ID NO: 70 |
| F1 optimized Vaccine candidate with no mutations and transmembrane domain | SEQ ID NO: 87 | SEQ ID NO: 88 | SEQ ID NO: 89 |

-continued

| SEQUENCES | | | |
|---|---|---|---|
| Designation | Amino Acid Sequence | DNA Sequence | RNA Sequence |
| F2 optimized Vaccine candidate with no mutations and no transmembrane domain | SEQ ID NO: 92 | SEQ ID NO: 93 | SEQ ID NO: 94 |
| F3 optimized Vaccine candidate with S155C, S190F, V207L, S290C and transmembrane domain | SEQ ID NO: 95 | SEQ ID NO: 96 | SEQ ID NO: 97 |
| F4 optimized Vaccine candidate with S155C, S190F, V207L, S290C and no transmembrane domain | SEQ ID NO: 98 | SEQ ID NO: 99 | SEQ ID NO: 100 |
| F5 optimized Vaccine candidate with S155C, S190F, V207L, S290C, D486H, E487Q, F484W, and D489H and TM Domain | SEQ ID NO: 101 | SEQ ID NO: 102 | SEQ ID NO: 103 |
| F6 optimized Vaccine candidate with S155C, S190F, V207L, S290C, D486H, E487Q, F484W, and D489H and no TM Domain | SEQ ID NO: 104 | SEQ ID NO: 105 | SEQ ID NO: 106 |
| 3'UTR | — | SEQ ID NO: 17 | SEQ ID NO: 18 |
| β-globulin 5'UTR | — | SEQ ID NO: 19 | SEQ ID NO: 20 |
| SYS UTR 2.0 | — | SEQ ID NO: 21 | SEQ ID NO: 22 |
| SYS UTR 1.0 | — | SEQ ID NO: 23 | SEQ ID NO: 24 |
| SYS4 5'UTR | — | SEQ ID NO: 25 | SEQ ID NO: 26 |
| polyA 40 | — | SEQ ID NO: 27 | SEQ ID NO: 27 |
| polyA 60 | — | SEQ ID NO: 28 | SEQ ID NO: 28 |
| polyA signal HSV | — | SEQ ID NO: 15 | SEQ ID NO: 16 |
| RNA sequence of an exemplified Protein with S155C, S190F, V207L, S290C, D486H, E487Q, F484W, and D489H and TM domain UTR-polyA | | | SEQ ID NO: 30 |
| Plasmid | — | SEQ ID NO: 29 | — |
| Side chains of HKP | SEQ ID NO: 31 to 44 | — | — |

SEQ ID NO: 1, Amino acid sequence of Optimized F glycoprotein fragment:
GFLLGVGSAIASGIAVSKVLHLEGEVNKIKSALLSTNKAVVSLSNGVSVLTSK

VLDLKNYIDKQLLPIVNKQSCSISNIETVIEFQQKNNRLLEITREFSVNAGVTTPVSTY

MLTNSELLSLINDMPITNDQKKLMSNNVQIVRQQSYSIMSIIKEEVLAYVVQLPLYGV

IDTPCWKLHTSPLCTTNTKEGSNICLTRTDRGWYCDNAGSVSFFPQADTCKVQSNRV

FCDTMNSLTLPSEVNLCNIDIFNPKYDCKIMTSKTDVSSSVITSLGAIVSCYGKTKCTA

SNKNRGIIKTFSNGCDYVSNKGVDTVSVGNTLYYVNKQEGKSLYVKGEPIINFYDPL

VFPSDEFDASISQVNEKINQSLAFIRKSDELLHNVNAGKSTTNIMITTIIIVIIVILLSLIA

VGLLLYCKARSTPVTLSKDQLSGINNIAFSN

-continued

SEQ ID NO: 2, Optimized F protein encoding DNA nucleotide sequence:
GGATTCCTGCTGGGCGTGGGAAGCGCTATCGCTTCTGGAATTGCCGTGAG

CAAGGTGCTGCACCTGGAAGGCGAGGTGAACAAGATCAAGTCTGCCCTGCTGTC

CACCAACAAGGCCGTAGTCAGCCTGAGCAATGGCGTGAGCGTCCTGACCAGTAA

GGTGCTGGACCTGAAGAACTACATCGACAAGCAGCTGCTGCCTATCGTGAACAA

GCAGAGCTGCTCCATCAGCAATATTGAGACTGTGATCGAATTCCAGCAGAAGAA

CAACCGGCTGCTGGAGATCACCAGAGAGTTCTCCGTGAACGCTGGCGTGACTAC

ACCTGTTTCAACCTACATGCTGACCAATTCTGAGCTGCTGAGCCTGATCAACGAC

ATGCCTATCACCAACGACCAGAAAAAACTGATGTCCAATAACGTTCAAATCGTG

CGGCAGCAAAGCTACAGCATCATGAGCATCATCAAGGAAGAAGTGCTTGCCTAC

GTGGTCCAGCTGCCACTTTATGGAGTTATCGATACACCCTGCTGGAAGCTGCACA

CCAGCCCTCTGTGTACAACCAACACCAAGGAAGGCAGCAACATCTGCCTGACCA

GAACAGATAGAGGCTGGTATTGTGATAACGCCGGCAGCGTGAGCTTCTTCCCCC

AGGCCGACACATGTAAAGTGCAGAGCAATAGAGTGTTCTGCGACACCATGAATA

GCCTGACCCTGCCCAGCGAGGTGAATCTGTGTAACATCGACATTTTCAACCCCAA

GTACGATTGCAAGATCATGACCTCCAAGACCGACGTGAGCAGCAGCGTGATCAC

CTCCCTGGGCGCCATCGTGTCTTGCTACGGCAAGACCAAGTGCACAGCCTCTAAC

AAAAATCGCGGCATCATCAAAACCTTCTCTAACGGTTGTGACTACGTGTCAAACA

AAGGCGTGGACACCGTGTCCGTGGGCAACACCCTGTATTACGTGAACAAGCAGG

AGGGCAAGAGCCTGTACGTGAAGGGCGAACCTATTATCAACTTCTACGACCCTCT

GGTGTTTCCTTCCGACGAGTTTGATGCTAGCATCTCTCAGGTGAACGAGAAGATC

AACCAGAGCCTGGCCTTTATCAGAAAGAGCGATGAGCTGCTGCACAACGTGAAC

GCCGGCAAGAGTACCACCAACATCATGATCACCACCATCATTATCGTGATCATCG

TGATCCTCCTGAGCCTGATCGCTGTCGGACTGCTGCTGTACTGCAAGGCCAGGAG

CACACCTGTGACCCTGAGCAAGGACCAACTGTCTGGCATCAACAACATCGCTTTT

AGCAAT

SEQ ID NO: 3, Optimized protein fragment with no transmembrane domain:
GFLLGVGSAIASGIAVSKVLHLEGEVNKIKSALLSTNKAVVSLSNGVSVLTSK

VLDLKNYIDKQLLPIVNKQSCSISNIETVIEFQQKNNRLLEITREFSVNAGVTTPVSTY

MLTNSELLSLINDMPITNDQKKLMSNNVQIVRQQSYSIMSIIKEEVLAYVVQLPLYGV

IDTPCWKLHTSPLCTTNTKEGSNICLTRTDRGWYCDNAGSVSFFPQADTCKVQSNRV

FCDTMNSLTLPSEVNLCNIDIFNPKYDCKIMTSKTDVSSSVITSLGAIVSCYGKTKCTA

SNKNRGIIKTFSNGCDYVSNKGVDTVSVGNTLYYVNKQEGKSLYVKGEPIINFYDPL

VFPSDEFDASISQVNEKINQSLAFIRKSDELLHNVNAGKSTTNIMITGYIPEAPRDGQA

YVRKDGEWVLLSTFLG

SEQ ID NO: 4, DNA sequence of Optimized protein without transmembrane domain:
GGATTCCTGCTGGGCGTGGGAAGCGCTATCGCTTCTGGAATTGCCGTGAG

CAAGGTGCTGCACCTGGAAGGCGAGGTGAACAAGATCAAGTCTGCCCTGCTGTC

CACCAACAAGGCCGTAGTCAGCCTGAGCAATGGCGTGAGCGTCCTGACCAGTAA

GGTGCTGGACCTGAAGAACTACATCGACAAGCAGCTGCTGCCTATCGTGAACAA

GCAGAGCTGCTCCATCAGCAATATTGAGACTGTGATCGAATTCCAGCAGAAGAA

CAACCGGCTGCTGGAGATCACCAGAGAGTTCTCCGTGAACGCTGGCGTGACTAC

-continued

ACCTGTTTCAACCTACATGCTGACCAATTCTGAGCTGCTGAGCCTGATCAACGAC

ATGCCTATCACCAACGACCAGAAAAAACTGATGTCCAATAACGTTCAAATCGTG

CGGCAGCAAAGCTACAGCATCATGAGCATCATCAAGGAAGAAGTGCTTGCCTAC

GTGGTCCAGCTGCCACTTTATGGAGTTATCGATACACCCTGCTGGAAGCTGCACA

CCAGCCCTCTGTGTACAACCAACACCAAGGAAGGCAGCAACATCTGCCTGACCA

GAACAGATAGAGGCTGGTATTGTGATAACGCCGGCAGCGTGAGCTTCTTCCCCC

AGGCCGACACATGTAAAGTGCAGAGCAATAGAGTGTTCTGCGACACCATGAATA

GCCTGACCCTGCCCAGCGAGGTGAATCTGTGTAACATCGACATTTTCAACCCCAA

GTACGATTGCAAGATCATGACCTCCAAGACCGACGTGAGCAGCAGCGTGATCAC

CTCCCTGGGCGCCATCGTGTCTTGCTACGGCAAGACCAAGTGCACAGCCTCTAAC

AAAAATCGCGGCATCATCAAAACCTTCTCTAACGGTTGTGACTACGTGTCAAACA

AAGGCGTGGACACCGTGTCCGTGGGCAACACCCTGTATTACGTGAACAAGCAGG

AGGGCAAGAGCCTGTACGTGAAGGGCGAACCTATTATCAACTTCTACGACCCTCT

GGTGTTTCCTTCCGACGAGTTTGATGCTAGCATCTCTCAGGTGAACGAGAAGATC

AACCAGAGCCTGGCCTTTATCAGAAAGAGCGATGAGCTGCTGCACAACGTGAAC

GCCGGCAAGAGTACCACCAACATCATGATCACCGGATACATCCCGGAGGCCCCT

AGGGACGGTCAAGCTTACGTGAGAAAGGACGGCGAATGGGTTCTGCTGTCGACC

TTCTTGGGA

SEQ ID NO 5, Optimized Vaccine F3 protein fragment with S155C, S190F, V207L S290C with transmembrane domain:
LGFLLGVGSAIASGIAVCKVLHLEGEVNKIKSALLSTNKAVVSLSNGVSVLTF

KVLDLKNYIDKQLLPILNKQSCSISNIETVIEFQQKNNRLLEITREFSVNAGVTTPVSTY

MLTNSELLSLINDMPITNDQKKLMSNNVQIVRQQSYSIMCIIKEEVLAYVVQLPLYGV

IDTPCWKLHTSPLCTTNTKEGSNICLTRTDRGWYCDNAGSVSFFPQADTCKVQSNRV

FCDTMNSLTLPSEVNLCNIDIFNPKYDCKIMTSKTDVSSSVITSLGAIVSCYGKTKCTA

SNKNRGIIKTFSNGCDYVSNKGVDTVSVGNTLYYVNKQEGKSLYVKGEPIINFYDPL

VFPSDEFDASISQVNEKINQSLAFIRKSDELLHNVNAGKSTTNIMITTIIIVIIVILLSLIA

VGLLLYCKARSTPVTLSKDQLSGINNIAFSN

SEQ ID NO: 6: DNA sequence of mutant F Optimized protein with S155C, S190F, V207L S290C:
GGATTCCTGCTGGGCGTGGGAAGCGCTATCGCTTCTGGAATTGCCGTGTG

CAAGGTGCTGCACCTGGAAGGCGAGGTGAACAAGATCAAGTCTGCCCTGCTGTC

CACCAACAAGGCCGTAGTCAGCCTGAGCAATGGCGTGAGCGTCCTGACCTTTAA

GGTGCTGGACCTGAAGAACTACATCGACAAGCAGCTGCTGCCTATCTTGAACAA

GCAGAGCTGCTCCATCAGCAATATTGAGACTGTGATCGAATTCCAGCAGAAGAA

CAACCGGCTGCTGGAGATCACCAGAGAGTTCTCCGTGAACGCTGGCGTGACTAC

ACCTGTTTCAACCTACATGCTGACCAATTCTGAGCTGCTGAGCCTGATCAACGAC

ATGCCTATCACCAACGACCAGAAAAAACTGATGTCCAATAACGTTCAAATCGTG

CGGCAGCAAAGCTACAGCATCATGTGCATCATCAAGGAAGAAGTGCTTGCCTAC

GTGGTCCAGCTGCCACTTTATGGAGTTATCGATACACCCTGCTGGAAGCTGCACA

CCAGCCCTCTGTGTACAACCAACACCAAGGAAGGCAGCAACATCTGCCTGACCA

GAACAGATAGAGGCTGGTATTGTGATAACGCCGGCAGCGTGAGCTTCTTCCCCC

-continued

AGGCCGACACATGTAAAGTGCAGAGCAATAGAGTGTTCTGCGACACCATGAATA

GCCTGACCCTGCCCAGCGAGGTGAATCTGTGTAACATCGACATTTTCAACCCCAA

GTACGATTGCAAGATCATGACCTCCAAGACCGACGTGAGCAGCAGCGTGATCAC

CTCCCTGGGCGCCATCGTGTCTTGCTACGGCAAGACCAAGTGCACAGCCTCTAAC

AAAAATCGCGGCATCATCAAAACCTTCTCTAACGGTTGTGACTACGTGTCAAACA

AAGGCGTGGACACCGTGTCCGTGGGCAACACCCTGTATTACGTGAACAAGCAGG

AGGGCAAGAGCCTGTACGTGAAGGGCGAACCTATTATCAACTTCTACGACCCTCT

GGTGTTTCCTTCCGACGAGTTTGATGCTAGCATCTCTCAGGTGAACGAGAAGATC

AACCAGAGCCTGGCCTTTATCAGAAAGAGCGATGAGCTGCTGCACAACGTGAAC

GCCGGCAAGAGTACCACCAACATCATGATCACCACCATCATTATCGTGATCATCG

TGATCCTCCTGAGCCTGATCGCTGTCGGACTGCTGCTGTACTGCAAGGCCAGGAG

CACACCTGTGACCCTGAGCAAGGACCAACTGTCTGGCATCAACAACATCGCTTTT

AGCAAT

SEQ ID NO: 7, mutant F Optimized protein fragment with S155C, S190F, V207L S290C and no transmembrane domain:
LGFLLGVGSAIASGIAVCKVLHLEGEVNKIKSALLSTNKAVVSLSNGVSVLTF

KVLDLKNYIDKQLLPILNKQSCSISNIETVIEFQQKNNRLLEITREFSVNAGVTTPVSTY

MLTNSELLSLINDMPITNDQKKLMSNNVQIVRQQSYSIMCIIKEEVLAYVVQLPLYGV

IDTPCWKLHTSPLCTTNTKEGSNICLTRTDRGWYCDNAGSVSFFPQADTCKVQSNRV

FCDTMNSLTLPSEVNLCNIDIFNPKYDCKIMTSKTDVSSSVITSLGAIVSCYGKTKCTA

SNKNRGIIKTFSNGCDYVSNKGVDTVSVGNTLYYVNKQEGKSLYVKGEPIINFYDPL

VFPSDEFDASISQVNEKINQSLAFIRKSDELLHNVNAGKSTTNIMITGYIPEAPRDGQA

YVRKDGEWVLLSTFLG

SEQ ID NO: 8: DNA sequence of , mutant F Optimized protein with S155C, S190F, V207L S290C and no transmembrane domain:
GGATTCCTGCTGGGCGTGGGAAGCGCTATCGCTTCTGGAATTGCCGTGTG

CAAGGTGCTGCACCTGGAAGGCGAGGTGAACAAGATCAAGTCTGCCCTGCTGTC

CACCAACAAGGCCGTAGTCAGCCTGAGCAATGGCGTGAGCGTCCTGACCTTTAA

GGTGCTGGACCTGAAGAACTACATCGACAAGCAGCTGCTGCCTATCTTGAACAA

GCAGAGCTGCTCCATCAGCAATATTGAGACTGTGATCGAATTCCAGCAGAAGAA

CAACCGGCTGCTGGAGATCACCAGAGAGTTCTCCGTGAACGCTGGCGTGACTAC

ACCTGTTTCAACCTACATGCTGACCAATTCTGAGCTGCTGAGCCTGATCAACGAC

ATGCCTATCACCAACGACCAGAAAAAACTGATGTCCAATAACGTTCAAATCGTG

CGGCAGCAAAGCTACAGCATCATGTGCATCATCAAGGAAGAAGTGCTTGCCTAC

GTGGTCCAGCTGCCACTTTATGGAGTTATCGATACACCCTGCTGGAAGCTGCACA

CCAGCCCTCTGTGTACAACCAACACCAAGGAAGGCAGCAACATCTGCCTGACCA

GAACAGATAGAGGCTGGTATTGTGATAACGCCGGCAGCGTGAGCTTCTTCCCCC

AGGCCGACACATGTAAAGTGCAGAGCAATAGAGTGTTCTGCGACACCATGAATA

GCCTGACCCTGCCCAGCGAGGTGAATCTGTGTAACATCGACATTTTCAACCCCAA

GTACGATTGCAAGATCATGACCTCCAAGACCGACGTGAGCAGCAGCGTGATCAC

CTCCCTGGGCGCCATCGTGTCTTGCTACGGCAAGACCAAGTGCACAGCCTCTAAC

AAAAATCGCGGCATCATCAAAACCTTCTCTAACGGTTGTGACTACGTGTCAAACA

AAGGCGTGGACACCGTGTCCGTGGGCAACACCCTGTATTACGTGAACAAGCAGG

-continued

AGGGCAAGAGCCTGTACGTGAAGGGCGAACCTATTATCAACTTCTACGACCCTCT

GGTGTTTCCTTCCGACGAGTTTGATGCTAGCATCTCTCAGGTGAACGAGAAGATC

AACCAGAGCCTGGCCTTTATCAGAAAGAGCGATGAGCTGCTGCACAACGTGAAC

GCCGGCAAGAGTACCACCAACATCATGATCACCGGATACATCCCGGAGGCCCCT

AGGGACGGTCAAGCTTACGTGAGAAAGGACGGCGAATGGGTTCTGCTGTCGACC

TTCTTGGGA

SEQ ID NO: 9, mutant F Optimized protein fragment with 155C, S190F, V207L, S290C, D486H, E487Q, F484W, and D489H with transmembrane domain:
LGFLLGVGSAIASGIAVCKVLHLEGEVNKIKSALLSTNKAVVSLSNGVSVLTF

KVLDLKNYIDKQLLPILNKQSCSISNIETVIEFQQKNNRLLEITREFSVNAGVTTPVSTY

MLTNSELLSLINDMPITNDQKKLMSNNVQIVRQQSYSIMCIIKEEVLAYVVQLPLYGV

IDTPCWKLHTSPLCTTNTKEGSNICLTRTDRGWYCDNAGSVSFFPQADTCKVQSNRV

FCDTMNSLTLPSEVNLCNIDIFNPKYDCKIMTSKTDVSSSVITSLGAIVSCYGKTKCTA

SNKNRGIIKTFSNGCDYVSNKGVDTVSVGNTLYYVNKQEGKSLYVKGEPIINFYDPL

VFPSHQWHASISQVNEKINQSLAFIRKSDELLHNVNAGKSTTNIMITTIIIVIIVILLSLIA

VGLLLYCKARSTPVTLSKDQLSGINNIAFSN

SEQ ID NO: 10: DNA Sequence of mutant F Optimized protein with 155C, S190F, V207L, S290C, D486H, E487Q, F484W, and D489H and transmembrane domain:
GGATTCCTGCTGGGCGTGGGAAGCGCTATCGCTTCTGGAATTGCCGTGTG

CAAGGTGCTGCACCTGGAAGGCGAGGTGAACAAGATCAAGTCTGCCCTGCTGTC

CACCAACAAGGCCGTAGTCAGCCTGAGCAATGGCGTGAGCGTCCTGACCTTTAA

GGTGCTGGACCTGAAGAACTACATCGACAAGCAGCTGCTGCCTATCTTGAACAA

GCAGAGCTGCTCCATCAGCAATATTGAGACTGTGATCGAATTCCAGCAGAAGAA

CAACCGGCTGCTGGAGATCACCAGAGAGTTCTCCGTGAACGCTGGCGTGACTAC

ACCTGTTTCAACCTACATGCTGACCAATTCTGAGCTGCTGAGCCTGATCAACGAC

ATGCCTATCACCAACGACCAGAAAAAACTGATGTCCAATAACGTTCAAATCGTG

CGGCAGCAAAGCTACAGCATCATGTGCATCATCAAGGAAGAAGTGCTTGCCTAC

GTGGTCCAGCTGCCACTTTATGGAGTTATCGATACACCCTGCTGGAAGCTGCACA

CCAGCCCTCTGTGTACAACCAACACCAAGGAAGGCAGCAACATCTGCCTGACCA

GAACAGATAGAGGCTGGTATTGTGATAACGCCGGCAGCGTGAGCTTCTTCCCCC

AGGCCGACACATGTAAAGTGCAGAGCAATAGAGTGTTCTGCGACACCATGAATA

GCCTGACCCTGCCCAGCGAGGTGAATCTGTGTAACATCGACATTTTCAACCCCAA

GTACGATTGCAAGATCATGACCTCCAAGACCGACGTGAGCAGCAGCGTGATCAC

CTCCCTGGGCGCCATCGTGTCTTGCTACGGCAAGACCAAGTGCACAGCCTCTAAC

AAAAATCGCGGCATCATCAAAACCTTCTCTAACGGTTGTGACTACGTGTCAAACA

AAGGCGTGGACACCGTGTCCGTGGGCAACACCCTGTATTACGTGAACAAGCAGG

AGGGCAAGAGCCTGTACGTGAAGGGCGAACCTATTATCAACTTCTACGACCCTCT

GGTGTTTCCTTCCCACCAGTGGCATGCTAGCATCTCTCAGGTGAACGAGAAGATC

AACCAGAGCCTGGCCTTTATCAGAAAGAGCGATGAGCTGCTGCACAACGTGAAC

GCCGGCAAGAGTACCACCAACATCATGATCACCACCATCATTATCGTGATCATCG

TGATCCTCCTGAGCCTGATCGCTGTCGGACTGCTGCTGTACTGCAAGGCCAGGAG

-continued

CACACCTGTGACCCTGAGCAAGGACCAACTGTCTGGCATCAACAACATCGCTTTT

AGCAAT

SEQ ID NO: 11, optimized F Protein fragment with s155C, S190F, V207L, S290C, D486H, E487Q, F484W, and D489H and no transmembrane domain:
LGFLLGVGSAIASGIAVCKVLHLEGEVNKIKSALLSTNKAVVSLSNGVSVLTF

KVLDLKNYIDKQLLPILNKQSCSISNIETVIEFQQKNNRLLEITREFSVNAGVTTPVSTY

MLTNSELLSLINDMPITNDQKKLMSNNVQIVRQQSYSIMCIIKEEVLAYVVQLPLYGV

IDTPCWKLHTSPLCTTNTKEGSNICLTRTDRGWYCDNAGSVSFFPQADTCKVQSNRV

FCDTMNSLTLPSEVNLCNIDIFNPKYDCKIMTSKTDVSSSVITSLGAIVSCYGKTKCTA

SNKNRGIIKTFSNGCDYVSNKGVDTVSVGNTLYYVNKQEGKSLYVKGEPIINFYDPL

VFPSHQWHASISQVNEKINQSLAFIRKSDELLHNVNAGKSTTNIMITGYIPEAPRDGQ

AYVRKDGEWVLLSTFLG

SEQ ID NO: 12, DNA sequence of F Protein Optimized with s155C, S190F, V207L, S290C, D486H, E487Q, F484W, and D489H and no transmembrane domain:
GGATTCCTGCTGGGCGTGGGAAGCGCTATCGCTTCTGGAATTGCCGTGTG

CAAGGTGCTGCACCTGGAAGGCGAGGTGAACAAGATCAAGTCTGCCCTGCTGTC

CACCAACAAGGCCGTAGTCAGCCTGAGCAATGGCGTGAGCGTCCTGACCTTTAA

GGTGCTGGACCTGAAGAACTACATCGACAAGCAGCTGCTGCCTATCTTGAACAA

GCAGAGCTGCTCCATCAGCAATATTGAGACTGTGATCGAATTCCAGCAGAAGAA

CAACCGGCTGCTGGAGATCACCAGAGAGTTCTCCGTGAACGCTGGCGTGACTAC

ACCTGTTTCAACCTACATGCTGACCAATTCTGAGCTGCTGAGCCTGATCAACGAC

ATGCCTATCACCAACGACCAGAAAAAACTGATGTCCAATAACGTTCAAATCGTG

CGGCAGCAAAGCTACAGCATCATGTGCATCATCAAGGAAGAAGTGCTTGCCTAC

GTGGTCCAGCTGCCACTTTATGGAGTTATCGATACACCCTGCTGGAAGCTGCACA

CCAGCCCTCTGTGTACAACCAACACCAAGGAAGGCAGCAACATCTGCCTGACCA

GAACAGATAGAGGCTGGTATTGTGATAACGCCGGCAGCGTGAGCTTCTTCCCCC

AGGCCGACACATGTAAAGTGCAGAGCAATAGAGTGTTCTGCGACACCATGAATA

GCCTGACCCTGCCCAGCGAGGTGAATCTGTGTAACATCGACATTTTCAACCCCAA

GTACGATTGCAAGATCATGACCTCCAAGACCGACGTGAGCAGCAGCGTGATCAC

CTCCCTGGGCGCCATCGTGTCTTGCTACGGCAAGACCAAGTGCACAGCCTCTAAC

AAAAATCGCGGCATCATCAAAACCTTCTCTAACGGTTGTGACTACGTGTCAAACA

AAGGCGTGGACACCGTGTCCGTGGGCAACACCCTGTATTACGTGAACAAGCAGG

AGGGCAAGAGCCTGTACGTGAAGGGCGAACCTATTATCAACTTCTACGACCCTCT

GGTGTTTCCTTCCCACCAGTGGCATGCTAGCATCTCTCAGGTGAACGAGAAGATC

AACCAGAGCCTGGCCTTTATCAGAAAGAGCGATGAGCTGCTGCACAACGTGAAC

GCCGGCAAGAGTACCACCAACATCATGATCACCGGATACATCCCGGAGGCCCCT

AGGGACGGTCAAGCTTACGTGAGAAAGGACGGCGAATGGGTTCTGCTGTCGACC

TTCTTGGGA

SEQ ID NO: 13 RNA Sequence of optimized F Protein fragment with s155C, S190F, V207L, S290C, D486H, E487Q, F484W, and D489H and TM domain:
GGAUUCCUGCUGGGCGUGGGAAGCGCUAUCGCUUCUGGAAUUGCCGUG

UGCAAGGUGCUGCACCUGGAAGGCGAGGUGAACAAGAUCAAGUCUGCCCUGCU

GUCCACCAACAAGGCCGUAGUCAGCCUGAGCAAUGGCGUGAGCGUCCUGACCU

-continued

UUAAGGUGCUGGACCUGAAGAACUACAUCGACAAGCAGCUGCUGCCUAUCUUG

AACAAGCAGAGCUGCUCCAUCAGCAAUAUUGAGACUGUGAUCGAAUUCCAGCA

GAAGAACAACCGGCUGCUGGAGAUCACCAGAGAGUUCUCCGUGAACGCUGGCG

UGACUACACCUGUUUCAACCUACAUGCUGACCAAUUCUGAGCUGCUGAGCCUG

AUCAACGACAUGCCUAUCACCAACGACCAGAAAAAACUGAUGUCCAAUAACGU

UCAAAUCGUGCGGCAGCAAAGCUACAGCAUCAUGUGCAUCAUCAAGGAAGAA

GUGCUUGCCUACGUGGUCCAGCUGCCACUUUAUGGAGUUAUCGAUACACCCUG

CUGGAAGCUGCACACCAGCCCUCUGUGUACAACCAACACCAAGGAAGGCAGCA

ACAUCUGCCUGACCAGAACAGAUAGAGGCUGGUAUUGUGAUAACGCCGGCAGC

GUGAGCUUCUUCCCCCAGGCCGACACAUGUAAAGUGCAGAGCAAUAGAGUGUU

CUGCGACACCAUGAAUAGCCUGACCCUGCCCAGCGAGGUGAAUCUGUGUAACA

UCGACAUUUUCAACCCCAAGUACGAUUGCAAGAUCAUGACCUCCAAGACCGAC

GUGAGCAGCAGCGUGAUCACCUCCCUGGGCGCCAUCGUGUCUUGCUACGGCAA

GACCAAGUGCACAGCCUCUAACAAAAAUCGCGGCAUCAUCAAAACCUUCUCUA

ACGGUUGUGACUACGUGUCAAACAAAGGCGUGGACACCGUGUCCGUGGGCAAC

ACCCUGUAUUACGUGAACAAGCAGGAGGGCAAGAGCCUGUACGUGAAGGGCG

AACCUAUUAUCAACUUCUACGACCCUCUGGUGUUUCCUUCCCACCAGUGGCAU

GCUAGCAUCUCUCAGGUGAACGAGAAGAUCAACCAGAGCCUGGCCUUUAUCAG

AAAGAGCGAUGAGCUGCUGCACAACGUGAACGCCGGCAAGAGUACCACCAACA

UCAUGAUCACCACCAUCAUUAUCGUGAUCAUCGUGAUCCUCCUGAGCCUGAUC

GCUGUCGGACUGCUGCUGUACUGCAAGGCCAGGAGCACACCUGUGACCCUGAG

CAAGGACCAACUGUCUGGCAUCAACAACAUCGCUUUUAGCAAU

SEQ ID NO: 14: RSV transmembrane domain
MITTIIIVIIVILLSLIAVGLLLYC

SEQ ID NO: 15, DNA sequence of polyA signal HSV:
CGGCAATAAAAAGACAGAATAAAACGCACGGTGTTGGGTCGTTTGTTC SEQ ID NO: 16, RNA sequence of polyA signal HSV:
CGGCAAUAAAAAGACAGAAUAAAACGCACGGUGUUGGGUCGUUUGUUC SEQ ID NO: 17, DNA sequence of 3' UTR:
GCTCGCTTTCTTGCTGTCCAATTTCTATTAAAGGTTCCTTTGTTCCCTAAGTCC

AACTACTAAACTGGGGGATATTATGAAGGGCCTTGAGCATCTGGATTCTGCCTAATA

AAAAACATTTATTTTCATTGC

SEQ ID NO: 18, RNA sequence of 3' UTR:
GCUCGCUUUCUUGCUGUCCAAUUUCUAUUAAAGGUUCCUUUGUUCCCUAA

GUCCAACUACUAAACUGGGGGAUAUUAUGAAGGGCCUUGAGCAUCUGGAUUCUGC

CUAAUAAAAAACAUUUAUUUUCAUUGC

SEQ ID NO: 19, DNA sequence of ß-globulin 5'UTR:
ACATTTGCTTCTGACACAACTGTGTTCACTAGCAACCTCAAACAGACACC SEQ ID NO: 20, RNA sequence of ß-globulin 5'UTR:
ACAUUUGCUUCUGACACAACUGUGUUCACUAGCAACCUCAAACAGACACC SEQ ID NO: 21, DNA sequence of SYS UTR 2.0:
GGCGCTCGAGCAGGTTCAGAAGGAGATCAAAAACCCCCAAGGATCAAACGC

CACC

-continued

SEQ ID NO: 22, RNA sequence of SYS UTR 2.0:
GGCGCUCGAGCAGGUUCAGAAGGAGAUCAAAAACCCCCAAGGAUCAAACGC

CACC

SEQ ID NO: 23, DNA sequence of SYS UTR 1.0:
GGGCGCTCGAGCAGGTTCAGAAGGAGATCAAAAACCCCCAAGGATCAAAC SEQ ID NO: 24, RNA sequence of SYS UTR 1.0:
GGGCGCUCGAGCAGGUUCAGAAGGAGAUCAAAAACCCCCAAGGAUCAAAC SEQ ID NO: 25, DNA sequence of SYS4 5'UTR:
GGCGCACGAGCAGGGAGAGAAGGAGATCAAAAACCCCCAAGGATCAAACGC

CACC

SEQ ID NO: 26, RNA sequence of SYS4 5'UTR:
GGCGCACGAGCAGGGAGAGAAGGAGAUCAAAAACCCCCAAGGAUCAAACG

CCACC

SEQ ID NO: 27, DNA and RNA sequence of polyA 40:
AAAAAAAAAAAAAAAAAAAAAAAAAAAAAAAAAAAAAAAA SEQ ID NO: 28, DNA and RNA sequence of polyA 60:
AAAAAAAAAAAAAAAAAAAAAAAAAAAAAAAAAAAAAAAAAAAAAAAAAA

AAAAAAAAAAGAAAAAAAAAAAAAAAAAAAAAAAAAAAAAAAAAAAAAAAAAAA

AAAAAAAAAAAAAAAAA

SEQ ID NO: 29, plasmid DNA sequence:
TCGCGCGTTTCGGTGATGACGGTGAAAACCTCTGACACATGCAGCTCCCGGA

GACGGTCACAGCTTGTCTGTAAGCGGATGCCGGGAGCAGACAAGCCCGTCAGGGCG

CGTCAGCGGGTGTTGGCGGGTGTCGGGGCTGGCTTAACTATGCGGCATCAGAGCAGA

TTGTACTGAGAGTGCACCATATGCGGTGTGAAATACCGCACAGATGCGTAAGGAGA

AAATACCGCATCAGGCGCCATTCGCCATTCAGGCTGCGCAACTGTTGGGAAGGGCGA

TCGGTGCGGGCCTCTTCGCTATTACGCCAGCTGGCGAAAGGGGGATGTGCTGCAAGG

CGATTAAGTTGGGTAACGCCAGGGTTTTCCCAGTCACGACGTTGTAAAACGACGGCC

AGTGAATTCGAGCTCGGTACCTCGCGAATGCATCTAGATATCGGATCCCGGGCCCGT

CGACTGCAGAGGCCTGCATGCAAGCTTTAATACGACTCACTATAAGGACATTTGCTT

CTGACACAACTGTGTTCACTAGCAACCTCAAACAGACACCGCCACCATGTTCGTGTT

CCTGGTGCTGCTGCCTCTGGTCAGCAGCCAGTGCGTGAACCTGAGAACAAGAACACA

GCTTCCTCCAGCCTACACAAACTCTTTTACACGGGGCGTGTACTATCCTGACAAGGTG

TTCCGGTCCAGCGTGCTGCACTCAACCCAAGACCTGTTCCTGCCCTTCTTCAGCAACG

TCACCTGGTTCCACGCCATCCACGTGTCTGGCACCAATGGCACAAAGCGATTCGATA

ACCCCGTGCTGCCTTTCAACGACGGCGTGTACTTTGCCTCCATCGAGAAGTCCAACAT

CATCCGGGGCTGGATCTTCGGGACCACACTGGATAGCAAGACCCAGTCTCTGCTGAT

CGTAAACAACGCCACCAACGTGGTCATCAAGGTGTGCGAGTTCCAGTTCTGCAACGA

CCCTTTCCTCGATGTGTACTACCACAAGAACAACAAGTCTTGGATGGAATCGGGCGT

GTATAGCAGCGCCAACAACTGCACCTTCGAATACGTGAGCCAGCCTTTCCTGATGGA

CCTGGAAGGCAAACAAGGCAATTTTAAGAACCTGAGAGAATTCGTGTTCAAAAATAT

AGACGGCTATTTCAAGATCTACAGCAAGCACACCCCTATTAATCTGGTGCGGGATCT

GCCTCAGGGCTTCAGCGCCCTCGAACCTCTGGTGGACCTGCCAATCGGCATCAACAT

TACAAGATTCCAGACGCTGCTCGCTCTGCACAGATCTTACCTGACCCCTGGCGACAG

CAGCAGCGGCTGGACCGCCGGCGCCGCCGCTTACTACGTGGGCTACCTGCAGCCTAG

-continued

AACCTTTCTGCTGAAGTACAACGAGAACGGCACCATCACTGATGCCGTGGATTGCGC

CCTGGACCCTCTGTCCGAAACCAAATGTACACTGAAGTCTTTTACCGTGGAAAAAGG

AATCTACCAGACTTCCAACTTCCGGGTGCAGCCGACCGAGAGCATCGTGCGGTTCCC

TAACATCACAAACCTGTGCCCCTTTGGCGAGGTGTTCAACGCCACAAGATTTGCTAG

CGTGTACGCCTGGAATAGAAAGAGAATCAGCAACTGCGTGGCCGATTACAGCGTGCT

GTACAATAGCGCCTCTTTCAGCACCTTCAAATGCTACGGCGTGAGCCCCACCAAGCT

GAACGATCTGTGTTTTACAAACGTGTATGCCGACTCATTCGTAATCAGGGGCGATGA

GGTGAGACAGATCGCTCCTGGACAGACAGGCAAAATCGCGGACTACAACTATAAGC

TGCCTGATGACTTCACAGGATGTGTGATCGCATGGAACTCCAATAACCTCGACAGCA

AGGTGGGCGGAAATTACAATTACCGCTACAGACTGTTTAGAAAGAGCAATCTGAAA

CCTTTCGAGAGAGACATCAGCACAGAGATCTACCAGGCCGGCAGCAAGCCCTGTAA

CGGCGTCGAGGGCTTCAACTGCTACTTCCCCCTGCAGAGCTACGGCTTCCAGCCTAC

CAACGGCGTGGGATACCAGCCTTACAGAGTGGTGGTGCTGAGCTTCGAGCTGCTGCA

TGCTCCTGCTACAGTGTGTGGTCCTAAGAAGAGCACCAACCTGGTTAAGAACAAGTG

CGTGAATTTTAACTTCAATGGACTGACCGGAACCGGCGTGCTGACCGAAAGCAACAA

GAAATTCCTGCCTTTTCAGCAGTTTGGCAGAGACATCGCCGACACCACCGACGCCGT

GAGAGATCCACAAACCCTGGAAATCCTGGACATCACACCTTGCTCATTTGGAGGGGT

GTCGGTGATCACACCTGGCACCAACACCAGCAACCAGGTGGCCGTGCTGTACCAGGG

AGTGAATTGTACCGAGGTCCCCGTGGCCATTCACGCCGACCAGCTGACCCCTACCTG

GCGGGTGTACTCCACCGGCTCTAACGTATTCCAGACCAGAGCCGGCTGTCTGATCGG

CGCAGAACACGTGAACAATAGCTACGAGTGCGACATCCCTATCGGAGCCGGGATCT

GCGCTAGCTACCAGACCCAGACAAACTCCAGAAGCAGAGCCGGAAGCGTGGCCAGC

CAGTCTATCATCGCCTACACCATGAGCCTGGGCGCCGAAAACAGCGTTGCCTACAGC

AACAATTCTATCGCCATCCCTACAAACTTCACCATCTCCGTGACCACCGAGATCCTGC

CTGTCAGCATGACAAAGACCAGCGTAGACTGCACAATGTACATCTGCGGAGATTCCA

CCGAGTGTAGTAACCTCCTGCTGCAATACGGATCTTTCTGTACTCAGCTGAACAGAG

CCCTGACCGGCATCGCCGTTGAACAGGACAAGAACACCCAGGAGGTTTTCGCCCAGG

TTAAGCAGATCTACAAAACCCCTCCTATCAAGGACTTCGGAGGCTTTAACTTCTCCCA

GATCCTGCCCGACCCCAGCAAGCCCAGCAAGCGGAGCCCCATCGAGGACCTGCTGTT

CAACAAGGTGACCCTGGCCGACGCCGGCTTCATCAAACAGTACGGCGATTGCCTGGG

AGACATCGCCGCTAGAGATCTAATTTGCGCCCAAAAGTTTAACGGCCTGACAGTGCT

GCCTCCACTGCTGACAGACGAGATGATCGCCCAGTACACATCTGCCCTGCTGGCTGG

TACCATCACATCTGGCTGGACCTTTGGCGCCGGCCCCGCCCTCCAGATCCCTTTCCCC

ATGCAGATGGCCTACCGGTTCAACGGCATCGGCGTGACCCAGAACGTGCTGTACGAA

AACCAGAAACTGATCGCCAACCAGTTCAATAGCGCGATCGGCAAAATCCAGGATAG

CCTCAGCTCTACACCCAGCGCTCTTGGCAAGCTGCAAAACGTGGTGAACCAGAATGC

CCAGGCCCTTAACACCCTGGTGAAGCAGCTATCCTCTAATTTCGGTGCCATCAGCAG

CGTGCTGAATGATATCCTGAGCAGACTGGACCCCCCTGAGGCCGAAGTGCAGATCGA

CAGACTGATCACCGGAAGACTGCAGAGCCTGCAAACCTACGTGACCCAGCAACTGA

TCCGGGCCGCAGAAATCCGGGCCTCCGCTAACCTGGCCGCTACCAAGATGAGCGAGT

GCGTGCTGGGTCAAAGCAAGCGCGTGGACTTCTGTGGAAAAGGCTACCACCTGATGA

-continued

GCTTCCCTCAGAGCGCTCCACACGGCGTGGTGTTCCTGCATGTGACTTACGTGCCTGC

CCAGGAAAAGAACTTCACCACCGCCCCTGCCATTTGTCACGACGGCAAGGCCCACTT

CCCCCGGGAAGGCGTGTTTGTGTCTAACGGAACACACTGGTTTGTGACTCAAAGAAA

CTTCTACGAGCCACAGATCATCACCACAGATAACACCTTCGTCAGCGGCAACTGCGA

CGTGGTGATCGGCATCGTGAACAATACTGTGTACGACCCCCTGCAGCCAGAGCTCGA

TTCTTTCAAAGAGGAACTGGATAAGTACTTCAAGAACCACACATCCCCCGACGTCGA

CCTGGGCGATATCAGCGGCATTAACGCCAGCGTGGTGAACATCCAGAAGGAAATCG

ATAGACTGAACGAGGTGGCAAAGAACCTGAATGAGTCCCTGATTGACCTGCAAGAG

CTCGGGAAGTACGAGCAGTATATCAAGTGGCCTTGGTACATCTGGCTGGGCTTCATC

GCGGGCCTGATCGCCATCGTTATGGTGACGATCATGCTGTGCTGCATGACCAGTTGC

TGTAGCTGCCTGAAGGGCTGCTGCAGCTGCGGCAGCTGTTGCAAGTTCGACGAGGAC

GACAGCGAGCCTGTGCTGAAGGGCGTTAAGCTGCACTACACCTGAGCTCGCTTTCTT

GCTGTCCAATTTCTATTAAAGGTTCCTTTGTTCCCTAAGTCCAACTACTAAACTGGGG

GATATTATGAAGGGCCTTGAGCATCTGGATTCTGCCTAATAAAAAACATTTATTTTCA

TTGCCAATAGGCCGAAATCGGCAAGCGCGATCGCAAAAAAAAAAAAAAAAAAAAAAA

AAAAAAAAAAAAAAAAAAAAAAAAAAAAAAGAAAAAAAAAAAAAAAAAAAAAAAAA

AAAAAAAAAAAAAAAAAAAAAAAAAAAAAAAAAAAAAAGAATTCCTCGAGATTTAAA

TTCGCGAGTACTATGCATATGGGCCCAATATTAATTAAGCGCTAGCACGCGTTTAAA

CAGGCCTCGAGGCGCGCCCGCTTCCTCGCTCACTGACTCGCTGCGCTCGGTCGTTCGG

CTGCGGCGAGCGGTATCAGCTCACTCAAAGGCGGTAATACGGTTATCCACAGAATCA

GGGGATAACGCAGGAAAGAACATGTGAGCAAAAGGCCAGCAAAAGGCCAGGAACC

GTAAAAAGGCCGCGTTGCTGGCGTTTTTCCATAGGCTCCGCCCCCCTGACGAGCATC

ACAAAAATCGACGCTCAAGTCAGAGGTGGCGAAACCCGACAGGACTATAAAGATAC

CAGGCGTTTCCCCCTGGAAGCTCCCTCGTGCGCTCTCCTGTTCCGACCCTGCCGCTTA

CCGGATACCTGTCCGCCTTTCTCCCTTCGGGAAGCGTGGCGCTTTCTCATAGCTCACG

CTGTAGGTATCTCAGTTCGGTGTAGGTCGTTCGCTCCAAGCTGGGCTGTGTGCACGA

ACCCCCCGTTCAGCCCGACCGCTGCGCCTTATCCGGTAACTATCGTCTTGAGTCCAAC

CCGGTAAGACACGACTTATCGCCACTGGCAGCAGCCACTGGTAACAGGATTAGCAG

AGCGAGGTATGTAGGCGGTGCTACAGAGTTCTTGAAGTGGTGGCCTAACTACGGCTA

CACTAGAAGAACAGTATTTGGTATCTGCGCTCTGCTGAAGCCAGTTACCTTCGGAAA

AAGAGTTGGTAGCTCTTGATCCGGCAAACAAACCACCGCTGGTAGCGGTGGTTTTTT

TGTTTGCAAGCAGCAGATTACGCGCAGAAAAAAAGGATCTCAAGAAGATCCTTTGAT

CTTTTCTACGGGGTCTGACGCTCAGTGGAACGAAAACTCACGTTAAGGGATTTTGGT

CATGAGATTATCAAAAAGGATCTTCACCTAGATCCTTTTAAATTAAAAATGAAGTTTT

AAATCAAGCCCAATCTGAATAATGTTACAACCAATTAACCAATTCTGATTAGAAAAA

CTCATCGAGCATCAAATGAAACTGCAATTTATTCATATCAGGATTATCAATACCATAT

TTTTGAAAAAGCCGTTTCTGTAATGAAGGAGAAAACTCACCGAGGCAGTTCCATAGG

ATGGCAAGATCCTGGTATCGGTCTGCGATTCCGACTCGTCCAACATCAATACAACCT

ATTAATTTCCCCTCGTCAAAAATAAGGTTATCAAGTGAGAAATCACCATGAGTGACG

ACTGAATCCGGTGAGAATGGCAAAAGTTTATGCATTTCTTTCCAGACTTGTTCAACA

-continued

GGCCAGCCATTACGCTCGTCATCAAAATCACTCGCATCAACCAAACCGTTATTCATTC

GTGATTGCGCCTGAGCGAGACGAAATACGCGATCGCTGTTAAAAGGACAATTACAA

ACAGGAATCGAATGCAACCGGCGCAGGAACACTGCCAGCGCATCAACAATATTTTC

ACCTGAATCAGGATATTCTTCTAATACCTGGAATGCTGTTTTTCCGGGGATCGCAGTG

GTGAGTAACCATGCATCATCAGGAGTACGGATAAAATGCTTGATGGTCGGAAGAGG

CATAAATTCCGTCAGCCAGTTTAGTCTGACCATCTCATCTGTAACATCATTGGCAACG

CTACCTTTGCCATGTTTCAGAAACAACTCTGGCGCATCGGGCTTCCCATACAAGCGAT

AGATTGTCGCACCTGATTGCCCGACATTATCGCGAGCCCATTTATACCCATATAAATC

AGCATCCATGTTGGAATTTAATCGCGGCCTCGACGTTTCCCGTTGAATATGGCTCATA

ACACCCCTTGTATTACTGTTTATGTAAGCAGACAGTTTTATTGTTCATGATGATATAT

TTTTATCTTGTGCAATGTAACATCAGAGATTTTGAGACACGGGCCAGAGCTGCA

SEQ ID NO: 30, RNA sequence of an exemplified Protein with s155C, S190F, V207L, S290C, and TM domain UTR-polyA:
AUGGAACUGCCUGUGCUGAAAACAAACGCCAUCACAACAAUCCUGGCA

GCAGUGACACUGUGCUUCGCCAGCAGCCAGAAUAUUACAGAAGAGUUCUACCA

GAGCACAUGCAGCGCCGUGUCUAAGGGCUACCUGAGCGCCCUGAGAACAGGCU

GGUACACCAGCGUCAUCACGAUCGAGCUGAGUAAUAUCAAGGAGAACAAAUG

CAACGGCACCGACGCCAAGGUGAAGCUGAUCAAGCAGGAGCUGGAUAAAUACA

AGAACGCCGUGACCGAGUUGCAGCUGCUGAUGCAGUCUACCCCAGCCGCCAAC

AACAGAGCCAGACGGGAACUACCCAGAUUCAUGAACUACACACUGAACAACAC

UAAGAACACCAACGUGACACUGUCUAAGAAAAGAAAGCGGCGGUUCCUGGGA

UUCCUGCUGGGCGUGGGAAGCGCUAUCGCUUCUGGAAUUGCCGUGUGCAAGG

UGCUGCACCUGGAAGGCGAGGUGAACAAGAUCAAGUCUGCCCUGCUGUCCACC

AACAAGGCCGUAGUCAGCCUGAGCAAUGGCGUGAGCGUCCUGACCUUUAAGGU

GCUGGACCUGAAGAACUACAUCGACAAGCAGCUGCUGCCUAUCUUGAACAAGC

AGAGCUGCUCCAUCAGCAAUAUUGAGACUGUGAUCGAAUUCCAGCAGAAGAA

CAACCGGCUGCUGGAGAUCACCAGAGAGUUCUCCGUGAACGCUGGCGUGACUA

CACCUGUUUCAACCUACAUGCUGACCAAUUCUGAGCUGCUGAGCCUGAUCAAC

GACAUGCCUAUCACCAACGACCAGAAAAAACUGAUGUCCAAUAACGUUCAAAU

CGUGCGGCAGCAAAGCUACAGCAUCAUGUGCAUCAUCAAGGAAGAAGUGCUU

GCCUACGUGGUCCAGCUGCCACUUUAUGGAGUUAUCGAUACACCCUGCUGGAA

GCUGCACACCAGCCCUCUGUGUACAACCAACACCAAGGAAGGCAGCAACAUCU

GCCUGACCAGAACAGAUAGAGGCUGGUAUUGUGAUAACGCCGGCAGCGUGAG

CUUCUUCCCCCAGGCCGACACAUGUAAAGUGCAGAGCAAUAGAGUGUUCUGCG

ACACCAUGAAUAGCCUGACCCUGCCCAGCGAGGUGAAUCUGUGUAACAUCGAC

AUUUUCAACCCCAAGUACGAUUGCAAGAUCAUGACCUCCAAGACCGACGUGAG

CAGCAGCGUGAUCACCUCCCUGGGCGCCAUCGUGUCUUGCUACGGCAAGACCA

AGUGCACAGCCUCUAACAAAAAUCGCGGCAUCAUCAAAACCUUCUCUAACGGU

UGUGACUACGUGUCAAACAAAGGCGUGGACACCGUGUCCGUGGGCAACACCCU

GUAUUACGUGAACAAGCAGGAGGGCAAGAGCCUGUACGUGAAGGGCGAACCU

AUUAUCAACUUCUACGACCCUCUGGUGUUUCCUUCCGACGAGUUUGAUGCUAG

CAUCUCUCAGGUGAACGAGAAGAUCAACCAGAGCCUGGCCUUUAUCAGAAAGA

-continued

GCGAUGAGCUGCUGCACAACGUGAACGCCGGCAAGAGUACCACCAACAUCAUG

AUCACCACCAUCAUUAUCGUGAUCAUCGUGAUCCUCCUGAGCCUGAUCGCUGU

CGGACUGCUGCUGUACUGCAAGGCCAGGAGCACACCUGUGACCCUGAGCAAGG

ACCAACUGUCUGGCAUCAACAACAUCGCUUUUAGCAAUUAGAAAAAAAAAAAA

AAAAAAAAAAAAAAAAAAAAAAAAAAAAAAAAAAAAAGAAAAAAAAAAAAAAA

AAAAAAAAAAAAAAAAAAAAAAAAAAAAAAAAAAAAAAAAAAAA

SEQ ID NO: 107, HKP side chain:
KHKHKHKHK

SEQ ID NO: 108, HKP side chain:
HKHKHKHKHK

SEQ ID NO: 109, HKP side chain:
KHKHKHKHKH

SEQ ID NO: 110, HKP side chain:
HKHKHKHKHKH

SEQ ID NO: 111, HKP side chain:
KHKHHKHHKHHKHHKHHKHK

SEQ ID NO: 112, HKP side chain:
KHHHKHHHKHHHKHHHK

SEQ ID NO: 113, HKP side chain:
KHHHKHHHKHHHHKHHHK

SEQ ID NO: 114, HKP side chain:
KHHHKHHHKHHHHKHHHK, wherein the $1^{st}$, $5^{th}$, $9^{th}$, $14^{th}$ and $18^{th}$ amino acids are D-amino acids.

SEQ ID NO: 115, HKP side chain:
HKHHHKHHHKHHHHKHHHK

SEQ ID NO: 116, HKP side chain:
HHKHHHKHHHKHHHHKHHHK

SEQ ID NO: 41, HKP side chain:
KHHHHKHHHHKHHHHKHHHHK

SEQ ID NO: 42, HKP side chain:
KHHHKHHHKHHHKHHHHK

SEQ ID NO: 43, HKP side chain:
KHHHKHHHHKHHHKHHHK

SEQ ID NO: 44, HKP side chain:
KHHHKHHHHKHHHKHHHHK

SEQ ID NO: 45:
-HHHK-
RX(K/R)R

SEQ ID NO: 47:
TAATACGACTCACTATAA

SEQ ID NO: 48: RNA sequence of SEQ ID NO: 1:
GGAUUCCUGCUGGGCGUGGGAAGCGCUAUCGCUUCUGGAAUUGCCGUGAGCA

AGGUGCUGCACCUGGAAGGCGAGGUGAACAAGAUCAAGUCUGCCCUGCUGUCC

ACCAACAAGGCCGUAGUCAGCCUGAGCAAUGGCGUGAGCGUCCUGACCAGUAA

GGUGCUGGACCUGAAGAACUACAUCGACAAGCAGCUGCUGCCUAUCGUGAACA

AGCAGAGCUGCUCCAUCAGCAAUAUUGAGACUGUGAUCGAAUUCCAGCAGAA

GAACAACCGGCUGCUGGAGAUCACCAGAGAGUUCUCCGUGAACGCUGGCGUGA

CUACACCUGUUUCAACCUACAUGCUGACCAAUUCUGAGCUGCUGAGCCUGAUC

AACGACAUGCCUAUCACCAACGACCAGAAAAAACUGAUGUCCAAUAACGUUCA

AAUCGUGCGGCAGCAAAGCUACAGCAUCAUGAGCAUCAUCAAGGAAGAAGUG

-continued

CUUGCCUACGUGGUCCAGCUGCCACUUUAUGGAGUUAUCGAUACACCCUGCUG

GAAGCUGCACACCAGCCCUCUGUGUACAACCAACACCAAGGAAGGCAGCAACA

UCUGCCUGACCAGAACAGAUAGAGGCUGGUAUUGUGAUAACGCCGGCAGCGU

GAGCUUCUUCCCCCAGGCCGACACAUGUAAAGUGCAGAGCAAUAGAGUGUUCU

GCGACACCAUGAAUAGCCUGACCCUGCCCAGCGAGGUGAAUCUGUGUAACAUC

GACAUUUUCAACCCCAAGUACGAUUGCAAGAUCAUGACCUCCAAGACCGACGU

GAGCAGCAGCGUGAUCACCUCCCUGGGCGCCAUCGUGUCUUGCUACGGCAAGA

CCAAGUGCACAGCCUCUAACAAAAAUCGCGGCAUCAUCAAAACCUUCUCUAAC

GGUUGUGACUACGUGUCAAACAAAGGCGUGGACACCGUGUCCGUGGGCAACAC

CCUGUAUUACGUGAACAAGCAGGAGGGCAAGAGCCUGUACGUGAAGGGCGAA

CCUAUUAUCAACUUCUACGACCCUCUGGUGUUUCCUUCCGACGAGUUUGAUGC

UAGCAUCUCUCAGGUGAACGAGAAGAUCAACCAGAGCCUGGCCUUUAUCAGAA

AGAGCGAUGAGCUGCUGCACAACGUGAACGCCGGCAAGAGUACCACCAACAUC

AUGAUCACCACCAUCAUUAUCGUGAUCAUCGUGAUCCUCCUGAGCCUGAUCGC

UGUCGGACUGCUGCUGUACUGCAAGGCCAGGAGCACACCUGUGACCCUGAGCA

AGGACCAACUGUCUGGCAUCAACAACAUCGCUUUUAGCAAU

SEQ ID NO: 49, RNA sequence of SEQ ID NO: 3:
GGAUUCCUGCUGGGCGUGGGAAGCGCUAUCGCUUCUGGAAUUGCCGUG

AGCAAGGUGCUGCACCUGGAAGGCGAGGUGAACAAGAUCAAGUCUGCCCUGCU

GUCCACCAACAAGGCCGUAGUCAGCCUGAGCAAUGGCGUGAGCGUCCUGACCA

GUAAGGUGCUGGACCUGAAGAACUACAUCGACAAGCAGCUGCUGCCUAUCGUG

AACAAGCAGAGCUGCUCCAUCAGCAAUAUUGAGACUGUGAUCGAAUUCCAGCA

GAAGAACAACCGGCUGCUGGAGAUCACCAGAGAGUUCUCCGUGAACGCUGGCG

UGACUACACCUGUUUCAACCUACAUGCUGACCAAUUCUGAGCUGCUGAGCCUG

AUCAACGACAUGCCUAUCACCAACGACCAGAAAAAACUGAUGUCCAAUAACGU

UCAAAUCGUGCGGCAGCAAAGCUACAGCAUCAUGAGCAUCAUCAAGGAAGAA

GUGCUUGCCUACGUGGUCCAGCUGCCACUUUAUGGAGUUAUCGAUACACCCUG

CUGGAAGCUGCACACCAGCCCUCUGUGUACAACCAACACCAAGGAAGGCAGCA

ACAUCUGCCUGACCAGAACAGAUAGAGGCUGGUAUUGUGAUAACGCCGGCAGC

GUGAGCUUCUUCCCCCAGGCCGACACAUGUAAAGUGCAGAGCAAUAGAGUGUU

CUGCGACACCAUGAAUAGCCUGACCCUGCCCAGCGAGGUGAAUCUGUGUAACA

UCGACAUUUUCAACCCCAAGUACGAUUGCAAGAUCAUGACCUCCAAGACCGAC

GUGAGCAGCAGCGUGAUCACCUCCCUGGGCGCCAUCGUGUCUUGCUACGGCAA

GACCAAGUGCACAGCCUCUAACAAAAAUCGCGGCAUCAUCAAAACCUUCUCUA

ACGGUUGUGACUACGUGUCAAACAAAGGCGUGGACACCGUGUCCGUGGGCAAC

ACCCUGUAUUACGUGAACAAGCAGGAGGGCAAGAGCCUGUACGUGAAGGGCG

AACCUAUUAUCAACUUCUACGACCCUCUGGUGUUUCCUUCCGACGAGUUUGAU

GCUAGCAUCUCUCAGGUGAACGAGAAGAUCAACCAGAGCCUGGCCUUUAUCAG

AAAGAGCGAUGAGCUGCUGCACAACGUGAACGCCGGCAAGAGUACCACCAACA

UCAUGAUCACCGGAUACAUCCCGGAGGCCCCUAGGGACGGUCAAGCUUACGUG

AGAAAGGACGGCGAAUGGGUUCUGCUGUCGACCUUCUUGGGA

-continued

SEQ ID NO: 50, RNA sequence of SEQ ID NO: 5:
GGAUUCCUGCUGGGCGUGGGAAGCGCUAUCGCUUCUGGAAUUGCCGUG

UGCAAGGUGCUGCACCUGGAAGGCGAGGUGAACAAGAUCAAGUCUGCCCUGCU

GUCCACCAACAAGGCCGUAGUCAGCCUGAGCAAUGGCGUGAGCGUCCUGACCU

UUAAGGUGCUGGACCUGAAGAACUACAUCGACAAGCAGCUGCUGCCUAUCUUG

AACAAGCAGAGCUGCUCCAUCAGCAAUAUUGAGACUGUGAUCGAAUUCCAGCA

GAAGAACAACCGGCUGCUGGAGAUCACCAGAGAGUUCUCCGUGAACGCUGGCG

UGACUACACCUGUUUCAACCUACAUGCUGACCAAUUCUGAGCUGCUGAGCCUG

AUCAACGACAUGCCUAUCACCAACGACCAGAAAAAACUGAUGUCCAAUAACGU

UCAAAUCGUGCGGCAGCAAAGCUACAGCAUCAUGUGCAUCAUCAAGGAAGAA

GUGCUUGCCUACGUGGUCCAGCUGCCACUUUAUGGAGUUAUCGAUACACCCUG

CUGGAAGCUGCACACCAGCCCUCUGUGUACAACCAACACCAAGGAAGGCAGCA

ACAUCUGCCUGACCAGAACAGAUAGAGGCUGGUAUUGUGAUAACGCCGGCAGC

GUGAGCUUCUUCCCCCAGGCCGACACAUGUAAAGUGCAGAGCAAUAGAGUGUU

CUGCGACACCAUGAAUAGCCUGACCCUGCCCAGCGAGGUGAAUCUGUGUAACA

UCGACAUUUUCAACCCCAAGUACGAUUGCAAGAUCAUGACCUCCAAGACCGAC

GUGAGCAGCAGCGUGAUCACCUCCCUGGGCGCCAUCGUGUCUUGCUACGGCAA

GACCAAGUGCACAGCCUCUAACAAAAAUCGCGGCAUCAUCAAAACCUUCUCUA

ACGGUUGUGACUACGUGUCAAACAAAGGCGUGGACACCGUGUCCGUGGGCAAC

ACCCUGUAUUACGUGAACAAGCAGGAGGGCAAGAGCCUGUACGUGAAGGGCG

AACCUAUUAUCAACUUCUACGACCCUCUGGUGUUUCCUUCCGACGAGUUUGAU

GCUAGCAUCUCUCAGGUGAACGAGAAGAUCAACCAGAGCCUGGCCUUUAUCAG

AAAGAGCGAUGAGCUGCUGCACAACGUGAACGCCGGCAAGAGUACCACCAACA

UCAUGAUCACCACCAUCAUUAUCGUGAUCAUCGUGAUCCUCCUGAGCCUGAUC

GCUGUCGGACUGCUGCUGUACUGCAAGGCCAGGAGCACACCUGUGACCCUGAG

CAAGGACCAACUGUCUGGCAUCAACAACAUCGCUUUUAGCAAU

SEQ ID NO: 51, RNA sequence of SEQ ID NO: 7:
GGAUUCCUGCUGGGCGUGGGAAGCGCUAUCGCUUCUGGAAUUGCCGUG

UGCAAGGUGCUGCACCUGGAAGGCGAGGUGAACAAGAUCAAGUCUGCCCUGCU

GUCCACCAACAAGGCCGUAGUCAGCCUGAGCAAUGGCGUGAGCGUCCUGACCU

UUAAGGUGCUGGACCUGAAGAACUACAUCGACAAGCAGCUGCUGCCUAUCUUG

AACAAGCAGAGCUGCUCCAUCAGCAAUAUUGAGACUGUGAUCGAAUUCCAGCA

GAAGAACAACCGGCUGCUGGAGAUCACCAGAGAGUUCUCCGUGAACGCUGGCG

UGACUACACCUGUUUCAACCUACAUGCUGACCAAUUCUGAGCUGCUGAGCCUG

AUCAACGACAUGCCUAUCACCAACGACCAGAAAAAACUGAUGUCCAAUAACGU

UCAAAUCGUGCGGCAGCAAAGCUACAGCAUCAUGUGCAUCAUCAAGGAAGAA

GUGCUUGCCUACGUGGUCCAGCUGCCACUUUAUGGAGUUAUCGAUACACCCUG

CUGGAAGCUGCACACCAGCCCUCUGUGUACAACCAACACCAAGGAAGGCAGCA

ACAUCUGCCUGACCAGAACAGAUAGAGGCUGGUAUUGUGAUAACGCCGGCAGC

GUGAGCUUCUUCCCCCAGGCCGACACAUGUAAAGUGCAGAGCAAUAGAGUGUU

CUGCGACACCAUGAAUAGCCUGACCCUGCCCAGCGAGGUGAAUCUGUGUAACA

-continued

UCGACAUUUUCAACCCCAAGUACGAUUGCAAGAUCAUGACCUCCAAGACCGAC

GUGAGCAGCAGCGUGAUCACCUCCCUGGGCGCCAUCGUGUCUUGCUACGGCAA

GACCAAGUGCACAGCCUCUAACAAAAAUCGCGGCAUCAUCAAAACCUUCUCUA

ACGGUUGUGACUACGUGUCAAACAAAGGCGUGGACACCGUGUCCGUGGGCAAC

ACCCUGUAUUACGUGAACAAGCAGGAGGGCAAGAGCCUGUACGUGAAGGGCG

AACCUAUUAUCAACUUCUACGACCCUCUGGUGUUUCCUUCCGACGAGUUUGAU

GCUAGCAUCUCUCAGGUGAACGAGAAGAUCAACCAGAGCCUGGCCUUUAUCAG

AAAGAGCGAUGAGCUGCUGCACAACGUGAACGCCGGCAAGAGUACCACCAACA

UCAUGAUCACCGGAUACAUCCCGGAGGCCCCUAGGGACGGUCAAGCUUACGUG

AGAAAGGACGGCGAAUGGGUUCUGCUGUCGACCUUCUUGGGA

SEQ ID NO: 52, RNA sequence of SEQ ID NO: 11:
GGAUUCCUGCUGGGCGUGGGAAGCGCUAUCGCUUCUGGAAUUGCCGUG

UGCAAGGUGCUGCACCUGGAAGGCGAGGUGAACAAGAUCAAGUCUGCCCUGCU

GUCCACCAACAAGGCCGUAGUCAGCCUGAGCAAUGGCGUGAGCGUCCUGACCU

UUAAGGUGCUGGACCUGAAGAACUACAUCGACAAGCAGCUGCUGCCUAUCUUG

AACAAGCAGAGCUGCUCCAUCAGCAAUAUUGAGACUGUGAUCGAAUUCCAGCA

GAAGAACAACCGGCUGCUGGAGAUCACCAGAGAGUUCUCCGUGAACGCUGGCG

UGACUACACCUGUUUCAACCUACAUGCUGACCAAUUCUGAGCUGCUGAGCCUG

AUCAACGACAUGCCUAUCACCAACGACCAGAAAAAACUGAUGUCCAAUAACGU

UCAAAUCGUGCGGCAGCAAAGCUACAGCAUCAUGUGCAUCAUCAAGGAAGAA

GUGCUUGCCUACGUGGUCCAGCUGCCACUUUAUGGAGUUAUCGAUACACCCUG

CUGGAAGCUGCACACCAGCCCUCUGUGUACAACCAACACCAAGGAAGGCAGCA

ACAUCUGCCUGACCAGAACAGAUAGAGGCUGGUAUUGUGAUAACGCCGGCAGC

GUGAGCUUCUUCCCCCAGGCCGACACAUGUAAAGUGCAGAGCAAUAGAGUGUU

CUGCGACACCAUGAAUAGCCUGACCCUGCCCAGCGAGGUGAAUCUGUGUAACA

UCGACAUUUUCAACCCCAAGUACGAUUGCAAGAUCAUGACCUCCAAGACCGAC

GUGAGCAGCAGCGUGAUCACCUCCCUGGGCGCCAUCGUGUCUUGCUACGGCAA

GACCAAGUGCACAGCCUCUAACAAAAAUCGCGGCAUCAUCAAAACCUUCUCUA

ACGGUUGUGACUACGUGUCAAACAAAGGCGUGGACACCGUGUCCGUGGGCAAC

ACCCUGUAUUACGUGAACAAGCAGGAGGGCAAGAGCCUGUACGUGAAGGGCG

AACCUAUUAUCAACUUCUACGACCCUCUGGUGUUUCCUUCCCACCAGUGGCAU

GCUAGCAUCUCUCAGGUGAACGAGAAGAUCAACCAGAGCCUGGCCUUUAUCAG

AAAGAGCGAUGAGCUGCUGCACAACGUGAACGCCGGCAAGAGUACCACCAACA

UCAUGAUCACCGGAUACAUCCCGGAGGCCCCUAGGGACGGUCAAGCUUACGUG

AGAAAGGACGGCGAAUGGGUUCUGCUGUCGACCUUCUUGGGA

SEQ ID NO: 53, Amino acid sequence of A2 glycoprotein (A2-1):
MELLILKANAITTILTAVTFCFASGQNITEEFYQSTCSAVSKGYLSALRTGWYT

SVITIELSNIKENKCNGTDAKVKLIKQELDKYKNAVTELQLLMQSTPATNNRARRELP

RFMNYTLNNAKKTNVTLSKKRKRRFLGFLLGVGSAIASGVAVSKVLHLEGEVNKIK

SALLSTNKAVVSLSNGVSVLTFKVLDLKNYIDKQLLPILNKQSCSISNIETVIEFQQKN

NRLLEITREFSVNAGVTTPVSTYMLTNSELLSLINDMPITNDQKKLMSNNVQIVRQQS

YSIMSIIKEEVLAYVVQLPLYGVIDTPCWKLHTSPLCTTNTKEGSNICLTRTDRGWYC

-continued

DNAGSVSFFPQAETCKVQSNRVFCDTMNSLTLPSEVNLCNVDIFNPKYDCKIMTSKT

DVSSSVITSLGAIVSCYGKTKCTASNKNRGIIKTFSNGCDYVSNKGVDTVSVGNTLYY

VNKQEGKSLYVKGEPIINFYDPLVFPSDEFDASISQVNEKINQSLAFIRKSDELLHNVN

AGKSTTNIMITTIIIVIIVILLSLIAVGLLLYCKARSTPVTLSKDQLSGINNIAFSN

SEQ ID NO: 54, DNA sequence of A2 glycoprotein (A2-1):
ATGGAACTGCTGATCCTGAAGGCCAACGCTATCACCACAATCCTGACCGC

CGTGACCTTTTGCTTCGCCTCTGGCCAGAACATCACGGAAGAGTTTTACCAGAGC

ACCTGCAGCGCTGTGTCCAAAGGTTATCTGAGCGCTCTGAGAACCGGATGGTATA

CCAGCGTCATCACAATCGAGTTGTCCAATATCAAGGAAAACAAGTGTAACGGAA

CAGATGCCAAGGTGAAGCTGATCAAGCAGGAACTGGATAAGTACAAGAACGCC

GTGACCGAGCTGCAGCTGTTGATGCAGAGCACTCCTGCCACCAACAACAGAGCC

CGGAGAGAGCTGCCTAGATTCATGAACTACACCCTCAACAACGCCAAGAAGACC

AACGTGACACTGAGCAAGAAGCGGAAAAGACGGTTCCTGGGATTCCTGCTGGGC

GTTGGAAGCGCCATCGCCAGCGGCGTGGCCGTGTCTAAGGTGCTGCACCTGGAA

GGAGAGGTGAACAAAATCAAATCTGCCCTGCTTAGCACCAACAAAGCCGTTGTG

AGTTTGAGCAACGGTGTGTCCGTGCTGACATTTAAGGTGCTGGACCTGAAGAACT

ACATCGACAAGCAACTGCTGCCCATCCTGAACAAGCAATCCTGTTCCATCAGCAA

CATCGAGACAGTTATCGAGTTCCAGCAGAAGAACAACCGGCTGCTGGAAATCAC

CAGAGAATTCAGCGTGAATGCTGGCGTGACTACCCCAGTGTCTACCTACATGCTG

ACAAATTCTGAGCTGCTGAGCCTGATCAACGACATGCCTATCACAAATGATCAG

AAAAAGCTGATGAGCAACAATGTCCAGATCGTGCGGCAGCAAAGCTACAGCATC

ATGAGCATCATTAAGGAAGAAGTGCTGGCCTACGTGGTGCAGCTGCCTCTGTAC

GGCGTGATCGACACCCCTTGCTGGAAGCTGCACACCTCTCCTCTGTGTACCACAA

ACACCAAGGAGGGCAGCAACATCTGCCTGACAAGAACCGATAGAGGCTGGTACT

GCGATAACGCCGGCTCTGTCTCATTCTTCCCTCAGGCCGAGACATGCAAGGTCCA

GAGCAACAGAGTGTTTTGTGATACCATGAACAGCCTGACCCTGCCAAGCGAAGT

GAATCTGTGCAATGTGGACATCTTCAACCCCAAGTACGACTGCAAGATCATGACC

AGCAAGACAGACGTGTCCAGCAGCGTTATCACCAGCCTGGGCGCCATTGTGTCTT

GCTACGGCAAAACCAAGTGCACCGCATCTAACAAAAATCGCGGCATCATCAAGA

CATTCAGCAACGGCTGTGACTACGTCAGCAATAAGGGCGTGGACACCGTGAGCG

TGGGCAACACACTGTACTACGTGAATAAGCAGGAGGGCAAGTCTCTCTACGTGA

AAGGCGAGCCTATCATCAATTTCTACGACCCCCTGGTGTTCCCCTCCGACGAGTT

CGACGCCTCTATTAGCCAGGTGAACGAGAAGATTAACCAGAGCCTGGCTTTCATC

AGAAAGAGCGACGAGCTGCTGCACAACGTGAACGCTGGCAAGTCCACAACCAAC

ATCATGATCACCACCATCATCATCGTGATCATCGTGATTCTGCTGAGCCTCATCG

CCGTGGGCCTGCTGCTGTATTGCAAAGCCAGAAGCACACCTGTGACCCTGAGCA

AGGACCAGCTGTCTGGCATCAACAACATCGCCTTCTCTAACTAG

SEQ ID NO: 55, RNA sequence of A2 glycoprotein (A2-1):
AUGGAACUGCUGAUCCUGAAGGCCAACGCUAUCACCACAAUCCUGACCG

CCGUGACCUUUUGCUUCGCCUCUGGCCAGAACAUCACGGAAGAGUUUUACCAG

AGCACCUGCAGCGCUGUGUCCAAAGGUUAUCUGAGCGCUCUGAGAACCGGAUG

-continued

GUAUACCAGCGUCAUCACAAUCGAGUUGUCCAAUAUCAAGGAAAACAAGUGU

AACGGAACAGAUGCCAAGGUGAAGCUGAUCAAGCAGGAACUGGAUAAGUACA

AGAACGCCGUGACCGAGCUGCAGCUGUUGAUGCAGAGCACUCCUGCCACCAAC

AACAGAGCCCGGAGAGAGCUGCCUAGAUUCAUGAACUACACCCUCAACAACGC

CAAGAAGACCAACGUGACACUGAGCAAGAAGCGGAAAAGACGGUUCCUGGGA

UUCCUGCUGGGCGUUGGAAGCGCCAUCGCCAGCGGCGUGGCCGUGUCUAAGGU

GCUGCACCUGGAAGGAGAGGUGAACAAAAUCAAAUCUGCCCUGCUUAGCACCA

ACAAAGCCGUUGUGAGUUUGAGCAACGGUGUGUCCGUGCUGACAUUUAAGGU

GCUGGACCUGAAGAACUACAUCGACAAGCAACUGCUGCCCAUCCUGAACAAGC

AAUCCUGUUCCAUCAGCAACAUCGAGACAGUUAUCGAGUUCCAGCAGAAGAAC

AACCGGCUGCUGGAAAUCACCAGAGAAUUCAGCGUGAAUGCUGGCGUGACUAC

CCCAGUGUCUACCUACAUGCUGACAAAUUCUGAGCUGCUGAGCCUGAUCAACG

ACAUGCCUAUCACAAAUGAUCAGAAAAAGCUGAUGAGCAACAAUGUCCAGAU

CGUGCGGCAGCAAAGCUACAGCAUCAUGAGCAUCAUUAAGGAAGAAGUGCUG

GCCUACGUGGUGCAGCUGCCUCUGUACGGCGUGAUCGACACCCCUUGCUGGAA

GCUGCACACCUCUCCUCUGUGUACCACAAACACCAAGGAGGGCAGCAACAUCU

GCCUGACAAGAACCGAUAGAGGCUGGUACUGCGAUAACGCCGGCUCUGUCUCA

UUCUUCCCUCAGGCCGAGACAUGCAAGGUCCAGAGCAACAGAGUGUUUUGUGA

UACCAUGAACAGCCUGACCCUGCCAAGCGAAGUGAAUCUGUGCAAUGUGGACA

UCUUCAACCCCAAGUACGACUGCAAGAUCAUGACCAGCAAGACAGACGUGUCC

AGCAGCGUUAUCACCAGCCUGGGCGCCAUUGUGUCUUGCUACGGCAAAACCAA

GUGCACCGCAUCUAACAAAAAUCGCGGCAUCAUCAAGACAUUCAGCAACGGCU

GUGACUACGUCAGCAAUAAGGGCGUGGACACCGUGAGCGUGGGCAACACACUG

UACUACGUGAAUAAGCAGGAGGGCAAGUCUCUCUACGUGAAAGGCGAGCCUA

UCAUCAAUUUCUACGACCCCCUGGUGUUCCCCUCCGACGAGUUCGACGCCUCU

AUUAGCCAGGUGAACGAGAAGAUUAACCAGAGCCUGGCUUUCAUCAGAAAGA

GCGACGAGCUGCUGCACAACGUGAACGCUGGCAAGUCCACAACCAACAUCAUG

AUCACCACCAUCAUCAUCGUGAUCAUCGUGAUUCUGCUGAGCCUCAUCGCCGU

GGGCCUGCUGCUGUAUUGCAAAGCCAGAAGCACACCUGUGACCCUGAGCAAGG

ACCAGCUGUCUGGCAUCAACAACAUCGCCUUCUCUAACUAG

SEQ ID NO: 56, Protein sequence of A2 glycoprotein without transmembrane domain (A2-2):

MELLILKANAITTILTAVTFCFASGQNITEEFYQSTCSAVSKGYLSALRTGWYT

SVITIELSNIKENKCNGTDAKVKLIKQELDKYKNAVTELQLLMQSTPATNNRARRELP

RFMNYTLNNAKKTNVTLSKKRKRRFLGFLLGVGSAIASGVAVSKVLHLEGEVNKIK

SALLSTNKAVVSLSNGVSVLTFKVLDLKNYIDKQLLPILNKQSCSISNIETVIEFQQKN

NRLLEITREFSVNAGVTTPVSTYMLTNSELLSLINDMPITNDQKKLMSNNVQIVRQQS

YSIMSIIKEEVLAYVVQLPLYGVIDTPCWKLHTSPLCTTNTKEGSNICLTRTDRGWYC

DNAGSVSFFPQAETCKVQSNRVFCDTMNSLTLPSEVNLCNVDIFNPKYDCKIMTSKT

DVSSSVITSLGAIVSCYGKTKCTASNKNRGIIKTFSNGCDYVSNKGVDTVSVGNTLYY

VNKQEGKSLYVKGEPIINFYDPLVFPSDEFDASISQVNEKINQSLAFIRKSDELLHNVN

AGKSTTNIMIT

-continued

SEQ ID NO: 57, DNA sequence of A2 glycoprotein without transmembrane domain (A2-2):

ATGGAACTGCTGATCCTGAAGGCCAACGCTATCACCACAATCCTGACCGC

CGTGACCTTTTGCTTCGCCTCTGGCCAGAACATCACGGAAGAGTTTTACCAGAGC

ACCTGCAGCGCTGTGTCCAAAGGTTATCTGAGCGCTCTGAGAACCGGATGGTATA

CCAGCGTCATCACAATCGAGTTGTCCAATATCAAGGAAAACAAGTGTAACGGAA

CAGATGCCAAGGTGAAGCTGATCAAGCAGGAACTGGATAAGTACAAGAACGCC

GTGACCGAGCTGCAGCTGTTGATGCAGAGCACTCCTGCCACCAACAACAGAGCC

CGGAGAGAGCTGCCTAGATTCATGAACTACACCCTCAACAACGCCAAGAAGACC

AACGTGACACTGAGCAAGAAGCGGAAAAGACGGTTCCTGGGATTCCTGCTGGGC

GTTGGAAGCGCCATCGCCAGCGGCGTGGCCGTGTGTAAGGTGCTGCACCTGGAA

GGAGAGGTGAACAAAATCAAATCTGCCCTGCTTAGCACCAACAAAGCCGTTGTG

AGTTTGAGCAACGGTGTGTCCGTGCTGACATTTAAGGTGCTGGACCTGAAGAACT

ACATCGACAAGCAACTGCTGCCCATCCTGAACAAGCAATCCTGTTCCATCAGCAA

CATCGAGACAGTTATCGAGTTCCAGCAGAAGAACAACCGGCTGCTGGAAATCAC

CAGAGAATTCAGCGTGAATGCTGGCGTGACTACCCCAGTGTCTACCTACATGCTG

ACAAATTCTGAGCTGCTGAGCCTGATCAACGACATGCCTATCACAAATGATCAG

AAAAAGCTGATGAGCAACAATGTCCAGATCGTGCGGCAGCAAAGCTACAGCATC

ATGTGCATCATTAAGGAAGAAGTGCTGGCCTACGTGGTGCAGCTGCCTCTGTACG

GCGTGATCGACACCCCTTGCTGGAAGCTGCACACCTCTCCTCTGTGTACCACAAA

CACCAAGGAGGGCAGCAACATCTGCCTGACAAGAACCGATAGAGGCTGGTACTG

CGATAACGCCGGCTCTGTCTCATTCTTCCCTCAGGCCGAGACATGCAAGGTCCAG

AGCAACAGAGTGTTTTGTGATACCATGAACAGCCTGACCCTGCCAAGCGAAGTG

AATCTGTGCAATGTGGACATCTTCAACCCCAAGTACGACTGCAAGATCATGACCA

GCAAGACAGACGTGTCCAGCAGCGTTATCACCAGCCTGGGCGCCATTGTGTCTTG

CTACGGCAAAACCAAGTGCACCGCATCTAACAAAAATCGCGGCATCATCAAGAC

ATTCAGCAACGGCTGTGACTACGTCAGCAATAAGGGCGTGGACACCGTGAGCGT

GGGCAACACACTGTACTACGTGAATAAGCAGGAGGGCAAGTCTCTCTACGTGAA

AGGCGAGCCTATCATCAATTTCTACGACCCCCTGGTGTTCCCCTCCGACGAGTTC

GACGCCTCTATTAGCCAGGTGAACGAGAAGATTAACCAGAGCCTGGCTTTCATC

AGAAAGAGCGACGAGCTGCTGCACAACGTGAACGCTGGCAAGTCCACAACCAAC

ATCATGATCACCACCATCATCATCGTGATCATCGTGATTCTGCTGAGCCTCATCG

CCGTGGGCCTGCTGCTGTATTGCAAAGCCAGAAGCACACCTGTGACCCTGAGCA

AGGACCAGCTGTCTGGCATCAACAACATCGCCTTCTCTAACTAG

SEQ ID NO: 58 RNA sequence of A2 glycoprotein without transmembrane domain (A2-2):

AUGGAACUGCUGAUCCUGAAGGCCAACGCUAUCACCACAAUCCUGACCG

CCGUGACCUUUUGCUUCGCCUCUGGCCAGAACAUCACGGAAGAGUUUUACCAG

AGCACCUGCAGCGCUGUGUCCAAAGGUUAUCUGAGCGCUCUGAGAACCGGAUG

GUAUACCAGCGUCAUCACAAUCGAGUUGUCCAAUAUCAAGGAAAACAAGUGU

AACGGAACAGAUGCCAAGGUGAAGCUGAUCAAGCAGGAACUGGAUAAGUACA

AGAACGCCGUGACCGAGCUGCAGCUGUUGAUGCAGAGCACUCCUGCCACCAAC

-continued
AACAGAGCCCGGAGAGAGCUGCCUAGAUUCAUGAACUACACCCUCAACAACGC

CAAGAAGACCAACGUGACACUGAGCAAGAAGCGGAAAAGACGGUUCCUGGGA

UUCCUGCUGGGCGUUGGAAGCGCCAUCGCCAGCGGCGUGGCCGUGUGUAAGGU

GCUGCACCUGGAAGGAGAGGUGAACAAAAUCAAAUCUGCCCUGCUUAGCACCA

ACAAAGCCGUUGUGAGUUUGAGCAACGGUGUGUCCGUGCUGACAUUUAAGGU

GCUGGACCUGAAGAACUACAUCGACAAGCAACUGCUGCCCAUCCUGAACAAGC

AAUCCUGUUCCAUCAGCAACAUCGAGACAGUUAUCGAGUUCCAGCAGAAGAAC

AACCGGCUGCUGGAAAUCACCAGAGAAUUCAGCGUGAAUGCUGGCGUGACUAC

CCCAGUGUCUACCUACAUGCUGACAAAUUCUGAGCUGCUGAGCCUGAUCAACG

ACAUGCCUAUCACAAAUGAUCAGAAAAAGCUGAUGAGCAACAAUGUCCAGAU

CGUGCGGCAGCAAAGCUACAGCAUCAUGUGCAUCAUUAAGGAAGAAGUGCUG

GCCUACGUGGUGCAGCUGCCUCUGUACGGCGUGAUCGACACCCCUUGCUGGAA

GCUGCACACCUCUCCUCUGUGUACCACAAACACCAAGGAGGGCAGCAACAUCU

GCCUGACAAGAACCGAUAGAGGCUGGUACUGCGAUAACGCCGGCUCUGUCUCA

UUCUUCCCUCAGGCCGAGACAUGCAAGGUCCAGAGCAACAGAGUGUUUUGUGA

UACCAUGAACAGCCUGACCCUGCCAAGCGAAGUGAAUCUGUGCAAUGUGGACA

UCUUCAACCCCAAGUACGACUGCAAGAUCAUGACCAGCAAGACAGACGUGUCC

AGCAGCGUUAUCACCAGCCUGGGCGCCAUUGUGUCUUGCUACGGCAAAACCAA

GUGCACCGCAUCUAACAAAAAUCGCGGCAUCAUCAAGACAUUCAGCAACGGCU

GUGACUACGUCAGCAAUAAGGGCGUGGACACCGUGAGCGUGGGCAACACACUG

UACUACGUGAAUAAGCAGGAGGGCAAGUCUCUCUACGUGAAAGGCGAGCCUA

UCAUCAAUUUCUACGACCCCCUGGUGUUCCCCUCCGACGAGUUCGACGCCUCU

AUUAGCCAGGUGAACGAGAAGAUUAACCAGAGCCUGGCUUUCAUCAGAAAGA

GCGACGAGCUGCUGCACAACGUGAACGCUGGCAAGUCCACAACCAACAUCAUG

AUCACCACCAUCAUCAUCGUGAUCAUCGUGAUUCUGCUGAGCCUCAUCGCCGU

GGGCCUGCUGCUGUAUUGCAAAGCCAGAAGCACACCUGUGACCCUGAGCAAGG

ACCAGCUGUCUGGCAUCAACAACAUCGCCUUCUCUAACUAG

SEQ ID NO: 59, Mutant A2 protein with S155C, S190F, V207L S290C (A2-3):
MELLILKANAITTILTAVTFCFASGQNITEEFYQSTCSAVSKGYLSALRTGWYT

SVITIELSNIKENKCNGTDAKVKLIKQELDKYKNAVTELQLLMQSTPATNNRARRELP

RFMNYTLNNAKKTNVTLSKKRKRRFLGFLLGVGSAIASGVAVCKVLHLEGEVNKIK

SALLSTNKAVVSLSNGVSVLTFKVLDLKNYIDKQLLPILNKQSCSISNIETVIEFQQKN

NRLLEITREFSVNAGVTTPVSTYMLTNSELLSLINDMPITNDQKKLMSNNVQIVRQQS

YSIMCIIKEEVLAYVVQLPLYGVIDTPCWKLHTSPLCTTNTKEGSNICLTRTDRGWYC

DNAGSVSFFPQAETCKVQSNRVFCDTMNSLTLPSEVNLCNVDIFNPKYDCKIMTSKT

DVSSSVITSLGAIVSCYGKTKCTASNKNRGIIKTFSNGCDYVSNKGVDTVSVGNTLYY

VNKQEGKSLYVKGEPIINFYDPLVFPSDEFDASISQVNEKINQSLAFIRKSDELLHNVN

AGKSTTNIMITTIIIVIIVILLSLIAVGLLLYCKARSTPVTLSKDQLSGINNIAFSN

SEQ ID NO: 60, DNA sequence of amino acid SEQ ID NO: 59 (A2-3):
ATGGAACTGCTGATCCTGAAGGCCAACGCTATCACCACAATCCTGACCGC

CGTGACCTTTTGCTTCGCCTCTGGCCAGAACATCACGGAAGAGTTTTACCAGAGC

ACCTGCAGCGCTGTGTCCAAAGGTTATCTGAGCGCTCTGAGAACCGGATGGTATA

-continued

CCAGCGTCATCACAATCGAGTTGTCCAATATCAAGGAAAACAAGTGTAACGGAA

CAGATGCCAAGGTGAAGCTGATCAAGCAGGAACTGGATAAGTACAAGAACGCC

GTGACCGAGCTGCAGCTGTTGATGCAGAGCACTCCTGCCACCAACAACAGAGCC

CGGAGAGAGCTGCCTAGATTCATGAACTACACCCTCAACAACGCCAAGAAGACC

AACGTGACACTGAGCAAGAAGCGGAAAAGACGGTTCCTGGGATTCCTGCTGGGC

GTTGGAAGCGCCATCGCCAGCGGCGTGGCCGTGTGTAAGGTGCTGCACCTGGAA

GGAGAGGTGAACAAAATCAAATCTGCCCTGCTTAGCACCAACAAAGCCGTTGTG

AGTTTGAGCAACGGTGTGTCCGTGCTGACATTTAAGGTGCTGGACCTGAAGAACT

ACATCGACAAGCAACTGCTGCCCATCCTGAACAAGCAATCCTGTTCCATCAGCAA

CATCGAGACAGTTATCGAGTTCCAGCAGAAGAACAACCGGCTGCTGGAAATCAC

CAGAGAATTCAGCGTGAATGCTGGCGTGACTACCCCAGTGTCTACCTACATGCTG

ACAAATTCTGAGCTGCTGAGCCTGATCAACGACATGCCTATCACAAATGATCAG

AAAAAGCTGATGAGCAACAATGTCCAGATCGTGCGGCAGCAAAGCTACAGCATC

ATGTGCATCATTAAGGAAGAAGTGCTGGCCTACGTGGTGCAGCTGCCTCTGTACG

GCGTGATCGACACCCCTTGCTGGAAGCTGCACACCTCTCCTCTGTGTACCACAAA

CACCAAGGAGGGCAGCAACATCTGCCTGACAAGAACCGATAGAGGCTGGTACTG

CGATAACGCCGGCTCTGTCTCATTCTTCCCTCAGGCCGAGACATGCAAGGTCCAG

AGCAACAGAGTGTTTTGTGATACCATGAACAGCCTGACCCTGCCAAGCGAAGTG

AATCTGTGCAATGTGGACATCTTCAACCCCAAGTACGACTGCAAGATCATGACCA

GCAAGACAGACGTGTCCAGCAGCGTTATCACCAGCCTGGGCGCCATTGTGTCTTG

CTACGGCAAAACCAAGTGCACCGCATCTAACAAAAATCGCGGCATCATCAAGAC

ATTCAGCAACGGCTGTGACTACGTCAGCAATAAGGGCGTGGACACCGTGAGCGT

GGGCAACACACTGTACTACGTGAATAAGCAGGAGGGCAAGTCTCTCTACGTGAA

AGGCGAGCCTATCATCAATTTCTACGACCCCCTGGTGTTCCCCTCCGACGAGTTC

GACGCCTCTATTAGCCAGGTGAACGAGAAGATTAACCAGAGCCTGGCTTTCATC

AGAAAGAGCGACGAGCTGCTGCACAACGTGAACGCTGGCAAGTCCACAACCAAC

ATCATGATCACCACCATCATCATCGTGATCATCGTGATTCTGCTGAGCCTCATCG

CCGTGGGCCTGCTGCTGTATTGCAAAGCCAGAAGCACACCTGTGACCCTGAGCA

AGGACCAGCTGTCTGGCATCAACAACATCGCCTTCTCTAACTAG

SEQ ID NO: 61, RNA sequence of amino acid SEQ ID NO: 59 (A2-3):
AUGGAACUGCUGAUCCUGAAGGCCAACGCUAUCACCACAAUCCUGACCG

CCGUGACCUUUUGCUUCGCCUCUGGCCAGAACAUCACGGAAGAGUUUUACCAG

AGCACCUGCAGCGCUGUGUCCAAAGGUUAUCUGAGCGCUCUGAGAACCGGAUG

GUAUACCAGCGUCAUCACAAUCGAGUUGUCCAAUAUCAAGGAAAACAAGUGU

AACGGAACAGAUGCCAAGGUGAAGCUGAUCAAGCAGGAACUGGAUAAGUACA

AGAACGCCGUGACCGAGCUGCAGCUGUUGAUGCAGAGCACUCCUGCCACCAAC

AACAGAGCCCGGAGAGAGCUGCCUAGAUUCAUGAACUACACCCUCAACAACGC

CAAGAAGACCAACGUGACACUGAGCAAGAAGCGGAAAAGACGGUUCCUGGGA

UUCCUGCUGGGCGUUGGAAGCGCCAUCGCCAGCGGCGUGGCCGUGUGUAAGGU

GCUGCACCUGGAAGGAGAGGUGAACAAAAUCAAAUCUGCCCUGCUUAGCACCA

ACAAAGCCGUUGUGAGUUUGAGCAACGGUGUGUCCGUGCUGACAUUUAAGGU

-continued

GCUGGACCUGAAGAACUACAUCGACAAGCAACUGCUGCCCAUCCUGAACAAGC

AAUCCUGUUCCAUCAGCAACAUCGAGACAGUUAUCGAGUUCCAGCAGAAGAAC

AACCGGCUGCUGGAAAUCACCAGAGAAUUCAGCGUGAAUGCUGGCGUGACUAC

CCCAGUGUCUACCUACAUGCUGACAAAUUCUGAGCUGCUGAGCCUGAUCAACG

ACAUGCCUAUCACAAAUGAUCAGAAAAAGCUGAUGAGCAACAAUGUCCAGAU

CGUGCGGCAGCAAAGCUACAGCAUCAUGUGCAUCAUUAAGGAAGAAGUGCUG

GCCUACGUGGUGCAGCUGCCUCUGUACGGCGUGAUCGACACCCCUUGCUGGAA

GCUGCACACCUCUCCUCUGUGUACCACAAACACCAAGGAGGGCAGCAACAUCU

GCCUGACAAGAACCGAUAGAGGCUGGUACUGCGAUAACGCCGGCUCUGUCUCA

UUCUUCCCUCAGGCCGAGACAUGCAAGGUCCAGAGCAACAGAGUGUUUUGUGA

UACCAUGAACAGCCUGACCCUGCCAAGCGAAGUGAAUCUGUGCAAUGUGGACA

UCUUCAACCCCAAGUACGACUGCAAGAUCAUGACCAGCAAGACAGACGUGUCC

AGCAGCGUUAUCACCAGCCUGGGCGCCAUUGUGUCUUGCUACGGCAAAACCAA

GUGCACCGCAUCUAACAAAAAUCGCGGCAUCAUCAAGACAUUCAGCAACGGCU

GUGACUACGUCAGCAAUAAGGGCGUGGACACCGUGAGCGUGGGCAACACACUG

UACUACGUGAAUAAGCAGGAGGGCAAGUCUCUCUACGUGAAAGGCGAGCCUA

UCAUCAAUUUCUACGACCCCCUGGUGUUCCCCUCCGACGAGUUCGACGCCUCU

AUUAGCCAGGUGAACGAGAAGAUUAACCAGAGCCUGGCUUUCAUCAGAAAGA

GCGACGAGCUGCUGCACAACGUGAACGCUGGCAAGUCCACAACCAACAUCAUG

AUCACCACCAUCAUCAUCGUGAUCAUCGUGAUUCUGCUGAGCCUCAUCGCCGU

GGGCCUGCUGCUGUAUUGCAAAGCCAGAAGCACACCUGUGACCCUGAGCAAGG

ACCAGCUGUCUGGCAUCAACAACAUCGCCUUCUCUAACUAG

SEQ ID NO: 62, Mutant A2 protein with S155C, S190F, V207L S290C and no transmembrane domain (A2-4):
MELLILKANAITTILTAVTFCFASGQNITEEFYQSTCSAVSKGYLSALRTGWYT

SVITIELSNIKENKCNGTDAKVKLIKQELDKYKNAVTELQLLMQSTPATNNRARRELP

RFMNYTLNNAKKTNVTLSKKRKRRFLGFLLGVGSAIASGVAVCKVLHLEGEVNKIK

SALLSTNKAVVSLSNGVSVLTFKVLDLKNYIDKQLLPILNKQSCSISNIETVIEFQQKN

NRLLEITREFSVNAGVTTPVSTYMLTNSELLSLINDMPITNDQKKLMSNNVQIVRQQS

YSIMCIIKEEVLAYVVQLPLYGVIDTPCWKLHTSPLCTTNTKEGSNICLTRTDRGWYC

DNAGSVSFFPQAETCKVQSNRVFCDTMNSLTLPSEVNLCNVDIFNPKYDCKIMTSKT

DVSSSVITSLGAIVSCYGKTKCTASNKNRGIIKTFSNGCDYVSNKGVDTVSVGNTLYY

VNKQEGKSLYVKGEPIINFYDPLVFPSDEFDASISQVNEKINQSLAFIRKSDELLHNVN

AGKSTTNIMIT

SEQ ID NO: 63, DNA sequence of amino acid SEQ ID NO: 62 (A2-4):
ATGGAACTGCTGATCCTGAAGGCCAACGCTATCACCACAATCCTGACCGC

CGTGACCTTTTGCTTCGCCTCTGGCCAGAACATCACGGAAGAGTTTTACCAGAGC

ACCTGCAGCGCTGTGTCCAAAGGTTATCTGAGCGCTCTGAGAACCGGATGGTATA

CCAGCGTCATCACAATCGAGTTGTCCAATATCAAGGAAAACAAGTGTAACGGAA

CAGATGCCAAGGTGAAGCTGATCAAGCAGGAACTGGATAAGTACAAGAACGCC

GTGACCGAGCTGCAGCTGTTGATGCAGAGCACTCCTGCCACCAACAACAGAGCC

CGGAGAGAGCTGCCTAGATTCATGAACTACACCCTCAACAACGCCAAGAAGACC

-continued

AACGTGACACTGAGCAAGAAGCGGAAAAGACGGTTCCTGGGATTCCTGCTGGGC

GTTGGAAGCGCCATCGCCAGCGGCGTGGCCGTGTGTAAGGTGCTGCACCTGGAA

GGAGAGGTGAACAAAATCAAATCTGCCCTGCTTAGCACCAACAAAGCCGTTGTG

AGTTTGAGCAACGGTGTGTCCGTGCTGACATTTAAGGTGCTGGACCTGAAGAACT

ACATCGACAAGCAACTGCTGCCCATCCTGAACAAGCAATCCTGTTCCATCAGCAA

CATCGAGACAGTTATCGAGTTCCAGCAGAAGAACAACCGGCTGCTGGAAATCAC

CAGAGAATTCAGCGTGAATGCTGGCGTGACTACCCCAGTGTCTACCTACATGCTG

ACAAATTCTGAGCTGCTGAGCCTGATCAACGACATGCCTATCACAAATGATCAG

AAAAAGCTGATGAGCAACAATGTCCAGATCGTGCGGCAGCAAAGCTACAGCATC

ATGTGCATCATTAAGGAAGAAGTGCTGGCCTACGTGGTGCAGCTGCCTCTGTACG

GCGTGATCGACACCCCTTGCTGGAAGCTGCACACCTCTCCTCTGTGTACCACAAA

CACCAAGGAGGGCAGCAACATCTGCCTGACAAGAACCGATAGAGGCTGGTACTG

CGATAACGCCGGCTCTGTCTCATTCTTCCCTCAGGCCGAGACATGCAAGGTCCAG

AGCAACAGAGTGTTTTGTGATACCATGAACAGCCTGACCCTGCCAAGCGAAGTG

AATCTGTGCAATGTGGACATCTTCAACCCCAAGTACGACTGCAAGATCATGACCA

GCAAGACAGACGTGTCCAGCAGCGTTATCACCAGCCTGGGCGCCATTGTGTCTTG

CTACGGCAAAACCAAGTGCACCGCATCTAACAAAAATCGCGGCATCATCAAGAC

ATTCAGCAACGGCTGTGACTACGTCAGCAATAAGGGCGTGGACACCGTGAGCGT

GGGCAACACACTGTACTACGTGAATAAGCAGGAGGGCAAGTCTCTCTACGTGAA

AGGCGAGCCTATCATCAATTTCTACGACCCCCTGGTGTTCCCCTCCGACGAGTTC

GACGCCTCTATTAGCCAGGTGAACGAGAAGATTAACCAGAGCCTGGCTTTCATC

AGAAAGAGCGACGAGCTGCTGCACAACGTGAACGCTGGCAAGTCCACAACCAAC

ATCATGATCACCGGATACATCCCGGAGGCCCCTAGGGACGGTCAAGCTTACGTG

AGAAAGGACGGCGAATGGGTTCTGCTGTCGACCTTCTTGGGATAA

SEQ ID NO: 64, RNA sequence of amino acid SEQ ID NO: 62 (A2-4):
AUGGAACUGCUGAUCCUGAAGGCCAACGCUAUCACCACAAUCCUGACCG

CCGUGACCUUUUGCUUCGCCUCUGGCCAGAACAUCACGGAAGAGUUUUACCAG

AGCACCUGCAGCGCUGUGUCCAAAGGUUAUCUGAGCGCUCUGAGAACCGGAUG

GUAUACCAGCGUCAUCACAAUCGAGUUGUCCAAUAUCAAGGAAAACAAGUGU

AACGGAACAGAUGCCAAGGUGAAGCUGAUCAAGCAGGAACUGGAUAAGUACA

AGAACGCCGUGACCGAGCUGCAGCUGUUGAUGCAGAGCACUCCUGCCACCAAC

AACAGAGCCCGGAGAGAGCUGCCUAGAUUCAUGAACUACACCCUCAACAACGC

CAAGAAGACCAACGUGACACUGAGCAAGAAGCGGAAAAGACGGUUCCUGGGA

UUCCUGCUGGGCGUUGGAAGCGCCAUCGCCAGCGGCGUGGCCGUGUGUAAGGU

GCUGCACCUGGAAGGAGAGGUGAACAAAAUCAAAUCUGCCCUGCUUAGCACCA

ACAAAGCCGUUGUGAGUUUGAGCAACGGUGUGUCCGUGCUGACAUUUAAGGU

GCUGGACCUGAAGAACUACAUCGACAAGCAACUGCUGCCCAUCCUGAACAAGC

AAUCCUGUUCCAUCAGCAACAUCGAGACAGUUAUCGAGUUCCAGCAGAAGAAC

AACCGGCUGCUGGAAAUCACCAGAGAAUUCAGCGUGAAUGCUGGCGUGACUAC

CCCAGUGUCUACCUACAUGCUGACAAAUUCUGAGCUGCUGAGCCUGAUCAACG

ACAUGCCUAUCACAAAUGAUCAGAAAAAGCUGAUGAGCAACAAUGUCCAGAU

-continued

CGUGCGGCAGCAAAGCUACAGCAUCAUGUGCAUCAUUAAGGAAGAAGUGCUG

GCCUACGUGGUGCAGCUGCCUCUGUACGGCGUGAUCGACACCCCUUGCUGGAA

GCUGCACACCUCUCCUCUGUGUACCACAAACACCAAGGAGGGCAGCAACAUCU

GCCUGACAAGAACCGAUAGAGGCUGGUACUGCGAUAACGCCGGCUCUGUCUCA

UUCUUCCCUCAGGCCGAGACAUGCAAGGUCCAGAGCAACAGAGUGUUUUGUGA

UACCAUGAACAGCCUGACCCUGCCAAGCGAAGUGAAUCUGUGCAAUGUGGACA

UCUUCAACCCCAAGUACGACUGCAAGAUCAUGACCAGCAAGACAGACGUGUCC

AGCAGCGUUAUCACCAGCCUGGGCGCCAUUGUGUCUUGCUACGGCAAAACCAA

GUGCACCGCAUCUAACAAAAAUCGCGGCAUCAUCAAGACAUUCAGCAACGGCU

GUGACUACGUCAGCAAUAAGGGCGUGGACACCGUGAGCGUGGGCAACACACUG

UACUACGUGAAUAAGCAGGAGGGCAAGUCUCUCUACGUGAAAGGCGAGCCUA

UCAUCAAUUUCUACGACCCCCUGGUGUUCCCCUCCGACGAGUUCGACGCCUCU

AUUAGCCAGGUGAACGAGAAGAUUAACCAGAGCCUGGCUUUCAUCAGAAAGA

GCGACGAGCUGCUGCACAACGUGAACGCUGGCAAGUCCACAACCAACAUCAUG

AUCACCGGAUACAUCCCGGAGGCCCCUAGGGACGGUCAAGCUUACGUGAGAAA

GGACGGCGAAUGGGUUCUGCUGUCGACCUUCUUGGGAUAA

SEQ ID NO: 65, mutantA2 protein with 155C, S190F, V207L, S290C, D486H, E487Q, F484W, and D489H and transmembrane domain (A2-5):
MELLILKANAITTILTAVTFCFASGQNITEEFYQSTCSAVSKGYLSALRTGWYT

SVITIELSNIKENKCNGTDAKVKLIKQELDKYKNAVTELQLLMQSTPATNNRARRELP

RFMNYTLNNAKKTNVTLSKKRKRRFLGFLLGVGSAIASGVAVCKVLHLEGEVNKIK

SALLSTNKAVVSLSNGVSVLTFKVLDLKNYIDKQLLPILNKQSCSISNIETVIEFQQKN

NRLLEITREFSVNAGVTTPVSTYMLTNSELLSLINDMPITNDQKKLMSNNVQIVRQQS

YSIMCIIKEEVLAYVVQLPLYGVIDTPCWKLHTSPLCTTNTKEGSNICLTRTDRGWYC

DNAGSVSFFPQAETCKVQSNRVFCDTMNSLTLPSEVNLCNVDIFNPKYDCKIMTSKT

DVSSSVITSLGAIVSCYGKTKCTASNKNRGIIKTFSNGCDYVSNKGVDTVSVGNTLYY

VNKQEGKSLYVKGEPIINFYDPLVFPSHQWHASISQVNEKINQSLAFIRKSDELLHNV

NAGKSTTNIMITTIIIVIIVILLSLIAVGLLLYCKARSTPVTLSKDQLSGINNIAFSN

SEQ ID NO: 66, DNA sequence of amino acid SEQ ID NO: 65 (A2-5):
ATGGAACTGCTGATCCTGAAGGCCAACGCTATCACCACAATCCTGACCGC

CGTGACCTTTTGCTTCGCCTCTGGCCAGAACATCACGGAAGAGTTTTACCAGAGC

ACCTGCAGCGCTGTGTCCAAAGGTTATCTGAGCGCTCTGAGAACCGGATGGTATA

CCAGCGTCATCACAATCGAGTTGTCCAATATCAAGGAAAACAAGTGTAACGGAA

CAGATGCCAAGGTGAAGCTGATCAAGCAGGAACTGGATAAGTACAAGAACGCC

GTGACCGAGCTGCAGCTGTTGATGCAGAGCACTCCTGCCACCAACAACAGAGCC

CGGAGAGAGCTGCCTAGATTCATGAACTACACCCTCAACAACGCCAAGAAGACC

AACGTGACACTGAGCAAGAAGCGGAAAAGACGGTTCCTGGGATTCCTGCTGGGC

GTTGGAAGCGCCATCGCCAGCGGCGTGGCCGTGTGTAAGGTGCTGCACCTGGAA

GGAGAGGTGAACAAAATCAAATCTGCCCTGCTTAGCACCAACAAAGCCGTTGTG

AGTTTGAGCAACGGTGTGTCCGTGCTGACATTTAAGGTGCTGGACCTGAAGAACT

ACATCGACAAGCAACTGCTGCCCATCCTGAACAAGCAATCCTGTTCCATCAGCAA

CATCGAGACAGTTATCGAGTTCCAGCAGAAGAACAACCGGCTGCTGGAAATCAC

-continued

CAGAGAATTCAGCGTGAATGCTGGCGTGACTACCCCAGTGTCTACCTACATGCTG

ACAAATTCTGAGCTGCTGAGCCTGATCAACGACATGCCTATCACAAATGATCAG

AAAAAGCTGATGAGCAACAATGTCCAGATCGTGCGGCAGCAAAGCTACAGCATC

ATGTGCATCATTAAGGAAGAAGTGCTGGCCTACGTGGTGCAGCTGCCTCTGTACG

GCGTGATCGACACCCCTTGCTGGAAGCTGCACACCTCTCCTCTGTGTACCACAAA

CACCAAGGAGGGCAGCAACATCTGCCTGACAAGAACCGATAGAGGCTGGTACTG

CGATAACGCCGGCTCTGTCTCATTCTTCCCTCAGGCCGAGACATGCAAGGTCCAG

AGCAACAGAGTGTTTTGTGATACCATGAACAGCCTGACCCTGCCAAGCGAAGTG

AATCTGTGCAATGTGGACATCTTCAACCCCAAGTACGACTGCAAGATCATGACCA

GCAAGACAGACGTGTCCAGCAGCGTTATCACCAGCCTGGGCGCCATTGTGTCTTG

CTACGGCAAAACCAAGTGCACCGCATCTAACAAAAATCGCGGCATCATCAAGAC

ATTCAGCAACGGCTGTGACTACGTCAGCAATAAGGGCGTGGACACCGTGAGCGT

GGGCAACACACTGTACTACGTGAATAAGCAGGAGGGCAAGTCTCTCTACGTGAA

AGGCGAGCCTATCATCAATTTCTACGACCCCCTGGTGTTCCCCTCCCACCAGTGG

CACGCCTCTATTAGCCAGGTGAACGAGAAGATTAACCAGAGCCTGGCTTTCATCA

GAAAGAGCGACGAGCTGCTGCACAACGTGAACGCTGGCAAGTCCACAACCAACA

TCATGATCACCACCATCATCATCGTGATCATCGTGATTCTGCTGAGCCTCATCGC

CGTGGGCCTGCTGCTGTATTGCAAAGCCAGAAGCACACCTGTGACCCTGAGCAA

GGACCAGCTGTCTGGCATCAACAACATCGCCTTCTCTAACTAG

SEQ ID NO: 67, RNA sequence of amino acid SEQ ID NO: 65 (A2-5):
AUGGAACUGCUGAUCCUGAAGGCCAACGCUAUCACCACAAUCCUGACCG

CCGUGACCUUUUGCUUCGCCUCUGGCCAGAACAUCACGGAAGAGUUUUACCAG

AGCACCUGCAGCGCUGUGUCCAAAGGUUAUCUGAGCGCUCUGAGAACCGGAUG

GUAUACCAGCGUCAUCACAAUCGAGUUGUCCAAUAUCAAGGAAAACAAGUGU

AACGGAACAGAUGCCAAGGUGAAGCUGAUCAAGCAGGAACUGGAUAAGUACA

AGAACGCCGUGACCGAGCUGCAGCUGUUGAUGCAGAGCACUCCUGCCACCAAC

AACAGAGCCCGGAGAGAGCUGCCUAGAUUCAUGAACUACACCCUCAACAACGC

CAAGAAGACCAACGUGACACUGAGCAAGAAGCGGAAAAGACGGUUCCUGGGA

UUCCUGCUGGGCGUUGGAAGCGCCAUCGCCAGCGGCGUGGCCGUGUGUAAGGU

GCUGCACCUGGAAGGAGAGGUGAACAAAAUCAAAUCUGCCCUGCUUAGCACCA

ACAAAGCCGUUGUGAGUUUGAGCAACGGUGUGUCCGUGCUGACAUUUAAGGU

GCUGGACCUGAAGAACUACAUCGACAAGCAACUGCUGCCCAUCCUGAACAAGC

AAUCCUGUUCCAUCAGCAACAUCGAGACAGUUAUCGAGUUCCAGCAGAAGAAC

AACCGGCUGCUGGAAAUCACCAGAGAAUUCAGCGUGAAUGCUGGCGUGACUAC

CCCAGUGUCUACCUACAUGCUGACAAAUUCUGAGCUGCUGAGCCUGAUCAACG

ACAUGCCUAUCACAAAUGAUCAGAAAAAGCUGAUGAGCAACAAUGUCCAGAU

CGUGCGGCAGCAAAGCUACAGCAUCAUGUGCAUCAUUAAGGAAGAAGUGCUG

GCCUACGUGGUGCAGCUGCCUCUGUACGGCGUGAUCGACACCCCUUGCUGGAA

GCUGCACACCUCUCCUCUGUGUACCACAAACACCAAGGAGGGCAGCAACAUCU

GCCUGACAAGAACCGAUAGAGGCUGGUACUGCGAUAACGCCGGCUCUGUCUCA

UUCUUCCCUCAGGCCGAGACAUGCAAGGUCCAGAGCAACAGAGUGUUUUGUGA

-continued

UACCAUGAACAGCCUGACCCUGCCAAGCGAAGUGAAUCUGUGCAAUGUGGACA

UCUUCAACCCCAAGUACGACUGCAAGAUCAUGACCAGCAAGACAGACGUGUCC

AGCAGCGUUAUCACCAGCCUGGGCGCCAUUGUGUCUUGCUACGGCAAAACCAA

GUGCACCGCAUCUAACAAAAAUCGCGGCAUCAUCAAGACAUUCAGCAACGGCU

GUGACUACGUCAGCAAUAAGGGCGUGGACACCGUGAGCGUGGGCAACACACUG

UACUACGUGAAUAAGCAGGAGGGCAAGUCUCUCUACGUGAAAGGCGAGCCUA

UCAUCAAUUUCUACGACCCCCUGGUGUUCCCCUCCCACCAGUGGCACGCCUCU

AUUAGCCAGGUGAACGAGAAGAUUAACCAGAGCCUGGCUUUCAUCAGAAAGA

GCGACGAGCUGCUGCACAACGUGAACGCUGGCAAGUCCACAACCAACAUCAUG

AUCACCACCAUCAUCAUCGUGAUCAUCGUGAUUCUGCUGAGCCUCAUCGCCGU

GGGCCUGCUGCUGUAUUGCAAAGCCAGAAGCACACCUGUGACCCUGAGCAAGG

ACCAGCUGUCUGGCAUCAACAACAUCGCCUUCUCUAACUAG

SEQ ID NO: 68, mutant A2 Protein with S155C, S190F, V207L, S290C, D486H, E487Q, F484W, and D489H and no transmembrane domain (A2-6):
MELLILKANAITTILTAVTFCFASGQNITEEFYQSTCSAVSKGYLSALRTGWYT

SVITIELSNIKENKCNGTDAKVKLIKQELDKYKNAVTELQLLMQSTPATNNRARRELP

RFMNYTLNNAKKTNVTLSKKRKRRFLGFLLGVGSAIASGVAVCKVLHLEGEVNKIK

SALLSTNKAVVSLSNGVSVLTFKVLDLKNYIDKQLLPILNKQSCSISNIETVIEFQQKN

NRLLEITREFSVNAGVTTPVSTYMLTNSELLSLINDMPITNDQKKLMSNNVQIVRQQS

YSIMCIIKEEVLAYVVQLPLYGVIDTPCWKLHTSPLCTTNTKEGSNICLTRTDRGWYC

DNAGSVSFFPQAETCKVQSNRVFCDTMNSLTLPSEVNLCNVDIFNPKYDCKIMTSKT

DVSSSVITSLGAIVSCYGKTKCTASNKNRGIIKTFSNGCDYVSNKGVDTVSVGNTLYY

VNKQEGKSLYVKGEPIINFYDPLVFPSHQWHASISQVNEKINQSLAFIRKSDELLHNV

NAGKSTTNIMIT

SEQ ID NO: 69, DNA sequence of amino acid SEQ ID NO: 68 (A2-6):
ATGGAACTGCTGATCCTGAAGGCCAACGCTATCACCACAATCCTGACCGC

CGTGACCTTTTGCTTCGCCTCTGGCCAGAACATCACGGAAGAGTTTTACCAGAGC

ACCTGCAGCGCTGTGTCCAAAGGTTATCTGAGCGCTCTGAGAACCGGATGGTATA

CCAGCGTCATCACAATCGAGTTGTCCAATATCAAGGAAAACAAGTGTAACGGAA

CAGATGCCAAGGTGAAGCTGATCAAGCAGGAACTGGATAAGTACAAGAACGCC

GTGACCGAGCTGCAGCTGTTGATGCAGAGCACTCCTGCCACCAACAACAGAGCC

CGGAGAGAGCTGCCTAGATTCATGAACTACACCCTCAACAACGCCAAGAAGACC

AACGTGACACTGAGCAAGAAGCGGAAAAGACGGTTCCTGGGATTCCTGCTGGGC

GTTGGAAGCGCCATCGCCAGCGGCGTGGCCGTGTGTAAGGTGCTGCACCTGGAA

GGAGAGGTGAACAAAATCAAATCTGCCCTGCTTAGCACCAACAAAGCCGTTGTG

AGTTTGAGCAACGGTGTGTCCGTGCTGACATTTAAGGTGCTGGACCTGAAGAACT

ACATCGACAAGCAACTGCTGCCCATCCTGAACAAGCAATCCTGTTCCATCAGCAA

CATCGAGACAGTTATCGAGTTCCAGCAGAAGAACAACCGGCTGCTGGAAATCAC

CAGAGAATTCAGCGTGAATGCTGGCGTGACTACCCCAGTGTCTACCTACATGCTG

ACAAATTCTGAGCTGCTGAGCCTGATCAACGACATGCCTATCACAAATGATCAG

AAAAAGCTGATGAGCAACAATGTCCAGATCGTGCGGCAGCAAAGCTACAGCATC

ATGTGCATCATTAAGGAAGAAGTGCTGGCCTACGTGGTGCAGCTGCCTCTGTACG

-continued

GCGTGATCGACACCCCTTGCTGGAAGCTGCACACCTCTCCTCTGTGTACCACAAA

CACCAAGGAGGGCAGCAACATCTGCCTGACAAGAACCGATAGAGGCTGGTACTG

CGATAACGCCGGCTCTGTCTCATTCTTCCCTCAGGCCGAGACATGCAAGGTCCAG

AGCAACAGAGTGTTTTGTGATACCATGAACAGCCTGACCCTGCCAAGCGAAGTG

AATCTGTGCAATGTGGACATCTTCAACCCCAAGTACGACTGCAAGATCATGACCA

GCAAGACAGACGTGTCCAGCAGCGTTATCACCAGCCTGGGCGCCATTGTGTCTTG

CTACGGCAAAACCAAGTGCACCGCATCTAACAAAAATCGCGGCATCATCAAGAC

ATTCAGCAACGGCTGTGACTACGTCAGCAATAAGGGCGTGGACACCGTGAGCGT

GGGCAACACACTGTACTACGTGAATAAGCAGGAGGGCAAGTCTCTCTACGTGAA

AGGCGAGCCTATCATCAATTTCTACGACCCCCTGGTGTTCCCCTCCCACCAGTGG

CACGCCTCTATTAGCCAGGTGAACGAGAAGATTAACCAGAGCCTGGCTTTCATCA

GAAAGAGCGACGAGCTGCTGCACAACGTGAACGCTGGCAAGTCCACAACCAACA

TCATGATCACCGGATACATCCCGGAGGCCCCTAGGGACGGTCAAGCTTACGTGA

GAAAGGACGGCGAATGGGTTCTGCTGTCGACCTTCTTGGGATAA

SEQ ID NO: 70, DNA sequence of amino acid SEQ ID NO: 68 (A2-6):
AUGGAACUGCUGAUCCUGAAGGCCAACGCUAUCACCACAAUCCUGACCG

CCGUGACCUUUUGCUUCGCCUCUGGCCAGAACAUCACGGAAGAGUUUUACCAG

AGCACCUGCAGCGCUGUGUCCAAAGGUUAUCUGAGCGCUCUGAGAACCGGAUG

GUAUACCAGCGUCAUCACAAUCGAGUUGUCCAAUAUCAAGGAAAACAAGUGU

AACGGAACAGAUGCCAAGGUGAAGCUGAUCAAGCAGGAACUGGAUAAGUACA

AGAACGCCGUGACCGAGCUGCAGCUGUUGAUGCAGAGCACUCCUGCCACCAAC

AACAGAGCCCGGAGAGAGCUGCCUAGAUUCAUGAACUACACCCUCAACAACGC

CAAGAAGACCAACGUGACACUGAGCAAGAAGCGGAAAAGACGGUUCCUGGGA

UUCCUGCUGGGCGUUGGAAGCGCCAUCGCCAGCGGCGUGGCCGUGUGUAAGGU

GCUGCACCUGGAAGGAGAGGUGAACAAAAUCAAAUCUGCCCUGCUUAGCACCA

ACAAAGCCGUUGUGAGUUUGAGCAACGGUGUGUCCGUGCUGACAUUUAAGGU

GCUGGACCUGAAGAACUACAUCGACAAGCAACUGCUGCCCAUCCUGAACAAGC

AAUCCUGUUCCAUCAGCAACAUCGAGACAGUUAUCGAGUUCCAGCAGAAGAAC

AACCGGCUGCUGGAAAUCACCAGAGAAUUCAGCGUGAAUGCUGGCGUGACUAC

CCCAGUGUCUACCUACAUGCUGACAAAUUCUGAGCUGCUGAGCCUGAUCAACG

ACAUGCCUAUCACAAAUGAUCAGAAAAAGCUGAUGAGCAACAAUGUCCAGAU

CGUGCGGCAGCAAAGCUACAGCAUCAUGUGCAUCAUUAAGGAAGAAGUGCUG

GCCUACGUGGUGCAGCUGCCUCUGUACGGCGUGAUCGACACCCCUUGCUGGAA

GCUGCACACCUCUCCUCUGUGUACCACAAACACCAAGGAGGGCAGCAACAUCU

GCCUGACAAGAACCGAUAGAGGCUGGUACUGCGAUAACGCCGGCUCUGUCUCA

UUCUUCCCUCAGGCCGAGACAUGCAAGGUCCAGAGCAACAGAGUGUUUUGUGA

UACCAUGAACAGCCUGACCCUGCCAAGCGAAGUGAAUCUGUGCAAUGUGGACA

UCUUCAACCCCAAGUACGACUGCAAGAUCAUGACCAGCAAGACAGACGUGUCC

AGCAGCGUUAUCACCAGCCUGGGCGCCAUUGUGUCUUGCUACGGCAAAACCAA

GUGCACCGCAUCUAACAAAAAUCGCGGCAUCAUCAAGACAUUCAGCAACGGCU

GUGACUACGUCAGCAAUAAGGGCGUGGACACCGUGAGCGUGGGCAACACACUG

-continued

UACUACGUGAAUAAGCAGGAGGGCAAGUCUCUCUACGUGAAAGGCGAGCCUA

UCAUCAAUUUCUACGACCCCCUGGUGUUCCCCUCCCACCAGUGGCACGCCUCU

AUUAGCCAGGUGAACGAGAAGAUUAACCAGAGCCUGGCUUUCAUCAGAAAGA

GCGACGAGCUGCUGCACAACGUGAACGCUGGCAAGUCCACAACCAACAUCAUG

AUCACCGGAUACAUCCCGGAGGCCCCUAGGGACGGUCAAGCUUACGUGAGAAA

GGACGGCGAAUGGGUUCUGCUGUCGACCUUCUUGGGAUAA

SEQ ID NO: 71, Optimized Signal peptide:
MELPVLKTNAITTILAAVTLCFASSQ

SEQ ID NO: 72, DNA of SEQ ID NO: 71:
ATGGAACTGCCTGTGCTGAAAACAAACGCCATCACAACAATCCTGGCAGC

AGTGACACTGTGCTTCGCCAGCAGCCAG

SEQ ID NO: 73, RNA of SEQ ID NO: 71:
AUGGAACUGCCUGUGCUGAAAACAAACGCCAUCACAACAAUCCUGGCA

GCAGUGACACUGUGCUUCGCCAGCAGCCAG

SEQ ID NO: 74, Optimized Heptad repeat C:
NITEEFYQSTCSAVSKGYLSALRTGWYTSVITIELSNIKENKCNGTDAKVKLIK

QELDKYKNAVTELQLLMQSTPAANNRARR

SEQ ID NO: 75, DNA of SEQ ID NO: 74:
AATATTACAGAAGAGTTCTACCAGAGCACATGCAGCGCCGTGTCTAAGGG

CTACCTGAGCGCCCTGAGAACAGGCTGGTACACCAGCGTCATCACGATCGAGCT

GAGTAATATCAAGGAGAACAAATGCAACGGCACCGACGCCAAGGTGAAGCTGA

TCAAGCAGGAGCTGGATAAATACAAGAACGCCGTGACCGAGTTGCAGCTGCTGA

TGCAGTCTACCCCAGCCGCCAACAACAGAGCCAGACGG

SEQ ID NO: 76, RNA of SEQ ID NO: 74:
AAUAUUACAGAAGAGUUCUACCAGAGCACAUGCAGCGCCGUGUCUAAG

GGCUACCUGAGCGCCCUGAGAACAGGCUGGUACACCAGCGUCAUCACGAUCGA

GCUGAGUAAUAUCAAGGAGAACAAAUGCAACGGCACCGACGCCAAGGUGAAG

CUGAUCAAGCAGGAGCUGGAUAAAUACAAGAACGCCGUGACCGAGUUGCAGC

UGCUGAUGCAGUCUACCCCAGCCGCCAACAACAGAGCCAGACGG

SEQ ID NO: 77, Optimized p27 fragment:
ELPRFMNYTLNNTKNTNVTLSKKRKRRF

SEQ ID NO: 78, DNA of SEQ ID NO: 77:
GAACTACCCAGATTCATGAACTACACACTGAACAACACTAAGAACACCAA

CGTGACACTGTCTAAGAAAAGAAAGCGGCGGTTC

SEQ ID NO: 79, RNA of SEQ ID NO: 77:
GAACUACCCAGAUUCAUGAACUACACACUGAACAACACUAAGAACACCA

ACGUGACACUGUCUAAGAAAAGAAAGCGGCGGUUC

SEQ ID NO: 80, S155 fusion peptide:
LGFLLGVGSAIASGIAVS

SEQ ID NO: 81, DNA of SEQ ID NO: 80:
CTGGGATTCCTGCTGGGCGTGGGAAGCGCTATCGCTTCTGGAATTGCCGT

GAGC

SEQ ID NO: 82, RNA of SEQ ID NO: 80:
CUGGGAUUCCUGCUGGGCGUGGGAAGCGCUAUCGCUUCUGGAAUUGCC

GUGAGC

SEQ ID NO: 83, trimerization domain:
TGYIPEAPRDGQAYVRKDGEWVLLSTFLG

-continued

SEQ ID NO: 84, DNA of SEQ ID NO: 83:
ACCGGATACATCCCGGAGGCCCCTAGGGACGGTCAAGCTTACGTGAGAAA

GGACGGCGAATGGGTTCTGCTGTCGACCTTCTTGGGA

SEQ ID NO: 85, RNA of SEQ ID NO: 83:
ACCGGAUACAUCCCGGAGGCCCCUAGGGACGGUCAAGCUUACGUGAGA

AAGGACGGCGAAUGGGUUCUGCUGUCGACCUUCUUGGGA

SEQ ID NO: 86, promoter region
TAATACGACTCACTATAA

SEQ ID NO: 87, optimized F protein Vaccine F1 sequence lacking any mutations with transmembrane domain:
MELPVLKTNAITTILAAVTLCFASSQNITEEFYQSTCSAVSKGYLSALRTGWY

TSVITIELSNIKENKCNGTDAKVKLIKQELDKYKNAVTELQLLMQSTPAANNRARRE

LPRFMNYTLNNTKNTNVTLSKKRKRRFLGFLLGVGSAIASGIAVSKVLHLEGEVNKI

KSALLSTNKAVVSLSNGVSVLTSKVLDLKNYIDKQLLPIVNKQSCSISNIETVIEFQQK

NNRLLEITREFSVNAGVTTPVSTYMLTNSELLSLINDMPITNDQKKLMSNNVQIVRQQ

SYSIMSIIKEEVLAYVVQLPLYGVIDTPCWKLHTSPLCTTNTKEGSNICLTRTDRGWY

CDNAGSVSFFPQADTCKVQSNRVFCDTMNSLTLPSEVNLCNIDIFNPKYDCKIMTSKT

DVSSSVITSLGAIVSCYGKTKCTASNKNRGIIKTFSNGCDYVSNKGVDTVSVGNTLYY

VNKQEGKSLYVKGEPIINFYDPLVFPSDEFDASISQVNEKINQSLAFIRKSDELLHNVN

AGKSTTNIMITTIIIVIIVILLSLIAVGLLLYCKARSTPVTLSKDQLSGINNIAFSN

SEQ ID NO: 88, DNA sequence for SEQ ID NO: 87,
ATGGAACTGCCTGTGCTGAAAACAAACGCCATCACAACAATCCTGGCAGC

AGTGACACTGTGCTTCGCCAGCAGCCAGAATATTACAGAAGAGTTCTACCAGAG

CACATGCAGCGCCGTGTCTAAGGGCTACCTGAGCGCCCTGAGAACAGGCTGGTA

CACCAGCGTCATCACGATCGAGCTGAGTAATATCAAGGAGAACAAATGCAACGG

CACCGACGCCAAGGTGAAGCTGATCAAGCAGGAGCTGGATAAATACAAGAACG

CCGTGACCGAGTTGCAGCTGCTGATGCAGTCTACCCCAGCCGCCAACAACAGAG

CCAGACGGGAACTACCCAGATTCATGAACTACACACTGAACAACACTAAGAACA

CCAACGTGACACTGTCTAAGAAAAGAAAGCGGCGGTTCCTGGGATTCCTGCTGG

GCGTGGGAAGCGCTATCGCTTCTGGAATTGCCGTGAGCAAGGTGCTGCACCTGG

AAGGCGAGGTGAACAAGATCAAGTCTGCCCTGCTGTCCACCAACAAGGCCGTAG

TCAGCCTGAGCAATGGCGTGAGCGTCCTGACCAGTAAGGTGCTGGACCTGAAGA

ACTACATCGACAAGCAGCTGCTGCCTATCGTGAACAAGCAGAGCTGCTCCATCA

GCAATATTGAGACTGTGATCGAATTCCAGCAGAAGAACAACCGGCTGCTGGAGA

TCACCAGAGAGTTCTCCGTGAACGCTGGCGTGACTACACCTGTTTCAACCTACAT

GCTGACCAATTCTGAGCTGCTGAGCCTGATCAACGACATGCCTATCACCAACGAC

CAGAAAAAACTGATGTCCAATAACGTTCAAATCGTGCGGCAGCAAAGCTACAGC

ATCATGAGCATCATCAAGGAAGAAGTGCTTGCCTACGTGGTCCAGCTGCCACTTT

ATGGAGTTATCGATACACCCTGCTGGAAGCTGCACACCAGCCCTCTGTGTACAAC

CAACACCAAGGAAGGCAGCAACATCTGCCTGACCAGAACAGATAGAGGCTGGTA

TTGTGATAACGCCGGCAGCGTGAGCTTCTTCCCCCAGGCCGACACATGTAAAGTG

CAGAGCAATAGAGTGTTCTGCGACACCATGAATAGCCTGACCCTGCCCAGCGAG

GTGAATCTGTGTAACATCGACATTTTCAACCCCAAGTACGATTGCAAGATCATGA

-continued

CCTCCAAGACCGACGTGAGCAGCAGCGTGATCACCTCCCTGGGCGCCATCGTGTC

TTGCTACGGCAAGACCAAGTGCACAGCCTCTAACAAAAATCGCGGCATCATCAA

AACCTTCTCTAACGGTTGTGACTACGTGTCAAACAAAGGCGTGGACACCGTGTCC

GTGGGCAACACCCTGTATTACGTGAACAAGCAGGAGGGCAAGAGCCTGTACGTG

AAGGGCGAACCTATTATCAACTTCTACGACCCTCTGGTGTTTCCTTCCGACGAGT

TTGATGCTAGCATCTCTCAGGTGAACGAGAAGATCAACCAGAGCCTGGCCTTTAT

CAGAAAGAGCGATGAGCTGCTGCACAACGTGAACGCCGGCAAGAGTACCACCA

ACATCATGATCACCACCATCATTATCGTGATCATCGTGATCCTCCTGAGCCTGAT

CGCTGTCGGACTGCTGCTGTACTGCAAGGCCAGGAGCACACCTGTGACCCTGAG

CAAGGACCAACTGTCTGGCATCAACAACATCGCTTTTAGCAAT

SEQ ID NO: 89, RNA of SEQ ID NO: 87:
AUGGAACUGCCUGUGCUGAAAACAAACGCCAUCACAACAAUCCUGGCA

GCAGUGACACUGUGCUUCGCCAGCAGCCAGAAUAUUACAGAAGAGUUCUACCA

GAGCACAUGCAGCGCCGUGUCUAAGGGCUACCUGAGCGCCCUGAGAACAGGCU

GGUACACCAGCGUCAUCACGAUCGAGCUGAGUAAUAUCAAGGAGAACAAAUG

CAACGGCACCGACGCCAAGGUGAAGCUGAUCAAGCAGGAGCUGGAUAAAUACA

AGAACGCCGUGACCGAGUUGCAGCUGCUGAUGCAGUCUACCCCAGCCGCCAAC

AACAGAGCCAGACGGGAACUACCCAGAUUCAUGAACUACACACUGAACAACAC

UAAGAACACCAACGUGACACUGUCUAAGAAAAGAAAGCGGCGGUUCCUGGGA

UUCCUGCUGGGCGUGGGAAGCGCUAUCGCUUCUGGAAUUGCCGUGAGCAAGG

UGCUGCACCUGGAAGGCGAGGUGAACAAGAUCAAGUCUGCCCUGCUGUCCACC

AACAAGGCCGUAGUCAGCCUGAGCAAUGGCGUGAGCGUCCUGACCAGUAAGGU

GCUGGACCUGAAGAACUACAUCGACAAGCAGCUGCUGCCUAUCGUGAACAAGC

AGAGCUGCUCCAUCAGCAAUAUUGAGACUGUGAUCGAAUUCCAGCAGAAGAA

CAACCGGCUGCUGGAGAUCACCAGAGAGUUCUCCGUGAACGCUGGCGUGACUA

CACCUGUUUCAACCUACAUGCUGACCAAUUCUGAGCUGCUGAGCCUGAUCAAC

GACAUGCCUAUCACCAACGACCAGAAAAAACUGAUGUCCAAUAACGUUCAAAU

CGUGCGGCAGCAAAGCUACAGCAUCAUGAGCAUCAUCAAGGAAGAAGUGCUU

GCCUACGUGGUCCAGCUGCCACUUUAUGGAGUUAUCGAUACACCCUGCUGGAA

GCUGCACACCAGCCCUCUGUGUACAACCAACACCAAGGAAGGCAGCAACAUCU

GCCUGACCAGAACAGAUAGAGGCUGGUAUUGUGAUAACGCCGGCAGCGUGAG

CUUCUUCCCCCAGGCCGACACAUGUAAAGUGCAGAGCAAUAGAGUGUUCUGCG

ACACCAUGAAUAGCCUGACCCUGCCCAGCGAGGUGAAUCUGUGUAACAUCGAC

AUUUUCAACCCCAAGUACGAUUGCAAGAUCAUGACCUCCAAGACCGACGUGAG

CAGCAGCGUGAUCACCUCCCUGGGCGCCAUCGUGUCUUGCUACGGCAAGACCA

AGUGCACAGCCUCUAACAAAAAUCGCGGCAUCAUCAAAACCUUCUCUAACGGU

UGUGACUACGUGUCAAACAAAGGCGUGGACACCGUGUCCGUGGGCAACACCCU

GUAUUACGUGAACAAGCAGGAGGGCAAGAGCCUGUACGUGAAGGGCGAACCU

AUUAUCAACUUCUACGACCCUCUGGUGUUUCCUUCCGACGAGUUUGAUGCUAG

CAUCUCUCAGGUGAACGAGAAGAUCAACCAGAGCCUGGCCUUUAUCAGAAAGA

GCGAUGAGCUGCUGCACAACGUGAACGCCGGCAAGAGUACCACCAACAUCAUG

-continued

AUCACCACCAUCAUUAUCGUGAUCAUCGUGAUCCUCCUGAGCCUGAUCGCUGU

CGGACUGCUGCUGUACUGCAAGGCCAGGAGCACACCUGUGACCCUGAGCAAGG

ACCAACUGUCUGGCAUCAACAACAUCGCUUUUAGCAAU

SEQ ID NO: 90, RSV cytoplasmic domain
KARSTPVTLSKDQLSGINNIAFSN

SEQ ID NO: 91, RSV trimerization domain
MITGYIPEAPRDGQAYVRKDGEWVLLSTFLG

SEQ ID NO: 92, optimized F protein Vaccine F2 sequence lacking any mutations without transmembrane domain:
MELPVLKTNAITTILAAVTLCFASSQNITEEFYQSTCSAVSKGYLSALRTGWY

TSVITIELSNIKENKCNGTDAKVKLIKQELDKYKNAVTELQLLMQSTPAANNRARRE

LPRFMNYTLNNTKNTNVTLSKKRKRRFLGFLLGVGSAIASGIA VSKVLHLEGEVNKI

KSALLSTNKAVVSLSNGVSVLTSKVLDLKNYIDKQLLPIVNKQSCSISNIETVIEFQQK

NNRLLEITREFSVNAGVTTPVSTYMLTNSELLSLINDMPITNDQKKLMSNNVQIVRQQ

SYSIMSIIKEEVLAYVVQLPLYGVIDTPCWKLHTSPLCTTNTKEGSNICLTRTDRGWY

CDNAGSVSFFPQADTCKVQSNRVFCDTMNSLTLPSEVNLCNIDIFNPKYDCKIMTSKT

DVSSSVITSLGAIVSCYGKTKCTASNKNRGIIKTFSNGCDYVSNKGVDTVSVGNTLYY

VNKQEGKSLYVKGEPIINFYDPLVFPSDEFDASISQVNEKINQSLAFIRKSDELLHNVN

AGKSTTNIMITGYIPEAPRDGQAYVRKDGEWVLLSTFLG

SEQ ID NO: 93, DNA for SEQ ID NO: 92:
ATGGAACTGCCTGTGCTGAAAACAAACGCCATCACAACAATCCTGGCAGC

AGTGACACTGTGCTTCGCCAGCAGCCAGAATATTACAGAAGAGTTCTACCAGAG

CACATGCAGCGCCGTGTCTAAGGGCTACCTGAGCGCCCTGAGAACAGGCTGGTA

CACCAGCGTCATCACGATCGAGCTGAGTAATATCAAGGAGAACAAATGCAACGG

CACCGACGCCAAGGTGAAGCTGATCAAGCAGGAGCTGGATAAATACAAGAACG

CCGTGACCGAGTTGCAGCTGCTGATGCAGTCTACCCCAGCCGCCAACAACAGAG

CCAGACGGGAACTACCCAGATTCATGAACTACACACTGAACAACACTAAGAACA

CCAACGTGACACTGTCTAAGAAAAGAAAGCGGCGGTTCCTGGGATTCCTGCTGG

GCGTGGGAAGCGCTATCGCTTCTGGAATTGCCGTGAGCAAGGTGCTGCACCTGG

AAGGCGAGGTGAACAAGATCAAGTCTGCCCTGCTGTCCACCAACAAGGCCGTAG

TCAGCCTGAGCAATGGCGTGAGCGTCCTGACCAGTAAGGTGCTGGACCTGAAGA

ACTACATCGACAAGCAGCTGCTGCCTATCGTGAACAAGCAGAGCTGCTCCATCA

GCAATATTGAGACTGTGATCGAATTCCAGCAGAAGAACAACCGGCTGCTGGAGA

TCACCAGAGAGTTCTCCGTGAACGCTGGCGTGACTACACCTGTTTCAACCTACAT

GCTGACCAATTCTGAGCTGCTGAGCCTGATCAACGACATGCCTATCACCAACGAC

CAGAAAAAACTGATGTCCAATAACGTTCAAATCGTGCGGCAGCAAAGCTACAGC

ATCATGAGCATCATCAAGGAAGAAGTGCTTGCCTACGTGGTCCAGCTGCCACTTT

ATGGAGTTATCGATACACCCTGCTGGAAGCTGCACACCAGCCCTCTGTGTACAAC

CAACACCAAGGAAGGCAGCAACATCTGCCTGACCAGAACAGATAGAGGCTGGTA

TTGTGATAACGCCGGCAGCGTGAGCTTCTTCCCCCAGGCCGACACATGTAAAGTG

CAGAGCAATAGAGTGTTCTGCGACACCATGAATAGCCTGACCCTGCCCAGCGAG

GTGAATCTGTGTAACATCGACATTTTCAACCCCAAGTACGATTGCAAGATCATGA

CCTCCAAGACCGACGTGAGCAGCAGCGTGATCACCTCCCTGGGCGCCATCGTGTC

-continued

TTGCTACGGCAAGACCAAGTGCACAGCCTCTAACAAAAATCGCGGCATCATCAA

AACCTTCTCTAACGGTTGTGACTACGTGTCAAACAAAGGCGTGGACACCGTGTCC

GTGGGCAACACCCTGTATTACGTGAACAAGCAGGAGGGCAAGAGCCTGTACGTG

AAGGGCGAACCTATTATCAACTTCTACGACCCTCTGGTGTTTCCTTCCGACGAGT

TTGATGCTAGCATCTCTCAGGTGAACGAGAAGATCAACCAGAGCCTGGCCTTTAT

CAGAAAGAGCGATGAGCTGCTGCACAACGTGAACGCCGGCAAGAGTACCACCA

ACATCATGATCACCGGATACATCCCGGAGGCCCCTAGGGACGGTCAAGCTTACG

TGAGAAAGGACGGCGAATGGGTTCTGCTGTCGACCTTCTTGGGA

SEQ ID NO: 94, RNA for SEQ ID NO: 92
AUGGAACUGCCUGUGCUGAAAACAAACGCCAUCACAACAAUCCUGGCA

GCAGUGACACUGUGCUUCGCCAGCAGCCAGAAUAUUACAGAAGAGUUCUACCA

GAGCACAUGCAGCGCCGUGUCUAAGGGCUACCUGAGCGCCCUGAGAACAGGCU

GGUACACCAGCGUCAUCACGAUCGAGCUGAGUAAUAUCAAGGAGAACAAAUG

CAACGGCACCGACGCCAAGGUGAAGCUGAUCAAGCAGGAGCUGGAUAAAUACA

AGAACGCCGUGACCGAGUUGCAGCUGCUGAUGCAGUCUACCCCAGCCGCCAAC

AACAGAGCCAGACGGGAACUACCCAGAUUCAUGAACUACACACUGAACAACAC

UAAGAACACCAACGUGACACUGUCUAAGAAAAGAAAGCGGCGGUUCCUGGGA

UUCCUGCUGGGCGUGGGAAGCGCUAUCGCUUCUGGAAUUGCCGUGAGCAAGG

UGCUGCACCUGGAAGGCGAGGUGAACAAGAUCAAGUCUGCCCUGCUGUCCACC

AACAAGGCCGUAGUCAGCCUGAGCAAUGGCGUGAGCGUCCUGACCAGUAAGGU

GCUGGACCUGAAGAACUACAUCGACAAGCAGCUGCUGCCUAUCGUGAACAAGC

AGAGCUGCUCCAUCAGCAAUAUUGAGACUGUGAUCGAAUUCCAGCAGAAGAA

CAACCGGCUGCUGGAGAUCACCAGAGAGUUCUCCGUGAACGCUGGCGUGACUA

CACCUGUUUCAACCUACAUGCUGACCAAUUCUGAGCUGCUGAGCCUGAUCAAC

GACAUGCCUAUCACCAACGACCAGAAAAAACUGAUGUCCAAUAACGUUCAAAU

CGUGCGGCAGCAAAGCUACAGCAUCAUGAGCAUCAUCAAGGAAGAAGUGCUU

GCCUACGUGGUCCAGCUGCCACUUUAUGGAGUUAUCGAUACACCCUGCUGGAA

GCUGCACACCAGCCCUCUGUGUACAACCAACACCAAGGAAGGCAGCAACAUCU

GCCUGACCAGAACAGAUAGAGGCUGGUAUUGUGAUAACGCCGGCAGCGUGAG

CUUCUUCCCCCAGGCCGACACAUGUAAAGUGCAGAGCAAUAGAGUGUUCUGCG

ACACCAUGAAUAGCCUGACCCUGCCCAGCGAGGUGAAUCUGUGUAACAUCGAC

AUUUUCAACCCCAAGUACGAUUGCAAGAUCAUGACCUCCAAGACCGACGUGAG

CAGCAGCGUGAUCACCUCCCUGGGCGCCAUCGUGUCUUGCUACGGCAAGACCA

AGUGCACAGCCUCUAACAAAAAUCGCGGCAUCAUCAAAACCUUCUCUAACGGU

UGUGACUACGUGUCAAACAAAGGCGUGGACACCGUGUCCGUGGGCAACACCCU

GUAUUACGUGAACAAGCAGGAGGGCAAGAGCCUGUACGUGAAGGGCGAACCU

AUUAUCAACUUCUACGACCCUCUGGUGUUUCCUUCCGACGAGUUUGAUGCUAG

CAUCUCUCAGGUGAACGAGAAGAUCAACCAGAGCCUGGCCUUUAUCAGAAAGA

GCGAUGAGCUGCUGCACAACGUGAACGCCGGCAAGAGUACCACCAACAUCAUG

AUCACCGGAUACAUCCCGGAGGCCCCUAGGGACGGUCAAGCUUACGUGAGAAA

GGACGGCGAAUGGGUUCUGCUGUCGACCUUCUUGGGA

-continued

SEQ ID NO: 95, Optimized Vaccine F3 full construct with S155C, S190F, V207L S290C with transmembrane domain:

MELPVLKTNAITTILAAVTLCFASSQNITEEFYQSTCSAVSKGYLSALRTGWY

TSVITIELSNIKENKCNGTDAKVKLIKQELDKYKNAVTELQLLMQSTPAANNRARRE

LPRFMNYTLNNTKNTNVTLSKKRKRRFLGFLLGVGSAIASGIAVCKVLHLEGEVNKI

KSALLSTNKAVVSLSNGVSVLTFKVLDLKNYIDKQLLPILNKQSCSISNIETVIEFQQK

NNRLLEITREFSVNAGVTTPVSTYMLTNSELLSLINDMPITNDQKKLMSNNVQIVRQQ

SYSIMCIIKEEVLAYVVQLPLYGVIDTPCWKLHTSPLCTTNTKEGSNICLTRTDRGWY

CDNAGSVSFFPQADTCKVQSNRVFCDTMNSLTLPSEVNLCNIDIFNPKYDCKIMTSKT

DVSSSVITSLGAIVSCYGKTKCTASNKNRGIIKTFSNGCDYVSNKGVDTVSVGNTLYY

VNKQEGKSLYVKGEPIINFYDPLVFPSDEFDASISQVNEKINQSLAFIRKSDELLHNVN

AGKSTTNIMITTIIIVIIVILLSLIAVGLLLYCKARSTPVTLSKDQLSGINNIAFSN

SEQ ID NO: 96, DNA of SEQ ID NO: 95

ATGGAACTGCCTGTGCTGAAAACAAACGCCATCACAACAATCCTGGCAGC

AGTGACACTGTGCTTCGCCAGCAGCCAGAATATTACAGAAGAGTTCTACCAGAG

CACATGCAGCGCCGTGTCTAAGGGCTACCTGAGCGCCCTGAGAACAGGCTGGTA

CACCAGCGTCATCACGATCGAGCTGAGTAATATCAAGGAGAACAAATGCAACGG

CACCGACGCCAAGGTGAAGCTGATCAAGCAGGAGCTGGATAAATACAAGAACG

CCGTGACCGAGTTGCAGCTGCTGATGCAGTCTACCCCAGCCGCCAACAACAGAG

CCAGACGGGAACTACCCAGATTCATGAACTACACACTGAACAACACTAAGAACA

CCAACGTGACACTGTCTAAGAAAAGAAAGCGGCGGTTCCTGGGATTCCTGCTGG

GCGTGGGAAGCGCTATCGCTTCTGGAATTGCCGTGTGCAAGGTGCTGCACCTGGA

AGGCGAGGTGAACAAGATCAAGTCTGCCCTGCTGTCCACCAACAAGGCCGTAGT

CAGCCTGAGCAATGGCGTGAGCGTCCTGACCTTTAAGGTGCTGGACCTGAAGAA

CTACATCGACAAGCAGCTGCTGCCTATCTTGAACAAGCAGAGCTGCTCCATCAGC

AATATTGAGACTGTGATCGAATTCCAGCAGAAGAACAACCGGCTGCTGGAGATC

ACCAGAGAGTTCTCCGTGAACGCTGGCGTGACTACACCTGTTTCAACCTACATGC

TGACCAATTCTGAGCTGCTGAGCCTGATCAACGACATGCCTATCACCAACGACCA

GAAAAAACTGATGTCCAATAACGTTCAAATCGTGCGGCAGCAAAGCTACAGCAT

CATGTGCATCATCAAGGAAGAAGTGCTTGCCTACGTGGTCCAGCTGCCACTTTAT

GGAGTTATCGATACACCCTGCTGGAAGCTGCACACCAGCCCTCTGTGTACAACCA

ACACCAAGGAAGGCAGCAACATCTGCCTGACCAGAACAGATAGAGGCTGGTATT

GTGATAACGCCGGCAGCGTGAGCTTCTTCCCCCAGGCCGACACATGTAAAGTGC

AGAGCAATAGAGTGTTCTGCGACACCATGAATAGCCTGACCCTGCCCAGCGAGG

TGAATCTGTGTAACATCGACATTTTCAACCCCAAGTACGATTGCAAGATCATGAC

CTCCAAGACCGACGTGAGCAGCAGCGTGATCACCTCCCTGGGCGCCATCGTGTCT

TGCTACGGCAAGACCAAGTGCACAGCCTCTAACAAAAATCGCGGCATCATCAAA

ACCTTCTCTAACGGTTGTGACTACGTGTCAAACAAAGGCGTGGACACCGTGTCCG

TGGGCAACACCCTGTATTACGTGAACAAGCAGGAGGGCAAGAGCCTGTACGTGA

AGGGCGAACCTATTATCAACTTCTACGACCCTCTGGTGTTTCCTTCCGACGAGTTT

GATGCTAGCATCTCTCAGGTGAACGAGAAGATCAACCAGAGCCTGGCCTTTATC

AGAAAGAGCGATGAGCTGCTGCACAACGTGAACGCCGGCAAGAGTACCACCAA

-continued

CATCATGATCACCACCATCATTATCGTGATCATCGTGATCCTCCTGAGCCTGATC

GCTGTCGGACTGCTGCTGTACTGCAAGGCCAGGAGCACACCTGTGACCCTGAGC

AAGGACCAACTGTCTGGCATCAACAACATCGCTTTTAGCAAT

SEQ ID NO: 97, RNA of SEQ ID NO: 95
AUGGAACUGCCUGUGCUGAAAACAAACGCCAUCACAACAAUCCUGGCA

GCAGUGACACUGUGCUUCGCCAGCAGCCAGAAUAUUACAGAAGAGUUCUACCA

GAGCACAUGCAGCGCCGUGUCUAAGGGCUACCUGAGCGCCCUGAGAACAGGCU

GGUACACCAGCGUCAUCACGAUCGAGCUGAGUAAUAUCAAGGAGAACAAAUG

CAACGGCACCGACGCCAAGGUGAAGCUGAUCAAGCAGGAGCUGGAUAAAUACA

AGAACGCCGUGACCGAGUUGCAGCUGCUGAUGCAGUCUACCCCAGCCGCCAAC

AACAGAGCCAGACGGGAACUACCCAGAUUCAUGAACUACACACUGAACAACAC

UAAGAACACCAACGUGACACUGUCUAAGAAAAGAAAGCGGCGGUUCCUGGGA

UUCCUGCUGGGCGUGGGAAGCGCUAUCGCUUCUGGAAUUGCCGUGUGCAAGG

UGCUGCACCUGGAAGGCGAGGUGAACAAGAUCAAGUCUGCCCUGCUGUCCACC

AACAAGGCCGUAGUCAGCCUGAGCAAUGGCGUGAGCGUCCUGACCUUUAAGGU

GCUGGACCUGAAGAACUACAUCGACAAGCAGCUGCUGCCUAUCUUGAACAAGC

AGAGCUGCUCCAUCAGCAAUAUUGAGACUGUGAUCGAAUUCCAGCAGAAGAA

CAACCGGCUGCUGGAGAUCACCAGAGAGUUCUCCGUGAACGCUGGCGUGACUA

CACCUGUUUCAACCUACAUGCUGACCAAUUCUGAGCUGCUGAGCCUGAUCAAC

GACAUGCCUAUCACCAACGACCAGAAAAAACUGAUGUCCAAUAACGUUCAAAU

CGUGCGGCAGCAAAGCUACAGCAUCAUGUGCAUCAUCAAGGAAGAAGUGCUU

GCCUACGUGGUCCAGCUGCCACUUUAUGGAGUUAUCGAUACACCCUGCUGGAA

GCUGCACACCAGCCCUCUGUGUACAACCAACACCAAGGAAGGCAGCAACAUCU

GCCUGACCAGAACAGAUAGAGGCUGGUAUUGUGAUAACGCCGGCAGCGUGAG

CUUCUUCCCCCAGGCCGACACAUGUAAAGUGCAGAGCAAUAGAGUGUUCUGCG

ACACCAUGAAUAGCCUGACCCUGCCCAGCGAGGUGAAUCUGUGUAACAUCGAC

AUUUUCAACCCCAAGUACGAUUGCAAGAUCAUGACCUCCAAGACCGACGUGAG

CAGCAGCGUGAUCACCUCCCUGGGCGCCAUCGUGUCUUGCUACGGCAAGACCA

AGUGCACAGCCUCUAACAAAAAUCGCGGCAUCAUCAAAACCUUCUCUAACGGU

UGUGACUACGUGUCAAACAAAGGCGUGGACACCGUGUCCGUGGGCAACACCCU

GUAUUACGUGAACAAGCAGGAGGGCAAGAGCCUGUACGUGAAGGGCGAACCU

AUUAUCAACUUCUACGACCCUCUGGUGUUUCCUUCCGACGAGUUUGAUGCUAG

CAUCUCUCAGGUGAACGAGAAGAUCAACCAGAGCCUGGCCUUUAUCAGAAAGA

GCGAUGAGCUGCUGCACAACGUGAACGCCGGCAAGAGUACCACCAACAUCAUG

AUCACCACCAUCAUUAUCGUGAUCAUCGUGAUCCUCCUGAGCCUGAUCGCUGU

CGGACUGCUGCUGUACUGCAAGGCCAGGAGCACACCUGUGACCCUGAGCAAGG

ACCAACUGUCUGGCAUCAACAACAUCGCUUUUAGCAAU

SEQ ID NO: 98, Optimized Vaccine F4 full construct with S155C, S190F, V207L S290C without transmembrane domain:
MELPVLKTNAITTILAAVTLCFASSQNITEEFYQSTCSAVSKGYLSALRTGWY

TSVITIELSNIKENKCNGTDAKVKLIKQELDKYKNAVTELQLLMQSTPAANNRARRE

LPRFMNYTLNNTKNTNVTLSKKRKRRFLGFLLGVGSAIASGIAVCKVLHLEGEVNKI

-continued

KSALLSTNKAVVSLSNGVSVLTFKVLDLKNYIDKQLLPILNKQSCSISNIETVIEFQQK

NNRLLEITREFSVNAGVTTPVSTYMLTNSELLSLINDMPITNDQKKLMSNNVQIVRQQ

SYSIMCIIKEEVLAYVVQLPLYGVIDTPCWKLHTSPLCTTNTKEGSNICLTRTDRGWY

CDNAGSVSFFPQADTCKVQSNRVFCDTMNSLTLPSEVNLCNIDIFNPKYDCKIMTSKT

DVSSSVITSLGAIVSCYGKTKCTASNKNRGIIKTFSNGCDYVSNKGVDTVSVGNTLYY

VNKQEGKSLYVKGEPIINFYDPLVFPSDEFDASISQVNEKINQSLAFIRKSDELLHNVN

AGKSTTNIMITGYIPEAPRDGQAYVRKDGEWVLLSTFLG

SEQ ID NO: 99, DNA of SEQ ID NO: 98
ATGGAACTGCCTGTGCTGAAAACAAACGCCATCACAACAATCCTGGCAGC

AGTGACACTGTGCTTCGCCAGCAGCCAGAATATTACAGAAGAGTTCTACCAGAG

CACATGCAGCGCCGTGTCTAAGGGCTACCTGAGCGCCCTGAGAACAGGCTGGTA

CACCAGCGTCATCACGATCGAGCTGAGTAATATCAAGGAGAACAAATGCAACGG

CACCGACGCCAAGGTGAAGCTGATCAAGCAGGAGCTGGATAAATACAAGAACG

CCGTGACCGAGTTGCAGCTGCTGATGCAGTCTACCCCAGCCGCCAACAACAGAG

CCAGACGGGAACTACCCAGATTCATGAACTACACACTGAACAACACTAAGAACA

CCAACGTGACACTGTCTAAGAAAAGAAAGCGGCGGTTCCTGGGATTCCTGCTGG

GCGTGGGAAGCGCTATCGCTTCTGGAATTGCCGTGTGCAAGGTGCTGCACCTGGA

AGGCGAGGTGAACAAGATCAAGTCTGCCCTGCTGTCCACCAACAAGGCCGTAGT

CAGCCTGAGCAATGGCGTGAGCGTCCTGACCTTTAAGGTGCTGGACCTGAAGAA

CTACATCGACAAGCAGCTGCTGCCTATCTTGAACAAGCAGAGCTGCTCCATCAGC

AATATTGAGACTGTGATCGAATTCCAGCAGAAGAACAACCGGCTGCTGGAGATC

ACCAGAGAGTTCTCCGTGAACGCTGGCGTGACTACACCTGTTTCAACCTACATGC

TGACCAATTCTGAGCTGCTGAGCCTGATCAACGACATGCCTATCACCAACGACCA

GAAAAAACTGATGTCCAATAACGTTCAAATCGTGCGGCAGCAAAGCTACAGCAT

CATGTGCATCATCAAGGAAGAAGTGCTTGCCTACGTGGTCCAGCTGCCACTTTAT

GGAGTTATCGATACACCCTGCTGGAAGCTGCACACCAGCCCTCTGTGTACAACCA

ACACCAAGGAAGGCAGCAACATCTGCCTGACCAGAACAGATAGAGGCTGGTATT

GTGATAACGCCGGCAGCGTGAGCTTCTTCCCCCAGGCCGACACATGTAAAGTGC

AGAGCAATAGAGTGTTCTGCGACACCATGAATAGCCTGACCCTGCCCAGCGAGG

TGAATCTGTGTAACATCGACATTTTCAACCCCAAGTACGATTGCAAGATCATGAC

CTCCAAGACCGACGTGAGCAGCAGCGTGATCACCTCCCTGGGCGCCATCGTGTCT

TGCTACGGCAAGACCAAGTGCACAGCCTCTAACAAAAATCGCGGCATCATCAAA

ACCTTCTCTAACGGTTGTGACTACGTGTCAAACAAAGGCGTGGACACCGTGTCCG

TGGGCAACACCCTGTATTACGTGAACAAGCAGGAGGGCAAGAGCCTGTACGTGA

AGGGCGAACCTATTATCAACTTCTACGACCCTCTGGTGTTTCCTTCCGACGAGTTT

GATGCTAGCATCTCTCAGGTGAACGAGAAGATCAACCAGAGCCTGGCCTTTATC

AGAAAGAGCGATGAGCTGCTGCACAACGTGAACGCCGGCAAGAGTACCACCAA

CATCATGATCACCGGATACATCCCGGAGGCCCCTAGGGACGGTCAAGCTTACGT

GAGAAAGGACGGCGAATGGGTTCTGCTGTCGACCTTCTTGGGA

SEQ ID NO: 100, RNA of SEQ ID NO: 98:
AUGGAACUGCCUGUGCUGAAAACAAACGCCAUCACAACAAUCCUGGCA

GCAGUGACACUGUGCUUCGCCAGCAGCCAGAAUAUUACAGAAGAGUUCUACCA

-continued

GAGCACAUGCAGCGCCGUGUCUAAGGGCUACCUGAGCGCCCUGAGAACAGGCU

GGUACACCAGCGUCAUCACGAUCGAGCUGAGUAAUAUCAAGGAGAACAAAUG

CAACGGCACCGACGCCAAGGUGAAGCUGAUCAAGCAGGAGCUGGAUAAAUACA

AGAACGCCGUGACCGAGUUGCAGCUGCUGAUGCAGUCUACCCCAGCCGCCAAC

AACAGAGCCAGACGGGAACUACCCAGAUUCAUGAACUACACACUGAACAACAC

UAAGAACACCAACGUGACACUGUCUAAGAAAAGAAAGCGGCGGUUCCUGGGA

UUCCUGCUGGGCGUGGGAAGCGCUAUCGCUUCUGGAAUUGCCGUGUGCAAGG

UGCUGCACCUGGAAGGCGAGGUGAACAAGAUCAAGUCUGCCCUGCUGUCCACC

AACAAGGCCGUAGUCAGCCUGAGCAAUGGCGUGAGCGUCCUGACCUUUAAGGU

GCUGGACCUGAAGAACUACAUCGACAAGCAGCUGCUGCCUAUCUUGAACAAGC

AGAGCUGCUCCAUCAGCAAUAUUGAGACUGUGAUCGAAUUCCAGCAGAAGAA

CAACCGGCUGCUGGAGAUCACCAGAGAGUUCUCCGUGAACGCUGGCGUGACUA

CACCUGUUUCAACCUACAUGCUGACCAAUUCUGAGCUGCUGAGCCUGAUCAAC

GACAUGCCUAUCACCAACGACCAGAAAAAACUGAUGUCCAAUAACGUUCAAAU

CGUGCGGCAGCAAAGCUACAGCAUCAUGUGCAUCAUCAAGGAAGAAGUGCUU

GCCUACGUGGUCCAGCUGCCACUUUAUGGAGUUAUCGAUACACCCUGCUGGAA

GCUGCACACCAGCCCUCUGUGUACAACCAACACCAAGGAAGGCAGCAACAUCU

GCCUGACCAGAACAGAUAGAGGCUGGUAUUGUGAUAACGCCGGCAGCGUGAG

CUUCUUCCCCCAGGCCGACACAUGUAAAGUGCAGAGCAAUAGAGUGUUCUGCG

ACACCAUGAAUAGCCUGACCCUGCCCAGCGAGGUGAAUCUGUGUAACAUCGAC

AUUUUCAACCCCAAGUACGAUUGCAAGAUCAUGACCUCCAAGACCGACGUGAG

CAGCAGCGUGAUCACCUCCCUGGGCGCCAUCGUGUCUUGCUACGGCAAGACCA

AGUGCACAGCCUCUAACAAAAAUCGCGGCAUCAUCAAAACCUUCUCUAACGGU

UGUGACUACGUGUCAAACAAAGGCGUGGACACCGUGUCCGUGGGCAACACCCU

GUAUUACGUGAACAAGCAGGAGGGCAAGAGCCUGUACGUGAAGGGCGAACCU

AUUAUCAACUUCUACGACCCUCUGGUGUUUCCUUCCGACGAGUUUGAUGCUAG

CAUCUCUCAGGUGAACGAGAAGAUCAACCAGAGCCUGGCCUUUAUCAGAAAGA

GCGAUGAGCUGCUGCACAACGUGAACGCCGGCAAGAGUACCACCAACAUCAUG

AUCACCGGAUACAUCCCGGAGGCCCCUAGGGACGGUCAAGCUUACGUGAGAAA

GGACGGCGAAUGGGUUCUGCUGUCGACCUUCUUGGGA

SEQ ID NO: 101, Optimized F5 Vaccine with mutations 155C, S190F, V207L, S290C, D486H, E487Q, F484W, and D489H with transmembrane domain:
MELPVLKTNAITTILAAVTLCFASSQNITEEFYQSTCSAVSKGYLSALRTGWY

TSVITIELSNIKENKCNGTDAKVKLIKQELDKYKNAVTELQLLMQSTPAANNRARRE

LPRFMNYTLNNTKNTNVTLSKKRKRRFLGFLLGVGSAIASGIAVCKVLHLEGEVNKI

KSALLSTNKAVVSLSNGVSVLTFKVLDLKNYIDKQLLPILNKQSCSISNIETVIEFQQK

NNRLLEITREFSVNAGVTTPVSTYMLTNSELLSLINDMPITNDQKKLMSNNVQIVRQQ

SYSIMCIIKEEVLAYVVQLPLYGVIDTPCWKLHTSPLCTTNTKEGSNICLTRTDRGWY

CDNAGSVSFFPQADTCKVQSNRVFCDTMNSLTLPSEVNLCNIDIFNPKYDCKIMTSKT

DVSSSVITSLGAIVSCYGKTKCTASNKNRGIIKTFSNGCDYVSNKGVDTVSVGNTLYY

-continued

VNKQEGKSLYVKGEPIINFYDPLVFPSHQWHASISQVNEKINQSLAFIRKSDELLHNV

NAGKSTTNIMITTIIIVIIVILLSLIAVGLLLYCKARSTPVTLSKDQLSGINNIAFSN

SEQ ID NO: 102, DNA of SEQ ID NO: 101:
ATGGAACTGCCTGTGCTGAAAACAAACGCCATCACAACAATCCTGGCAGC

AGTGACACTGTGCTTCGCCAGCAGCCAGAATATTACAGAAGAGTTCTACCAGAG

CACATGCAGCGCCGTGTCTAAGGGCTACCTGAGCGCCCTGAGAACAGGCTGGTA

CACCAGCGTCATCACGATCGAGCTGAGTAATATCAAGGAGAACAAATGCAACGG

CACCGACGCCAAGGTGAAGCTGATCAAGCAGGAGCTGGATAAATACAAGAACG

CCGTGACCGAGTTGCAGCTGCTGATGCAGTCTACCCCAGCCGCCAACAACAGAG

CCAGACGGGAACTACCCAGATTCATGAACTACACACTGAACAACACTAAGAACA

CCAACGTGACACTGTCTAAGAAAAGAAAGCGGCGGTTCCTGGGATTCCTGCTGG

GCGTGGGAAGCGCTATCGCTTCTGGAATTGCCGTGTGCAAGGTGCTGCACCTGGA

AGGCGAGGTGAACAAGATCAAGTCTGCCCTGCTGTCCACCAACAAGGCCGTAGT

CAGCCTGAGCAATGGCGTGAGCGTCCTGACCTTTAAGGTGCTGGACCTGAAGAA

CTACATCGACAAGCAGCTGCTGCCTATCTTGAACAAGCAGAGCTGCTCCATCAGC

AATATTGAGACTGTGATCGAATTCCAGCAGAAGAACAACCGGCTGCTGGAGATC

ACCAGAGAGTTCTCCGTGAACGCTGGCGTGACTACACCTGTTTCAACCTACATGC

TGACCAATTCTGAGCTGCTGAGCCTGATCAACGACATGCCTATCACCAACGACCA

GAAAAAACTGATGTCCAATAACGTTCAAATCGTGCGGCAGCAAAGCTACAGCAT

CATGTGCATCATCAAGGAAGAAGTGCTTGCCTACGTGGTCCAGCTGCCACTTTAT

GGAGTTATCGATACACCCTGCTGGAAGCTGCACACCAGCCCTCTGTGTACAACCA

ACACCAAGGAAGGCAGCAACATCTGCCTGACCAGAACAGATAGAGGCTGGTATT

GTGATAACGCCGGCAGCGTGAGCTTCTTCCCCCAGGCCGACACATGTAAAGTGC

AGAGCAATAGAGTGTTCTGCGACACCATGAATAGCCTGACCCTGCCCAGCGAGG

TGAATCTGTGTAACATCGACATTTTCAACCCCAAGTACGATTGCAAGATCATGAC

CTCCAAGACCGACGTGAGCAGCAGCGTGATCACCTCCCTGGGCGCCATCGTGTCT

TGCTACGGCAAGACCAAGTGCACAGCCTCTAACAAAAATCGCGGCATCATCAAA

ACCTTCTCTAACGGTTGTGACTACGTGTCAAACAAAGGCGTGGACACCGTGTCCG

TGGGCAACACCCTGTATTACGTGAACAAGCAGGAGGGCAAGAGCCTGTACGTGA

AGGGCGAACCTATTATCAACTTCTACGACCCTCTGGTGTTTCCTTCCCACCAGTG

GCATGCTAGCATCTCTCAGGTGAACGAGAAGATCAACCAGAGCCTGGCCTTTATC

AGAAAGAGCGATGAGCTGCTGCACAACGTGAACGCCGGCAAGAGTACCACCAA

CATCATGATCACCACCATCATTATCGTGATCATCGTGATCCTCCTGAGCCTGATC

GCTGTCGGACTGCTGCTGTACTGCAAGGCCAGGAGCACACCTGTGACCCTGAGC

AAGGACCAACTGTCTGGCATCAACAACATCGCTTTTAGCAAT

SEQ ID NO: 103, RNA of SEQ ID NO: 101
AUGGAACUGCCUGUGCUGAAAACAAACGCCAUCACAACAAUCCUGGCA

GCAGUGACACUGUGCUUCGCCAGCAGCCAGAAUAUUACAGAAGAGUUCUACCA

GAGCACAUGCAGCGCCGUGUCUAAGGGCUACCUGAGCGCCCUGAGAACAGGCU

GGUACACCAGCGUCAUCACGAUCGAGCUGAGUAAUAUCAAGGAGAACAAAUG

CAACGGCACCGACGCCAAGGUGAAGCUGAUCAAGCAGGAGCUGGAUAAAUACA

-continued

AGAACGCCGUGACCGAGUUGCAGCUGCUGAUGCAGUCUACCCCAGCCGCCAAC

AACAGAGCCAGACGGGAACUACCCAGAUUCAUGAACUACACACUGAACAACAC

UAAGAACACCAACGUGACACUGUCUAAGAAAAGAAAGCGGCGGUUCCUGGGA

UUCCUGCUGGGCGUGGGAAGCGCUAUCGCUUCUGGAAUUGCCGUGUGCAAGG

UGCUGCACCUGGAAGGCGAGGUGAACAAGAUCAAGUCUGCCCUGCUGUCCACC

AACAAGGCCGUAGUCAGCCUGAGCAAUGGCGUGAGCGUCCUGACCUUUAAGGU

GCUGGACCUGAAGAACUACAUCGACAAGCAGCUGCUGCCUAUCUUGAACAAGC

AGAGCUGCUCCAUCAGCAAUAUUGAGACUGUGAUCGAAUUCCAGCAGAAGAA

CAACCGGCUGCUGGAGAUCACCAGAGAGUUCUCCGUGAACGCUGGCGUGACUA

CACCUGUUUCAACCUACAUGCUGACCAAUUCUGAGCUGCUGAGCCUGAUCAAC

GACAUGCCUAUCACCAACGACCAGAAAAAACUGAUGUCCAAUAACGUUCAAAU

CGUGCGGCAGCAAAGCUACAGCAUCAUGUGCAUCAUCAAGGAAGAAGUGCUU

GCCUACGUGGUCCAGCUGCCACUUUAUGGAGUUAUCGAUACACCCUGCUGGAA

GCUGCACACCAGCCCUCUGUGUACAACCAACACCAAGGAAGGCAGCAACAUCU

GCCUGACCAGAACAGAUAGAGGCUGGUAUUGUGAUAACGCCGGCAGCGUGAG

CUUCUUCCCCCAGGCCGACACAUGUAAAGUGCAGAGCAAUAGAGUGUUCUGCG

ACACCAUGAAUAGCCUGACCCUGCCCAGCGAGGUGAAUCUGUGUAACAUCGAC

AUUUUCAACCCCAAGUACGAUUGCAAGAUCAUGACCUCCAAGACCGACGUGAG

CAGCAGCGUGAUCACCUCCCUGGGCGCCAUCGUGUCUUGCUACGGCAAGACCA

AGUGCACAGCCUCUAACAAAAAUCGCGGCAUCAUCAAAACCUUCUCUAACGGU

UGUGACUACGUGUCAAACAAAGGCGUGGACACCGUGUCCGUGGGCAACACCCU

GUAUUACGUGAACAAGCAGGAGGGCAAGAGCCUGUACGUGAAGGGCGAACCU

AUUAUCAACUUCUACGACCCUCUGGUGUUUCCUUCCCACCAGUGGCAUGCUAG

CAUCUCUCAGGUGAACGAGAAGAUCAACCAGAGCCUGGCCUUUAUCAGAAAGA

GCGAUGAGCUGCUGCACAACGUGAACGCCGGCAAGAGUACCACCAACAUCAUG

AUCACCACCAUCAUUAUCGUGAUCAUCGUGAUCCUCCUGAGCCUGAUCGCUGU

CGGACUGCUGCUGUACUGCAAGGCCAGGAGCACACCUGUGACCCUGAGCAAGG

ACCAACUGUCUGGCAUCAACAACAUCGCUUUUAGCAAU

SEQ ID NO: 104, Optimized F6 Vaccine with mutations 155C, S190F, V207L, S290C, D486H, E487Q, F484W, and D489H without transmembrane domain:
MELPVLKTNAITTILAAVTLCFASSQNITEEFYQSTCSAVSKGYLSALRTGWY

TSVITIELSNIKENKCNGTDAKVKLIKQELDKYKNAVTELQLLMQSTPAANNRARRE

LPRFMNYTLNNTKNTNVTLSKKRKRRFLGFLLGVGSAIASGIAVCKVLHLEGEVNKI

KSALLSTNKAVVSLSNGVSVLTFKVLDLKNYIDKQLLPILNKQSCSISNIETVIEFQQK

NNRLLEITREFSVNAGVTTPVSTYMLTNSELLSLINDMPITNDQKKLMSNNVQIVRQQ

SYSIMCIIKEEVLAYVVQLPLYGVIDTPCWKLHTSPLCTTNTKEGSNICLTRTDRGWY

CDNAGSVSFFPQADTCKVQSNRVFCDTMNSLTLPSEVNLCNIDIFNPKYDCKIMTSKT

DVSSSVITSLGAIVSCYGKTKCTASNKNRGIIKTFSNGCDYVSNKGVDTVSVGNTLYY

VNKQEGKSLYVKGEPIINFYDPLVFPSHQWHASISQVNEKINQSLAFIRKSDELLHNV

NAGKSTTNIMITGYIPEAPRDGQAYVRKDGEWVLLSTFLG

-continued

SEQ ID NO: 105, DNA of SEQ ID NO: 104
ATGGAACTGCCTGTGCTGAAAACAAACGCCATCACAACAATCCTGGCAGC

AGTGACACTGTGCTTCGCCAGCAGCCAGAATATTACAGAAGAGTTCTACCAGAG

CACATGCAGCGCCGTGTCTAAGGGCTACCTGAGCGCCCTGAGAACAGGCTGGTA

CACCAGCGTCATCACGATCGAGCTGAGTAATATCAAGGAGAACAAATGCAACGG

CACCGACGCCAAGGTGAAGCTGATCAAGCAGGAGCTGGATAAATACAAGAACG

CCGTGACCGAGTTGCAGCTGCTGATGCAGTCTACCCCAGCCGCCAACAACAGAG

CCAGACGGGAACTACCCAGATTCATGAACTACACACTGAACAACACTAAGAACA

CCAACGTGACACTGTCTAAGAAAAGAAAGCGGCGGTTCCTGGGATTCCTGCTGG

GCGTGGGAAGCGCTATCGCTTCTGGAATTGCCGTGTGCAAGGTGCTGCACCTGGA

AGGCGAGGTGAACAAGATCAAGTCTGCCCTGCTGTCCACCAACAAGGCCGTAGT

CAGCCTGAGCAATGGCGTGAGCGTCCTGACCTTTAAGGTGCTGGACCTGAAGAA

CTACATCGACAAGCAGCTGCTGCCTATCTTGAACAAGCAGAGCTGCTCCATCAGC

AATATTGAGACTGTGATCGAATTCCAGCAGAAGAACAACCGGCTGCTGGAGATC

ACCAGAGAGTTCTCCGTGAACGCTGGCGTGACTACACCTGTTTCAACCTACATGC

TGACCAATTCTGAGCTGCTGAGCCTGATCAACGACATGCCTATCACCAACGACCA

GAAAAAACTGATGTCCAATAACGTTCAAATCGTGCGGCAGCAAAGCTACAGCAT

CATGTGCATCATCAAGGAAGAAGTGCTTGCCTACGTGGTCCAGCTGCCACTTTAT

GGAGTTATCGATACACCCTGCTGGAAGCTGCACACCAGCCCTCTGTGTACAACCA

ACACCAAGGAAGGCAGCAACATCTGCCTGACCAGAACAGATAGAGGCTGGTATT

GTGATAACGCCGGCAGCGTGAGCTTCTTCCCCCAGGCCGACACATGTAAAGTGC

AGAGCAATAGAGTGTTCTGCGACACCATGAATAGCCTGACCCTGCCCAGCGAGG

TGAATCTGTGTAACATCGACATTTTCAACCCCAAGTACGATTGCAAGATCATGAC

CTCCAAGACCGACGTGAGCAGCAGCGTGATCACCTCCCTGGGCGCCATCGTGTCT

TGCTACGGCAAGACCAAGTGCACAGCCTCTAACAAAAATCGCGGCATCATCAAA

ACCTTCTCTAACGGTTGTGACTACGTGTCAAACAAAGGCGTGGACACCGTGTCCG

TGGGCAACACCCTGTATTACGTGAACAAGCAGGAGGGCAAGAGCCTGTACGTGA

AGGGCGAACCTATTATCAACTTCTACGACCCTCTGGTGTTTCCTTCCCACCAGTG

GCATGCTAGCATCTCTCAGGTGAACGAGAAGATCAACCAGAGCCTGGCCTTTATC

AGAAAGAGCGATGAGCTGCTGCACAACGTGAACGCCGGCAAGAGTACCACCAA

CATCATGATCACCGGATACATCCCGGAGGCCCCTAGGGACGGTCAAGCTTACGT

GAGAAAGGACGGCGAATGGGTTCTGCTGTCGACCTTCTTGGGA

SEQ ID NO: 106, RNA of SEQ ID NO: 104:
AUGGAACUGCCUGUGCUGAAAACAAACGCCAUCACAACAAUCCUGGCA

GCAGUGACACUGUGCUUCGCCAGCAGCCAGAAUAUUACAGAAGAGUUCUACCA

GAGCACAUGCAGCGCCGUGUCUAAGGGCUACCUGAGCGCCCUGAGAACAGGCU

GGUACACCAGCGUCAUCACGAUCGAGCUGAGUAAUAUCAAGGAGAACAAAUG

CAACGGCACCGACGCCAAGGUGAAGCUGAUCAAGCAGGAGCUGGAUAAAUACA

AGAACGCCGUGACCGAGUUGCAGCUGCUGAUGCAGUCUACCCCAGCCGCCAAC

AACAGAGCCAGACGGGAACUACCCAGAUUCAUGAACUACACACUGAACAACAC

UAAGAACACCAACGUGACACUGUCUAAGAAAAGAAAGCGGCGGUUCCUGGGA

-continued

UUCCUGCUGGGCGUGGGAAGCGCUAUCGCUUCUGGAAUUGCCGUGUGCAAGG

UGCUGCACCUGGAAGGCGAGGUGAACAAGAUCAAGUCUGCCCUGCUGUCCACC

AACAAGGCCGUAGUCAGCCUGAGCAAUGGCGUGAGCGUCCUGACCUUUAAGGU

GCUGGACCUGAAGAACUACAUCGACAAGCAGCUGCUGCCUAUCUUGAACAAGC

AGAGCUGCUCCAUCAGCAAUAUUGAGACUGUGAUCGAAUUCCAGCAGAAGAA

CAACCGGCUGCUGGAGAUCACCAGAGAGUUCUCCGUGAACGCUGGCGUGACUA

CACCUGUUUCAACCUACAUGCUGACCAAUUCUGAGCUGCUGAGCCUGAUCAAC

GACAUGCCUAUCACCAACGACCAGAAAAAACUGAUGUCCAAUAACGUUCAAAU

CGUGCGGCAGCAAAGCUACAGCAUCAUGUGCAUCAUCAAGGAAGAAGUGCUU

GCCUACGUGGUCCAGCUGCCACUUUAUGGAGUUAUCGAUACACCCUGCUGGAA

GCUGCACACCAGCCCUCUGUGUACAACCAACACCAAGGAAGGCAGCAACAUCU

GCCUGACCAGAACAGAUAGAGGCUGGUAUUGUGAUAACGCCGGCAGCGUGAG

CUUCUUCCCCCAGGCCGACACAUGUAAAGUGCAGAGCAAUAGAGUGUUCUGCG

ACACCAUGAAUAGCCUGACCCUGCCCAGCGAGGUGAAUCUGUGUAACAUCGAC

AUUUUCAACCCCAAGUACGAUUGCAAGAUCAUGACCUCCAAGACCGACGUGAG

CAGCAGCGUGAUCACCUCCCUGGGCGCCAUCGUGUCUUGCUACGGCAAGACCA

AGUGCACAGCCUCUAACAAAAAUCGCGGCAUCAUCAAAACCUUCUCUAACGGU

UGUGACUACGUGUCAAACAAAGGCGUGGACACCGUGUCCGUGGGCAACACCCU

GUAUUACGUGAACAAGCAGGAGGGCAAGAGCCUGUACGUGAAGGGCGAACCU

AUUAUCAACUUCUACGACCCUCUGGUGUUUCCUUCCCACCAGUGGCAUGCUAG

CAUCUCUCAGGUGAACGAGAAGAUCAACCAGAGCCUGGCCUUUAUCAGAAAGA

GCGAUGAGCUGCUGCACAACGUGAACGCCGGCAAGAGUACCACCAACAUCAUG

AUCACCGGAUACAUCCCGGAGGCCCCUAGGGACGGUCAAGCUUACGUGAGAAA

GGACGGCGAAUGGGUUCUGCUGUCGACCUUCUUGGGA

D

---

What is claimed is:

1. A respiratory syncytial virus (RSV) ribonucleic acid (RNA) encoding an RSV fusion glycoprotein (F) protein or an immunogenic fragment thereof, wherein the RSV RNA comprises SEQ ID NO: 97.

2. The RNA of claim 1, wherein the F protein further comprises one or more non-naturally occurring amino acid mutations selected from:

- a histidine (H) as the amino acid corresponding to D486 of SEQ ID NO: 87 (D486H),
- a glutamine (Q) as the amino acid corresponding to E487 of SEQ ID NO: 87 (E487Q),
- a tryptophan (W) as the amino acid corresponding to F488 of SEQ ID NO: 87 (F488W), or
- a H as the amino acid corresponding to D489 of SEQ ID NO: 87 (D489H).

3. The RNA of claim 1, further comprising

- a 3' UTR, optionally wherein the 3'UTR is selected from SEQ ID NOs: 18, 22, or 24;
- a 5' UTR, optionally wherein the 5' UTR comprises SEQ ID NO: 20 or 26; or
- a polyA tail, optionally wherein the polyA tail is selected from SEQ ID NOs: 27, 28, or 16.

4. The RNA of claim 1, wherein the RNA further comprises a 3' UTR selected from SEQ ID NOs: 18, 22, or 24, a 5' UTR selected from SEQ ID NOs: 20 or 26, and a polyA tail selected from SEQ ID NOs: 27, 28, or 16.

5. The RNA of claim 1, wherein the RNA is chemically modified and optionally comprises one or more of: an N1-methyl-pseudouridine residue or a pseudouridine residue, and optionally wherein at least about 50%, or at least about 70%, or about 100% of the uridine residues in the RNA are N1-methyl pseudouridine or pseudouridine.

6. A polypeptide encoded by the RNA of claim 1, wherein the polypeptide comprises SEQ ID NO: 95.

7. A polynucleotide encoding the RNA of claim 1, wherein the polynucleotide comprises SEQ ID NO: 96.

8. A polynucleotide encoding the RNA of claim 1, or a polynucleotide complementary thereto, optionally wherein the polynucleotide is selected from the group of: a deoxyribonucleic acid (DNA), an RNA, a hybrid of DNA and RNA, or an analog of each thereof.

9. A vector or isolated cell comprising the polynucleotide of claim 8.

10. A composition comprising a carrier and the RNA of claim 1.

11. The composition of claim 10, wherein the carrier is a pharmaceutically acceptable carrier.

12. A method of producing the RNA of claim 1, comprising culturing a cell comprising a polynucleotide encoding the RNA of claim 1 under conditions suitable for expressing the RNA.

13. A method of producing the RNA of claim 1, comprising contacting a DNA polynucleotide encoding the RNA of claim 1 with an RNA polymerase, adenosine triphosphate (ATP), cytidine triphosphate (CTP), guanosine-5'-triphosphate (GTP), and uridine triphosphate (UTP) or a chemically modified UTP under conditions suitable for expressing the RNA.

14. The method of claim 13, further comprising isolating the RNA.

15. A composition comprising the RNA of claim 1 and a pharmaceutically acceptable carrier.

16. The composition of claim 15, wherein the pharmaceutically acceptable carrier comprises a polymeric nanoparticle that comprises a Histidine-Lysine co-polymer (HKP), optionally wherein the HKP comprises a side chain selected from SEQ ID NOs: 31-44; optionally wherein the pharmaceutically acceptable carrier further comprises a lipid, optionally wherein the lipid comprises a cationic lipid, optionally wherein the cationic lipid is ionizable, optionally wherein the cationic lipid comprises Dlin-MC3-DMA (MC3) or dioleoyloxy-3-(trimethylammonio)propane (DOTAP) or both, or optionally wherein the lipid further comprises one or more of: a helper lipid, a cholesterol, or a PEGylated lipid, and further optionally wherein the pharmaceutically acceptable carrier comprises a lipid nanoparticle (LNP) and optionally wherein the LNP comprises one or more of: 9-Heptadecanyl 8-{(2-hydroxyethyl)[6-oxo-6-(undecyloxy)hexyl]amino}octanoate (SM-102), 2,2-dilinoleyl-4-dimethylaminoethyl-[1,3]-dioxolane (DLin-KC2-DMA), dilinoleyl-methyl-4-dimethylaminobutyrate (DLin-MC3-DMA), di((Z)-non-2-en-1-yl) 9-((4-(dimethylamino)butanoyl)oxy)heptadecanedioate (L319), or an equivalent of each thereof, and optionally wherein the LNP further comprises one or more of: a helper lipid, a cholesterol, or a PEGylated lipid, and optionally wherein the helper lipid comprises one or more of: disteroylphosphatidyl choline (DSPC), Dipalmitoylphosphatidylcholine (DPPC), (2R)-3-(Hexadecanoyloxy)-2-{[(9Z)-octadec-9-enoyl]oxy}propyl 2-(trimethylazaniumyl)ethyl phosphate (POPC), or dioleoyl phosphatidylethanolamine (DOPE), and optionally wherein the cholesterol comprises a plant cholesterol or an animal cholesterol or both and further optionally wherein the PEGylated lipid comprises one or more of: PEG-c-DOMG (R-3-[(ω-methoxy-poly(ethyleneglycol)2000)carbamoyl)]-1,2-dimyristyloxypropyl-3-amine), PEG-DSG (1,2-Distearoyl-sn-glycerol, methoxypolyethylene glycol), PEG-DMG (1,2-Dimyristoyl-sn-glycerol) optionally PEG2000-DMG ((1,2-dimyristoyl-sn-glycero-3-phophoethanolamine-N-[methoxy(polyethylene glycol)-2000)], or PEG-DPG (1,2-Dipalmitoyl-sn-glycerol, methoxypolyethylene glycol), and optionally the LNP comprises SM-102, DSPC, cholesterol and PEG2000-DMG, and further optionally wherein the mass ratio of the SM-102, DSPC, cholesterol and PEG200-DMG is about 1:1:1:1 and/or wherein the molar ratio of the SM-102, DSPC, cholesterol and PEG2000-DMG is about 50:10:38.5:1.5.

17. A method of producing the composition comprising contacting the RNA of claim 1 with an HKP, thereby the RNA and the HKP are self-assembled into nanoparticles, and optionally wherein the mass ratio of HKP and the RNA in the contacting step is about 10:1 to about 1:10, optionally 2.5:1, and optionally further comprising contacting the HKP and RNA with cationic lipid, and further optionally wherein the cationic lipid comprises Dlin-MC3-DMA (MC3) or DOTAP (dioleoyloxy-3-(trimethylammonio)propane) or both, and optionally wherein the mass ratio of the cationic lipid and the RNA in the contacting step is about 10:1 to about 1:10, optionally 1:1, and optionally wherein the mass ratio of the HKP, the mRNA and the cationic lipid in the contacting step is about 4:1:1 and optionally comprising contacting the RNA of claim 1 with a lipid, thereby the RNA and the lipid are self-assembled into lipid nanoparticles (LNPs), optionally wherein the LNPs comprise one or more of: 9-Heptadecanyl 8-{(2-hydroxyethyl)[6-oxo-6-(undecyloxy)hexyl]amino}octanoate (SM-102), 2,2-dilinoleyl-4-dimethylaminoethyl-[1,3]-dioxolane (DLin-KC2-DMA), dilinoleyl-methyl-4-dimethylaminobutyrate (DLin-MC3-DMA), di((Z)-non-2-en-1-yl) 9-((4-(dimethylamino)butanoyl)oxy)heptadecanedioate (L319), or an equivalent of each thereof, the LNPs further comprise one or more of: a helper lipid, a cholesterol, or a PEGylated lipid;

the helper lipid comprises one or more of: disteroylphosphatidyl choline (DSPC), Dipalmitoylphosphatidylcholine (DPPC), (2R)-3-(Hexadecanoyloxy)-2-{[(9Z)-octadec-9-enoyl]oxy}propyl 2-(trimethylazaniumyl)ethyl phosphate (POPC), or dioleoyl phosphatidylethanolamine (DOPE);

the cholesterol comprises a plant cholesterol or an animal cholesterol or both;

the PEGylated lipid comprises one or more of: PEG-c-DOMG (R-3-[(ω-methoxy-poly(ethyleneglycol)2000)carbamoyl)]-1,2-dimyristyloxypropyl-3-amine), PEG-DSG (1,2-Distearoyl-sn-glycerol, methoxypolyethylene glycol), PEG-DMG (1,2-Dimyristoyl-sn-glycerol) optionally PEG2000-DMG ((1,2-dimyristoyl-sn-glycero-3-phophoethanolamine-N-[methoxy(polyethylene glycol)-2000)], or PEG-DPG (1,2-Dipalmitoyl-sn-glycerol, methoxypolyethylene glycol);

the LNPs comprise SM-102, DSPC, cholesterol and PEG2000-DMG;

the mass ratio of the SM-102, DSPC, cholesterol and PEG200-DMG is about 1:1:1:1 and/or wherein the molar ratio of the SM-102, DSPC, cholesterol and PEG2000-DMG is about 50:10:38.5:1.5 the contacting step is performed in a microfluidic mixer, optionally selected from a slit interdigital micromixer, or a staggered herringbone micromixer (SHM).

18. In a subject in need thereof, a method of one or more of:

(a) preventing symptomatic RSV infection, (b) inducing an immune response to RSV, (c) treating a subject infected with RSV, or (d) reducing a RSV viral load, comprising administering to the subject the RNA of claim 1, and optionally wherein the subject is a human patient, selected from an infant, a pediatric patient, or a pregnant human or an adult 60 years old or older and optionally further comprising treating the subject with an additional therapeutic agent or an additional prophylactic agent, optionally selected from one or more of an influenza virus, a corona virus, an Ebola virus, a Human Immunodeficiency Virus (HIV), or a COVID-19, and optionally wherein the additional therapeutic agent comprises a RNA polynucleotide from another infectious virus, optionally selected from one or more of an influenza virus vaccine, a corona virus vaccine, an Ebola virus vaccine, a Human Immunodeficiency Virus (HIV) vaccine, or a COVID-19 vaccine and further optionally wherein the subject does not have, or exhibit symptoms of a RSV infection when administrated with the RNA or the composition.

* * * * *

SEQUENCE LISTING

```
Sequence total quantity: 118
SEQ ID NO: 1            moltype = AA  length = 436
FEATURE                 Location/Qualifiers
source                  1..436
                        mol_type = protein
                        organism = synthetic construct
SEQUENCE: 1
GFLLGVGSAI ASGIAVSKVL HLEGEVNKIK SALLSTNKAV VSLSNGVSVL TSKVLDLKNY  60
IDKQLLPIVN KQSCSISNIE TVIEFQQKNN RLLEITREFS VNAGVTTPVS TYMLTNSELL  120
SLINDMPITN DQKKLMSNNV QIVRQQSYSI MSIIKEEVLA YVVQLPLYGV IDTPCWKLHT  180
SPLCTTNTKE GSNICLTRTD RGWYCDNAGS VSFFPQADTC KVQSNRVFCD TMNSLTLPSE  240
VNLCNIDIFN PKYDCKIMTS KTDVSSSVIT SLGAIVSCYG KTKCTASNKN RGIIKTFSNG  300
CDYVSNKGVD TVSVGNTLYY VNKQEGKSLY VKGEPIINFY DPLVFPSDEF DASISQVNEK  360
INQSLAFIRK SDELLHNVNA GKSTTNIMIT TIIIVIIVIL LSLIAVGLLL YCKARSTPVT  420
LSKDQLSGIN NIAFSN                                                  436

SEQ ID NO: 2            moltype = DNA  length = 1308
FEATURE                 Location/Qualifiers
source                  1..1308
                        mol_type = other DNA
                        organism = synthetic construct
SEQUENCE: 2
ggattcctgc tgggcgtggg aagcgctatc gcttctggaa ttgccgtgag caaggtgctg  60
cacctggaag gcgaggtgaa caagatcaag tctgccctgc tgtccaccaa caaggccgta  120
gtcagcctga gcaatggcgt gagcgtcctg accagtaagg tgctggacct gaagaactac  180
```

```
atcgacaagc agctgctgcc tatcgtgaac aagcagagct gctccatcag caatattgag  240
actgtgatcg aattccagca gaagaacaac cggctgctgg agatcaccag agagttctcc  300
gtgaacgctg gcgtgactac acctgtttca acctacatgc tgaccaattc tgagctgctg  360
agcctgatca acgacatgcc tatcaccaac gaccagaaaa aactgatgtc caataacgtt  420
caaatcgtgc ggcagcaaag ctacagcatc atgagcatca tcaaggaaga agtgcttgcc  480
tacgtggtcc agctgccact ttatggagtt atcgatacac cctgctggaa gctgcacacc  540
agccctctgt gtacaaccaa caccaaggaa ggcagcaaca tctgcctgac cagaacagat  600
agaggctggt attgtgataa cgccggcagc gtgagcttct tcccccaggc cgacacatgt  660
aaagtgcaga gcaatagagt gttctgcgac accatgaata gcctgaccct gcccagcgag  720
gtgaatctgt gtaacatcga cattttcaac cccaagtacg attgcaagat catgacctcc  780
aagaccgacg tgagcagcag cgtgatcacc tccctgggcg ccatcgtgtc ttgctacggc  840
aagaccaagt gcacagcctc taacaaaaat cgcggcatca tcaaaacctt ctctaacggt  900
tgtgactacg tgtcaaacaa aggcgtggac accgtgtccg tgggcaacac cctgtattac  960
gtgaacaagc aggagggcaa gagcctgtac gtgaagggcg aacctattat caacttctac  1020
gaccctctgg tgtttccttc cgacgagttt gatgctagca tctctcaggt gaacgagaag  1080
atcaaccaga gcctggcctt tatcagaaag agcgatgagc tgctgcacaa cgtgaacgcc  1140
ggcaagagta ccaccaacat catgatcacc accatcatta tcgtgatcat cgtgatcctc  1200
ctgagcctga tcgctgtcgg actgctgctg tactgcaagg ccaggagcac acctgtgacc  1260
ctgagcaagg accaactgtc tggcatcaac aacatcgctt ttagcaat              1308

SEQ ID NO: 3            moltype = AA  length = 418
FEATURE                 Location/Qualifiers
source                  1..418
                        mol_type = protein
                        organism = synthetic construct
SEQUENCE: 3
GFLLGVGSAI ASGIAVSKVL HLEGEVNKIK SALLSTNKAV VSLSNGVSVL TSKVLDLKNY  60
IDKQLLPIVN KQSCSISNIE TVIEFQQKNN RLLEITREFS VNAGVTTPVS TYMLTNSELL  120
SLINDMPITN DQKKLMSNNV QIVRQQSYSI MSIIKEEVLA YVVQLPLYGV IDTPCWKLHT  180
SPLCTTNTKE GSNICLTRTD RGWYCDNAGS VSFFPQADTC KVQSNRVFCD TMNSLTLPSE  240
VNLCNIDIFN PKYDCKIMTS KTDVSSSVIT SLGAIVSCYG KTKCTASNKN RGIIKTFSNG  300
CDYVSNKGVD TVSVGNTLYY VNKQEGKSLY VKGEPIINFY DPLVFPSDEF DASISQVNEK  360
INQSLAFIRK SDELLHNVNA GKSTTNIMIT GYIPEAPRDG QAYVRKDGEW VLLSTFLG    418

SEQ ID NO: 4            moltype = DNA  length = 1254
FEATURE                 Location/Qualifiers
source                  1..1254
                        mol_type = other DNA
                        organism = synthetic construct
SEQUENCE: 4
ggattcctgc tgggcgtggg aagcgctatc gcttctggaa ttgccgtgag caaggtgctg  60
cacctggaag gcgaggtgaa caagatcaag tctgccctgc tgtccaccaa caaggccgta  120
gtcagcctga gcaatggcgt gagcgtcctg accagtaagg tgctggacct gaagaactac  180
atcgacaagc agctgctgcc tatcgtgaac aagcagagct gctccatcag caatattgag  240
actgtgatcg aattccagca gaagaacaac cggctgctgg agatcaccag agagttctcc  300
gtgaacgctg gcgtgactac acctgtttca acctacatgc tgaccaattc tgagctgctg  360
agcctgatca acgacatgcc tatcaccaac gaccagaaaa aactgatgtc caataacgtt  420
caaatcgtgc ggcagcaaag ctacagcatc atgagcatca tcaaggaaga agtgcttgcc  480
tacgtggtcc agctgccact ttatggagtt atcgatacac cctgctggaa gctgcacacc  540
agccctctgt gtacaaccaa caccaaggaa ggcagcaaca tctgcctgac cagaacagat  600
agaggctggt attgtgataa cgccggcagc gtgagcttct tcccccaggc cgacacatgt  660
aaagtgcaga gcaatagagt gttctgcgac accatgaata gcctgaccct gcccagcgag  720
gtgaatctgt gtaacatcga cattttcaac cccaagtacg attgcaagat catgacctcc  780
aagaccgacg tgagcagcag cgtgatcacc tccctgggcg ccatcgtgtc ttgctacggc  840
aagaccaagt gcacagcctc taacaaaaat cgcggcatca tcaaaacctt ctctaacggt  900
tgtgactacg tgtcaaacaa aggcgtggac accgtgtccg tgggcaacac cctgtattac  960
gtgaacaagc aggagggcaa gagcctgtac gtgaagggcg aacctattat caacttctac  1020
gaccctctgg tgtttccttc cgacgagttt gatgctagca tctctcaggt gaacgagaag  1080
atcaaccaga gcctggcctt tatcagaaag agcgatgagc tgctgcacaa cgtgaacgcc  1140
ggcaagagta ccaccaacat catgatcacc ggatacatcc cggaggcccc tagggacggt  1200
caagcttacg tgagaaagga cggcgaatgg gttctgctgt cgaccttctt ggga        1254

SEQ ID NO: 5            moltype = AA  length = 437
FEATURE                 Location/Qualifiers
source                  1..437
                        mol_type = protein
                        organism = synthetic construct
SEQUENCE: 5
LGFLLGVGSA IASGIAVCKV LHLEGEVNKI KSALLSTNKA VVSLSNGVSV LTFKVLDLKN  60
YIDKQLLPIL NKQSCSISNI ETVIEFQQKN NRLLEITREF SVNAGVTTPV STYMLTNSEL  120
LSLINDMPIT NDQKKLMSNN VQIVRQQSYS IMCIIKEEVL AYVVQLPLYG VIDTPCWKLH  180
TSPLCTTNTK EGSNICLTRT DRGWYCDNAG SVSFFPQADT CKVQSNRVFC DTMNSLTLPS  240
EVNLCNIDIF NPKYDCKIMT SKTDVSSSVI TSLGAIVSCY GKTKCTASNK NRGIIKTFSN  300
GCDYVSNKGV DTVSVGNTLY YVNKQEGKSL YVKGEPIINF YDPLVFPSDE FDASISQVNE  360
KINQSLAFIR KSDELLHNVN AGKSTTNIMI TTIIIVIIVI LLSLIAVGLL LYCKARSTPV  420
TLSKDQLSGI NNIAFSN                                                 437

SEQ ID NO: 6            moltype = DNA  length = 1308
FEATURE                 Location/Qualifiers
```

-continued

```
source                  1..1308
                        mol_type = other DNA
                        organism = synthetic construct
SEQUENCE: 6
ggattcctgc tgggcgtggg aagcgctatc gcttctggaa ttgccgtgtg caaggtgctg  60
cacctggaag gcgaggtgaa caagatcaag tctgccctgc tgtccaccaa caaggccgta  120
gtcagcctga gcaatggcgt gagcgtcctg acctttaagg tgctggacct gaagaactac  180
atcgacaagc agctgctgcc tatcttgaac aagcagagct gctccatcag caatattgag  240
actgtgatcg aattccagca gaagaacaac cggctgctgg agatcaccag agagttctcc  300
gtgaacgctg gcgtgactac acctgtttca acctacatgc tgaccaattc tgagctgctg  360
agcctgatca acgacatgcc tatcaccaac gaccagaaaa aactgatgtc caataacgtt  420
caaatcgtgc ggcagcaaag ctacagcatc atgtgcatca tcaaggaaga agtgcttgcc  480
tacgtggtcc agctgccact ttatggagtt atcgatacac cctgctggaa gctgcacacc  540
agccctctgt gtacaaccaa caccaaggaa ggcagcaaca tctgcctgac cagaacagat  600
agaggctggt attgtgataa cgccggcagc gtgagcttct tcccccaggc cgacacatgt  660
aaagtgcaga gcaatagagt gttctgcgac accatgaata gcctgaccct gcccagcgag  720
gtgaatctgt gtaacatcga cattttcaac cccaagtacg attgcaagat catgacctcc  780
aagaccgacg tgagcagcag cgtgatcacc tccctgggcg ccatcgtgtc ttgctacggc  840
aagaccaagt gcacagcctc taacaaaaat cgcggcatca tcaaaacctt ctctaacggt  900
tgtgactacg tgtcaaacaa aggcgtggac accgtgtccg tgggcaacac cctgtattac  960
gtgaacaagc aggagggcaa gagcctgtac gtgaagggcg aacctattat caacttctac  1020
gaccctctgg tgtttccttc cgacgagttt gatgctagca tctctcaggt gaacgagaag  1080
atcaaccaga gcctggcctt tatcagaaag agcgatgagc tgctgcacaa cgtgaacgcc  1140
ggcaagagta ccaccaacat catgatcacc accatcatta tcgtgatcat cgtgatcctc  1200
ctgagcctga tcgctgtcgg actgctgctg tactgcaagg ccaggagcac acctgtgacc  1260
ctgagcaagg accaactgtc tggcatcaac aacatcgctt ttagcaat              1308

SEQ ID NO: 7            moltype = AA  length = 419
FEATURE                 Location/Qualifiers
source                  1..419
                        mol_type = protein
                        organism = synthetic construct
SEQUENCE: 7
LGFLLGVGSA IASGIAVCKV LHLEGEVNKI KSALLSTNKA VVSLSNGVSV LTFKVLDLKN  60
YIDKQLLPIL NKQSCSISNI ETVIEFQQKN NRLLEITREF SVNAGVTTPV STYMLTNSEL  120
LSLINDMPIT NDQKKLMSNN VQIVRQQSYS IMCIIKEEVL AYVVQLPLYG VIDTPCWKLH  180
TSPLCTTNTK EGSNICLTRT DRGWYCDNAG SVSFFPQADT CKVQSNRVFC DTMNSLTLPS  240
EVNLCNIDIF NPKYDCKIMT SKTDVSSSVI TSLGAIVSCY GKTKCTASNK NRGIIKTFSN  300
GCDYVSNKGV DTVSVGNTLY YVNKQEGKSL YVKGEPIINF YDPLVFPSDE FDASISQVNE  360
KINQSLAFIR KSDELLHNVN AGKSTTNIMI TGYIPEAPRD GQAYVRKDGE WVLLSTFLG   419

SEQ ID NO: 8            moltype = DNA  length = 1254
FEATURE                 Location/Qualifiers
source                  1..1254
                        mol_type = other DNA
                        organism = synthetic construct
SEQUENCE: 8
ggattcctgc tgggcgtggg aagcgctatc gcttctggaa ttgccgtgtg caaggtgctg  60
cacctggaag gcgaggtgaa caagatcaag tctgccctgc tgtccaccaa caaggccgta  120
gtcagcctga gcaatggcgt gagcgtcctg acctttaagg tgctggacct gaagaactac  180
atcgacaagc agctgctgcc tatcttgaac aagcagagct gctccatcag caatattgag  240
actgtgatcg aattccagca gaagaacaac cggctgctgg agatcaccag agagttctcc  300
gtgaacgctg gcgtgactac acctgtttca acctacatgc tgaccaattc tgagctgctg  360
agcctgatca acgacatgcc tatcaccaac gaccagaaaa aactgatgtc caataacgtt  420
caaatcgtgc ggcagcaaag ctacagcatc atgtgcatca tcaaggaaga agtgcttgcc  480
tacgtggtcc agctgccact ttatggagtt atcgatacac cctgctggaa gctgcacacc  540
agccctctgt gtacaaccaa caccaaggaa ggcagcaaca tctgcctgac cagaacagat  600
agaggctggt attgtgataa cgccggcagc gtgagcttct tcccccaggc cgacacatgt  660
aaagtgcaga gcaatagagt gttctgcgac accatgaata gcctgaccct gcccagcgag  720
gtgaatctgt gtaacatcga cattttcaac cccaagtacg attgcaagat catgacctcc  780
aagaccgacg tgagcagcag cgtgatcacc tccctgggcg ccatcgtgtc ttgctacggc  840
aagaccaagt gcacagcctc taacaaaaat cgcggcatca tcaaaacctt ctctaacggt  900
tgtgactacg tgtcaaacaa aggcgtggac accgtgtccg tgggcaacac cctgtattac  960
gtgaacaagc aggagggcaa gagcctgtac gtgaagggcg aacctattat caacttctac  1020
gaccctctgg tgtttccttc cgacgagttt gatgctagca tctctcaggt gaacgagaag  1080
atcaaccaga gcctggcctt tatcagaaag agcgatgagc tgctgcacaa cgtgaacgcc  1140
ggcaagagta ccaccaacat catgatcacc ggatacatcc cggaggcccc tagggacggt  1200
caagcttacg tgagaaagga cggcgaatgg gttctgctgt cgaccttctt ggga        1254

SEQ ID NO: 9            moltype = AA  length = 437
FEATURE                 Location/Qualifiers
source                  1..437
                        mol_type = protein
                        organism = synthetic construct
SEQUENCE: 9
LGFLLGVGSA IASGIAVCKV LHLEGEVNKI KSALLSTNKA VVSLSNGVSV LTFKVLDLKN  60
YIDKQLLPIL NKQSCSISNI ETVIEFQQKN NRLLEITREF SVNAGVTTPV STYMLTNSEL  120
LSLINDMPIT NDQKKLMSNN VQIVRQQSYS IMCIIKEEVL AYVVQLPLYG VIDTPCWKLH  180
TSPLCTTNTK EGSNICLTRT DRGWYCDNAG SVSFFPQADT CKVQSNRVFC DTMNSLTLPS  240
```

```
EVNLCNIDIF NPKYDCKIMT SKTDVSSSVI TSLGAIVSCY GKTKCTASNK NRGIIKTFSN  300
GCDYVSNKGV DTVSVGNTLY YVNKQEGKSL YVKGEPIINF YDPLVFPSHQ WHASISQVNE  360
KINQSLAFIR KSDELLHNVN AGKSTTNIMI TTIIIVIIVI LLSLIAVGLL LYCKARSTPV  420
TLSKDQLSGI NNIAFSN                                                 437

SEQ ID NO: 10          moltype = DNA  length = 1308
FEATURE                Location/Qualifiers
source                 1..1308
                       mol_type = other DNA
                       organism = synthetic construct
SEQUENCE: 10
ggattcctgc tgggcgtggg aagcgctatc gcttctggaa ttgccgtgtg caaggtgctg  60
cacctggaag gcgaggtgaa caagatcaag tctgccctgc tgtccaccaa caaggccgta  120
gtcagcctga gcaatggcgt gagcgtcctg acctttaagg tgctggacct gaagaactac  180
atcgacaagc agctgctgcc tatcttgaac aagcagagct gctccatcag caatattgag  240
actgtgatcg aattccagca gaagaacaac cggctgctgg agatcaccag agagttctcc  300
gtgaacgctg gcgtgactac acctgtttca acctacatgc tgaccaattc tgagctgctg  360
agcctgatca acgacatgcc tatcaccaac gaccagaaaa aactgatgtc caataacgtt  420
caaatcgtgc ggcagcaaag ctacagcatc atgtgcatca tcaaggaaga agtgcttgcc  480
tacgtggtcc agctgccact ttatggagtt atcgatacac cctgctggaa gctgcacacc  540
agccctctgt gtacaaccaa caccaaggaa ggcagcaaca tctgcctgac cagaacagat  600
agaggctggt attgtgataa cgccggcagc gtgagcttct tcccccaggc cgacacatgt  660
aaagtgcaga gcaatagagt gttctgcgac accatgaata gcctgaccct gcccagcgag  720
gtgaatctgt gtaacatcga cattttcaac cccaagtacg attgcaagat catgacctcc  780
aagaccgacg tgagcagcag cgtgatcacc tccctgggcg ccatcgtgtc ttgctacggc  840
aagaccaagt gcacagcctc taacaaaaat cgcggcatca tcaaaacctt ctctaacggt  900
tgtgactacg tgtcaaacaa aggcgtggac accgtgtccg tgggcaacac cctgtattac  960
gtgaacaagc aggagggcaa gagcctgtac gtgaagggcg aacctattat caacttctac  1020
gaccctctgg tgtttccttc ccaccagtgg catgctagca tctctcaggt gaacgagaag  1080
atcaaccaga gcctggcctt tatcagaaag agcgatgagc tgctgcacaa cgtgaacgcc  1140
ggcaagagta ccaccaacat catgatcacc accatcatta tcgtgatcat cgtgatcctc  1200
ctgagcctga tcgctgtcgg actgctgctg tactgcaagg ccaggagcac acctgtgacc  1260
ctgagcaagg accaactgtc tggcatcaac aacatcgctt ttagcaat               1308

SEQ ID NO: 11          moltype = AA  length = 419
FEATURE                Location/Qualifiers
source                 1..419
                       mol_type = protein
                       organism = synthetic construct
SEQUENCE: 11
LGFLLGVGSA IASGIAVCKV LHLEGEVNKI KSALLSTNKA VVSLSNGVSV LTFKVLDLKN  60
YIDKQLLPIL NKQSCSISNI ETVIEFQQKN NRLLEITREF SVNAGVTTPV STYMLTNSEL  120
LSLINDMPIT NDQKKLMSNN VQIVRQQSYS IMCIIKEEVL AYVVQLPLYG VIDTPCWKLH  180
TSPLCTTNTK EGSNICLTRT DRGWYCDNAG SVSFFPQADT CKVQSNRVFC DTMNSLTLPS  240
EVNLCNIDIF NPKYDCKIMT SKTDVSSSVI TSLGAIVSCY GKTKCTASNK NRGIIKTFSN  300
GCDYVSNKGV DTVSVGNTLY YVNKQEGKSL YVKGEPIINF YDPLVFPSHQ WHASISQVNE  360
KINQSLAFIR KSDELLHNVN AGKSTTNIMI TGYIPEAPRD GQAYVRKDGE WVLLSTFLG   419

SEQ ID NO: 12          moltype = DNA  length = 1254
FEATURE                Location/Qualifiers
source                 1..1254
                       mol_type = other DNA
                       organism = synthetic construct
SEQUENCE: 12
ggattcctgc tgggcgtggg aagcgctatc gcttctggaa ttgccgtgtg caaggtgctg  60
cacctggaag gcgaggtgaa caagatcaag tctgccctgc tgtccaccaa caaggccgta  120
gtcagcctga gcaatggcgt gagcgtcctg acctttaagg tgctggacct gaagaactac  180
atcgacaagc agctgctgcc tatcttgaac aagcagagct gctccatcag caatattgag  240
actgtgatcg aattccagca gaagaacaac cggctgctgg agatcaccag agagttctcc  300
gtgaacgctg gcgtgactac acctgtttca acctacatgc tgaccaattc tgagctgctg  360
agcctgatca acgacatgcc tatcaccaac gaccagaaaa aactgatgtc caataacgtt  420
caaatcgtgc ggcagcaaag ctacagcatc atgtgcatca tcaaggaaga agtgcttgcc  480
tacgtggtcc agctgccact ttatggagtt atcgatacac cctgctggaa gctgcacacc  540
agccctctgt gtacaaccaa caccaaggaa ggcagcaaca tctgcctgac cagaacagat  600
agaggctggt attgtgataa cgccggcagc gtgagcttct tcccccaggc cgacacatgt  660
aaagtgcaga gcaatagagt gttctgcgac accatgaata gcctgaccct gcccagcgag  720
gtgaatctgt gtaacatcga cattttcaac cccaagtacg attgcaagat catgacctcc  780
aagaccgacg tgagcagcag cgtgatcacc tccctgggcg ccatcgtgtc ttgctacggc  840
aagaccaagt gcacagcctc taacaaaaat cgcggcatca tcaaaacctt ctctaacggt  900
tgtgactacg tgtcaaacaa aggcgtggac accgtgtccg tgggcaacac cctgtattac  960
gtgaacaagc aggagggcaa gagcctgtac gtgaagggcg aacctattat caacttctac  1020
gaccctctgg tgtttccttc ccaccagtgg catgctagca tctctcaggt gaacgagaag  1080
atcaaccaga gcctggcctt tatcagaaag agcgatgagc tgctgcacaa cgtgaacgcc  1140
ggcaagagta ccaccaacat catgatcacc ggatacatcc cggaggcccc tagggacggt  1200
caagcttacg tgagaaagga cggcgaatgg gttctgctgt cgaccttctt ggga        1254

SEQ ID NO: 13          moltype = RNA  length = 1308
FEATURE                Location/Qualifiers
source                 1..1308
```

```
                       mol_type = other RNA
                       organism = synthetic construct
SEQUENCE: 13
ggattcctgc tgggcgtggg aagcgctatc gcttctggaa ttgccgtgtg caaggtgctg  60
cacctggaag gcgaggtgaa caagatcaag tctgccctgc tgtccaccaa caaggccgta  120
gtcagcctga gcaatggcgt gagcgtcctg acctttaagg tgctggacct gaagaactac  180
atcgacaagc agctgctgcc tatcttgaac aagcagagct gctccatcag caatattgag  240
actgtgatcg aattccagca gaagaacaac cggctgctgg agatcaccag agagttctcc  300
gtgaacgctg gcgtgactac acctgtttca acctacatgc tgaccaattc tgagctgctg  360
agcctgatca acgacatgcc tatcaccaac gaccagaaaa aactgatgtc caataacgtt  420
caaatcgtgc ggcagcaaag ctacagcatc atgtgcatca tcaaggaaga agtgcttgcc  480
tacgtggtcc agctgccact ttatggagtt atcgatacac cctgctggaa gctgcacacc  540
agccctctgt gtacaaccaa caccaaggaa ggcagcaaca tctgcctgac cagaacagat  600
agaggctggt attgtgataa cgccggcagc gtgagcttct tcccccaggc cgacacatgt  660
aaagtgcaga gcaatagagt gttctgcgac accatgaata gcctgaccct gcccagcgag  720
gtgaatctgt gtaacatcga cattttcaac cccaagtacg attgcaagat catgacctcc  780
aagaccgacg tgagcagcag cgtgatcacc tccctgggcg ccatcgtgtc ttgctacggc  840
aagaccaagt gcacagcctc taacaaaaat cgcggcatca tcaaaacctt ctctaacggt  900
tgtgactacg tgtcaaacaa aggcgtggac accgtgtccg tgggcaacac cctgtattac  960
gtgaacaagc aggagggcaa gagcctgtac gtgaagggcg aacctattat caacttctac  1020
gaccctctgg tgtttccttc ccaccagtgg catgctagca tctctcaggt gaacgagaag  1080
atcaaccaga gcctggcctt tatcagaaag agcgatgagc tgctgcacaa cgtgaacgcc  1140
ggcaagagta ccaccaacat catgatcacc accatcatta tcgtgatcat cgtgatcctc  1200
ctgagcctga tcgctgtcgg actgctgctg tactgcaagg ccaggagcac acctgtgacc  1260
ctgagcaagg accaactgtc tggcatcaac aacatcgctt ttagcaat              1308

SEQ ID NO: 14          moltype = AA  length = 25
FEATURE                Location/Qualifiers
source                 1..25
                       mol_type = protein
                       organism = unidentified
SEQUENCE: 14
MITTIIIVII VILLSLIAVG LLLYC                                        25

SEQ ID NO: 15          moltype = DNA  length = 48
FEATURE                Location/Qualifiers
source                 1..48
                       mol_type = genomic DNA
                       organism = Herpes Simplex Virus
SEQUENCE: 15
cggcaataaa aagacagaat aaaacgcacg gtgttgggtc gtttgttc               48

SEQ ID NO: 16          moltype = RNA  length = 48
FEATURE                Location/Qualifiers
source                 1..48
                       mol_type = genomic RNA
                       organism = Herpes Simplex Virus
SEQUENCE: 16
cggcaataaa aagacagaat aaaacgcacg gtgttgggtc gtttgttc               48

SEQ ID NO: 17          moltype = DNA  length = 132
FEATURE                Location/Qualifiers
source                 1..132
                       mol_type = other DNA
                       organism = synthetic construct
SEQUENCE: 17
gctcgctttc ttgctgtcca atttctatta aaggttcctt tgttccctaa gtccaactac  60
taaactgggg gatattatga agggccttga gcatctggat tctgcctaat aaaaaacatt  120
tattttcatt gc                                                      132

SEQ ID NO: 18          moltype = RNA  length = 132
FEATURE                Location/Qualifiers
source                 1..132
                       mol_type = other RNA
                       organism = synthetic construct
SEQUENCE: 18
gctcgctttc ttgctgtcca atttctatta aaggttcctt tgttccctaa gtccaactac  60
taaactgggg gatattatga agggccttga gcatctggat tctgcctaat aaaaaacatt  120
tattttcatt gc                                                      132

SEQ ID NO: 19          moltype = DNA  length = 50
FEATURE                Location/Qualifiers
source                 1..50
                       mol_type = genomic DNA
                       organism = Homo sapiens
SEQUENCE: 19
acatttgctt ctgacacaac tgtgttcact agcaacctca aacagacacc             50

SEQ ID NO: 20          moltype = RNA  length = 50
```

```
FEATURE                 Location/Qualifiers
source                  1..50
                        mol_type = genomic RNA
                        organism = Homo sapiens
SEQUENCE: 20
acatttgctt ctgacacaac tgtgttcact agcaacctca aacagacacc             50

SEQ ID NO: 21           moltype = DNA  length = 55
FEATURE                 Location/Qualifiers
source                  1..55
                        mol_type = other DNA
                        organism = synthetic construct
SEQUENCE: 21
ggcgctcgag caggttcaga aggagatcaa aaaccccaa ggatcaaacg ccacc       55

SEQ ID NO: 22           moltype = RNA  length = 55
FEATURE                 Location/Qualifiers
source                  1..55
                        mol_type = other RNA
                        organism = synthetic construct
SEQUENCE: 22
ggcgctcgag caggttcaga aggagatcaa aaaccccaa ggatcaaacg ccacc       55

SEQ ID NO: 23           moltype = DNA  length = 50
FEATURE                 Location/Qualifiers
source                  1..50
                        mol_type = other DNA
                        organism = synthetic construct
SEQUENCE: 23
gggcgctcga gcaggttcag aaggagatca aaaaccccca aggatcaaac             50

SEQ ID NO: 24           moltype = RNA  length = 50
FEATURE                 Location/Qualifiers
source                  1..50
                        mol_type = other RNA
                        organism = synthetic construct
SEQUENCE: 24
gggcgctcga gcaggttcag aaggagatca aaaaccccca aggatcaaac             50

SEQ ID NO: 25           moltype = DNA  length = 55
FEATURE                 Location/Qualifiers
source                  1..55
                        mol_type = other DNA
                        organism = synthetic construct
SEQUENCE: 25
ggcgcacgag cagggagaga aggagatcaa aaaccccaa ggatcaaacg ccacc       55

SEQ ID NO: 26           moltype = RNA  length = 55
FEATURE                 Location/Qualifiers
source                  1..55
                        mol_type = other RNA
                        organism = synthetic construct
SEQUENCE: 26
ggcgcacgag cagggagaga aggagatcaa aaaccccaa ggatcaaacg ccacc       55

SEQ ID NO: 27           moltype = RNA  length = 40
FEATURE                 Location/Qualifiers
source                  1..40
                        mol_type = other RNA
                        organism = synthetic construct
SEQUENCE: 27
aaaaaaaaaa aaaaaaaaaa aaaaaaaaaa aaaaaaaaaa                        40

SEQ ID NO: 28           moltype = RNA  length = 121
FEATURE                 Location/Qualifiers
source                  1..121
                        mol_type = other RNA
                        organism = synthetic construct
SEQUENCE: 28
aaaaaaaaaa aaaaaaaaaa aaaaaaaaaa aaaaaaaaaa aaaaaaaaaa aaaaaaaaaa  60
gaaaaaaaaa aaaaaaaaaa aaaaaaaaaa aaaaaaaaaa aaaaaaaaaa aaaaaaaaaa  120
a                                                                  121

SEQ ID NO: 29           moltype = DNA  length = 6601
FEATURE                 Location/Qualifiers
source                  1..6601
                        mol_type = other DNA
                        organism = synthetic construct
SEQUENCE: 29
```

-continued

```
tcgcgcgttt cggtgatgac ggtgaaaacc tctgacacat gcagctcccg gagacggtca  60
cagcttgtct gtaagcggat gccgggagca gacaagcccg tcagggcgcg tcagcgggtg  120
ttggcgggtg tcggggctgg cttaactatg cggcatcaga gcagattgta ctgagagtgc  180
accatatgcg gtgtgaaata ccgcacagat gcgtaaggag aaaataccgc atcaggcgcc  240
attcgccatt caggctgcgc aactgttggg aagggcgatc ggtgcgggcc tcttcgctat  300
tacgccagct ggcgaaaggg ggatgtgctg caaggcgatt aagttgggta acgccagggt  360
tttcccagtc acgacgttgt aaaacgacgg ccagtgaatt cgagctcggt acctcgcgaa  420
tgcatctaga tatcggatcc cgggcccgtc gactgcagag gcctgcatgc aagctttaat  480
acgactcact ataaggacat ttgcttctga cacaactgtg ttcactagca acctcaaaca  540
gacaccgcca ccatgttcgt gttcctggtg ctgctgcctc tggtcagcag ccagtgcgtg  600
aacctgagaa caagaacaca gcttcctcca gcctacacaa actcttttac acggggcgtg  660
tactatcctg acaaggtgtt ccggtccagc gtgctgcact caacccaaga cctgttcctg  720
cccttcttca gcaacgtcac ctggttccac gccatccacg tgtctggcac caatggcaca  780
aagcgattcg ataaccccgt gctgcctttc aacgacggcg tgtactttgc ctccatcgag  840
aagtccaaca tcatccgggg ctggatcttc gggaccacac tggatagcaa gacccagtct  900
ctgctgatcg taaacaacgc caccaacgtg gtcatcaagg tgtgcgagtt ccagttctgc  960
aacgacccct tcctcgatgt gtactaccac aagaacaaca agtcttggat ggaatcgggc  1020
gtgtatagca gcgccaacaa ctgcaccttc gaatacgtga gccagccttt cctgatggac  1080
ctggaaggca aacaaggcaa ttttaagaac ctgagagaat tcgtgttcaa aaatatagac  1140
ggctatttca agatctacag caagcacacc cctattaatc tggtgcggga tctgcctcag  1200
ggcttcagcg ccctcgaacc tctggtggac ctgccaatcg gcatcaacat tacaagattc  1260
cagacgctgc tcgctctgca cagatcttac ctgacccctg gcgacagcag cagcggctgg  1320
accgccggcg ccgccgctta ctacgtgggc tacctgcagc ctagaacctt tctgctgaag  1380
tacaacgaga acggcaccat cactgatgcc gtggattgcg ccctggaccc tctgtccgaa  1440
accaaatgta cactgaagtc ttttaccgtg gaaaaaggaa tctaccagac ttccaacttc  1500
cgggtgcagc cgaccgagag catcgtgcgg ttccctaaca tcacaaacct gtgccccttt  1560
ggcgaggtgt tcaacgccac aagatttgct agcgtgtacg cctggaatag aaagagaatc  1620
agcaactgcg tggccgatta cagcgtgctg tacaatagcg cctctttcag caccttcaaa  1680
tgctacggcg tgagccccac caagctgaac gatctgtgtt ttacaaacgt gtatgccgac  1740
tcattcgtaa tcaggggcga tgaggtgaga cagatcgctc ctggacagac aggcaaaatc  1800
gcggactaca actataagct gcctgatgac ttcacaggat gtgtgatcgc atggaactcc  1860
aataacctcg acagcaaggt gggcggaaat tacaattacc gctacagact gtttagaaag  1920
agcaatctga aacctttcga gagagacatc agcacagaga tctaccaggc cggcagcaag  1980
ccctgtaacg gcgtcgaggg cttcaactgc tacttccccc tgcagagcta cggcttccag  2040
cctaccaacg gcgtgggata ccagccttac agagtggtgg tgctgagctt cgagctgctg  2100
catgctcctg ctacagtgtg tggtcctaag aagagcacca acctggttaa gaacaagtgc  2160
gtgaatttta acttcaatgg actgaccgga accggcgtgc tgaccgaaag caacaagaaa  2220
ttcctgcctt ttcagcagtt tggcagagac atcgccgaca ccaccgacgc cgtgagagat  2280
ccacaaaccc tggaaatcct ggacatcaca ccttgctcat ttggaggggt gtcggtgatc  2340
acacctggca ccaacaccag caaccaggtg gccgtgctgt accagggagt gaattgtacc  2400
gaggtccccg tggccattca cgccgaccag ctgacccccta cctggcgggt gtactccacc  2460
ggctctaacg tattccagac cagagccggc tgtctgatcg gcgcagaaca cgtgaacaat  2520
agctacgagt gcgacatccc tatcggagcc gggatctgcg ctagctacca gacccagaca  2580
aactccagaa gcagagccgg aagcgtggcc agccagtcta tcatcgccta caccatgagc  2640
ctgggcgccg aaaacagcgt tgcctacagc aacaattcta tcgccatccc tacaaacttc  2700
accatctccg tgaccaccga gatcctgcct gtcagcatga caaagaccag cgtagactgc  2760
acaatgtaca tctgcggaga ttccaccgag tgtagtaacc tcctgctgca atacggatct  2820
ttctgtactc agctgaacag agccctgacc ggcatcgccg ttgaacagga caagaacacc  2880
caggaggttt tcgcccaggt taagcagatc tacaaaaccc ctcctatcaa ggacttcgga  2940
ggctttaact tctcccagat cctgcccgac cccagcaagc ccagcaagcg gagccccatc  3000
gaggacctgc tgttcaacaa ggtgaccctg gccgacgccg gcttcatcaa acagtacggc  3060
gattgcctgg gagacatcgc cgctagagat ctaatttgcg cccaaaagtt taacggcctg  3120
acagtgctgc ctccactgct gacagacgag atgatcgccc agtacacatc tgccctgctg  3180
gctggtacca tcacatctgg ctggaccttt ggcgccggcc ccgccctcca gatccctttc  3240
cccatgcaga tggcctaccg gttcaacggc atcggcgtga cccagaacgt gctgtacgaa  3300
aaccagaaac tgatcgccaa ccagttcaat agcgcgatcg gcaaaatcca ggatagcctc  3360
agctctacac ccagcgctct tggcaagctg caaaacgtgg tgaaccagaa tgcccaggcc  3420
cttaacaccc tggtgaagca gctatcctct aatttcggtg ccatcagcag cgtgctgaat  3480
gatatcctga gcagactgga cccccctgag gccgaagtgc agatcgacag actgatcacc  3540
ggaagactgc agagcctgca aacctacgtg acccagcaac tgatccgggc cgcagaaatc  3600
cgggcctccg ctaacctggc cgctaccaag atgagcgagt gcgtgctggg tcaaagcaag  3660
cgcgtggact tctgtggaaa aggctaccac ctgatgagct tccctcagag cgctccacac  3720
ggcgtggtgt tcctgcatgt gacttacgtg cctgcccagg aaaagaactt caccaccgcc  3780
cctgccattt gtcacgacgg caaggcccac ttcccccggg aaggcgtgtt tgtgtctaac  3840
ggaacacact ggtttgtgac tcaaagaaac ttctacgagc cacagatcat caccacagat  3900
aacaccttcg tcagcggcaa ctgcgacgtg gtgatcggca tcgtgaacaa tactgtgtac  3960
gacccccctgc agccagagct cgattctttc aaagaggaac tggataagta cttcaagaac  4020
cacacatccc ccgacgtcga cctgggcgat atcagcggca ttaacgccag cgtggtgaac  4080
atccagaagg aaatcgatag actgaacgag gtggcaaaga acctgaatga gtccctgatt  4140
gacctgcaag agctcgggaa gtacgagcag tatatcaagt ggccttggta catctggctg  4200
ggcttcatcg cgggcctgat cgccatcgtt atggtgacga tcatgctgtg ctgcatgacc  4260
agttgctgta gctgcctgaa gggctgctgc agctgcggca gctgttgcaa gttcgacgag  4320
gacgacagcg agcctgtgct gaagggcgtt aagctgcact acacctgagc tcgctttctt  4380
gctgtccaat ttctattaaa ggttcctttg ttccctaagt ccaactacta aactgggggga  4440
tattatgaag ggccttgagc atctggattc tgcctaataa aaaacattta ttttcattgc  4500
caataggccg aaatcggcaa gcgcgatcgc aaaaaaaaaa aaaaaaaaaa aaaaaaaaaa  4560
aaaaaaaaaa aaaaaaaaaa gaaaaaaaaa aaaaaaaaaa aaaaaaaaaa aaaaaaaaaa  4620
aaaaaaaaaa aaaaaaaaaa agaattcctc gagatttaaa ttcgcgagta ctatgcatat  4680
gggcccaata ttaattaagc gctagcacgc gtttaaacag gcctcgaggc gcgcccgctt  4740
```

-continued

```
cctcgctcac tgactcgctg cgctcggtcg ttcggctgcg gcgagcggta tcagctcact  4800
caaaggcggt aatacggtta tccacagaat caggggataa cgcaggaaag aacatgtgag  4860
caaaaggcca gcaaaaggcc aggaaccgta aaaaggccgc gttgctggcg tttttccata  4920
ggctccgccc ccctgacgag catcacaaaa atcgacgctc aagtcagagg tggcgaaacc  4980
cgacaggact ataaagatac caggcgtttc cccctggaag ctccctcgtg cgctctcctg  5040
ttccgaccct gccgcttacc ggatacctgt ccgcctttct cccttcggga agcgtggcgc  5100
tttctcatag ctcacgctgt aggtatctca gttcggtgta ggtcgttcgc tccaagctgg  5160
gctgtgtgca cgaacccccc gttcagcccg accgctgcgc cttatccggt aactatcgtc  5220
ttgagtccaa cccggtaaga cacgacttat cgccactggc agcagccact ggtaacagga  5280
ttagcagagc gaggtatgta ggcggtgcta cagagttctt gaagtggtgg cctaactacg  5340
gctacactag aagaacagta tttggtatct gcgctctgct gaagccagtt accttcggaa  5400
aaagagttgg tagctcttga tccggcaaac aaaccaccgc tggtagcggt ggtttttttg  5460
tttgcaagca gcagattacg cgcagaaaaa aaggatctca agaagatcct ttgatctttt  5520
ctacggggtc tgacgctcag tggaacgaaa actcacgtta agggattttg gtcatgagat  5580
tatcaaaaag gatcttcacc tagatccttt taaattaaaa atgaagtttt aaatcaagcc  5640
caatctgaat aatgttacaa ccaattaacc aattctgatt agaaaaactc atcgagcatc  5700
aaatgaaact gcaatttatt catatcagga ttatcaatac catatttttg aaaaagccgt  5760
ttctgtaatg aaggagaaaa ctcaccgagg cagttccata ggatggcaag atcctggtat  5820
cggtctgcga ttccgactcg tccaacatca atacaaccta ttaatttccc ctcgtcaaaa  5880
ataaggttat caagtgagaa atcaccatga gtgacgactg aatccggtga gaatggcaaa  5940
agtttatgca tttctttcca gacttgttca acaggccagc cattacgctc gtcatcaaaa  6000
tcactcgcat caaccaaacc gttattcatt cgtgattgcg cctgagcgag acgaaatacg  6060
cgatcgctgt taaaaggaca attacaaaca ggaatcgaat gcaaccggcg caggaacact  6120
gccagcgcat caacaatatt ttcacctgaa tcaggatatt cttctaatac ctggaatgct  6180
gtttttccgg ggatcgcagt ggtgagtaac catgcatcat caggagtacg gataaaatgc  6240
ttgatggtcg gaagaggcat aaattccgtc agccagttta gtctgaccat ctcatctgta  6300
acatcattgg caacgctacc tttgccatgt ttcagaaaca actctggcgc atcgggcttc  6360
ccatacaagc gatagattgt cgcacctgat tgcccgacat tatcgcgagc ccatttatac  6420
ccatataaat cagcatccat gttggaattt aatcgcggcc tcgacgtttc ccgttgaata  6480
tggctcataa caccccttgt attactgttt atgtaagcag acagttttat tgttcatgat  6540
gatatatttt tatcttgtgc aatgtaacat cagagatttt gagacacggg ccagagctgc  6600
a                                                                   6601
```

```
SEQ ID NO: 30          moltype = RNA  length = 1835
FEATURE                Location/Qualifiers
source                 1..1835
                       mol_type = other RNA
                       organism = synthetic construct
SEQUENCE: 30
atggaactgc ctgtgctgaa aacaaacgcc atcacaacaa tcctggcagc agtgacactg  60
tgcttcgcca gcagccagaa tattacagaa gagttctacc agagcacatg cagcgccgtg  120
tctaagggct acctgagcgc cctgagaaca ggctggtaca ccagcgtcat cacgatcgag  180
ctgagtaata tcaaggagaa caaatgcaac ggcaccgacg ccaaggtgaa gctgatcaag  240
caggagctgg ataaatacaa gaacgccgtg accgagttgc agctgctgat gcagtctacc  300
ccagccgcca acaacagagc cagacgggaa ctacccagat tcatgaacta cacactgaac  360
aacactaaga acaccaacgt gacactgtct aagaaaagaa agcggcggtt cctgggattc  420
ctgctgggcg tgggaagcgc tatcgcttct ggaattgccg tgtgcaaggt gctgcacctg  480
gaaggcgagg tgaacaagat caagtctgcc ctgctgtcca ccaacaaggc cgtagtcagc  540
ctgagcaatg gcgtgagcgt cctgaccttt aaggtgctgg acctgaagaa ctacatcgac  600
aagcagctgc tgcctatctt gaacaagcag agctgctcca tcagcaatat tgagactgtg  660
atcgaattcc agcagaagaa caaccggctg ctggagatca ccagagagtt ctccgtgaac  720
gctggcgtga ctacacctgt ttcaacctac atgctgacca attctgagct gctgagcctg  780
atcaacgaca tgcctatcac caacgaccag aaaaaactga tgtccaataa cgttcaaatc  840
gtgcggcagc aaagctacag catcatgtgc atcatcaagg aagaagtgct tgcctacgtg  900
gtccagctgc cactttatgg agttatcgat acaccctgct ggaagctgca caccagccct  960
ctgtgtacaa ccaacaccaa ggaaggcagc aacatctgcc tgaccagaac agatagaggc  1020
tggtattgtg ataacgccgg cagcgtgagc ttcttccccc aggccgacac atgtaaagtg  1080
cagagcaata gagtgttctg cgacaccatg aatagcctga ccctgcccag cgaggtgaat  1140
ctgtgtaaca tcgacatttt caaccccaag tacgattgca agatcatgac ctccaagacc  1200
gacgtgagca gcagcgtgat cacctccctg ggcgccatcg tgtcttgcta cggcaagacc  1260
aagtgcacag cctctaacaa aaatcgcggc atcatcaaaa ccttctctaa cggttgtgac  1320
tacgtgtcaa acaaaggcgt ggacaccgtg tccgtgggca acaccctgta ttacgtgaac  1380
aagcaggagg gcaagagcct gtacgtgaag ggcgaaccta ttatcaactt ctacgaccct  1440
ctggtgtttc cttccgacga gtttgatgct agcatctctc aggtgaacga gaagatcaac  1500
cagagcctgg cctttatcag aaagagcgat gagctgctgc acaacgtgaa cgccggcaag  1560
agtaccacca acatcatgat caccaccatc attatcgtga tcatcgtgat cctcctgagc  1620
ctgatcgctg tcggactgct gctgtactgc aaggccagga gcacacctgt gaccctgagc  1680
aaggaccaac tgtctggcat caacaacatc gcttttagca attagaaaaa aaaaaaaaaa  1740
aaaaaaaaaa aaaaaaaaaa aaaaaaaaaa aaaaagaaaa aaaaaaaaaa aaaaaaaaaa  1800
aaaaaaaaaa aaaaaaaaaa aaaaaaaaaa aaaaa                            1835
```

```
SEQ ID NO: 31          moltype = AA  length = 20
FEATURE                Location/Qualifiers
source                 1..20
                       mol_type = protein
                       organism = synthetic construct
REGION                 1..20
                       note = This sequence is one part of a branched amino acid
                        sequence
```

-continued

```
SEQUENCE: 31
KHKHHKHHKH HKHHKHHKHK                                        20

SEQ ID NO: 32          moltype = AA  length = 17
FEATURE                Location/Qualifiers
source                 1..17
                       mol_type = protein
                       organism = synthetic construct
REGION                 1..17
                       note = This sequence is one part of a branched amino acid
                        sequence
SEQUENCE: 32
KHHHKHHHKH HHKHHHK                                           17

SEQ ID NO: 33          moltype = AA  length = 18
FEATURE                Location/Qualifiers
source                 1..18
                       mol_type = protein
                       organism = synthetic construct
REGION                 1..18
                       note = This sequence is one part of a branched amino acid
                        sequence
SEQUENCE: 33
KHHHKHHHKH HHHKHHHK                                          18

SEQ ID NO: 34          moltype = AA  length = 18
FEATURE                Location/Qualifiers
source                 1..18
                       mol_type = protein
                       organism = synthetic construct
SITE                   1
                       note = D-amino acid
SITE                   5
                       note = D-amino acid
SITE                   9
                       note = D-amino acid
SITE                   14
                       note = D-amino acid
SITE                   18
                       note = D-amino acid
REGION                 1..18
                       note = This sequence is one part of a branched amino acid
                        sequence
SEQUENCE: 34
KHHHKHHHKH HHHKHHHK                                          18

SEQ ID NO: 35          moltype = AA  length = 19
FEATURE                Location/Qualifiers
source                 1..19
                       mol_type = protein
                       organism = synthetic construct
REGION                 1..19
                       note = This sequence is one part of a branched amino acid
                        sequence
SEQUENCE: 35
HKHHHKHHHK HHHHKHHHK                                         19

SEQ ID NO: 36          moltype = AA  length = 20
FEATURE                Location/Qualifiers
source                 1..20
                       mol_type = protein
                       organism = synthetic construct
REGION                 1..20
                       note = This sequence is one part of a branched amino acid
                        sequence
SEQUENCE: 36
HHKHHHKHHH KHHHHKHHHK                                        20

SEQ ID NO: 37          moltype = AA  length = 21
FEATURE                Location/Qualifiers
source                 1..21
                       mol_type = protein
                       organism = synthetic construct
REGION                 1..21
                       note = This sequence is one part of a branched amino acid
                        sequence
SEQUENCE: 37
KHHHHKHHHH KHHHHKHHHH K                                      21
```

-continued

```
SEQ ID NO: 38          moltype = AA  length = 18
FEATURE                Location/Qualifiers
source                 1..18
                       mol_type = protein
                       organism = synthetic construct
REGION                 1..18
                       note = This sequence is one part of a branched amino acid
                        sequence
SEQUENCE: 38
KHHHKHHHKH HHKHHHHK                                                18

SEQ ID NO: 39          moltype = AA  length = 18
FEATURE                Location/Qualifiers
source                 1..18
                       mol_type = protein
                       organism = synthetic construct
REGION                 1..18
                       note = This sequence is one part of a branched amino acid
                        sequence
SEQUENCE: 39
KHHHKHHHHK HHHKHHHK                                                18

SEQ ID NO: 40          moltype = AA  length = 19
FEATURE                Location/Qualifiers
source                 1..19
                       mol_type = protein
                       organism = synthetic construct
REGION                 1..19
                       note = This sequence is one part of a branched amino acid
                        sequence
SEQUENCE: 40
KHHHKHHHHK HHHKHHHHK                                               19

SEQ ID NO: 41          moltype = AA  length = 21
FEATURE                Location/Qualifiers
source                 1..21
                       mol_type = protein
                       organism = synthetic construct
SEQUENCE: 41
KHHHHKHHHH KHHHHKHHHH K                                            21

SEQ ID NO: 42          moltype = AA  length = 18
FEATURE                Location/Qualifiers
source                 1..18
                       mol_type = protein
                       organism = synthetic construct
SEQUENCE: 42
KHHHKHHHKH HHKHHHHK                                                18

SEQ ID NO: 43          moltype = AA  length = 18
FEATURE                Location/Qualifiers
source                 1..18
                       mol_type = protein
                       organism = synthetic construct
SEQUENCE: 43
KHHHKHHHHK HHHKHHHK                                                18

SEQ ID NO: 44          moltype = AA  length = 19
FEATURE                Location/Qualifiers
source                 1..19
                       mol_type = protein
                       organism = synthetic construct
SEQUENCE: 44
KHHHKHHHHK HHHKHHHHK                                               19

SEQ ID NO: 45          moltype = AA  length = 4
FEATURE                Location/Qualifiers
source                 1..4
                       mol_type = protein
                       organism = synthetic construct
SEQUENCE: 45
HHHK                                                               4

SEQ ID NO: 46          moltype =   length =
SEQUENCE: 46
000

SEQ ID NO: 47          moltype = DNA  length = 18
FEATURE                Location/Qualifiers
```

```
source                  1..18
                        mol_type = other DNA
                        organism = synthetic construct
SEQUENCE: 47
taatacgact cactataa                                                18

SEQ ID NO: 48           moltype = RNA  length = 1308
FEATURE                 Location/Qualifiers
source                  1..1308
                        mol_type = other RNA
                        organism = synthetic construct
SEQUENCE: 48
ggattcctgc tgggcgtggg aagcgctatc gcttctggaa ttgccgtgag caaggtgctg  60
cacctggaag gcgaggtgaa caagatcaag tctgccctgc tgtccaccaa caaggccgta  120
gtcagcctga gcaatggcgt gagcgtcctg accagtaagg tgctggacct gaagaactac  180
atcgacaagc agctgctgcc tatcgtgaac aagcagagct gctccatcag caatattgag  240
actgtgatcg aattccagca gaagaacaac cggctgctgg agatcaccag agagttctcc  300
gtgaacgctg gcgtgactac acctgtttca acctacatgc tgaccaattc tgagctgctg  360
agcctgatca acgacatgcc tatcaccaac gaccagaaaa aactgatgtc caataacgtt  420
caaatcgtgc ggcagcaaag ctacagcatc atgagcatca tcaaggaaga agtgcttgcc  480
tacgtggtcc agctgccact ttatggagtt atcgatacac cctgctggaa gctgcacacc  540
agccctctgt gtacaaccaa caccaaggaa ggcagcaaca tctgcctgac cagaacagat  600
agaggctggt attgtgataa cgccggcagc gtgagcttct tcccccaggc cgacacatgt  660
aaagtgcaga gcaatagagt gttctgcgac accatgaata gcctgaccct gcccagcgag  720
gtgaatctgt gtaacatcga cattttcaac cccaagtacg attgcaagat catgacctcc  780
aagaccgacg tgagcagcag cgtgatcacc tccctgggcg ccatcgtgtc ttgctacggc  840
aagaccaagt gcacagcctc taacaaaaat cgcggcatca tcaaaacctt ctctaacggt  900
tgtgactacg tgtcaaacaa aggcgtggac accgtgtccg tgggcaacac cctgtattac  960
gtgaacaagc aggagggcaa gagcctgtac gtgaagggcg aacctattat caacttctac  1020
gaccctctgg tgtttccttc cgacgagttt gatgctagca tctctcaggt gaacgagaag  1080
atcaaccaga gcctggcctt tatcagaaag agcgatgagc tgctgcacaa cgtgaacgcc  1140
ggcaagagta ccaccaacat catgatcacc accatcatta tcgtgatcat cgtgatcctc  1200
ctgagcctga tcgctgtcgg actgctgctg tactgcaagg ccaggagcac acctgtgacc  1260
ctgagcaagg accaactgtc tggcatcaac aacatcgctt ttagcaat               1308

SEQ ID NO: 49           moltype = RNA  length = 1254
FEATURE                 Location/Qualifiers
source                  1..1254
                        mol_type = other RNA
                        organism = synthetic construct
SEQUENCE: 49
ggattcctgc tgggcgtggg aagcgctatc gcttctggaa ttgccgtgag caaggtgctg  60
cacctggaag gcgaggtgaa caagatcaag tctgccctgc tgtccaccaa caaggccgta  120
gtcagcctga gcaatggcgt gagcgtcctg accagtaagg tgctggacct gaagaactac  180
atcgacaagc agctgctgcc tatcgtgaac aagcagagct gctccatcag caatattgag  240
actgtgatcg aattccagca gaagaacaac cggctgctgg agatcaccag agagttctcc  300
gtgaacgctg gcgtgactac acctgtttca acctacatgc tgaccaattc tgagctgctg  360
agcctgatca acgacatgcc tatcaccaac gaccagaaaa aactgatgtc caataacgtt  420
caaatcgtgc ggcagcaaag ctacagcatc atgagcatca tcaaggaaga agtgcttgcc  480
tacgtggtcc agctgccact ttatggagtt atcgatacac cctgctggaa gctgcacacc  540
agccctctgt gtacaaccaa caccaaggaa ggcagcaaca tctgcctgac cagaacagat  600
agaggctggt attgtgataa cgccggcagc gtgagcttct tcccccaggc cgacacatgt  660
aaagtgcaga gcaatagagt gttctgcgac accatgaata gcctgaccct gcccagcgag  720
gtgaatctgt gtaacatcga cattttcaac cccaagtacg attgcaagat catgacctcc  780
aagaccgacg tgagcagcag cgtgatcacc tccctgggcg ccatcgtgtc ttgctacggc  840
aagaccaagt gcacagcctc taacaaaaat cgcggcatca tcaaaacctt ctctaacggt  900
tgtgactacg tgtcaaacaa aggcgtggac accgtgtccg tgggcaacac cctgtattac  960
gtgaacaagc aggagggcaa gagcctgtac gtgaagggcg aacctattat caacttctac  1020
gaccctctgg tgtttccttc cgacgagttt gatgctagca tctctcaggt gaacgagaag  1080
atcaaccaga gcctggcctt tatcagaaag agcgatgagc tgctgcacaa cgtgaacgcc  1140
ggcaagagta ccaccaacat catgatcacc ggatacatcc cggaggcccc tagggacggt  1200
caagcttacg tgagaaagga cggcgaatgg gttctgctgt cgaccttctt ggga        1254

SEQ ID NO: 50           moltype = RNA  length = 1308
FEATURE                 Location/Qualifiers
source                  1..1308
                        mol_type = other RNA
                        organism = synthetic construct
SEQUENCE: 50
ggattcctgc tgggcgtggg aagcgctatc gcttctggaa ttgccgtgtg caaggtgctg  60
cacctggaag gcgaggtgaa caagatcaag tctgccctgc tgtccaccaa caaggccgta  120
gtcagcctga gcaatggcgt gagcgtcctg acctttaagg tgctggacct gaagaactac  180
atcgacaagc agctgctgcc tatcttgaac aagcagagct gctccatcag caatattgag  240
actgtgatcg aattccagca gaagaacaac cggctgctgg agatcaccag agagttctcc  300
gtgaacgctg gcgtgactac acctgtttca acctacatgc tgaccaattc tgagctgctg  360
agcctgatca acgacatgcc tatcaccaac gaccagaaaa aactgatgtc caataacgtt  420
caaatcgtgc ggcagcaaag ctacagcatc atgtgcatca tcaaggaaga agtgcttgcc  480
tacgtggtcc agctgccact ttatggagtt atcgatacac cctgctggaa gctgcacacc  540
agccctctgt gtacaaccaa caccaaggaa ggcagcaaca tctgcctgac cagaacagat  600
```

-continued

```
agaggctggt attgtgataa cgccggcagc gtgagcttct tcccccaggc cgacacatgt  660
aaagtgcaga gcaatagagt gttctgcgac accatgaata gcctgaccct gcccagcgag  720
gtgaatctgt gtaacatcga cattttcaac cccaagtacg attgcaagat catgacctcc  780
aagaccgacg tgagcagcag cgtgatcacc tccctgggcg ccatcgtgtc ttgctacggc  840
aagaccaagt gcacagcctc taacaaaaat cgcggcatca tcaaaacctt ctctaacggt  900
tgtgactacg tgtcaaacaa aggcgtggac accgtgtccg tgggcaacac cctgtattac  960
gtgaacaagc aggagggcaa gagcctgtac gtgaagggcg aacctattat caacttctac  1020
gaccctctgg tgtttccttc cgacgagttt gatgctagca tctctcaggt gaacgagaag  1080
atcaaccaga gcctggcctt tatcagaaag agcgatgagc tgctgcacaa cgtgaacgcc  1140
ggcaagagta ccaccaacat catgatcacc accatcatta tcgtgatcat cgtgatcctc  1200
ctgagcctga tcgctgtcgg actgctgctg tactgcaagg ccaggagcac acctgtgacc  1260
ctgagcaagg accaactgtc tggcatcaac aacatcgctt ttagcaat              1308
```

```
SEQ ID NO: 51          moltype = RNA  length = 1254
FEATURE                Location/Qualifiers
source                 1..1254
                       mol_type = other RNA
                       organism = synthetic construct
SEQUENCE: 51
ggattcctgc tgggcgtggg aagcgctatc gcttctggaa ttgccgtgtg caaggtgctg  60
cacctggaag gcgaggtgaa caagatcaag tctgccctgc tgtccaccaa caaggccgta  120
gtcagcctga gcaatggcgt gagcgtcctg acctttaagg tgctggacct gaagaactac  180
atcgacaagc agctgctgcc tatcttgaac aagcagagct gctccatcag caatattgag  240
actgtgatcg aattccagca gaagaacaac cggctgctgg agatcaccag agagttctcc  300
gtgaacgctg gcgtgactac acctgtttca acctacatgc tgaccaattc tgagctgctg  360
agcctgatca acgacatgcc tatcaccaac gaccagaaaa aactgatgtc caataacgtt  420
caaatcgtgc ggcagcaaag ctacagcatc atgtgcatca tcaaggaaga agtgcttgcc  480
tacgtggtcc agctgccact ttatggagtt atcgatacac cctgctggaa gctgcacacc  540
agccctctgt gtacaaccaa caccaaggaa ggcagcaaca tctgcctgac cagaacagat  600
agaggctggt attgtgataa cgccggcagc gtgagcttct tcccccaggc cgacacatgt  660
aaagtgcaga gcaatagagt gttctgcgac accatgaata gcctgaccct gcccagcgag  720
gtgaatctgt gtaacatcga cattttcaac cccaagtacg attgcaagat catgacctcc  780
aagaccgacg tgagcagcag cgtgatcacc tccctgggcg ccatcgtgtc ttgctacggc  840
aagaccaagt gcacagcctc taacaaaaat cgcggcatca tcaaaacctt ctctaacggt  900
tgtgactacg tgtcaaacaa aggcgtggac accgtgtccg tgggcaacac cctgtattac  960
gtgaacaagc aggagggcaa gagcctgtac gtgaagggcg aacctattat caacttctac  1020
gaccctctgg tgtttccttc cgacgagttt gatgctagca tctctcaggt gaacgagaag  1080
atcaaccaga gcctggcctt tatcagaaag agcgatgagc tgctgcacaa cgtgaacgcc  1140
ggcaagagta ccaccaacat catgatcacc ggatacatcc cggaggcccc tagggacggt  1200
caagcttacg tgagaaagga cggcgaatgg gttctgctgt cgaccttctt ggga        1254
```

```
SEQ ID NO: 52          moltype = RNA  length = 1254
FEATURE                Location/Qualifiers
source                 1..1254
                       mol_type = other RNA
                       organism = synthetic construct
SEQUENCE: 52
ggattcctgc tgggcgtggg aagcgctatc gcttctggaa ttgccgtgtg caaggtgctg  60
cacctggaag gcgaggtgaa caagatcaag tctgccctgc tgtccaccaa caaggccgta  120
gtcagcctga gcaatggcgt gagcgtcctg acctttaagg tgctggacct gaagaactac  180
atcgacaagc agctgctgcc tatcttgaac aagcagagct gctccatcag caatattgag  240
actgtgatcg aattccagca gaagaacaac cggctgctgg agatcaccag agagttctcc  300
gtgaacgctg gcgtgactac acctgtttca acctacatgc tgaccaattc tgagctgctg  360
agcctgatca acgacatgcc tatcaccaac gaccagaaaa aactgatgtc caataacgtt  420
caaatcgtgc ggcagcaaag ctacagcatc atgtgcatca tcaaggaaga agtgcttgcc  480
tacgtggtcc agctgccact ttatggagtt atcgatacac cctgctggaa gctgcacacc  540
agccctctgt gtacaaccaa caccaaggaa ggcagcaaca tctgcctgac cagaacagat  600
agaggctggt attgtgataa cgccggcagc gtgagcttct tcccccaggc cgacacatgt  660
aaagtgcaga gcaatagagt gttctgcgac accatgaata gcctgaccct gcccagcgag  720
gtgaatctgt gtaacatcga cattttcaac cccaagtacg attgcaagat catgacctcc  780
aagaccgacg tgagcagcag cgtgatcacc tccctgggcg ccatcgtgtc ttgctacggc  840
aagaccaagt gcacagcctc taacaaaaat cgcggcatca tcaaaacctt ctctaacggt  900
tgtgactacg tgtcaaacaa aggcgtggac accgtgtccg tgggcaacac cctgtattac  960
gtgaacaagc aggagggcaa gagcctgtac gtgaagggcg aacctattat caacttctac  1020
gaccctctgg tgtttccttc ccaccagtgg catgctagca tctctcaggt gaacgagaag  1080
atcaaccaga gcctggcctt tatcagaaag agcgatgagc tgctgcacaa cgtgaacgcc  1140
ggcaagagta ccaccaacat catgatcacc ggatacatcc cggaggcccc tagggacggt  1200
caagcttacg tgagaaagga cggcgaatgg gttctgctgt cgaccttctt ggga        1254
```

```
SEQ ID NO: 53          moltype = AA  length = 574
FEATURE                Location/Qualifiers
source                 1..574
                       mol_type = protein
                       organism = synthetic construct
SEQUENCE: 53
MELLILKANA ITTILTAVTF CFASGQNITE EFYQSTCSAV SKGYLSALRT GWYTSVITIE  60
LSNIKENKCN GTDAKVKLIK QELDKYKNAV TELQLLMQST PATNNRARRE LPRFMNYTLN  120
NAKKTNVTLS KKRKRRFLGF LLGVGSAIAS GVAVSKVLHL EGEVNKIKSA LLSTNKAVVS  180
LSNGVSVLTF KVLDLKNYID KQLLPILNKQ SCSISNIETV IEFQQKNNRL LEITREFSVN  240
```

-continued

```
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNVDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNAGK STTNIMITTI IIVIIVILLS  540
LIAVGLLLYC KARSTPVTLS KDQLSGINNI AFSN                             574

SEQ ID NO: 54          moltype = DNA  length = 1725
FEATURE                Location/Qualifiers
source                 1..1725
                       mol_type = other DNA
                       organism = synthetic construct
SEQUENCE: 54
atggaactgc tgatcctgaa ggccaacgct atcaccacaa tcctgaccgc cgtgaccttt  60
tgcttcgcct ctggccagaa catcacggaa gagttttacc agagcacctg cagcgctgtg  120
tccaaaggtt atctgagcgc tctgagaacc ggatggtata ccagcgtcat cacaatcgag  180
ttgtccaata tcaaggaaaa caagtgtaac ggaacagatg ccaaggtgaa gctgatcaag  240
caggaactgg ataagtacaa gaacgccgtg accgagctgc agctgttgat gcagagcact  300
cctgccacca acaacagagc ccggagagag ctgcctagat tcatgaacta caccctcaac  360
aacgccaaga agaccaacgt gacactgagc aagaagcgga aaagacggtt cctgggattc  420
ctgctgggcg ttggaagcgc catcgccagc ggcgtggccg tgtctaaggt gctgcacctg  480
gaaggagagg tgaacaaaat caaatctgcc ctgcttagca ccaacaaagc cgttgtgagt  540
ttgagcaacg gtgtgtccgt gctgacattt aaggtgctgg acctgaagaa ctacatcgac  600
aagcaactgc tgcccatcct gaacaagcaa tcctgttcca tcagcaacat cgagacagtt  660
atcgagttcc agcagaagaa caaccggctg ctggaaatca ccagagaatt cagcgtgaat  720
gctggcgtga ctaccccagt gtctacctac atgctgacaa attctgagct gctgagcctg  780
atcaacgaca tgcctatcac aaatgatcag aaaaagctga tgagcaacaa tgtccagatc  840
gtgcggcagc aaagctacag catcatgagc atcattaagg aagaagtgct ggcctacgtg  900
gtgcagctgc ctctgtacgg cgtgatcgac accccttgct ggaagctgca cacctctcct  960
ctgtgtacca caaacaccaa ggagggcagc aacatctgcc tgacaagaac cgatagaggc  1020
tggtactgcg ataacgccgg ctctgtctca ttcttccctc aggccgagac atgcaaggtc  1080
cagagcaaca gagtgttttg tgataccatg aacagcctga ccctgccaag cgaagtgaat  1140
ctgtgcaatg tggacatctt caaccccaag tacgactgca agatcatgac cagcaagaca  1200
gacgtgtcca gcagcgttat caccagcctg ggcgccattg tgtcttgcta cggcaaaacc  1260
aagtgcaccg catctaacaa aaatcgcggc atcatcaaga cattcagcaa cggctgtgac  1320
tacgtcagca ataagggcgt ggacaccgtg agcgtgggca acacactgta ctacgtgaat  1380
aagcaggagg gcaagtctct ctacgtgaaa ggcgagccta tcatcaattt ctacgacccc  1440
ctggtgttcc cctccgacga gttcgacgcc tctattagcc aggtgaacga gaagattaac  1500
cagagcctgg ctttcatcag aaagagcgac gagctgctgc acaacgtgaa cgctggcaag  1560
tccacaacca acatcatgat caccaccatc atcatcgtga tcatcgtgat tctgctgagc  1620
ctcatcgccg tgggcctgct gctgtattgc aaagccagaa gcacacctgt gaccctgagc  1680
aaggaccagc tgtctggcat caacaacatc gccttctcta actag                 1725

SEQ ID NO: 55          moltype = RNA  length = 1725
FEATURE                Location/Qualifiers
source                 1..1725
                       mol_type = other RNA
                       organism = synthetic construct
SEQUENCE: 55
atggaactgc tgatcctgaa ggccaacgct atcaccacaa tcctgaccgc cgtgaccttt  60
tgcttcgcct ctggccagaa catcacggaa gagttttacc agagcacctg cagcgctgtg  120
tccaaaggtt atctgagcgc tctgagaacc ggatggtata ccagcgtcat cacaatcgag  180
ttgtccaata tcaaggaaaa caagtgtaac ggaacagatg ccaaggtgaa gctgatcaag  240
caggaactgg ataagtacaa gaacgccgtg accgagctgc agctgttgat gcagagcact  300
cctgccacca acaacagagc ccggagagag ctgcctagat tcatgaacta caccctcaac  360
aacgccaaga agaccaacgt gacactgagc aagaagcgga aaagacggtt cctgggattc  420
ctgctgggcg ttggaagcgc catcgccagc ggcgtggccg tgtctaaggt gctgcacctg  480
gaaggagagg tgaacaaaat caaatctgcc ctgcttagca ccaacaaagc cgttgtgagt  540
ttgagcaacg gtgtgtccgt gctgacattt aaggtgctgg acctgaagaa ctacatcgac  600
aagcaactgc tgcccatcct gaacaagcaa tcctgttcca tcagcaacat cgagacagtt  660
atcgagttcc agcagaagaa caaccggctg ctggaaatca ccagagaatt cagcgtgaat  720
gctggcgtga ctaccccagt gtctacctac atgctgacaa attctgagct gctgagcctg  780
atcaacgaca tgcctatcac aaatgatcag aaaaagctga tgagcaacaa tgtccagatc  840
gtgcggcagc aaagctacag catcatgagc atcattaagg aagaagtgct ggcctacgtg  900
gtgcagctgc ctctgtacgg cgtgatcgac accccttgct ggaagctgca cacctctcct  960
ctgtgtacca caaacaccaa ggagggcagc aacatctgcc tgacaagaac cgatagaggc  1020
tggtactgcg ataacgccgg ctctgtctca ttcttccctc aggccgagac atgcaaggtc  1080
cagagcaaca gagtgttttg tgataccatg aacagcctga ccctgccaag cgaagtgaat  1140
ctgtgcaatg tggacatctt caaccccaag tacgactgca agatcatgac cagcaagaca  1200
gacgtgtcca gcagcgttat caccagcctg ggcgccattg tgtcttgcta cggcaaaacc  1260
aagtgcaccg catctaacaa aaatcgcggc atcatcaaga cattcagcaa cggctgtgac  1320
tacgtcagca ataagggcgt ggacaccgtg agcgtgggca acacactgta ctacgtgaat  1380
aagcaggagg gcaagtctct ctacgtgaaa ggcgagccta tcatcaattt ctacgacccc  1440
ctggtgttcc cctccgacga gttcgacgcc tctattagcc aggtgaacga gaagattaac  1500
cagagcctgg ctttcatcag aaagagcgac gagctgctgc acaacgtgaa cgctggcaag  1560
tccacaacca acatcatgat caccaccatc atcatcgtga tcatcgtgat tctgctgagc  1620
ctcatcgccg tgggcctgct gctgtattgc aaagccagaa gcacacctgt gaccctgagc  1680
aaggaccagc tgtctggcat caacaacatc gccttctcta actag                 1725
```

```
SEQ ID NO: 56          moltype = AA  length = 528
FEATURE                Location/Qualifiers
source                 1..528
                       mol_type = protein
                       organism = synthetic construct
SEQUENCE: 56
MELLILKANA ITTILTAVTF CFASGQNITE EFYQSTCSAV SKGYLSALRT GWYTSVITIE  60
LSNIKENKCN GTDAKVKLIK QELDKYKNAV TELQLLMQST PATNNRARRE LPRFMNYTLN  120
NAKKTNVTLS KKRKRRFLGF LLGVGSAIAS GVAVSKVLHL EGEVNKIKSA LLSTNKAVVS  180
LSNGVSVLTF KVLDLKNYID KQLLPILNKQ SCSISNIETV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNVDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNAGK STTNIMIT               528

SEQ ID NO: 57          moltype = DNA  length = 1725
FEATURE                Location/Qualifiers
source                 1..1725
                       mol_type = other DNA
                       organism = synthetic construct
SEQUENCE: 57
atggaactgc tgatcctgaa ggccaacgct atcaccacaa tcctgaccgc cgtgaccttt  60
tgcttcgcct ctggccagaa catcacggaa gagttttacc agagcacctg cagcgctgtg  120
tccaaaggtt atctgagcgc tctgagaacc ggatggtata ccagcgtcat cacaatcgag  180
ttgtccaata tcaaggaaaa caagtgtaac ggaacagatg ccaaggtgaa gctgatcaag  240
caggaactgg ataagtacaa gaacgccgtg accgagctgc agctgttgat gcagagcact  300
cctgccacca acaacagagc ccggagagag ctgcctagat tcatgaacta caccctcaac  360
aacgccaaga agaccaacgt gacactgagc aagaagcgga aaagacggtt cctgggattc  420
ctgctgggcg ttggaagcgc catcgccagc ggcgtggccg tgtgtaaggt gctgcacctg  480
gaaggagagg tgaacaaaat caaatctgcc ctgcttagca ccaacaaagc cgttgtgagt  540
ttgagcaacg gtgtgtccgt gctgacattt aaggtgctgg acctgaagaa ctacatcgac  600
aagcaactgc tgcccatcct gaacaagcaa tcctgttcca tcagcaacat cgagacagtt  660
atcgagttcc agcagaagaa caaccggctg ctggaaatca ccagagaatt cagcgtgaat  720
gctggcgtga ctaccccagt gtctacctac atgctgacaa attctgagct gctgagcctg  780
atcaacgaca tgcctatcac aaatgatcag aaaaagctga tgagcaacaa tgtccagatc  840
gtgcggcagc aaagctacag catcatgtgc atcattaagg aagaagtgct ggcctacgtg  900
gtgcagctgc ctctgtacgg cgtgatcgac accccttgct ggaagctgca cacctctcct  960
ctgtgtacca caaacaccaa ggagggcagc aacatctgcc tgacaagaac cgatagaggc  1020
tggtactgcg ataacgccgg ctctgtctca ttcttccctc aggccgagac atgcaaggtc  1080
cagagcaaca gagtgttttg tgataccatg aacagcctga ccctgccaag cgaagtgaat  1140
ctgtgcaatg tggacatctt caaccccaag tacgactgca agatcatgac cagcaagaca  1200
gacgtgtcca gcagcgttat caccagcctg ggcgccattg tgtcttgcta cggcaaaacc  1260
aagtgcaccg catctaacaa aaatcgcggc atcatcaaga cattcagcaa cggctgtgac  1320
tacgtcagca ataagggcgt ggacaccgtg agcgtgggca acacactgta ctacgtgaat  1380
aagcaggagg gcaagtctct ctacgtgaaa ggcgagccta tcatcaattt ctacgacccc  1440
ctggtgttcc cctccgacga gttcgacgcc tctattagcc aggtgaacga gaagattaac  1500
cagagcctgg ctttcatcag aaagagcgac gagctgctgc acaacgtgaa cgctggcaag  1560
tccacaacca acatcatgat caccaccatc atcatcgtga tcatcgtgat tctgctgagc  1620
ctcatcgccg tgggcctgct gctgtattgc aaagccagaa gcacacctgt gaccctgagc  1680
aaggaccagc tgtctggcat caacaacatc gccttctcta actag                1725

SEQ ID NO: 58          moltype = RNA  length = 1725
FEATURE                Location/Qualifiers
source                 1..1725
                       mol_type = other RNA
                       organism = synthetic construct
SEQUENCE: 58
atggaactgc tgatcctgaa ggccaacgct atcaccacaa tcctgaccgc cgtgaccttt  60
tgcttcgcct ctggccagaa catcacggaa gagttttacc agagcacctg cagcgctgtg  120
tccaaaggtt atctgagcgc tctgagaacc ggatggtata ccagcgtcat cacaatcgag  180
ttgtccaata tcaaggaaaa caagtgtaac ggaacagatg ccaaggtgaa gctgatcaag  240
caggaactgg ataagtacaa gaacgccgtg accgagctgc agctgttgat gcagagcact  300
cctgccacca acaacagagc ccggagagag ctgcctagat tcatgaacta caccctcaac  360
aacgccaaga agaccaacgt gacactgagc aagaagcgga aaagacggtt cctgggattc  420
ctgctgggcg ttggaagcgc catcgccagc ggcgtggccg tgtgtaaggt gctgcacctg  480
gaaggagagg tgaacaaaat caaatctgcc ctgcttagca ccaacaaagc cgttgtgagt  540
ttgagcaacg gtgtgtccgt gctgacattt aaggtgctgg acctgaagaa ctacatcgac  600
aagcaactgc tgcccatcct gaacaagcaa tcctgttcca tcagcaacat cgagacagtt  660
atcgagttcc agcagaagaa caaccggctg ctggaaatca ccagagaatt cagcgtgaat  720
gctggcgtga ctaccccagt gtctacctac atgctgacaa attctgagct gctgagcctg  780
atcaacgaca tgcctatcac aaatgatcag aaaaagctga tgagcaacaa tgtccagatc  840
gtgcggcagc aaagctacag catcatgtgc atcattaagg aagaagtgct ggcctacgtg  900
gtgcagctgc ctctgtacgg cgtgatcgac accccttgct ggaagctgca cacctctcct  960
ctgtgtacca caaacaccaa ggagggcagc aacatctgcc tgacaagaac cgatagaggc  1020
tggtactgcg ataacgccgg ctctgtctca ttcttccctc aggccgagac atgcaaggtc  1080
cagagcaaca gagtgttttg tgataccatg aacagcctga ccctgccaag cgaagtgaat  1140
ctgtgcaatg tggacatctt caaccccaag tacgactgca agatcatgac cagcaagaca  1200
gacgtgtcca gcagcgttat caccagcctg ggcgccattg tgtcttgcta cggcaaaacc  1260
```

-continued

```
aagtgcaccg catctaacaa aaatcgcggc atcatcaaga cattcagcaa cggctgtgac  1320
tacgtcagca ataagggcgt ggacaccgtg agcgtgggca acacactgta ctacgtgaat  1380
aagcaggagg gcaagtctct ctacgtgaaa ggcgagccta tcatcaattt ctacgacccc  1440
ctggtgttcc cctccgacga gttcgacgcc tctattagcc aggtgaacga gaagattaac  1500
cagagcctgg ctttcatcag aaagagcgac gagctgctgc acaacgtgaa cgctggcaag  1560
tccacaacca acatcatgat caccaccatc atcatcgtga tcatcgtgat tctgctgagc  1620
ctcatcgccg tgggcctgct gctgtattgc aaagccagaa gcacacctgt gaccctgagc  1680
aaggaccagc tgtctggcat caacaacatc gccttctcta actag                  1725

SEQ ID NO: 59          moltype = AA  length = 574
FEATURE                Location/Qualifiers
source                 1..574
                       mol_type = protein
                       organism = synthetic construct
SEQUENCE: 59
MELLILKANA ITTILTAVTF CFASGQNITE EFYQSTCSAV SKGYLSALRT GWYTSVITIE  60
LSNIKENKCN GTDAKVKLIK QELDKYKNAV TELQLLMQST PATNNRARRE LPRFMNYTLN  120
NAKKTNVTLS KKRKRRFLGF LLGVGSAIAS GVAVCKVLHL EGEVNKIKSA LLSTNKAVVS  180
LSNGVSVLTF KVLDLKNYID KQLLPILNKQ SCSISNIETV IEFQQKNNRL LEITREFSVN  240
AGVTTPVSTY MLTNSELLSL INDMPITNDQ KKLMSNNVQI VRQQSYSIMC IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNVDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNAGK STTNIMITTI IIVIIVILLS  540
LIAVGLLLYC KARSTPVTLS KDQLSGINNI AFSN                              574

SEQ ID NO: 60          moltype = DNA  length = 1725
FEATURE                Location/Qualifiers
source                 1..1725
                       mol_type = other DNA
                       organism = synthetic construct
SEQUENCE: 60
atggaactgc tgatcctgaa ggccaacgct atcaccacaa tcctgaccgc cgtgaccttt  60
tgcttcgcct ctggccagaa catcacggaa gagttttacc agagcacctg cagcgctgtg  120
tccaaaggtt atctgagcgc tctgagaacc ggatggtata ccagcgtcat cacaatcgag  180
ttgtccaata tcaaggaaaa caagtgtaac ggaacagatg ccaaggtgaa gctgatcaag  240
caggaactgg ataagtacaa gaacgccgtg accgagctgc agctgttgat gcagagcact  300
cctgccacca acaacagagc ccggagagag ctgcctagat tcatgaacta caccctcaac  360
aacgccaaga agaccaacgt gacactgagc aagaagcgga aaagacggtt cctgggattc  420
ctgctgggcg ttggaagcgc catcgccagc ggcgtggccg tgtgtaaggt gctgcacctg  480
gaaggagagg tgaacaaaat caaatctgcc ctgcttagca ccaacaaagc cgttgtgagt  540
ttgagcaacg gtgtgtccgt gctgacattt aaggtgctgg acctgaagaa ctacatcgac  600
aagcaactgc tgcccatcct gaacaagcaa tcctgttcca tcagcaacat cgagacagtt  660
atcgagttcc agcagaagaa caaccggctg ctggaaatca ccagagaatt cagcgtgaat  720
gctggcgtga ctaccccagt gtctacctac atgctgacaa attctgagct gctgagcctg  780
atcaacgaca tgcctatcac aaatgatcag aaaaagctga tgagcaacaa tgtccagatc  840
gtgcggcagc aaagctacag catcatgtgc atcattaagg aagaagtgct ggcctacgtg  900
gtgcagctgc ctctgtacgg cgtgatcgac accccttgct ggaagctgca cacctctcct  960
ctgtgtacca caaacaccaa ggagggcagc aacatctgcc tgacaagaac cgatagaggc  1020
tggtactgcg ataacgccgg ctctgtctca ttcttccctc aggccgagac atgcaaggtc  1080
cagagcaaca gagtgttttg tgataccatg aacagcctga ccctgccaag cgaagtgaat  1140
ctgtgcaatg tggacatctt caaccccaag tacgactgca agatcatgac cagcaagaca  1200
gacgtgtcca gcagcgttat caccagcctg ggcgccattg tgtcttgcta cggcaaaacc  1260
aagtgcaccg catctaacaa aaatcgcggc atcatcaaga cattcagcaa cggctgtgac  1320
tacgtcagca ataagggcgt ggacaccgtg agcgtgggca acacactgta ctacgtgaat  1380
aagcaggagg gcaagtctct ctacgtgaaa ggcgagccta tcatcaattt ctacgacccc  1440
ctggtgttcc cctccgacga gttcgacgcc tctattagcc aggtgaacga gaagattaac  1500
cagagcctgg ctttcatcag aaagagcgac gagctgctgc acaacgtgaa cgctggcaag  1560
tccacaacca acatcatgat caccaccatc atcatcgtga tcatcgtgat tctgctgagc  1620
ctcatcgccg tgggcctgct gctgtattgc aaagccagaa gcacacctgt gaccctgagc  1680
aaggaccagc tgtctggcat caacaacatc gccttctcta actag                  1725

SEQ ID NO: 61          moltype = RNA  length = 1725
FEATURE                Location/Qualifiers
source                 1..1725
                       mol_type = other RNA
                       organism = synthetic construct
SEQUENCE: 61
atggaactgc tgatcctgaa ggccaacgct atcaccacaa tcctgaccgc cgtgaccttt  60
tgcttcgcct ctggccagaa catcacggaa gagttttacc agagcacctg cagcgctgtg  120
tccaaaggtt atctgagcgc tctgagaacc ggatggtata ccagcgtcat cacaatcgag  180
ttgtccaata tcaaggaaaa caagtgtaac ggaacagatg ccaaggtgaa gctgatcaag  240
caggaactgg ataagtacaa gaacgccgtg accgagctgc agctgttgat gcagagcact  300
cctgccacca acaacagagc ccggagagag ctgcctagat tcatgaacta caccctcaac  360
aacgccaaga agaccaacgt gacactgagc aagaagcgga aaagacggtt cctgggattc  420
ctgctgggcg ttggaagcgc catcgccagc ggcgtggccg tgtgtaaggt gctgcacctg  480
gaaggagagg tgaacaaaat caaatctgcc ctgcttagca ccaacaaagc cgttgtgagt  540
ttgagcaacg gtgtgtccgt gctgacattt aaggtgctgg acctgaagaa ctacatcgac  600
aagcaactgc tgcccatcct gaacaagcaa tcctgttcca tcagcaacat cgagacagtt  660
```

```
atcgagttcc agcagaagaa caaccggctg ctggaaatca ccagagaatt cagcgtgaat  720
gctggcgtga ctaccccagt gtctacctac atgctgacaa attctgagct gctgagcctg  780
atcaacgaca tgcctatcac aaatgatcag aaaaagctga tgagcaacaa tgtccagatc  840
gtgcggcagc aaagctacag catcatgtgc atcattaagg aagaagtgct ggcctacgtg  900
gtgcagctgc ctctgtacgg cgtgatcgac accccttgct ggaagctgca cacctctcct  960
ctgtgtacca caaacaccaa ggagggcagc aacatctgcc tgacaagaac cgatagaggc  1020
tggtactgcg ataacgccgg ctctgtctca ttcttccctc aggccgagac atgcaaggtc  1080
cagagcaaca gagtgttttg tgataccatg aacagcctga ccctgccaag cgaagtgaat  1140
ctgtgcaatg tggacatctt caaccccaag tacgactgca agatcatgac cagcaagaca  1200
gacgtgtcca gcagcgttat caccagcctg ggcgccattg tgtcttgcta cggcaaaacc  1260
aagtgcaccg catctaacaa aaatcgcggc atcatcaaga cattcagcaa cggctgtgac  1320
tacgtcagca ataagggcgt ggacaccgtg agcgtgggca acacactgta ctacgtgaat  1380
aagcaggagg gcaagtctct ctacgtgaaa ggcgagccta tcatcaattt ctacgacccc  1440
ctggtgttcc cctccgacga gttcgacgcc tctattagcc aggtgaacga gaagattaac  1500
cagagcctgg ctttcatcag aaagagcgac gagctgctgc acaacgtgaa cgctggcaag  1560
tccacaacca acatcatgat caccaccatc atcatcgtga tcatcgtgat tctgctgagc  1620
ctcatcgccg tgggcctgct gctgtattgc aaagccagaa gcacacctgt gaccctgagc  1680
aaggaccagc tgtctggcat caacaacatc gccttctcta actag  1725
```

```
SEQ ID NO: 62          moltype = AA  length = 528
FEATURE                Location/Qualifiers
source                 1..528
                       mol_type = protein
                       organism = synthetic construct
SEQUENCE: 62
MELLILKANA ITTILTAVTF CFASGQNITE EFYQSTCSAV SKGYLSALRT GWYTSVITIE  60
LSNIKENKCN GTDAKVKLIK QELDKYKNAV TELQLLMQST PATNNRARRE LPRFMNYTLN  120
NAKKTNVTLS KKRKRRFLGF LLGVGSAIAS GVAVCKVLHL EGEVNKIKSA LLSTNKAVVS  180
LSNGVSVLTF KVLDLKNYID KQLLPILNKQ SCSISNIETV IEFQQKNNRL LEITREFSVN  240
AGVTTPVSTY MLTNSELLSL INDMPITNDQ KKLMSNNVQI VRQQSYSIMC IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNVDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNAGK STTNIMIT  528
```

```
SEQ ID NO: 63          moltype = DNA  length = 1671
FEATURE                Location/Qualifiers
source                 1..1671
                       mol_type = other DNA
                       organism = synthetic construct
SEQUENCE: 63
atggaactgc tgatcctgaa ggccaacgct atcaccacaa tcctgaccgc cgtgaccttt  60
tgcttcgcct ctggccagaa catcacggaa gagttttacc agagcacctg cagcgctgtg  120
tccaaaggtt atctgagcgc tctgagaacc ggatggtata ccagcgtcat cacaatcgag  180
ttgtccaata tcaaggaaaa caagtgtaac ggaacagatg ccaaggtgaa gctgatcaag  240
caggaactgg ataagtacaa gaacgccgtg accgagctgc agctgttgat gcagagcact  300
cctgccacca acaacagagc ccggagagag ctgcctagat tcatgaacta caccctcaac  360
aacgccaaga agaccaacgt gacactgagc aagaagcgga aaagacggtt cctgggattc  420
ctgctgggcg ttggaagcgc catcgccagc ggcgtggccg tgtgtaaggt gctgcacctg  480
gaaggagagg tgaacaaaat caaatctgcc ctgcttagca ccaacaaagc cgttgtgagt  540
ttgagcaacg gtgtgtccgt gctgacattt aaggtgctgg acctgaagaa ctacatcgac  600
aagcaactgc tgcccatcct gaacaagcaa tcctgttcca tcagcaacat cgagacagtt  660
atcgagttcc agcagaagaa caaccggctg ctggaaatca ccagagaatt cagcgtgaat  720
gctggcgtga ctaccccagt gtctacctac atgctgacaa attctgagct gctgagcctg  780
atcaacgaca tgcctatcac aaatgatcag aaaaagctga tgagcaacaa tgtccagatc  840
gtgcggcagc aaagctacag catcatgtgc atcattaagg aagaagtgct ggcctacgtg  900
gtgcagctgc ctctgtacgg cgtgatcgac accccttgct ggaagctgca cacctctcct  960
ctgtgtacca caaacaccaa ggagggcagc aacatctgcc tgacaagaac cgatagaggc  1020
tggtactgcg ataacgccgg ctctgtctca ttcttccctc aggccgagac atgcaaggtc  1080
cagagcaaca gagtgttttg tgataccatg aacagcctga ccctgccaag cgaagtgaat  1140
ctgtgcaatg tggacatctt caaccccaag tacgactgca agatcatgac cagcaagaca  1200
gacgtgtcca gcagcgttat caccagcctg ggcgccattg tgtcttgcta cggcaaaacc  1260
aagtgcaccg catctaacaa aaatcgcggc atcatcaaga cattcagcaa cggctgtgac  1320
tacgtcagca ataagggcgt ggacaccgtg agcgtgggca acacactgta ctacgtgaat  1380
aagcaggagg gcaagtctct ctacgtgaaa ggcgagccta tcatcaattt ctacgacccc  1440
ctggtgttcc cctccgacga gttcgacgcc tctattagcc aggtgaacga gaagattaac  1500
cagagcctgg ctttcatcag aaagagcgac gagctgctgc acaacgtgaa cgctggcaag  1560
tccacaacca acatcatgat caccggatac atcccggagg cccctaggga cggtcaagct  1620
tacgtgagaa aggacggcga atgggttctg ctgtcgacct tcttgggata a  1671
```

```
SEQ ID NO: 64          moltype = RNA  length = 1671
FEATURE                Location/Qualifiers
source                 1..1671
                       mol_type = other RNA
                       organism = synthetic construct
SEQUENCE: 64
atggaactgc tgatcctgaa ggccaacgct atcaccacaa tcctgaccgc cgtgaccttt  60
tgcttcgcct ctggccagaa catcacggaa gagttttacc agagcacctg cagcgctgtg  120
tccaaaggtt atctgagcgc tctgagaacc ggatggtata ccagcgtcat cacaatcgag  180
```

-continued

```
ttgtccaata tcaaggaaaa caagtgtaac ggaacagatg ccaaggtgaa gctgatcaag  240
caggaactgg ataagtacaa gaacgccgtg accgagctgc agctgttgat gcagagcact  300
cctgccacca acaacagagc ccggagagag ctgcctagat tcatgaacta caccctcaac  360
aacgccaaga agaccaacgt gacactgagc aagaagcgga aaagacggtt cctgggattc  420
ctgctgggcg ttggaagcgc catcgccagc ggcgtggccg tgtgtaaggt gctgcacctg  480
gaaggagagg tgaacaaaat caaatctgcc ctgcttagca ccaacaaagc cgttgtgagt  540
ttgagcaacg gtgtgtccgt gctgacattt aaggtgctgg acctgaagaa ctacatcgac  600
aagcaactgc tgcccatcct gaacaagcaa tcctgttcca tcagcaacat cgagacagtt  660
atcgagttcc agcagaagaa caaccggctg ctggaaatca ccagagaatt cagcgtgaat  720
gctggcgtga ctaccccagt gtctacctac atgctgacaa attctgagct gctgagcctg  780
atcaacgaca tgcctatcac aaatgatcag aaaaagctga tgagcaacaa tgtccagatc  840
gtgcggcagc aaagctacag catcatgtgc atcattaagg aagaagtgct ggcctacgtg  900
gtgcagctgc ctctgtacgg cgtgatcgac accccttgct ggaagctgca cacctctcct  960
ctgtgtacca caaacaccaa ggagggcagc aacatctgcc tgacaagaac cgatagaggc  1020
tggtactgcg ataacgccgg ctctgtctca ttcttccctc aggccgagac atgcaaggtc  1080
cagagcaaca gagtgttttg tgataccatg aacagcctga ccctgccaag cgaagtgaat  1140
ctgtgcaatg tggacatctt caaccccaag tacgactgca agatcatgac cagcaagaca  1200
gacgtgtcca gcagcgttat caccagcctg ggcgccattg tgtcttgcta cggcaaaacc  1260
aagtgcaccg catctaacaa aaatcgcggc atcatcaaga cattcagcaa cggctgtgac  1320
tacgtcagca ataagggcgt ggacaccgtg agcgtgggca acacactgta ctacgtgaat  1380
aagcaggagg gcaagtctct ctacgtgaaa ggcgagccta tcatcaattt ctacgacccc  1440
ctggtgttcc cctccgacga gttcgacgcc tctattagcc aggtgaacga gaagattaac  1500
cagagcctgg ctttcatcag aaagagcgac gagctgctgc acaacgtgaa cgctggcaag  1560
tccacaacca acatcatgat caccggatac atcccggagg cccctaggga cggtcaagct  1620
tacgtgagaa aggacggcga atgggttctg ctgtcgacct tcttgggata a           1671

SEQ ID NO: 65          moltype = AA  length = 574
FEATURE                Location/Qualifiers
source                 1..574
                       mol_type = protein
                       organism = synthetic construct
SEQUENCE: 65
MELLILKANA ITTILTAVTF CFASGQNITE EFYQSTCSAV SKGYLSALRT GWYTSVITIE  60
LSNIKENKCN GTDAKVKLIK QELDKYKNAV TELQLLMQST PATNNRARRE LPRFMNYTLN  120
NAKKTNVTLS KKRKRRFLGF LLGVGSAIAS GVAVCKVLHL EGEVNKIKSA LLSTNKAVVS  180
LSNGVSVLTF KVLDLKNYID KQLLPILNKQ SCSISNIETV IEFQQKNNRL LEITREFSVN  240
AGVTTPVSTY MLTNSELLSL INDMPITNDQ KKLMSNNVQI VRQQSYSIMC IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNVDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSHQWHA SISQVNEKIN QSLAFIRKSD ELLHNVNAGK STTNIMITTI IVIIVILLS  540
LIAVGLLLYC KARSTPVTLS KDQLSGINNI AFSN                              574

SEQ ID NO: 66          moltype = DNA  length = 1725
FEATURE                Location/Qualifiers
source                 1..1725
                       mol_type = other DNA
                       organism = synthetic construct
SEQUENCE: 66
atggaactgc tgatcctgaa ggccaacgct atcaccacaa tcctgaccgc cgtgaccttt  60
tgcttcgcct ctggccagaa catcacggaa gagttttacc agagcacctg cagcgctgtg  120
tccaaaggtt atctgagcgc tctgagaacc ggatggtata ccagcgtcat cacaatcgag  180
ttgtccaata tcaaggaaaa caagtgtaac ggaacagatg ccaaggtgaa gctgatcaag  240
caggaactgg ataagtacaa gaacgccgtg accgagctgc agctgttgat gcagagcact  300
cctgccacca acaacagagc ccggagagag ctgcctagat tcatgaacta caccctcaac  360
aacgccaaga agaccaacgt gacactgagc aagaagcgga aaagacggtt cctgggattc  420
ctgctgggcg ttggaagcgc catcgccagc ggcgtggccg tgtgtaaggt gctgcacctg  480
gaaggagagg tgaacaaaat caaatctgcc ctgcttagca ccaacaaagc cgttgtgagt  540
ttgagcaacg gtgtgtccgt gctgacattt aaggtgctgg acctgaagaa ctacatcgac  600
aagcaactgc tgcccatcct gaacaagcaa tcctgttcca tcagcaacat cgagacagtt  660
atcgagttcc agcagaagaa caaccggctg ctggaaatca ccagagaatt cagcgtgaat  720
gctggcgtga ctaccccagt gtctacctac atgctgacaa attctgagct gctgagcctg  780
atcaacgaca tgcctatcac aaatgatcag aaaaagctga tgagcaacaa tgtccagatc  840
gtgcggcagc aaagctacag catcatgtgc atcattaagg aagaagtgct ggcctacgtg  900
gtgcagctgc ctctgtacgg cgtgatcgac accccttgct ggaagctgca cacctctcct  960
ctgtgtacca caaacaccaa ggagggcagc aacatctgcc tgacaagaac cgatagaggc  1020
tggtactgcg ataacgccgg ctctgtctca ttcttccctc aggccgagac atgcaaggtc  1080
cagagcaaca gagtgttttg tgataccatg aacagcctga ccctgccaag cgaagtgaat  1140
ctgtgcaatg tggacatctt caaccccaag tacgactgca agatcatgac cagcaagaca  1200
gacgtgtcca gcagcgttat caccagcctg ggcgccattg tgtcttgcta cggcaaaacc  1260
aagtgcaccg catctaacaa aaatcgcggc atcatcaaga cattcagcaa cggctgtgac  1320
tacgtcagca ataagggcgt ggacaccgtg agcgtgggca acacactgta ctacgtgaat  1380
aagcaggagg gcaagtctct ctacgtgaaa ggcgagccta tcatcaattt ctacgacccc  1440
ctggtgttcc cctcccacca gtggcacgcc tctattagcc aggtgaacga gaagattaac  1500
cagagcctgg ctttcatcag aaagagcgac gagctgctgc acaacgtgaa cgctggcaag  1560
tccacaacca acatcatgat caccaccatc atcatcgtga tcatcgtgat tctgctgagc  1620
ctcatcgccg tgggcctgct gctgtattgc aaagccagaa gcacacctgt gaccctgagc  1680
aaggaccagc tgtctggcat caacaacatc gccttctcta actag                 1725
```

-continued

```
SEQ ID NO: 67          moltype = RNA  length = 1725
FEATURE                Location/Qualifiers
source                 1..1725
                       mol_type = other RNA
                       organism = synthetic construct
SEQUENCE: 67
atggaactgc tgatcctgaa ggccaacgct atcaccacaa tcctgaccgc cgtgaccttt  60
tgcttcgcct ctggccagaa catcacggaa gagttttacc agagcacctg cagcgctgtg  120
tccaaaggtt atctgagcgc tctgagaacc ggatggtata ccagcgtcat cacaatcgag  180
ttgtccaata tcaaggaaaa caagtgtaac ggaacagatg ccaaggtgaa gctgatcaag  240
caggaactgg ataagtacaa gaacgccgtg accgagctgc agctgttgat gcagagcact  300
cctgccacca acaacagagc ccggagagag ctgcctagat tcatgaacta caccctcaac  360
aacgccaaga agaccaacgt gacactgagc aagaagcgga aaagacggtt cctgggattc  420
ctgctgggcg ttggaagcgc catcgccagc ggcgtggccg tgtgtaaggt gctgcacctg  480
gaaggagagg tgaacaaaat caaatctgcc ctgcttagca ccaacaaagc cgttgtgagt  540
ttgagcaacg gtgtgtccgt gctgacattt aaggtgctgg acctgaagaa ctacatcgac  600
aagcaactgc tgcccatcct gaacaagcaa tcctgttcca tcagcaacat cgagacagtt  660
atcgagttcc agcagaagaa caaccggctg ctggaaatca ccagagaatt cagcgtgaat  720
gctggcgtga ctaccccagt gtctacctac atgctgacaa attctgagct gctgagcctg  780
atcaacgaca tgcctatcac aaatgatcag aaaaagctga tgagcaacaa tgtccagatc  840
gtgcggcagc aaagctacag catcatgtgc atcattaagg aagaagtgct ggcctacgtg  900
gtgcagctgc ctctgtacgg cgtgatcgac accccttgct ggaagctgca cacctctcct  960
ctgtgtacca caaacaccaa ggagggcagc aacatctgcc tgacaagaac cgatagaggc  1020
tggtactgcg ataacgccgg ctctgtctca ttcttccctc aggccgagac atgcaaggtc  1080
cagagcaaca gagtgttttg tgataccatg aacagcctga ccctgccaag cgaagtgaat  1140
ctgtgcaatg tggacatctt caaccccaag tacgactgca agatcatgac cagcaagaca  1200
gacgtgtcca gcagcgttat caccagcctg ggcgccattg tgtcttgcta cggcaaaacc  1260
aagtgcaccg catctaacaa aaatcgcggc atcatcaaga cattcagcaa cggctgtgac  1320
tacgtcagca ataagggcgt ggacaccgtg agcgtgggca acacactgta ctacgtgaat  1380
aagcaggagg gcaagtctct ctacgtgaaa ggcgagccta tcatcaattt ctacgacccc  1440
ctggtgttcc cctcccacca gtggcacgcc tctattagcc aggtgaacga gaagattaac  1500
cagagcctgg ctttcatcag aaagagcgac gagctgctgc acaacgtgaa cgctggcaag  1560
tccacaacca acatcatgat caccaccatc atcatcgtga tcatcgtgat tctgctgagc  1620
ctcatcgccg tgggcctgct gctgtattgc aaagccagaa gcacacctgt gaccctgagc  1680
aaggaccagc tgtctggcat caacaacatc gccttctcta actag                1725

SEQ ID NO: 68          moltype = AA  length = 528
FEATURE                Location/Qualifiers
source                 1..528
                       mol_type = protein
                       organism = synthetic construct
SEQUENCE: 68
MELLILKANA ITTILTAVTF CFASGQNITE EFYQSTCSAV SKGYLSALRT GWYTSVITIE  60
LSNIKENKCN GTDAKVKLIK QELDKYKNAV TELQLLMQST PATNNRARRE LPRFMNYTLN  120
NAKKTNVTLS KKRKRRFLGF LLGVGSAIAS GVAVCKVLHL EGEVNKIKSA LLSTNKAVVS  180
LSNGVSVLTF KVLDLKNYID KQLLPILNKQ SCSISNIETV IEFQQKNNRL LEITREFSVN  240
AGVTTPVSTY MLTNSELLSL INDMPITNDQ KKLMSNNVQI VRQQSYSIMC IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNVDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSHQWHA SISQVNEKIN QSLAFIRKSD ELLHNVNAGK STTNIMIT                528

SEQ ID NO: 69          moltype = DNA  length = 1671
FEATURE                Location/Qualifiers
source                 1..1671
                       mol_type = other DNA
                       organism = synthetic construct
SEQUENCE: 69
atggaactgc tgatcctgaa ggccaacgct atcaccacaa tcctgaccgc cgtgaccttt  60
tgcttcgcct ctggccagaa catcacggaa gagttttacc agagcacctg cagcgctgtg  120
tccaaaggtt atctgagcgc tctgagaacc ggatggtata ccagcgtcat cacaatcgag  180
ttgtccaata tcaaggaaaa caagtgtaac ggaacagatg ccaaggtgaa gctgatcaag  240
caggaactgg ataagtacaa gaacgccgtg accgagctgc agctgttgat gcagagcact  300
cctgccacca acaacagagc ccggagagag ctgcctagat tcatgaacta caccctcaac  360
aacgccaaga agaccaacgt gacactgagc aagaagcgga aaagacggtt cctgggattc  420
ctgctgggcg ttggaagcgc catcgccagc ggcgtggccg tgtgtaaggt gctgcacctg  480
gaaggagagg tgaacaaaat caaatctgcc ctgcttagca ccaacaaagc cgttgtgagt  540
ttgagcaacg gtgtgtccgt gctgacattt aaggtgctgg acctgaagaa ctacatcgac  600
aagcaactgc tgcccatcct gaacaagcaa tcctgttcca tcagcaacat cgagacagtt  660
atcgagttcc agcagaagaa caaccggctg ctggaaatca ccagagaatt cagcgtgaat  720
gctggcgtga ctaccccagt gtctacctac atgctgacaa attctgagct gctgagcctg  780
atcaacgaca tgcctatcac aaatgatcag aaaaagctga tgagcaacaa tgtccagatc  840
gtgcggcagc aaagctacag catcatgtgc atcattaagg aagaagtgct ggcctacgtg  900
gtgcagctgc ctctgtacgg cgtgatcgac accccttgct ggaagctgca cacctctcct  960
ctgtgtacca caaacaccaa ggagggcagc aacatctgcc tgacaagaac cgatagaggc  1020
tggtactgcg ataacgccgg ctctgtctca ttcttccctc aggccgagac atgcaaggtc  1080
cagagcaaca gagtgttttg tgataccatg aacagcctga ccctgccaag cgaagtgaat  1140
ctgtgcaatg tggacatctt caaccccaag tacgactgca agatcatgac cagcaagaca  1200
gacgtgtcca gcagcgttat caccagcctg ggcgccattg tgtcttgcta cggcaaaacc  1260
```

-continued

```
aagtgcaccg catctaacaa aaatcgcggc atcatcaaga cattcagcaa cggctgtgac  1320
tacgtcagca ataagggcgt ggacaccgtg agcgtgggca acacactgta ctacgtgaat  1380
aagcaggagg gcaagtctct ctacgtgaaa ggcgagccta tcatcaattt ctacgacccc  1440
ctggtgttcc cctcccacca gtggcacgcc tctattagcc aggtgaacga gaagattaac  1500
cagagcctgg ctttcatcag aaagagcgac gagctgctgc acaacgtgaa cgctggcaag  1560
tccacaacca acatcatgat caccggatac atcccggagg cccctaggga cggtcaagct  1620
tacgtgagaa aggacggcga atgggttctg ctgtcgacct tcttgggata a           1671

SEQ ID NO: 70           moltype = RNA  length = 1671
FEATURE                 Location/Qualifiers
source                  1..1671
                        mol_type = other RNA
                        organism = synthetic construct
SEQUENCE: 70
atggaactgc tgatcctgaa ggccaacgct atcaccacaa tcctgaccgc cgtgaccttt  60
tgcttcgcct ctggccagaa catcacggaa gagttttacc agagcacctg cagcgctgtg  120
tccaaaggtt atctgagcgc tctgagaacc ggatggtata ccagcgtcat cacaatcgag  180
ttgtccaata tcaaggaaaa caagtgtaac ggaacagatg ccaaggtgaa gctgatcaag  240
caggaactgg ataagtacaa gaacgccgtg accgagctgc agctgttgat gcagagcact  300
cctgccacca acaacagagc ccggagagag ctgcctagat tcatgaacta caccctcaac  360
aacgccaaga agaccaacgt gacactgagc aagaagcgga aaagacggtt cctgggattc  420
ctgctgggcg ttggaagcgc catcgccagc ggcgtggccg tgtgtaaggt gctgcacctg  480
gaaggagagg tgaacaaaat caaatctgcc ctgcttagca ccaacaaagc cgttgtgagt  540
ttgagcaacg gtgtgtccgt gctgacattt aaggtgctgg acctgaagaa ctacatcgac  600
aagcaactgc tgcccatcct gaacaagcaa tcctgttcca tcagcaacat cgagacagtt  660
atcgagttcc agcagaagaa caaccggctg ctggaaatca ccagagaatt cagcgtgaat  720
gctggcgtga ctaccccagt gtctacctac atgctgacaa attctgagct gctgagcctg  780
atcaacgaca tgcctatcac aaatgatcag aaaaagctga tgagcaacaa tgtccagatc  840
gtgcggcagc aaagctacag catcatgtgc atcattaagg aagaagtgct ggcctacgtg  900
gtgcagctgc ctctgtacgg cgtgatcgac accccttgct ggaagctgca cacctctcct  960
ctgtgtacca caaacaccaa ggagggcagc aacatctgcc tgacaagaac cgatagaggc  1020
tggtactgcg ataacgccgg ctctgtctca ttcttccctc aggccgagac atgcaaggtc  1080
cagagcaaca gagtgttttg tgataccatg aacagcctga ccctgccaag cgaagtgaat  1140
ctgtgcaatg tggacatctt caaccccaag tacgactgca agatcatgac cagcaagaca  1200
gacgtgtcca gcagcgttat caccagcctg ggcgccattg tgtcttgcta cggcaaaacc  1260
aagtgcaccg catctaacaa aaatcgcggc atcatcaaga cattcagcaa cggctgtgac  1320
tacgtcagca ataagggcgt ggacaccgtg agcgtgggca acacactgta ctacgtgaat  1380
aagcaggagg gcaagtctct ctacgtgaaa ggcgagccta tcatcaattt ctacgacccc  1440
ctggtgttcc cctcccacca gtggcacgcc tctattagcc aggtgaacga gaagattaac  1500
cagagcctgg ctttcatcag aaagagcgac gagctgctgc acaacgtgaa cgctggcaag  1560
tccacaacca acatcatgat caccggatac atcccggagg cccctaggga cggtcaagct  1620
tacgtgagaa aggacggcga atgggttctg ctgtcgacct tcttgggata a           1671

SEQ ID NO: 71           moltype = AA  length = 26
FEATURE                 Location/Qualifiers
source                  1..26
                        mol_type = protein
                        organism = synthetic construct
SEQUENCE: 71
MELPVLKTNA ITTILAAVTL CFASSQ                                       26

SEQ ID NO: 72           moltype = DNA  length = 78
FEATURE                 Location/Qualifiers
source                  1..78
                        mol_type = other DNA
                        organism = synthetic construct
SEQUENCE: 72
atggaactgc ctgtgctgaa aacaaacgcc atcacaacaa tcctggcagc agtgacactg  60
tgcttcgcca gcagccag                                                78

SEQ ID NO: 73           moltype = RNA  length = 78
FEATURE                 Location/Qualifiers
source                  1..78
                        mol_type = other RNA
                        organism = synthetic construct
SEQUENCE: 73
atggaactgc ctgtgctgaa aacaaacgcc atcacaacaa tcctggcagc agtgacactg  60
tgcttcgcca gcagccag                                                78

SEQ ID NO: 74           moltype = AA  length = 83
FEATURE                 Location/Qualifiers
source                  1..83
                        mol_type = protein
                        organism = synthetic construct
SEQUENCE: 74
NITEEFYQST CSAVSKGYLS ALRTGWYTSV ITIELSNIKE NKCNGTDAKV KLIKQELDKY  60
KNAVTELQLL MQSTPAANNR ARR                                          83

SEQ ID NO: 75           moltype = DNA  length = 249
```

```
FEATURE                Location/Qualifiers
source                 1..249
                       mol_type = other DNA
                       organism = synthetic construct
SEQUENCE: 75
aatattacag aagagttcta ccagagcaca tgcagcgccg tgtctaaggg ctacctgagc  60
gccctgagaa caggctggta caccagcgtc atcacgatcg agctgagtaa tatcaaggag  120
aacaaatgca acggcaccga cgccaaggtg aagctgatca agcaggagct ggataaatac  180
aagaacgccg tgaccgagtt gcagctgctg atgcagtcta ccccagccgc caacaacaga  240
gccagacgg                                                          249

SEQ ID NO: 76          moltype = RNA  length = 249
FEATURE                Location/Qualifiers
source                 1..249
                       mol_type = other RNA
                       organism = synthetic construct
SEQUENCE: 76
aatattacag aagagttcta ccagagcaca tgcagcgccg tgtctaaggg ctacctgagc  60
gccctgagaa caggctggta caccagcgtc atcacgatcg agctgagtaa tatcaaggag  120
aacaaatgca acggcaccga cgccaaggtg aagctgatca agcaggagct ggataaatac  180
aagaacgccg tgaccgagtt gcagctgctg atgcagtcta ccccagccgc caacaacaga  240
gccagacgg                                                          249

SEQ ID NO: 77          moltype = AA  length = 28
FEATURE                Location/Qualifiers
source                 1..28
                       mol_type = protein
                       organism = synthetic construct
SEQUENCE: 77
ELPRFMNYTL NNTKNTNVTL SKKRKRRF                                     28

SEQ ID NO: 78          moltype = DNA  length = 84
FEATURE                Location/Qualifiers
source                 1..84
                       mol_type = other DNA
                       organism = synthetic construct
SEQUENCE: 78
gaactaccca gattcatgaa ctacacactg aacaacacta agaacaccaa cgtgacactg  60
tctaagaaaa gaaagcggcg gttc                                         84

SEQ ID NO: 79          moltype = RNA  length = 84
FEATURE                Location/Qualifiers
source                 1..84
                       mol_type = other RNA
                       organism = synthetic construct
SEQUENCE: 79
gaactaccca gattcatgaa ctacacactg aacaacacta agaacaccaa cgtgacactg  60
tctaagaaaa gaaagcggcg gttc                                         84

SEQ ID NO: 80          moltype = AA  length = 18
FEATURE                Location/Qualifiers
source                 1..18
                       mol_type = protein
                       organism = synthetic construct
SEQUENCE: 80
LGFLLGVGSA IASGIAVS                                                18

SEQ ID NO: 81          moltype = DNA  length = 54
FEATURE                Location/Qualifiers
source                 1..54
                       mol_type = other DNA
                       organism = synthetic construct
SEQUENCE: 81
ctgggattcc tgctgggcgt gggaagcgct atcgcttctg gaattgccgt gagc        54

SEQ ID NO: 82          moltype = RNA  length = 54
FEATURE                Location/Qualifiers
source                 1..54
                       mol_type = other RNA
                       organism = synthetic construct
SEQUENCE: 82
ctgggattcc tgctgggcgt gggaagcgct atcgcttctg gaattgccgt gagc        54

SEQ ID NO: 83          moltype = AA  length = 29
FEATURE                Location/Qualifiers
source                 1..29
                       mol_type = protein
                       organism = synthetic construct
SEQUENCE: 83
```

```
TGYIPEAPRD GQAYVRKDGE WVLLSTFLG                                     29

SEQ ID NO: 84           moltype = DNA  length = 87
FEATURE                 Location/Qualifiers
source                  1..87
                        mol_type = other DNA
                        organism = synthetic construct
SEQUENCE: 84
accggataca tcccggaggc ccctagggac ggtcaagctt acgtgagaaa ggacggcgaa  60
tgggttctgc tgtcgacctt cttggga                                       87

SEQ ID NO: 85           moltype = RNA  length = 87
FEATURE                 Location/Qualifiers
source                  1..87
                        mol_type = other RNA
                        organism = synthetic construct
SEQUENCE: 85
accggataca tcccggaggc ccctagggac ggtcaagctt acgtgagaaa ggacggcgaa  60
tgggttctgc tgtcgacctt cttggga                                       87

SEQ ID NO: 86           moltype = DNA  length = 18
FEATURE                 Location/Qualifiers
source                  1..18
                        mol_type = other DNA
                        organism = synthetic construct
SEQUENCE: 86
taatacgact cactataa                                                 18

SEQ ID NO: 87           moltype = AA  length = 574
FEATURE                 Location/Qualifiers
source                  1..574
                        mol_type = protein
                        organism = synthetic construct
SEQUENCE: 87
MELPVLKTNA ITTILAAVTL CFASSQNITE EFYQSTCSAV SKGYLSALRT GWYTSVITIE  60
LSNIKENKCN GTDAKVKLIK QELDKYKNAV TELQLLMQST PAANNRARRE LPRFMNYTLN  120
NTKNTNVTLS KKRKRRFLGF LLGVGSAIAS GIAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQADTCKV  360
QSNRVFCDTM NSLTLPSEVN LCNIDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNAGK STTNIMITTI IIVIIVILLS  540
LIAVGLLLYC KARSTPVTLS KDQLSGINNI AFSN                               574

SEQ ID NO: 88           moltype = DNA  length = 1722
FEATURE                 Location/Qualifiers
source                  1..1722
                        mol_type = other DNA
                        organism = synthetic construct
SEQUENCE: 88
atggaactgc ctgtgctgaa aacaaacgcc atcacaacaa tcctggcagc agtgacactg  60
tgcttcgcca gcagccagaa tattacagaa gagttctacc agagcacatg cagcgccgtg  120
tctaagggct acctgagcgc cctgagaaca ggctggtaca ccagcgtcat cacgatcgag  180
ctgagtaata tcaaggagaa caaatgcaac ggcaccgacg ccaaggtgaa gctgatcaag  240
caggagctgg ataaatacaa gaacgccgtg accgagttgc agctgctgat gcagtctacc  300
ccagccgcca acaacagagc cagacgggaa ctacccagat tcatgaacta cacactgaac  360
aacactaaga acaccaacgt gacactgtct aagaaaagaa agcggcggtt cctgggattc  420
ctgctgggcg tgggaagcgc tatcgcttct ggaattgccg tgagcaaggt gctgcacctg  480
gaaggcgagg tgaacaagat caagtctgcc ctgctgtcca ccaacaaggc cgtagtcagc  540
ctgagcaatg gcgtgagcgt cctgaccagt aaggtgctgg acctgaagaa ctacatcgac  600
aagcagctgc tgcctatcgt gaacaagcag agctgctcca tcagcaatat tgagactgtg  660
atcgaattcc agcagaagaa caaccggctg ctggagatca ccagagagtt ctccgtgaac  720
gctggcgtga ctacacctgt ttcaacctac atgctgacca attctgagct gctgagcctg  780
atcaacgaca tgcctatcac caacgaccag aaaaaactga tgtccaataa cgttcaaatc  840
gtgcggcagc aaagctacag catcatgagc atcatcaagg aagaagtgct tgcctacgtg  900
gtccagctgc cactttatgg agttatcgat acaccctgct ggaagctgca caccagccct  960
ctgtgtacaa ccaacaccaa ggaaggcagc aacatctgcc tgaccagaac agatagaggc  1020
tggtattgtg ataacgccgg cagcgtgagc ttcttccccc aggccgacac atgtaaagtg  1080
cagagcaata gagtgttctg cgacaccatg aatagcctga ccctgcccag cgaggtgaat  1140
ctgtgtaaca tcgacatttt caaccccaag tacgattgca agatcatgac ctccaagacc  1200
gacgtgagca gcagcgtgat cacctccctg ggcgccatcg tgtcttgcta cggcaagacc  1260
aagtgcacag cctctaacaa aaatcgcggc atcatcaaaa ccttctctaa cggttgtgac  1320
tacgtgtcaa acaaaggcgt ggacaccgtg tccgtgggca acaccctgta ttacgtgaac  1380
aagcaggagg gcaagagcct gtacgtgaag ggcgaaccta ttatcaactt ctacgaccct  1440
ctggtgtttc cttccgacga gtttgatgct agcatctctc aggtgaacga gaagatcaac  1500
cagagcctgg cctttatcag aaagagcgat gagctgctgc acaacgtgaa cgccggcaag  1560
agtaccacca acatcatgat caccaccatc attatcgtga tcatcgtgat cctcctgagc  1620
ctgatcgctg tcggactgct gctgtactgc aaggccagga gcacacctgt gaccctgagc  1680
```

```
aaggaccaac tgtctggcat caacaacatc gcttttagca at                    1722

SEQ ID NO: 89          moltype = RNA  length = 1722
FEATURE                Location/Qualifiers
source                 1..1722
                       mol_type = other RNA
                       organism = synthetic construct
SEQUENCE: 89
atggaactgc ctgtgctgaa aacaaacgcc atcacaacaa tcctggcagc agtgacactg  60
tgcttcgcca gcagccagaa tattacagaa gagttctacc agagcacatg cagcgccgtg  120
tctaagggct acctgagcgc cctgagaaca ggctggtaca ccagcgtcat cacgatcgag  180
ctgagtaata tcaaggagaa caaatgcaac ggcaccgacg ccaaggtgaa gctgatcaag  240
caggagctgg ataaatacaa gaacgccgtg accgagttgc agctgctgat gcagtctacc  300
ccagccgcca acaacagagc cagacgggaa ctacccagat tcatgaacta cacactgaac  360
aacactaaga acaccaacgt gacactgtct aagaaaagaa agcggcggtt cctgggattc  420
ctgctgggcg tgggaagcgc tatcgcttct ggaattgccg tgagcaaggt gctgcacctg  480
gaaggcgagg tgaacaagat caagtctgcc ctgctgtcca ccaacaaggc cgtagtcagc  540
ctgagcaatg gcgtgagcgt cctgaccagt aaggtgctgg acctgaagaa ctacatcgac  600
aagcagctgc tgcctatcgt gaacaagcag agctgctcca tcagcaatat tgagactgtg  660
atcgaattcc agcagaagaa caaccggctg ctggagatca ccagagagtt ctccgtgaac  720
gctggcgtga ctacacctgt ttcaacctac atgctgacca attctgagct gctgagcctg  780
atcaacgaca tgcctatcac caacgaccag aaaaaactga tgtccaataa cgttcaaatc  840
gtgcggcagc aaagctacag catcatgagc atcatcaagg aagaagtgct tgcctacgtg  900
gtccagctgc cactttatgg agttatcgat acaccctgct ggaagctgca caccagccct  960
ctgtgtacaa ccaacaccaa ggaaggcagc aacatctgcc tgaccagaac agatagaggc  1020
tggtattgtg ataacgccgg cagcgtgagc ttcttccccc aggccgacac atgtaaagtg  1080
cagagcaata gagtgttctg cgacaccatg aatagcctga ccctgcccag cgaggtgaat  1140
ctgtgtaaca tcgacatttt caaccccaag tacgattgca agatcatgac ctccaagacc  1200
gacgtgagca gcagcgtgat cacctccctg ggcgccatcg tgtcttgcta cggcaagacc  1260
aagtgcacag cctctaacaa aaatcgcggc atcatcaaaa ccttctctaa cggttgtgac  1320
tacgtgtcaa acaaaggcgt ggacaccgtg tccgtgggca acaccctgta ttacgtgaac  1380
aagcaggagg gcaagagcct gtacgtgaag ggcgaaccta ttatcaactt ctacgaccct  1440
ctggtgtttc cttccgacga gtttgatgct agcatctctc aggtgaacga gaagatcaac  1500
cagagcctgg cctttatcag aaagagcgat gagctgctgc acaacgtgaa cgccggcaag  1560
agtaccacca acatcatgat caccaccatc attatcgtga tcatcgtgat cctcctgagc  1620
ctgatcgctg tcggactgct gctgtactgc aaggccagga gcacacctgt gaccctgagc  1680
aaggaccaac tgtctggcat caacaacatc gcttttagca at                    1722

SEQ ID NO: 90          moltype = AA  length = 24
FEATURE                Location/Qualifiers
source                 1..24
                       mol_type = protein
                       organism = unidentified
SEQUENCE: 90
KARSTPVTLS KDQLSGINNI AFSN                                        24

SEQ ID NO: 91          moltype = AA  length = 31
FEATURE                Location/Qualifiers
source                 1..31
                       mol_type = protein
                       organism = unidentified
SEQUENCE: 91
MITGYIPEAP RDGQAYVRKD GEWVLLSTFL G                                31

SEQ ID NO: 92          moltype = AA  length = 556
FEATURE                Location/Qualifiers
source                 1..556
                       mol_type = protein
                       organism = synthetic construct
SEQUENCE: 92
MELPVLKTNA ITTILAAVTL CFASSQNITE EFYQSTCSAV SKGYLSALRT GWYTSVITIE  60
LSNIKENKCN GTDAKVKLIK QELDKYKNAV TELQLLMQST PAANNRARRE LPRFMNYTLN  120
NTKNTNVTLS KKRKRRFLGF LLGVGSAIAS GIAVSKVLHL EGEVNKIKSA LLSTNKAVVS  180
LSNGVSVLTS KVLDLKNYID KQLLPIVNKQ SCSISNIETV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQADTCKV  360
QSNRVFCDTM NSLTLPSEVN LCNIDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNAGK STTNIMITGY IPEAPRDGQA  540
YVRKDGEWVL LSTFLG                                                 556

SEQ ID NO: 93          moltype = DNA  length = 1668
FEATURE                Location/Qualifiers
source                 1..1668
                       mol_type = other DNA
                       organism = synthetic construct
SEQUENCE: 93
atggaactgc ctgtgctgaa aacaaacgcc atcacaacaa tcctggcagc agtgacactg  60
tgcttcgcca gcagccagaa tattacagaa gagttctacc agagcacatg cagcgccgtg  120
```

```
tctaagggct acctgagcgc cctgagaaca ggctggtaca ccagcgtcat cacgatcgag  180
ctgagtaata tcaaggagaa caaatgcaac ggcaccgacg ccaaggtgaa gctgatcaag  240
caggagctgg ataaatacaa gaacgccgtg accgagttgc agctgctgat gcagtctacc  300
ccagccgcca acaacagagc cagacgggaa ctacccagat tcatgaacta cacactgaac  360
aacactaaga acaccaacgt gacactgtct aagaaaagaa agcggcggtt cctgggattc  420
ctgctgggcg tgggaagcgc tatcgcttct ggaattgccg tgagcaaggt gctgcacctg  480
gaaggcgagg tgaacaagat caagtctgcc ctgctgtcca ccaacaaggc cgtagtcagc  540
ctgagcaatg gcgtgagcgt cctgaccagt aaggtgctgg acctgaagaa ctacatcgac  600
aagcagctgc tgcctatcgt gaacaagcag agctgctcca tcagcaatat tgagactgtg  660
atcgaattcc agcagaagaa caaccggctg ctggagatca ccagagagtt ctccgtgaac  720
gctggcgtga ctacacctgt ttcaacctac atgctgacca attctgagct gctgagcctg  780
atcaacgaca tgcctatcac caacgaccag aaaaaactga tgtccaataa cgttcaaatc  840
gtgcggcagc aaagctacag catcatgagc atcatcaagg aagaagtgct tgcctacgtg  900
gtccagctgc cactttatgg agttatcgat acaccctgct ggaagctgca caccagccct  960
ctgtgtacaa ccaacaccaa ggaaggcagc aacatctgcc tgaccagaac agatagaggc  1020
tggtattgtg ataacgccgg cagcgtgagc ttcttccccc aggccgacac atgtaaagtg  1080
cagagcaata gagtgttctg cgacaccatg aatagcctga ccctgcccag cgaggtgaat  1140
ctgtgtaaca tcgacatttt caaccccaag tacgattgca agatcatgac ctccaagacc  1200
gacgtgagca gcagcgtgat cacctccctg ggcgccatcg tgtcttgcta cggcaagacc  1260
aagtgcacag cctctaacaa aaatcgcggc atcatcaaaa ccttctctaa cggttgtgac  1320
tacgtgtcaa acaaaggcgt ggacaccgtg tccgtgggca acaccctgta ttacgtgaac  1380
aagcaggagg gcaagagcct gtacgtgaag ggcgaaccta ttatcaactt ctacgaccct  1440
ctggtgtttc cttccgacga gtttgatgct agcatctctc aggtgaacga gaagatcaac  1500
cagagcctgg cctttatcag aaagagcgat gagctgctgc acaacgtgaa cgccggcaag  1560
agtaccacca acatcatgat caccggatac atcccggagg cccctaggga cggtcaagct  1620
tacgtgagaa aggacggcga atgggttctg ctgtcgacct tcttggga              1668
```

```
SEQ ID NO: 94          moltype = RNA  length = 1668
FEATURE                Location/Qualifiers
source                 1..1668
                       mol_type = other RNA
                       organism = synthetic construct
SEQUENCE: 94
atggaactgc ctgtgctgaa aacaaacgcc atcacaacaa tcctggcagc agtgacactg  60
tgcttcgcca gcagccagaa tattacagaa gagttctacc agagcacatg cagcgccgtg  120
tctaagggct acctgagcgc cctgagaaca ggctggtaca ccagcgtcat cacgatcgag  180
ctgagtaata tcaaggagaa caaatgcaac ggcaccgacg ccaaggtgaa gctgatcaag  240
caggagctgg ataaatacaa gaacgccgtg accgagttgc agctgctgat gcagtctacc  300
ccagccgcca acaacagagc cagacgggaa ctacccagat tcatgaacta cacactgaac  360
aacactaaga acaccaacgt gacactgtct aagaaaagaa agcggcggtt cctgggattc  420
ctgctgggcg tgggaagcgc tatcgcttct ggaattgccg tgagcaaggt gctgcacctg  480
gaaggcgagg tgaacaagat caagtctgcc ctgctgtcca ccaacaaggc cgtagtcagc  540
ctgagcaatg gcgtgagcgt cctgaccagt aaggtgctgg acctgaagaa ctacatcgac  600
aagcagctgc tgcctatcgt gaacaagcag agctgctcca tcagcaatat tgagactgtg  660
atcgaattcc agcagaagaa caaccggctg ctggagatca ccagagagtt ctccgtgaac  720
gctggcgtga ctacacctgt ttcaacctac atgctgacca attctgagct gctgagcctg  780
atcaacgaca tgcctatcac caacgaccag aaaaaactga tgtccaataa cgttcaaatc  840
gtgcggcagc aaagctacag catcatgagc atcatcaagg aagaagtgct tgcctacgtg  900
gtccagctgc cactttatgg agttatcgat acaccctgct ggaagctgca caccagccct  960
ctgtgtacaa ccaacaccaa ggaaggcagc aacatctgcc tgaccagaac agatagaggc  1020
tggtattgtg ataacgccgg cagcgtgagc ttcttccccc aggccgacac atgtaaagtg  1080
cagagcaata gagtgttctg cgacaccatg aatagcctga ccctgcccag cgaggtgaat  1140
ctgtgtaaca tcgacatttt caaccccaag tacgattgca agatcatgac ctccaagacc  1200
gacgtgagca gcagcgtgat cacctccctg ggcgccatcg tgtcttgcta cggcaagacc  1260
aagtgcacag cctctaacaa aaatcgcggc atcatcaaaa ccttctctaa cggttgtgac  1320
tacgtgtcaa acaaaggcgt ggacaccgtg tccgtgggca acaccctgta ttacgtgaac  1380
aagcaggagg gcaagagcct gtacgtgaag ggcgaaccta ttatcaactt ctacgaccct  1440
ctggtgtttc cttccgacga gtttgatgct agcatctctc aggtgaacga gaagatcaac  1500
cagagcctgg cctttatcag aaagagcgat gagctgctgc acaacgtgaa cgccggcaag  1560
agtaccacca acatcatgat caccggatac atcccggagg cccctaggga cggtcaagct  1620
tacgtgagaa aggacggcga atgggttctg ctgtcgacct tcttggga              1668
```

```
SEQ ID NO: 95          moltype = AA  length = 574
FEATURE                Location/Qualifiers
source                 1..574
                       mol_type = protein
                       organism = synthetic construct
SEQUENCE: 95
MELPVLKTNA ITTILAAVTL CFASSQNITE EFYQSTCSAV SKGYLSALRT GWYTSVITIE  60
LSNIKENKCN GTDAKVKLIK QELDKYKNAV TELQLLMQST PAANNRARRE LPRFMNYTLN  120
NTKNTNVTLS KKRKRRFLGF LLGVGSAIAS GIAVCKVLHL EGEVNKIKSA LLSTNKAVVS  180
LSNGVSVLTF KVLDLKNYID KQLLPILNKQ SCSISNIETV IEFQQKNNRL LEITREFSVN  240
AGVTTPVSTY MLTNSELLSL INDMPITNDQ KKLMSNNVQI VRQQSYSIMC IIKEEVLAYV  300
VQLPLYGVID TPCWKLHTSP LCTTNTKEGS NICLTRTDRG WYCDNAGSVS FFPQADTCKV  360
QSNRVFCDTM NSLTLPSEVN LCNIDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNAGK STTNIMITTI IIVIIVILLS  540
LIAVGLLLYC KARSTPVTLS KDQLSGINNI AFSN                               574
```

```
SEQ ID NO: 96          moltype = DNA  length = 1722
FEATURE                Location/Qualifiers
source                 1..1722
                       mol_type = other DNA
                       organism = synthetic construct
SEQUENCE: 96
atggaactgc ctgtgctgaa aacaaacgcc atcacaacaa tcctggcagc agtgacactg  60
tgcttcgcca gcagccagaa tattacagaa gagttctacc agagcacatg cagcgccgtg  120
tctaagggct acctgagcgc cctgagaaca ggctggtaca ccagcgtcat cacgatcgag  180
ctgagtaata tcaaggagaa caaatgcaac ggcaccgacg ccaaggtgaa gctgatcaag  240
caggagctgg ataaatacaa gaacgccgtg accgagttgc agctgctgat gcagtctacc  300
ccagccgcca acaacagagc cagacgggaa ctacccagat tcatgaacta cacactgaac  360
aacactaaga acaccaacgt gacactgtct aagaaaagaa agcggcggtt cctgggattc  420
ctgctgggcg tgggaagcgc tatcgcttct ggaattgccg tgtgcaaggt gctgcacctg  480
gaaggcgagg tgaacaagat caagtctgcc ctgctgtcca ccaacaaggc cgtagtcagc  540
ctgagcaatg gcgtgagcgt cctgaccttt aaggtgctgg acctgaagaa ctacatcgac  600
aagcagctgc tgcctatctt gaacaagcag agctgctcca tcagcaatat tgagactgtg  660
atcgaattcc agcagaagaa caaccggctg ctggagatca ccagagagtt ctccgtgaac  720
gctggcgtga ctacacctgt ttcaacctac atgctgacca attctgagct gctgagcctg  780
atcaacgaca tgcctatcac caacgaccag aaaaaactga tgtccaataa cgttcaaatc  840
gtgcggcagc aaagctacag catcatgtgc atcatcaagg aagaagtgct tgcctacgtg  900
gtccagctgc cactttatgg agttatcgat acaccctgct ggaagctgca caccagccct  960
ctgtgtacaa ccaacaccaa ggaaggcagc aacatctgcc tgaccagaac agatagaggc  1020
tggtattgtg ataacgccgg cagcgtgagc ttcttccccc aggccgacac atgtaaagtg  1080
cagagcaata gagtgttctg cgacaccatg aatagcctga ccctgcccag cgaggtgaat  1140
ctgtgtaaca tcgacatttt caaccccaag tacgattgca agatcatgac ctccaagacc  1200
gacgtgagca gcagcgtgat cacctccctg ggcgccatcg tgtcttgcta cggcaagacc  1260
aagtgcacag cctctaacaa aaatcgcggc atcatcaaaa ccttctctaa cggttgtgac  1320
tacgtgtcaa acaaaggcgt ggacaccgtg tccgtgggca acaccctgta ttacgtgaac  1380
aagcaggagg gcaagagcct gtacgtgaag ggcgaaccta ttatcaactt ctacgaccct  1440
ctggtgtttc cttccgacga gtttgatgct agcatctctc aggtgaacga gaagatcaac  1500
cagagcctgg cctttatcag aaagagcgat gagctgctgc acaacgtgaa cgccggcaag  1560
agtaccacca acatcatgat caccaccatc attatcgtga tcatcgtgat cctcctgagc  1620
ctgatcgctg tcggactgct gctgtactgc aaggccagga gcacacctgt gaccctgagc  1680
aaggaccaac tgtctggcat caacaacatc gcttttagca at                    1722

SEQ ID NO: 97          moltype = RNA  length = 1722
FEATURE                Location/Qualifiers
source                 1..1722
                       mol_type = other RNA
                       organism = synthetic construct
SEQUENCE: 97
atggaactgc ctgtgctgaa aacaaacgcc atcacaacaa tcctggcagc agtgacactg  60
tgcttcgcca gcagccagaa tattacagaa gagttctacc agagcacatg cagcgccgtg  120
tctaagggct acctgagcgc cctgagaaca ggctggtaca ccagcgtcat cacgatcgag  180
ctgagtaata tcaaggagaa caaatgcaac ggcaccgacg ccaaggtgaa gctgatcaag  240
caggagctgg ataaatacaa gaacgccgtg accgagttgc agctgctgat gcagtctacc  300
ccagccgcca acaacagagc cagacgggaa ctacccagat tcatgaacta cacactgaac  360
aacactaaga acaccaacgt gacactgtct aagaaaagaa agcggcggtt cctgggattc  420
ctgctgggcg tgggaagcgc tatcgcttct ggaattgccg tgtgcaaggt gctgcacctg  480
gaaggcgagg tgaacaagat caagtctgcc ctgctgtcca ccaacaaggc cgtagtcagc  540
ctgagcaatg gcgtgagcgt cctgaccttt aaggtgctgg acctgaagaa ctacatcgac  600
aagcagctgc tgcctatctt gaacaagcag agctgctcca tcagcaatat tgagactgtg  660
atcgaattcc agcagaagaa caaccggctg ctggagatca ccagagagtt ctccgtgaac  720
gctggcgtga ctacacctgt ttcaacctac atgctgacca attctgagct gctgagcctg  780
atcaacgaca tgcctatcac caacgaccag aaaaaactga tgtccaataa cgttcaaatc  840
gtgcggcagc aaagctacag catcatgtgc atcatcaagg aagaagtgct tgcctacgtg  900
gtccagctgc cactttatgg agttatcgat acaccctgct ggaagctgca caccagccct  960
ctgtgtacaa ccaacaccaa ggaaggcagc aacatctgcc tgaccagaac agatagaggc  1020
tggtattgtg ataacgccgg cagcgtgagc ttcttccccc aggccgacac atgtaaagtg  1080
cagagcaata gagtgttctg cgacaccatg aatagcctga ccctgcccag cgaggtgaat  1140
ctgtgtaaca tcgacatttt caaccccaag tacgattgca agatcatgac ctccaagacc  1200
gacgtgagca gcagcgtgat cacctccctg ggcgccatcg tgtcttgcta cggcaagacc  1260
aagtgcacag cctctaacaa aaatcgcggc atcatcaaaa ccttctctaa cggttgtgac  1320
tacgtgtcaa acaaaggcgt ggacaccgtg tccgtgggca acaccctgta ttacgtgaac  1380
aagcaggagg gcaagagcct gtacgtgaag ggcgaaccta ttatcaactt ctacgaccct  1440
ctggtgtttc cttccgacga gtttgatgct agcatctctc aggtgaacga gaagatcaac  1500
cagagcctgg cctttatcag aaagagcgat gagctgctgc acaacgtgaa cgccggcaag  1560
agtaccacca acatcatgat caccaccatc attatcgtga tcatcgtgat cctcctgagc  1620
ctgatcgctg tcggactgct gctgtactgc aaggccagga gcacacctgt gaccctgagc  1680
aaggaccaac tgtctggcat caacaacatc gcttttagca at                    1722

SEQ ID NO: 98          moltype = AA  length = 556
FEATURE                Location/Qualifiers
source                 1..556
                       mol_type = protein
                       organism = synthetic construct
SEQUENCE: 98
MELPVLKTNA ITTILAAVTL CFASSQNITE EFYQSTCSAV SKGYLSALRT GWYTSVITIE  60
```

```
LSNIKENKCN GTDAKVKLIK QELDKYKNAV TELQLLMQST PAANNRARRE LPRFMNYTLN  120
NTKNTNVTLS KKRKRRFLGF LLGVGSAIAS GIAVCKVLHL EGEVNKIKSA LLSTNKAVVS  180
LSNGVSVLTF KVLDLKNYID KQLLPILNKQ SCSISNIETV IEFQQKNNRL LEITREFSVN  240
AGVTTPVSTY MLTNSELLSL INDMPITNDQ KKLMSNNVQI VRQQSYSIMC IIKEEVLAYV  300
VQLPLYGVID TPCWKLHTSP LCTTNTKEGS NICLTRTDRG WYCDNAGSVS FFPQADTCKV  360
QSNRVFCDTM NSLTLPSEVN LCNIDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHNVNAGK STTNIMITGY IPEAPRDGQA  540
YVRKDGEWVL LSTFLG                                                 556

SEQ ID NO: 99          moltype = DNA  length = 1668
FEATURE                Location/Qualifiers
source                 1..1668
                       mol_type = other DNA
                       organism = synthetic construct
SEQUENCE: 99
atggaactgc ctgtgctgaa aacaaacgcc atcacaacaa tcctggcagc agtgacactg  60
tgcttcgcca gcagccagaa tattacagaa gagttctacc agagcacatg cagcgccgtg  120
tctaagggct acctgagcgc cctgagaaca ggctggtaca ccagcgtcat cacgatcgag  180
ctgagtaata tcaaggagaa caaatgcaac ggcaccgacg ccaaggtgaa gctgatcaag  240
caggagctgg ataaatacaa gaacgccgtg accgagttgc agctgctgat gcagtctacc  300
ccagccgcca acaacagagc cagacgggaa ctacccagat tcatgaacta cacactgaac  360
aacactaaga acaccaacgt gacactgtct aagaaaagaa agcggcggtt cctgggattc  420
ctgctgggcg tgggaagcgc tatcgcttct ggaattgccg tgtgcaaggt gctgcacctg  480
gaaggcgagg tgaacaagat caagtctgcc ctgctgtcca ccaacaaggc cgtagtcagc  540
ctgagcaatg gcgtgagcgt cctgaccttt aaggtgctgg acctgaagaa ctacatcgac  600
aagcagctgc tgcctatctt gaacaagcag agctgctcca tcagcaatat tgagactgtg  660
atcgaattcc agcagaagaa caaccggctg ctggagatca ccagagagtt ctccgtgaac  720
gctggcgtga ctacacctgt ttcaacctac atgctgacca attctgagct gctgagcctg  780
atcaacgaca tgcctatcac caacgaccag aaaaaactga tgtccaataa cgttcaaatc  840
gtgcggcagc aaagctacag catcatgtgc atcatcaagg aagaagtgct tgcctacgtg  900
gtccagctgc cactttatgg agttatcgat acaccctgct ggaagctgca caccagccct  960
ctgtgtacaa ccaacaccaa ggaaggcagc aacatctgcc tgaccagaac agatagaggc  1020
tggtattgtg ataacgccgg cagcgtgagc ttcttccccc aggccgacac atgtaaagtg  1080
cagagcaata gagtgttctg cgacaccatg aatagcctga ccctgcccag cgaggtgaat  1140
ctgtgtaaca tcgacatttt caaccccaag tacgattgca agatcatgac ctccaagacc  1200
gacgtgagca gcagcgtgat cacctccctg ggcgccatcg tgtcttgcta cggcaagacc  1260
aagtgcacag cctctaacaa aaatcgcggc atcatcaaaa ccttctctaa cggttgtgac  1320
tacgtgtcaa acaaaggcgt ggacaccgtg tccgtgggca acaccctgta ttacgtgaac  1380
aagcaggagg gcaagagcct gtacgtgaag ggcgaaccta ttatcaactt ctacgaccct  1440
ctggtgtttc cttccgacga gtttgatgct agcatctctc aggtgaacga gaagatcaac  1500
cagagcctgg cctttatcag aaagagcgat gagctgctgc acaacgtgaa cgccggcaag  1560
agtaccacca acatcatgat caccggatac atcccggagg cccctaggga cggtcaagct  1620
tacgtgagaa aggacggcga atgggttctg ctgtcgacct tcttggga              1668

SEQ ID NO: 100         moltype = RNA  length = 1668
FEATURE                Location/Qualifiers
source                 1..1668
                       mol_type = other RNA
                       organism = synthetic construct
SEQUENCE: 100
atggaactgc ctgtgctgaa aacaaacgcc atcacaacaa tcctggcagc agtgacactg  60
tgcttcgcca gcagccagaa tattacagaa gagttctacc agagcacatg cagcgccgtg  120
tctaagggct acctgagcgc cctgagaaca ggctggtaca ccagcgtcat cacgatcgag  180
ctgagtaata tcaaggagaa caaatgcaac ggcaccgacg ccaaggtgaa gctgatcaag  240
caggagctgg ataaatacaa gaacgccgtg accgagttgc agctgctgat gcagtctacc  300
ccagccgcca acaacagagc cagacgggaa ctacccagat tcatgaacta cacactgaac  360
aacactaaga acaccaacgt gacactgtct aagaaaagaa agcggcggtt cctgggattc  420
ctgctgggcg tgggaagcgc tatcgcttct ggaattgccg tgtgcaaggt gctgcacctg  480
gaaggcgagg tgaacaagat caagtctgcc ctgctgtcca ccaacaaggc cgtagtcagc  540
ctgagcaatg gcgtgagcgt cctgaccttt aaggtgctgg acctgaagaa ctacatcgac  600
aagcagctgc tgcctatctt gaacaagcag agctgctcca tcagcaatat tgagactgtg  660
atcgaattcc agcagaagaa caaccggctg ctggagatca ccagagagtt ctccgtgaac  720
gctggcgtga ctacacctgt ttcaacctac atgctgacca attctgagct gctgagcctg  780
atcaacgaca tgcctatcac caacgaccag aaaaaactga tgtccaataa cgttcaaatc  840
gtgcggcagc aaagctacag catcatgtgc atcatcaagg aagaagtgct tgcctacgtg  900
gtccagctgc cactttatgg agttatcgat acaccctgct ggaagctgca caccagccct  960
ctgtgtacaa ccaacaccaa ggaaggcagc aacatctgcc tgaccagaac agatagaggc  1020
tggtattgtg ataacgccgg cagcgtgagc ttcttccccc aggccgacac atgtaaagtg  1080
cagagcaata gagtgttctg cgacaccatg aatagcctga ccctgcccag cgaggtgaat  1140
ctgtgtaaca tcgacatttt caaccccaag tacgattgca agatcatgac ctccaagacc  1200
gacgtgagca gcagcgtgat cacctccctg ggcgccatcg tgtcttgcta cggcaagacc  1260
aagtgcacag cctctaacaa aaatcgcggc atcatcaaaa ccttctctaa cggttgtgac  1320
tacgtgtcaa acaaaggcgt ggacaccgtg tccgtgggca acaccctgta ttacgtgaac  1380
aagcaggagg gcaagagcct gtacgtgaag ggcgaaccta ttatcaactt ctacgaccct  1440
ctggtgtttc cttccgacga gtttgatgct agcatctctc aggtgaacga gaagatcaac  1500
cagagcctgg cctttatcag aaagagcgat gagctgctgc acaacgtgaa cgccggcaag  1560
agtaccacca acatcatgat caccggatac atcccggagg cccctaggga cggtcaagct  1620
tacgtgagaa aggacggcga atgggttctg ctgtcgacct tcttggga              1668
```

```
SEQ ID NO: 101         moltype = AA  length = 574
FEATURE                Location/Qualifiers
source                 1..574
                       mol_type = protein
                       organism = synthetic construct
SEQUENCE: 101
MELPVLKTNA ITTILAAVTL CFASSQNITE EFYQSTCSAV SKGYLSALRT GWYTSVITIE  60
LSNIKENKCN GTDAKVKLIK QELDKYKNAV TELQLLMQST PAANNRARRE LPRFMNYTLN  120
NTKNTNVTLS KKRKRRFLGF LLGVGSAIAS GIAVCKVLHL EGEVNKIKSA LLSTNKAVVS  180
LSNGVSVLTF KVLDLKNYID KQLLPILNKQ SCSISNIETV IEFQQKNNRL LEITREFSVN  240
AGVTTPVSTY MLTNSELLSL INDMPITNDQ KKLMSNNVQI VRQQSYSIMC IIKEEVLAYV  300
VQLPLYGVID TPCWKLHTSP LCTTNTKEGS NICLTRTDRG WYCDNAGSVS FFPQADTCKV  360
QSNRVFCDTM NSLTLPSEVN LCNIDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSHQWHA SISQVNEKIN QSLAFIRKSD ELLHNVNAGK STTNIMITTI IIVIIVILLS  540
LIAVGLLLYC KARSTPVTLS KDQLSGINNI AFSN                             574

SEQ ID NO: 102         moltype = DNA  length = 1722
FEATURE                Location/Qualifiers
source                 1..1722
                       mol_type = other DNA
                       organism = synthetic construct
SEQUENCE: 102
atggaactgc ctgtgctgaa aacaaacgcc atcacaacaa tcctggcagc agtgacactg  60
tgcttcgcca gcagccagaa tattacagaa gagttctacc agagcacatg cagcgccgtg  120
tctaagggct acctgagcgc cctgagaaca ggctggtaca ccagcgtcat cacgatcgag  180
ctgagtaata tcaaggagaa caaatgcaac ggcaccgacg ccaaggtgaa gctgatcaag  240
caggagctgg ataaatacaa gaacgccgtg accgagttgc agctgctgat gcagtctacc  300
ccagccgcca acaacagagc cagacgggaa ctacccagat tcatgaacta cacactgaac  360
aacactaaga acaccaacgt gacactgtct aagaaaagaa agcggcggtt cctgggattc  420
ctgctgggcg tgggaagcgc tatcgcttct ggaattgccg tgtgcaaggt gctgcacctg  480
gaaggcgagg tgaacaagat caagtctgcc ctgctgtcca ccaacaaggc cgtagtcagc  540
ctgagcaatg gcgtgagcgt cctgaccttt aaggtgctgg acctgaagaa ctacatcgac  600
aagcagctgc tgcctatctt gaacaagcag agctgctcca tcagcaatat tgagactgtg  660
atcgaattcc agcagaagaa caaccggctg ctggagatca ccagagagtt ctccgtgaac  720
gctggcgtga ctacacctgt ttcaacctac atgctgacca attctgagct gctgagcctg  780
atcaacgaca tgcctatcac caacgaccag aaaaaactga tgtccaataa cgttcaaatc  840
gtgcggcagc aaagctacag catcatgtgc atcatcaagg aagaagtgct tgcctacgtg  900
gtccagctgc cactttatgg agttatcgat acaccctgct ggaagctgca caccagccct  960
ctgtgtacaa ccaacaccaa ggaaggcagc aacatctgcc tgaccagaac agatagaggc  1020
tggtattgtg ataacgccgg cagcgtgagc ttcttccccc aggccgacac atgtaaagtg  1080
cagagcaata gagtgttctg cgacaccatg aatagcctga ccctgcccag cgaggtgaat  1140
ctgtgtaaca tcgacatttt caaccccaag tacgattgca agatcatgac ctccaagacc  1200
gacgtgagca gcagcgtgat cacctccctg ggcgccatcg tgtcttgcta cggcaagacc  1260
aagtgcacag cctctaacaa aaatcgcggc atcatcaaaa ccttctctaa cggttgtgac  1320
tacgtgtcaa acaaaggcgt ggacaccgtg tccgtgggca acaccctgta ttacgtgaac  1380
aagcaggagg gcaagagcct gtacgtgaag ggcgaaccta ttatcaactt ctacgaccct  1440
ctggtgtttc cttcccacca gtggcatgct agcatctctc aggtgaacga gaagatcaac  1500
cagagcctgg cctttatcag aaagagcgat gagctgctgc acaacgtgaa cgccggcaag  1560
agtaccacca acatcatgat caccaccatc attatcgtga tcatcgtgat cctcctgagc  1620
ctgatcgctg tcggactgct gctgtactgc aaggccagga gcacacctgt gaccctgagc  1680
aaggaccaac tgtctggcat caacaacatc gcttttagca at                    1722

SEQ ID NO: 103         moltype = RNA  length = 1722
FEATURE                Location/Qualifiers
source                 1..1722
                       mol_type = other RNA
                       organism = synthetic construct
SEQUENCE: 103
atggaactgc ctgtgctgaa aacaaacgcc atcacaacaa tcctggcagc agtgacactg  60
tgcttcgcca gcagccagaa tattacagaa gagttctacc agagcacatg cagcgccgtg  120
tctaagggct acctgagcgc cctgagaaca ggctggtaca ccagcgtcat cacgatcgag  180
ctgagtaata tcaaggagaa caaatgcaac ggcaccgacg ccaaggtgaa gctgatcaag  240
caggagctgg ataaatacaa gaacgccgtg accgagttgc agctgctgat gcagtctacc  300
ccagccgcca acaacagagc cagacgggaa ctacccagat tcatgaacta cacactgaac  360
aacactaaga acaccaacgt gacactgtct aagaaaagaa agcggcggtt cctgggattc  420
ctgctgggcg tgggaagcgc tatcgcttct ggaattgccg tgtgcaaggt gctgcacctg  480
gaaggcgagg tgaacaagat caagtctgcc ctgctgtcca ccaacaaggc cgtagtcagc  540
ctgagcaatg gcgtgagcgt cctgaccttt aaggtgctgg acctgaagaa ctacatcgac  600
aagcagctgc tgcctatctt gaacaagcag agctgctcca tcagcaatat tgagactgtg  660
atcgaattcc agcagaagaa caaccggctg ctggagatca ccagagagtt ctccgtgaac  720
gctggcgtga ctacacctgt ttcaacctac atgctgacca attctgagct gctgagcctg  780
atcaacgaca tgcctatcac caacgaccag aaaaaactga tgtccaataa cgttcaaatc  840
gtgcggcagc aaagctacag catcatgtgc atcatcaagg aagaagtgct tgcctacgtg  900
gtccagctgc cactttatgg agttatcgat acaccctgct ggaagctgca caccagccct  960
ctgtgtacaa ccaacaccaa ggaaggcagc aacatctgcc tgaccagaac agatagaggc  1020
tggtattgtg ataacgccgg cagcgtgagc ttcttccccc aggccgacac atgtaaagtg  1080
cagagcaata gagtgttctg cgacaccatg aatagcctga ccctgcccag cgaggtgaat  1140
```

```
ctgtgtaaca tcgacatttt caaccccaag tacgattgca agatcatgac ctccaagacc  1200
gacgtgagca gcagcgtgat cacctccctg ggcgccatcg tgtcttgcta cggcaagacc  1260
aagtgcacag cctctaacaa aaatcgcggc atcatcaaaa ccttctctaa cggttgtgac  1320
tacgtgtcaa acaaaggcgt ggacaccgtg tccgtgggca acaccctgta ttacgtgaac  1380
aagcaggagg gcaagagcct gtacgtgaag ggcgaaccta ttatcaactt ctacgaccct  1440
ctggtgtttc cttcccacca gtggcatgct agcatctctc aggtgaacga gaagatcaac  1500
cagagcctgg cctttatcag aaagagcgat gagctgctgc acaacgtgaa cgccggcaag  1560
agtaccacca acatcatgat caccaccatc attatcgtga tcatcgtgat cctcctgagc  1620
ctgatcgctg tcggactgct gctgtactgc aaggccagga gcacacctgt gaccctgagc  1680
aaggaccaac tgtctggcat caacaacatc gcttttagca at                      1722

SEQ ID NO: 104          moltype = AA  length = 556
FEATURE                 Location/Qualifiers
source                  1..556
                        mol_type = protein
                        organism = synthetic construct
SEQUENCE: 104
MELPVLKTNA ITTILAAVTL CFASSQNITE EFYQSTCSAV SKGYLSALRT GWYTSVITIE  60
LSNIKENKCN GTDAKVKLIK QELDKYKNAV TELQLLMQST PAANNRARRE LPRFMNYTLN  120
NTKNTNVTLS KKRKRRFLGF LLGVGSAIAS GIAVCKVLHL EGEVNKIKSA LLSTNKAVVS  180
LSNGVSVLTF KVLDLKNYID KQLLPILNKQ SCSISNIETV IEFQQKNNRL LEITREFSVN  240
AGVTTPVSTY MLTNSELLSL INDMPITNDQ KKLMSNNVQI VRQQSYSIMC IIKEEVLAYV  300
VQLPLYGVID TPCWKLHTSP LCTTNTKEGS NICLTRTDRG WYCDNAGSVS FFPQADTCKV  360
QSNRVFCDTM NSLTLPSEVN LCNIDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSHQWHA SISQVNEKIN QSLAFIRKSD ELLHNVNAGK STTNIMITGY IPEAPRDGQA  540
YVRKDGEWVL LSTFLG                                                   556

SEQ ID NO: 105          moltype = DNA  length = 1668
FEATURE                 Location/Qualifiers
source                  1..1668
                        mol_type = other DNA
                        organism = synthetic construct
SEQUENCE: 105
atggaactgc ctgtgctgaa aacaaacgcc atcacaacaa tcctggcagc agtgacactg  60
tgcttcgcca gcagccagaa tattacagaa gagttctacc agagcacatg cagcgccgtg  120
tctaagggct acctgagcgc cctgagaaca ggctggtaca ccagcgtcat cacgatcgag  180
ctgagtaata tcaaggagaa caaatgcaac ggcaccgacg ccaaggtgaa gctgatcaag  240
caggagctgg ataaatacaa gaacgccgtg accgagttgc agctgctgat gcagtctacc  300
ccagccgcca acaacagagc cagacgggaa ctacccagat tcatgaacta cacactgaac  360
aacactaaga acaccaacgt gacactgtct aagaaaagaa agcggcggtt cctgggattc  420
ctgctgggcg tgggaagcgc tatcgcttct ggaattgccg tgtgcaaggt gctgcacctg  480
gaaggcgagg tgaacaagat caagtctgcc ctgctgtcca ccaacaaggc cgtagtcagc  540
ctgagcaatg gcgtgagcgt cctgaccttt aaggtgctgg acctgaagaa ctacatcgac  600
aagcagctgc tgcctatctt gaacaagcag agctgctcca tcagcaatat tgagactgtg  660
atcgaattcc agcagaagaa caaccggctg ctggagatca ccagagagtt ctccgtgaac  720
gctggcgtga ctacacctgt ttcaacctac atgctgacca attctgagct gctgagcctg  780
atcaacgaca tgcctatcac caacgaccag aaaaaactga tgtccaataa cgttcaaatc  840
gtgcggcagc aaagctacag catcatgtgc atcatcaagg aagaagtgct tgcctacgtg  900
gtccagctgc cactttatgg agttatcgat acaccctgct ggaagctgca caccagccct  960
ctgtgtacaa ccaacaccaa ggaaggcagc aacatctgcc tgaccagaac agatagaggc  1020
tggtattgtg ataacgccgg cagcgtgagc ttcttccccc aggccgacac atgtaaagtg  1080
cagagcaata gagtgttctg cgacaccatg aatagcctga ccctgcccag cgaggtgaat  1140
ctgtgtaaca tcgacatttt caaccccaag tacgattgca agatcatgac ctccaagacc  1200
gacgtgagca gcagcgtgat cacctccctg ggcgccatcg tgtcttgcta cggcaagacc  1260
aagtgcacag cctctaacaa aaatcgcggc atcatcaaaa ccttctctaa cggttgtgac  1320
tacgtgtcaa acaaaggcgt ggacaccgtg tccgtgggca acaccctgta ttacgtgaac  1380
aagcaggagg gcaagagcct gtacgtgaag ggcgaaccta ttatcaactt ctacgaccct  1440
ctggtgtttc cttcccacca gtggcatgct agcatctctc aggtgaacga gaagatcaac  1500
cagagcctgg cctttatcag aaagagcgat gagctgctgc acaacgtgaa cgccggcaag  1560
agtaccacca acatcatgat caccggatac atcccggagg cccctaggga cggtcaagct  1620
tacgtgagaa aggacggcga atgggttctg ctgtcgacct tcttggga               1668

SEQ ID NO: 106          moltype = RNA  length = 1668
FEATURE                 Location/Qualifiers
source                  1..1668
                        mol_type = other RNA
                        organism = synthetic construct
SEQUENCE: 106
atggaactgc ctgtgctgaa aacaaacgcc atcacaacaa tcctggcagc agtgacactg  60
tgcttcgcca gcagccagaa tattacagaa gagttctacc agagcacatg cagcgccgtg  120
tctaagggct acctgagcgc cctgagaaca ggctggtaca ccagcgtcat cacgatcgag  180
ctgagtaata tcaaggagaa caaatgcaac ggcaccgacg ccaaggtgaa gctgatcaag  240
caggagctgg ataaatacaa gaacgccgtg accgagttgc agctgctgat gcagtctacc  300
ccagccgcca acaacagagc cagacgggaa ctacccagat tcatgaacta cacactgaac  360
aacactaaga acaccaacgt gacactgtct aagaaaagaa agcggcggtt cctgggattc  420
ctgctgggcg tgggaagcgc tatcgcttct ggaattgccg tgtgcaaggt gctgcacctg  480
gaaggcgagg tgaacaagat caagtctgcc ctgctgtcca ccaacaaggc cgtagtcagc  540
ctgagcaatg gcgtgagcgt cctgaccttt aaggtgctgg acctgaagaa ctacatcgac  600
```

```
aagcagctgc tgcctatctt gaacaagcag agctgctcca tcagcaatat tgagactgtg  660
atcgaattcc agcagaagaa caaccggctg ctggagatca ccagagagtt ctccgtgaac  720
gctggcgtga ctacacctgt ttcaacctac atgctgacca attctgagct gctgagcctg  780
atcaacgaca tgcctatcac caacgaccag aaaaaactga tgtccaataa cgttcaaatc  840
gtgcggcagc aaagctacag catcatgtgc atcatcaagg aagaagtgct tgcctacgtg  900
gtccagctgc cactttatgg agttatcgat acaccctgct ggaagctgca caccagccct  960
ctgtgtacaa ccaacaccaa ggaaggcagc aacatctgcc tgaccagaac agatagaggc  1020
tggtattgtg ataacgccgg cagcgtgagc ttcttccccc aggccgacac atgtaaagtg  1080
cagagcaata gagtgttctg cgacaccatg aatagcctga ccctgcccag cgaggtgaat  1140
ctgtgtaaca tcgacatttt caaccccaag tacgattgca agatcatgac ctccaagacc  1200
gacgtgagca gcagcgtgat cacctccctg ggcgccatcg tgtcttgcta cggcaagacc  1260
aagtgcacag cctctaacaa aaatcgcggc atcatcaaaa ccttctctaa cggttgtgac  1320
tacgtgtcaa acaaaggcgt ggacaccgtg tccgtgggca acaccctgta ttacgtgaac  1380
aagcaggagg gcaagagcct gtacgtgaag ggcgaaccta ttatcaactt ctacgaccct  1440
ctggtgtttc cttcccacca gtggcatgct agcatctctc aggtgaacga gaagatcaac  1500
cagagcctgg cctttatcag aaagagcgat gagctgctgc acaacgtgaa cgccggcaag  1560
agtaccacca acatcatgat caccggatac atcccggagg cccctaggga cggtcaagct  1620
tacgtgagaa aggacggcga atgggttctg ctgtcgacct tcttggga              1668
```

```
SEQ ID NO: 107          moltype = AA  length = 9
FEATURE                 Location/Qualifiers
source                  1..9
                        mol_type = protein
                        organism = synthetic construct
SEQUENCE: 107
KHKHKHKHK                                                          9

SEQ ID NO: 108          moltype = AA  length = 10
FEATURE                 Location/Qualifiers
source                  1..10
                        mol_type = protein
                        organism = synthetic construct
SEQUENCE: 108
HKHKHKHKHK                                                         10

SEQ ID NO: 109          moltype = AA  length = 10
FEATURE                 Location/Qualifiers
source                  1..10
                        mol_type = protein
                        organism = synthetic construct
SEQUENCE: 109
KHKHKHKHKH                                                         10

SEQ ID NO: 110          moltype = AA  length = 11
FEATURE                 Location/Qualifiers
source                  1..11
                        mol_type = protein
                        organism = synthetic construct
SEQUENCE: 110
HKHKHKHKHK H                                                       11

SEQ ID NO: 111          moltype = AA  length = 20
FEATURE                 Location/Qualifiers
source                  1..20
                        mol_type = protein
                        organism = synthetic construct
SEQUENCE: 111
KHKHHKHHKH HKHHKHHKHK                                              20

SEQ ID NO: 112          moltype = AA  length = 17
FEATURE                 Location/Qualifiers
source                  1..17
                        mol_type = protein
                        organism = synthetic construct
SEQUENCE: 112
KHHHKHHHKH HHKHHHK                                                 17

SEQ ID NO: 113          moltype = AA  length = 18
FEATURE                 Location/Qualifiers
source                  1..18
                        mol_type = protein
                        organism = synthetic construct
SEQUENCE: 113
KHHHKHHHKH HHHKHHHK                                                18

SEQ ID NO: 114          moltype = AA  length = 18
FEATURE                 Location/Qualifiers
source                  1..18
                        mol_type = protein
```

-continued

```
                        organism = synthetic construct
SITE                    1
                        note = D-amino acid
SITE                    5
                        note = D-amino acid
SITE                    9
                        note = D-amino acid
SITE                    14
                        note = D-amino acid
SITE                    18
                        note = D-amino acid
SEQUENCE: 114
KHHHKHHHKH HHHKHHHK                                          18

SEQ ID NO: 115          moltype = AA  length = 19
FEATURE                 Location/Qualifiers
source                  1..19
                        mol_type = protein
                        organism = synthetic construct
SEQUENCE: 115
HKHHHKHHHK HHHHKHHHK                                         19

SEQ ID NO: 116          moltype = AA  length = 20
FEATURE                 Location/Qualifiers
source                  1..20
                        mol_type = protein
                        organism = synthetic construct
SEQUENCE: 116
HHKHHHKHHH KHHHHKHHHK                                        20

SEQ ID NO: 117          moltype = AA  length = 50
FEATURE                 Location/Qualifiers
source                  1..50
                        mol_type = protein
                        organism = unidentified
SEQUENCE: 117
IMITTIIIVI IVILLSLIAV GLLLYCKARS TPVTLSKDQL SGINNIAFSN       50

SEQ ID NO: 118          moltype = RNA  length = 300
FEATURE                 Location/Qualifiers
source                  1..300
                        mol_type = other RNA
                        organism = synthetic construct
misc_difference         1..300
                        note = This sequence may encompass 10-300 adenosine
                         monophosphate nucleotides
SEQUENCE: 118
aaaaaaaaaa aaaaaaaaaa aaaaaaaaaa aaaaaaaaaa aaaaaaaaaa aaaaaaaaaa  60
aaaaaaaaaa aaaaaaaaaa aaaaaaaaaa aaaaaaaaaa aaaaaaaaaa aaaaaaaaaa  120
aaaaaaaaaa aaaaaaaaaa aaaaaaaaaa aaaaaaaaaa aaaaaaaaaa aaaaaaaaaa  180
aaaaaaaaaa aaaaaaaaaa aaaaaaaaaa aaaaaaaaaa aaaaaaaaaa aaaaaaaaaa  240
aaaaaaaaaa aaaaaaaaaa aaaaaaaaaa aaaaaaaaaa aaaaaaaaaa aaaaaaaaaa  300
```